US009957247B2

(12) United States Patent
Wang et al.

(10) Patent No.: US 9,957,247 B2
(45) Date of Patent: May 1, 2018

(54) SECA INHIBITORS AND METHODS OF MAKING AND USING THEREOF

(71) Applicant: Georgia State University Research Foundation, Inc., Atlanta, GA (US)

(72) Inventors: Binghe Wang, Marietta, GA (US); Phang-Cheng Tai, Atlanta, GA (US); Jinshan Jin, Atlanta, GA (US); Yinghsin Hsieh, Atlanta, GA (US); Ying-Ju Ritter, Marietta, GA (US); Jianmei Cui, Kennesaw, GA (US); Arpana S. Chaudhary, Atlanta, GA (US); Chaofeng Dai, Atlanta, GA (US); Krishna Damera, Smyrna, GA (US); Weixuan Chen, Atlanta, GA (US)

(73) Assignee: Georgia State University Research Foundation, Inc., Atlanta, GA (US)

( * ) Notice: Subject to any disclaimer, the term of this patent is extended or adjusted under 35 U.S.C. 154(b) by 0 days. days.

(21) Appl. No.: 14/406,085

(22) PCT Filed: Jun. 5, 2013

(86) PCT No.: PCT/US2013/044243
§ 371 (c)(1),
(2) Date: Dec. 5, 2014

(87) PCT Pub. No.: WO2013/184755
PCT Pub. Date: Dec. 12, 2013

(65) Prior Publication Data
US 2015/0152077 A1 Jun. 4, 2015

Related U.S. Application Data

(60) Provisional application No. 61/656,793, filed on Jun. 7, 2012, provisional application No. 61/824,857, filed on May 17, 2013, provisional application No. 61/826,345, filed on May 22, 2013.

(51) Int. Cl.
| | | |
|---|---|---|
| C07D 239/38 | (2006.01) |
| C07D 239/20 | (2006.01) |
| C07D 239/22 | (2006.01) |
| A61K 31/496 | (2006.01) |
| C07D 311/86 | (2006.01) |
| C07D 413/14 | (2006.01) |
| C07D 401/14 | (2006.01) |
| C07D 311/58 | (2006.01) |
| C07D 311/82 | (2006.01) |
| C07D 403/14 | (2006.01) |
| C07D 417/14 | (2006.01) |
| C07D 249/12 | (2006.01) |
| C07D 471/10 | (2006.01) |
| C07D 491/20 | (2006.01) |
| C07D 495/04 | (2006.01) |
| C07C 63/331 | (2006.01) |
| C07D 239/56 | (2006.01) |
| C07D 239/60 | (2006.01) |
| C07D 311/74 | (2006.01) |
| C07D 493/10 | (2006.01) |
| C07D 497/04 | (2006.01) |

(Continued)

(52) U.S. Cl.
CPC .......... *C07D 311/86* (2013.01); *A61K 31/496* (2013.01); *C07C 63/331* (2013.01); *C07D 239/20* (2013.01); *C07D 239/22* (2013.01); *C07D 239/38* (2013.01); *C07D 239/56* (2013.01); *C07D 239/60* (2013.01); *C07D 249/12* (2013.01); *C07D 311/58* (2013.01); *C07D 311/74* (2013.01); *C07D 311/82* (2013.01); *C07D 401/14* (2013.01); *C07D 403/14* (2013.01); *C07D 413/14* (2013.01); *C07D 417/14* (2013.01); *C07D 471/10* (2013.01); *C07D 491/20* (2013.01); *C07D 493/10* (2013.01); *C07D 495/04* (2013.01); *C07D 497/04* (2013.01); *C09B 11/24* (2013.01); *G01N 33/6872* (2013.01); *G01N 2333/4706* (2013.01)

(58) Field of Classification Search
CPC .. C07D 401/14; C07D 311/82; C07D 311/86; C07D 403/14; C07D 239/38; C07D 417/14; C07D 239/20; C07D 239/22; A61K 31/496
USPC ...... 544/296, 300, 311; 548/304.1; 549/344, 549/391, 406; 562/466; 514/256
See application file for complete search history.

(56) References Cited

U.S. PATENT DOCUMENTS 3,142,668 A * 7/1964 Rattee .................... C09B 62/02
534/617
4,938,763 A 7/1990 Dunn
5,480,656 A 1/1996 Okada
(Continued)

FOREIGN PATENT DOCUMENTS

DE 2308210 9/1974
GB 871856 * 7/1961
(Continued)

OTHER PUBLICATIONS

English Abstract DN 73:87881, 1970.*
Caplus English Abstract DN 79:13470 Kline Ira et al . 1973.*
Babuchkina, et al., "Nuclear quadrupole resonance in polymers", J Mole Structure, 117(3-4):323-8 (1984).
Carr, et al., "Bis-basic-substituted polycyclic aromatic compounds. A new class of antiviral agents. 7. Bisalkamine esters of 9-oxoxanlhene-2,7-dicarboxylic acid, 3,6-bis-basic ethers of xanthen-9-one, and 2,7-bis(aminoacyl) xanthen-9-ones-xanthenes, and -thioxanthenes", J Med Chem., 19(9):1142-8 (1976).
Chen, et al., "Identification and characterization of protease-resistant SecA fragments: secA has two membrane-integral forms", J. Bacteriol., 180:527-37 (1998).
Chen, et al., "A significant fraction of functional SecA is permanently embedded in the membrane. SecA cycling on and off the membrane is not essential during protein translocation", J. Biol. Chem., 271:29698-706 (1996).
(Continued)

Primary Examiner — Rita J Desai
(74) Attorney, Agent, or Firm — Pabst Patent Group LLP

(57) ABSTRACT

Inhibitors of SecA, and methods of making and using thereof, are described herein. The compounds described herein can be used to treat or prevent microbial infections, such as bacterial infections.

17 Claims, 126 Drawing Sheets

(51) Int. Cl.
   *G01N 33/68* (2006.01)
   *C09B 11/24* (2006.01)

(56) References Cited

U.S. PATENT DOCUMENTS

| | | | | |
|---|---|---|---|---|
| 6,007,961 | A * | 12/1999 | Inomata | G03F 7/022 430/165 |
| 6,113,943 | A | 9/2000 | Okada | |
| 6,387,903 | B1 * | 5/2002 | Dinsmore | C07D 403/06 514/254.05 |
| 7,052,678 | B2 | 5/2006 | Vanbever | |
| 7,829,578 | B1 | 11/2010 | Riscoe | |

FOREIGN PATENT DOCUMENTS

| | | | |
|---|---|---|---|
| GB | 878646 | * | 10/1961 |
| GB | 885547 | * | 12/1961 |
| JP | H0511441 | | 1/1993 |
| JP | 06157516 | * | 6/1994 |
| WO | WO 9804548 | * | 2/1998 |
| WO | WO 98/14432 | * | 4/1998 |
| WO | WO 9818755 | * | 5/1998 |
| WO | 2008098143 | | 8/2008 |

OTHER PUBLICATIONS

Chen, et al., "The first low microM SecA inhibitors", Bioorg Med Chem., 18(4), 1617-25 (2010).
Cortesi, et al., "Sugar cross-linked gelatin for controlled release: microspheres and disks", Biomaterials, 19:1641-9 (1998).
Demidova, et al., "Effect of cell-photosensitizer binding and cell density on microbial photoinactivation", Antimicrob Agents Chemother, 49:2329-35 (2005).
Dodean, et al., "Synthesis and heme-binding correlation with antimalarial activity of 3,6-bis-(omega-N,N-diethylaminoamyloxy)-4,5-difluoroxanthorie", Bioorganic Med Chem., 16:1174-83 (2008).
Fitzpatrick, et al., "Further total sytheses of chlorine-containing lichen xanthones", J Chem Soc., 1:85-9 (1980).
Hassoon, et al., Electron transfer photoreduction of 5,7-Diiodo-3-butoxy-6-flourone with tetrabutylammonium triphenylbutyborate and N,N-Dimerthyl-2,6-diisopropylaniline, J Physical Chem., 99(23):9416-24 (1995).
Hsieh, et al., "SecA alone can promote protein translocation and ion channel activity: SecYEG increases efficiency and signal peptide specificity", J. Biol. Chem., 286: 44702-9 (2011).
Huang, et al., "Fluorescein analogues inhibit SecA ATPase: the first sub-micromolar inhibitor of bacterial protein translocation", ChemMedChem., 7 (4):571-7 (2012).
Inbaraj, et al., "Phloxine B phototoxicity: a mechanistic study using HaCaT keratinocytes", Photochem Photobiol, 81:81-8 (2005).
Kawaguchi, et al., "Phagocytosis of latex particles by leucocytes. I. Dependence of phagocytosis on the size and surface potential of particles", Biomaterials, '7: 61-6 (1986).
Langbein and Paetzold, "Photooxidation von leukofarvatoffen. III. Sensibilisierte photooxidation von leukofiuoreszein", J Fuer Praktische Chemie, 324(1):46-52 (19821 (English Abstract).
Levy, et al., "Active efflux, a common mechanism for biocide and antibiotic resistance" Symp Ser Soc Appl Microbiol, (31):65S-71S (2002).
Lin, et al., "Electrophysiological studies in Xenopus oocytes for the opening of *Escherichia coli* SecA-dependent protein-conducting channels", J. Membr. Biol., 214:103-13 (2006).
Lin, et al., "*Escherichia coil* membranes depleted of SecYEG elicit SecA-dependent ion-channel activity but lose signal peptide specificity", J. Membr. Biol., 245:747-57 (2012).
Markham, et al., "Efflux-mediated drug resistance in Gram-positive bacteria", Curr Opin Microbiol, 4:509-14 (2001).
Nikaido, et al., "Antibiotic efflux mechanisms", Curr Opin Infect Dis, 12:529-36 (1999).
Rautio, et al., "Prodrugs: design and clinical applications", Nat Rev Drug Discov., 7:255-270 (2008).
Rudt and Muller, "In vitro phagocytosis assay of nano- and microparticies by chemiluminescence. I. Effect of analytical parameters, particle size and particle concentration", J. Contr. Rel, 22:263-72 (1992).
Ruiz, et al., "Chemical conditionality: a genetic strategy to probe organelle assembly", Cell, 121:307-17 (2005).
Siegfried, et al., "Struktur and C-NMR-Spektroskopie von chlorhaltigen flechtenxanthonen", Tetrahedron, 34(16):2491-502 (1978) (English Abstract).
Sierecki, et al., "Discovery of small molecule inhibitors of the PH domain leucine-rich repeat protein phosphatase (PHLPP) by chemical and virtual screening", J Med. Chem., 53(19):6899-911 (2010).
Van Bambeke, et al., "Antibiotic efflux pumps", Biochem Pharmacol, 60:457-70 (2000).
Wang, et al., "The phototoxicity of xanthene derivatives against *Escherichia coli, Staphylococcus aureus*, and *Saccharomyces cerevisiae*", Curr. Microbial., 52:1-5 (2006).
Zhang, et al., "Design, synthesis, and evaluation of efflux substrate-metal chelator conjugates as potential antimicrobial agents", Bioorg Med Chem Lett, 17:707-11 (2007).
Delia, et al., "24,6-trichloropyrimidine. Reaction with 4-substituted phenolate ions", J Heterocyclic Chem., 35:69-73 (1998).
Ghosh, et al., "2,4-Bis (aryloxy)pyrimidines as antimicrobial agents", J Med Chem., 11:1237-8 (1968).

* cited by examiner

| Compounds | MW | Structure |
|---|---|---|
| RB | 1017.64 | Chemical Formula: $C_{20}H_2Cl_4Na_2O_5$<br>Molecular Weight: 1017.64 |
| SCA-41 | 282.33 | Chemical Formula: $C_{18}H_{19}O_3$<br>Molecular Weight: 282.3337 |
| SCA-42 | 597.92 | Chemical Formula: $C_{18}H_{14}Br_4O_3$<br>Molecular Weight: 597.9180 |
| SCA-44 | 785.92 | Chemical Formula: $C_{18}H_{14}I_4O_3$<br>Molecular Weight: 785.9198 |
| SCA-45 | 660.02 | Chemical Formula: $C_{18}H_{15}I_3O_3$<br>Molecular Weight: 660.0233 |
| SCA-46 | 256.30 | Chemical Formula: $C_{16}H_{16}O_3$<br>Molecular Weight: 256.2964 |
| SCA-47 | 759.88 | Chemical Formula: $C_{16}H_{12}I_4O_3$<br>Molecular Weight: 759.8826 |
| SCA-50 | 298.38 | Chemical Formula: $C_{19}H_{22}O_3$<br>Molecular Weight: 298.3762 |
| SCA-57 | 296.36 | Chemical Formula: $C_{19}H_{20}O_3$<br>Molecular Weight: 296.36 |

FIG. 7

SecA Inhibitors

Analog classes: A(Rose Bengal), B (Pyrimidine) and C(Triazole)

| ID & Class | Notebook No. | Structure | Results |
|---|---|---|---|
| BW-SCA-1-B | WX-I-153 | Chemical Formula: $C_{30}H_{20}N_6O_2S_2$<br>Molecular Weight: 560.6488 | |
| BW-SCA-2-B | WX-I-146-A | Chemical Formula: $C_{32}H_{24}N_6O_2S_2$<br>Molecular Weight: 588.7020 | |

FIG. 8-1

| | | |
|---|---|---|
| BW-SCA-5-B | WX-B-10-D | Chemical Formula: $C_{36}H_{32}N_6O_2S_2$<br>Molecular Weight: 644.8083 |
| BW-SCA-6-B | WX-I-146-C | Chemical Formula: $C_{32}H_{24}N_6O_4S_2$<br>Molecular Weight: 620.7008 |

FIG. 8-3

| | | BW-SCA-7-B |
|---|---|---|
| WX-I-143 WX-B-10-E | Structure: bis-pyrimidinone with two 4-bromophenyl groups, CN substituents, linked via -S-CH$_2$-C$_6$H$_4$-CH$_2$-S- bridge. Chemical Formula: C$_{30}$H$_{18}$Br$_2$N$_6$O$_2$S$_2$; Molecular Weight: 718.4409 | |

| | Proteins: | IC$_{50}$ (μM) |
|---|---|---|
| In vitro inhibition | EcSecAN68 | 2 |
| | EcSecA | 20 |
| | Cell lines: | IC$_{50}$ (μM) |
| toxicity | HeLa cell | very high |
| | HCT116 | 26.3 |

FIG. 8-4

| | | | In vitro inhibition | Proteins: EcSecAN68 | IC$_{50}$ (μM) | |
|---|---|---|---|---|---|---|
| | | | In vivo inhibition | Strains: E. coli NR698 | MIC$_{50}$ (μM) | MIC$_{95}$(μM) |
| | | | toxicity | Cell lines: HeLa cell | IC$_{50}$ (μM) 12.55 | |
| | | | | HCT116 | 26.3 | |

| | | |
|---|---|---|
| BW-SCA-9-B | WX-I-146-B / WX-B-10-F | Chemical Formula: C$_{38}$H$_{24}$N$_6$O$_2$S$_2$; Molecular Weight: 660.7662 |
| BW-SCA-10-B | WX-B-8-B | Chemical Formula: C$_{20}$H$_{17}$N$_3$OS; Molecular Weight: 347.4335 |
| BW-SCA-11-B | WX-B-8-D | Chemical Formula: C$_{21}$H$_{19}$N$_3$OS; Molecular Weight: 361.4601 |

FIG. 8-6

| | | |
|---|---|---|
| BW-SCA-12-B | WX-B-5 | 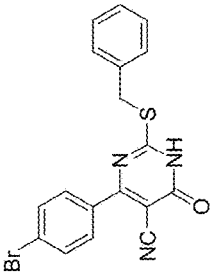 Chemical Formula: $C_{18}H_{12}BrN_3OS$<br>Molecular Weight: 398.2764 |
| BW-SCA-13-B | WX-B-8-C | 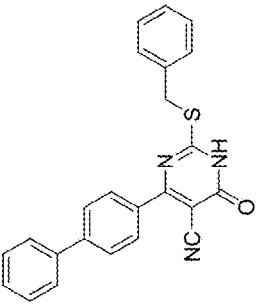 Chemical Formula: $C_{24}H_{17}N_3OS$<br>Molecular Weight: 395.4763 |

| | | | |
|---|---|---|---|
| In vitro inhibition | Proteins: | $IC_{50}$ (μM) | |
| | EcSecAN68 | 19 | |
| | EcSecA | >100 | |
| | EcSecA Tn | 75 | |
| | BsSecA | 100 | |
| | BaSecA1 | >200 | |
| | BaSecA2 | >100 | |
| | SaSecA2 | >200 | |
| | Ec-F$_0$F$_1$-H$^+$-ATPase | >200 | |
| In vivo inhibition | Strains: | $MIC_{50}$ (μM) | $MIC_{95}$ (μM) |
| | B. anthracis Sterne | 5 | 6 |
| | S. aureus 6538 | 52 | >70 |
| | S. aureus Mu50 | 65 | >100 |
| | S. aureus N315 | 60 | >100 |
| | S. aureus Mu3 | >100 | >100 |
| | E. coli NR698 | 55 | >70 |
| | B. subtilis 168 | 15/7 | /10 |

FIG. 8-7

| BW-SCA-15-B | AS-1-5 | | | |
|---|---|---|---|---|
| | | In vitro inhibition | Proteins: | IC$_{50}$ (μM) |
| | | | EcSecAN68 | 8 |
| | | | EcSecA | 30 |
| | | | EcSecA Tn | 30 |
| | | | BsSecA | >100 |
| | | | BaSecA1 | >200 |
| | | | BaSecA2 | 20 |
| | | | SaSecA1 | 140 |
| | | | SaSecA2 | 13 |
| | | | Ec-F$_1$F$_0$-H$^+$-ATPase | >100 |
| | | Ion Channel inhibition | Protein: | IC$_{50}$ (μM) |
| | | | EcSecA | 4.2 |
| | | | SaSecA1 | 2 |
| | | | BaSecA1 | 2.8 |
| | | | PaSecA | 3.2 |
| | | | BsSecA | 3 |
| | | | MsSecA | 3 |
| | | | MtbSecA | 3.1 |
| | | | SpSecA | 3.5 |
| | | In vivo inhibition | Strains: | MIC$_{50}$ (μM) | MIC$_{95}$ (μM) |
| | | | B. anthracis Sterne | 4 | 5 |
| | | | S. aureus 6538 | 12 | 15 |
| | | | S. aureus Mu50 | 22 | 38 |
| | | | S. aureus N315 | 9 | 25 |
| | | | S. aureus Mu3 | 35 | 100 |
| | | | E. coli NR698 | 35 | 50 (MIC$_{90}$) |
| | | | B. subtilis 168 | 7 | 10 |
| | | toxicity | Cell lins: | IC$_{50}$ (μM) |
| | | | HeLa cell | 35/40 |

Chemical Formula: C$_{24}$H$_{16}$N$_6$OS
Molecular Weight: 436.4884

| | | BW-SCA-16-B | AS-1-19 | (structure with two azide groups) Chemical Formula: C₃₁H₂₁N₉OS Molecular Weight: 567.6231 |

| | Proteins: | IC$_{50}$ (μM) | |
|---|---|---|---|
| In vitro inhibition | EcSecAN68 | ND | |
| | EcSecA | >100 | |
| | BaSecA2 | >200 | |
| | Strains: | MIC$_{50}$ (μM) | MIC (μM) |
| In vivo inhibition | B. anthracis Sterne | | >250 |
| | S. aureus 6538 | | >250 |
| | S. aureus Mu50 | | >250 |
| | E. coli NR698 | | >250 |
| | B. subtilis 168 | | >250 |

| | | BW-SCA-17-B | AS-2-53 | (structure with amine group) Chemical Formula: C₂₄H₁₈N₄OS Molecular Weight: 410.4909 |

| | Proteins: | IC$_{50}$ (μM) | |
|---|---|---|---|
| In vitro inhibition | EcSecAN68 | 11 | |
| | BaSecA | <100 | |
| | Strains: | MIC$_{50}$ (μM) | MIC$_{95}$ (μM) |
| In vivo inhibition | B. anthracis Sterne | >100 | >100 |
| | S. aureus 6538 | >100 | >100 |
| | S. aureus Mu50 | 20, 32%↓ | >20 |
| | E. coli NR698 | >100 | >100 |
| | B. subtilis 168 | >100 | >100 |

| | | BW-SCA-18-B | AS-2-37 | 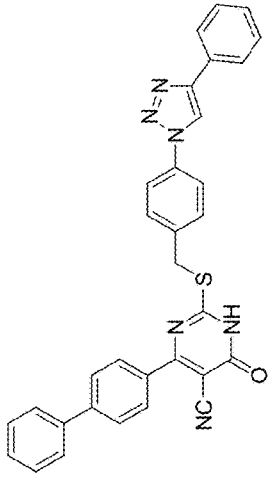 Chemical Formula: C$_{32}$H$_{22}$N$_6$OS<br>Molecular Weight: 538.6217 | | In vitro inhibition | Proteins: | IC$_{50}$ (μM) | |
|---|---|---|---|---|---|---|---|---|---|
| | | | | | | | EcSecAN68 | 2.5 | |
| | | | | | | | BsSecA | 25 μM 44%↓, no more increase | |
| | | | | | | | BaSecA1 | 100 μM 20%↓, no more increase | |
| | | | | | | | BaSecA2 | 13 | |
| | | | | | | | Ec-F$_1$F$_0$-H$^+$-ATPase | >100 | |
| | | | | | | In vivo inhibition | Strains: | MIC$_{50}$ (μM) | MIC$_{95}$(μM) |
| | | | | | | | B. anthracis Sterne | 21 | 25 |
| | | | |

| BW-SCA-20-C | C#34 | [Structure: pyrimidine with methylthio group, two thioether linkages to pyrazole rings bearing 3,5-dichlorophenyl substituents] Chemical Formula: $C_{21}H_{12}Cl_4N_8S_3$ Molecular Weight: 614.38 | | | |
|---|---|---|---|---|---|
| | | | | IC$_{50}$ (µM) | |
| | | | Proteins: | MIC$_{50}$ (µM) | MIC$_{95}$ (µM) |
| | | In vitro inhibition | EcSecAN68 | | 12.5 |
| | | | EcSecA | | 12.5, MIC90 |
| | | In vivo inhibition | Strains: | | |
| | | | B. an

| | | | |
|---|---|---|---|
| BW-SCA-21-C | C#85 | 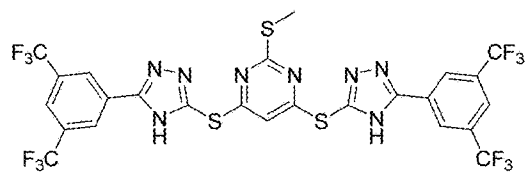  Chemical Formula: $C_{25}H_{12}F_{12}N_8S_3$ Molecular Weight: 748.59 | (see table below) |

| | | | |
|---|---|---|---|
| ***In vitro* inhibition** | Proteins: | $IC_{50}$ (μM) | |
| | EcSecAN68 | 18 | |
| | EcSecA | 45, 40°C, liposome +<br>>100, 30°C, liposome +<br>45, 40°C liposome −<br>20, 42°C liposome + | |
| | EcSecA Tn | 20 | |
| | BsSecA | >100 | |
| | BaSecA2 | 45 | |
| | SaSecA1 | >100, 25°C with liposome | |
| | SaSecA2 | 43 | |
| | Ec-$F_1F_0$-$H^+$-ATPase | 100 | |
| *Ion Channel inhibition* | Protein: | $IC_{50}$ (μM) | |
| | EcSecA | 2.4 | |
| | SaSecA1 | 1.6 | |
| | BaSecA1 | 1.5 | |
| | PaSecA | 1.5 | |
| | BsSecA | 2.6 | |
| | MsSecA | 2 | |
| | MtbSecA | 2 | |
| | SpSecA | 1 | |
| ***In vivo* inhibition** | *Strains:* | $MIC_{50}$ (μM) | MIC (μM) |
| | *B. anthracis* Sterne | 3 | 6.25 |
| | *S. aureus* 6538 | 1.5 | 12.5 |
| | *S. aureus* Mu50 | 0.75 | |
| | *S. aureus* N315 | 0.8 | |
| | *S. aureus* Mu3 | 1.5 | |
| | *E. coli* NR698 | 60 | 25 |
| | *B. subtilis* 168 | 3 | 6.25 |

$MIC9_5$: *B. anthracis* Sterne 4 μM; *S. aureus* 6538 4 μM; *S. aureus* Mu50 2 μM; *S. aureus* Mu3 2 μM; *S. aureus* N315 2 μM; *E. coli* NR698 75 μM (MIC90); *B. subtilis* 168 4 μM.

FIG. 8-13

| | | | |
|---|---|---|---|
| BW-SCA-22-A | MC181 & MCI-83 | 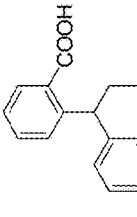<br>Chemical Formula: C₁₆H₁₄O₄<br>Molecular Weight: 270.09<br>270.28 | In vitro inhibition<br>Proteins: IC₅₀ (µM)<br>EcSecAN68: >100/>200<br>BsSecA: >200<br>BaSecA2: >200<br>In vivo inhibition<br>Strains: MIC₅₀ (µM) / MIC (µM)<br>E. coli NR698: >100 / >250*<br>B. subtilis 168: >100 |
| BW-SCA-23-A | MC197 | 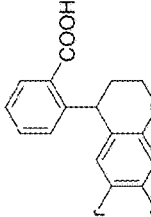<br>Chemical Formula: C₁₆H₁₂Br₂O₄<br>Molecular Weight: 425.91<br>428.0721 | In vitro inhibition<br>Proteins: IC₅₀ (µM)<br>EcSecAN68: 100, 75%↓/200<br>BsSecA: >200<br>BaSecA2: >200<br>In vivo inhibition<br>Strains: MIC₅₀ (µM) / MIC (µM)<br>E. coli NR698: 45 / >250*<br>B. subtilis 168: 75 |
| BW-SCA-24-A | MC198-1 | 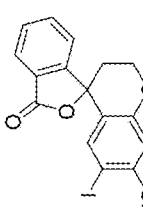<br>Chemical Formula: C₁₆H₁₀I₂O₄<br>Molecular Weight: 520.0571 | In vitro inhibition<br>Proteins: IC₅₀ (µM)<br>EcSecAN68: 140<br>BsSecA: >200<br>BaSecA2: >200<br>In vivo inhibition<br>Strains: MIC₅₀ (µ) / MIC₉₅(µM)<br>E. coli NR698: >100 / >250*<br>B. subtilis 168: 45 |

FIG. 8-14

| | | | | | |
|---|---|---|---|---|---|
| BW-SCA-36-A | MC2-43 | ![structure] Chemical Formula: $C_{13}H_8O_4$ Molecular Weight: 228.2002 | *In vitro* inhibition | Proteins: EcSecAN68 EcSecA BsSecA BaSecA2 | IC$_{50}$ (μM) 100, 96%↓/>200 >200 >200 |
| | | | *In vivo* inhibition | Strains: E. coli NR698 B. subtilis 168 | MIC$_{50}$ (μM) / MIC (μM) >100 / >250* >100 / >100 |
| BW-SCA-37-A | MC2-53 | ![structure] Chemical Formula: $C_{13}H_4Br_4O_4$ Molecular Weight: 543.7845 | *In vitro* inhibition | Proteins: EcSecAN68 EcSecA BsSecA BaSecA2 | IC$_{50}$ (μM) 30/70 >200 >200 |
| | | | *In vivo* inhibition | Strains: E. coli NR698 B. subtilis 168 | MIC$_{50}$ (μM) / MIC (μM) >100 / >250* 75 |
| BW-SCA-38-A | MC2-50 | ![structure] Chemical Formula: $C_{13}H_6I_2O_4$ Molecular Weight: 479.9933 | *In vitro* inhibition | Proteins: EcSecAN68 BsSecA BaSecA2 | IC$_{50}$ (μM) >100/>200 >200 >200 |
| | | | *In vivo* inhibition | Strains: E. coli NR698 B. subtilis 168 | MIC$_{50}$ (μM) / MIC (μM) 75 / >250* 79 |


FIG. 8-18

| | | MC2-83 | 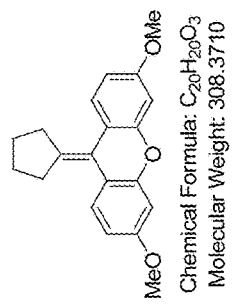 Chemical Formula: $C_{20}H_{20}O_3$<br>Molecular Weight: 308.3710 | *In vitro* inhibition | Proteins: | $IC_{50}$ (μM) |
|---|---|---|---|---|---|---|
| BW-SCA-39-A | | | | | EcSecAN68 | >100/>200 |
| | | | | | EcSecA | >100 |
| | | | | | BsSecA | >100 |
| | | | | | BaSecA | >200 |
| | | | | | Ec-$F_1F_0$-$H^+$-ATPase | >100 |
| | | | | *In vivo* inhibition | Strains: | $MIC_{50}$ (μM) / MIC (μM) |
| | | | | | *B. anthracis* Sterne | >10 |
| | | | | | *S. aureus* 6538 | >10 |
| | | | | | *S. aureus* Mu50 | >10 |
| | | | | | *E. coli* NR698 | >250* |
| | | | | | *B. subtilis* 168 | >100 |
| BW-SCA-40-A | | MC2-88 | 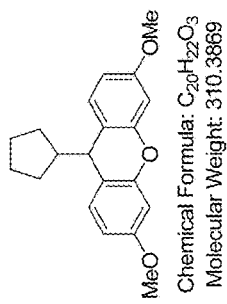 Chemical Formula: $C_{20}H_{22}O_3$<br>Molecular Weight: 310.3869 | *In vitro* inhibition | Proteins: | $IC_{50}$ (μM) |
| | | | | | EcSecAN68 | 100, 58%↓/>200 |
| | | | | | EcSecA | |
| | | | | | BsSecA | >200 |
| | | | | | BaSecA2 | >200 |
| | | | | *In vivo* inhibition | Strains: | $MIC_{50}$ (μM) / MIC (μM) |
| | | | | | *E. coli* NR698 | >250* |
| | | | | | *B. subtilis* 168 | >100 |

FIG. 8-19

| | | | | |
|---|---|---|---|---|
| BW-SCA-41-A | MC2-89 | 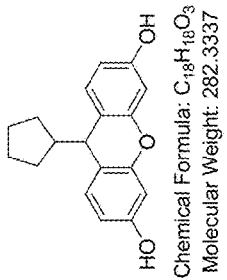<br>Chemical Formula: $C_{18}H_{18}O_3$<br>Molecular Weight: 282.3337 | *In vitro* inhibition | Proteins: | IC$_{50}$ (µM) |
| | | | | EcSecAN68 | 8 old/25 new |
| | | | | EcSecA | 43/180 |
| | | | | EcSecA Tn | 15/30 |
| | | | | BsSecA | 30/ |
| | | | | BaSecA1 | /100 |
| | | | | BaSecA2 | 30/ |
| | | | | SaSecA2 | 6/40 |
| | | | | Ec-F$_1$F$_0$-H$^+$-ATPase | 60/ |
| | | | Ion Channel inhibition | Protein: | IC$_{50}$ (µM) |
| | | | | EcSecA | /3.4 |
| | | | | SaSecA1 | /3.4 |
| | | | | BaSecA1 | /3.8 |
| | | | | aSecA | /3.6 |
| | | | | BsSecA | /3 |
| | | | | MsSecA | /3.5 |
| | | | | MtbSecA | /3.2 |
| | | | | SpSecA | /3 |
| | | | *In vivo* inhibition | Strains: | MIC$_{50}$ (µM) | MIC (µM) |
| | | | | *B. anthracis* Sterne | 3.2/ | |
| | | | | *S. aureus* 6538 | 5/7/27/21/22/23 | 25 |
| | | | | *S. aureus* Mu50 | 5.5/23 | 12.5/50 |
| | | | | *S. aureus* N315 | 5/ | |
| | | | | *S. aureus* Mu3 | 5/ | |
| | | | | *E. coli* NR698 | 8.5/32 | 25/50/50 |
| | | | | *B. subtilis* 168 | 7/20 | |
| | | | | *E. coli* MC4100 | >100 | |
| | | | toxicity | Cell lines: | IC$_{50}$ (µM) |
| | | | | HeLa cell | 10/22/20 |

FIG. 8-20

| | | | | |
|---|---|---|---|---|
| BW-SCA-42-A | MC2-92 | Structure: 9-cyclopentyl-xanthene with Br, Br, OH, Br, Br, OH substituents. Chemical Formula: $C_{18}H_{14}Br_4O_3$; Molecular Weight: 597.9180 | *In vitro* inhibition | Proteins: / EcSecAN68 / EcSecA / BsSecA / BaSecA2 / Ec-F$_1$F$_0$-H$^+$-ATPase — IC$_{50}$ (µM): 4.5/1 / >100 / >100 / 45 / 100 (70%↓) |
| | | | *In vivo* inhibition | Strains: / *B. anthracis* Sterne / *S. aureus* 6538 / *S. aureus* Mu50 / *E. coli* NR698 / *B. subtilis* 168 — MIC$_{50}$ (µM): 3.2 / 19 / 10 / 19 / 9 — MIC (µM): / 25 14h /250 20h / 12.5 /50 / 6.25/ 6.25/ 0.78 |
| BW-SCA-43-A | MC2-93 | Structure: 9-cyclopentyl-xanthene with I, OH, I, OH substituents. Chemical Formula: $C_{18}H_{16}I_2O_3$; Molecular Weight: 534.1268 | *In vitro* inhibition | Proteins: / EcSecAN68 / EcSecA / EcSecA Tn / BsSecA / BaSecA2 / Ec-F$_1$F$_0$-H$^+$-ATPase — IC$_{50}$ (µM): 2.4/2 / 200 / 9 / 100 / 13 / 17 |
| | | | *In vivo* inhibition | Strains: / *B. anthracis* Sterne / *S. aureus* 6538 / *S. aureus* Mu50 / *E. coli* NR698 / *B. subtilis* 168 / *E. coli* MC4100 — MIC$_{50}$ (µM): 1 / 4 / 2.7 / 8.2 / 3.2 / >100 — MIC (µM): 3.125 / 3.125 / 6.25/ 25/ 6.25 |

FIG. 8-21

| | | | | |
|---|---|---|---|---|
| BW-SCA-44-A | MC2-95-1<br>MCII-99-1<br>& MCII-101-1 | Chemical Formula: $C_{18}H_{14}I_4O_3$<br>Molecular Weight: 785.9198 | *In vitro*<br>inhibition | Proteins: | IC$_{50}$ (μM) |
| | | | | EcSecAN68 | 1.7 |
| | | | | EcSecA | >100 |
| | | | | BsSecA | >100 |
| | | | | BaSecA2 | 18 |
| | | | | Ec-F$_1$F$_0$-H$^+$-ATPase | >10 |
| | | | *In vivo*<br>inhibition | Strains: | MIC$_{50}$ (μM) / MIC (μM) |
| | | | | *B. anthracis* Sterne | 2 / 6.25/25 |
| | | | | *S. aureus* 6538 | 18 / 6.25/12.5 |
| | | | | *S. aureus* Mu50 | 7 / 3.125/1.56/ |
| | | | | *E. coli* NR698 | 3 / 0.78 |
| | | | | *B. subtilis* 168 | 5 / |
| BW-SCA-45-A | MC2-95-2<br>MCII-99-2 | Chemical Formula: $C_{18}H_{15}I_3O_3$<br>Molecular Weight: 660.0233 | *In vitro*<br>inhibition | Proteins: | IC$_{50}$ (μM) |
| | | | | EcSecAN68 | 1.3 |
| | | | | EcSecA | >100 |
| | | | | BsSecA | >100 |
| | | | | BaSecA2 | 17 |
| | | | | Ec-F$_1$F$_0$-H$^+$-ATPase | 100 (55%↓) |
| | | | *In vivo*<br>inhibition | Strains: | MIC$_{50}$ (μM) / MIC (μM) |
| | | | | *B. anthracis* Sterne | 2 / |
| | | | | *S. aureus* 6538 | 5 / 6.25 |
| | | | | *S. aureus* Mu50 | 4 / 1.56/6.25 |
| | | | | *E. coli* NR698 | 18 / 6.25/25/3.1 |
| | | | | *B. subtilis* 168 | 5 / 25 |

FIG. 8-22

| BW-SCA-46-A | MC2-122 | 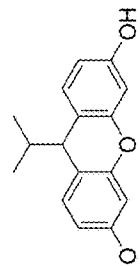 Chemical Formula: $C_{16}H_{16}O_3$<br>Molecular Weight: 256.2964 | In vitro inhibition | Proteins: | $IC_{50}$ (μM) |
|---|---|---|---|---|---|
| | | | | EcSecAN68 | 60 |
| | | | | EcSecA | |
| | | | | BsSecA | >200 |
| | | | | BaSecA2 | >20 |
| | | | In vivo inhibition | Strains: | $MIC_{50}$ (μM) | MIC (μM) |
| | | | | B. anthracis Sterne | | |
| | | | | S. aureus 6538 | 70 | |
| | | | | S. aureus Mu50 | 53 | 100/50/10 |
| | | | | E. coli NR698 | | 0/50 |
| | | | | B. subtilis 168 | 70 | |

| BW-SCA-47-A | MC2-135-1 | 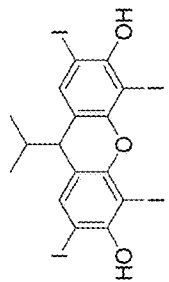 Chemical Formula: $C_{16}H_{12}I_4O_3$<br>Molecular Weight: 759.8826 | In vitro inhibition | Proteins: | $IC_{50}$ (μM) |
|---|---|---|---|---|---|
| | | | | EcSecAN68 | 2 |
| | | | | EcSecA | |
| | | | | BsSecA | >200 |
| | | | | BaSecA2 | >20 |
| | | | In vivo inhibition | Strains: | $MIC_{50}$ (μM) | MIC (μM) |
| | | | | B. anthracis Sterne | 1.6 | |
| | | | | S. aureus 6538 | 6.9 | 12.5 |
| | | | | S. aureus Mu50 | 9 | 6.25 |
| | | | | E. coli NR698 | 8.5 | 3.125/3.125/12.5 |
| | | | | B. subtilis 168 | 5.3 | /0.78 |

FIG. 8-23

| | | BW-SCA-48-A | MC2-135-2 | 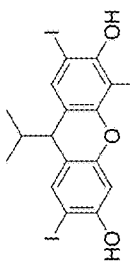 Chemical Formula: C$_{16}$H$_{13}$I$_3$O$_3$<br>Molecular Weight: 633.9860 | *In vitro* inhibition | Proteins: | IC$_{50}$ (μM) | |
|---|---|---|---|---|---|---|---|---|
| | | | | | | EcSecAN68 | 3.5 | |
| | | | | | | EcSecA | | |
| | | | | | | BsSecA | <200 | |
| | | | | | | BaSecA2 | <20 | |
| | | | | | *In vivo* inhibition | Strains: | MIC$_{50}$ (μM) | MIC (μM) |
| | | | | | | *B. anthracis* Sterne | 3.2 | |
| | | | | | | *S. aureus* 6538 | 7.4 | 6.25 |
| | | | | | | *S. aureus* Mu50 | 5.5 | 6.25 |
| | | | | | | *E. coli* NR698 | 32 | 12.5/12.5/6 |
| | | | | | | *B. subtilis* 168 | 5.1 | .25 |
| | | BW-SCA-49-A | MC2-131 | 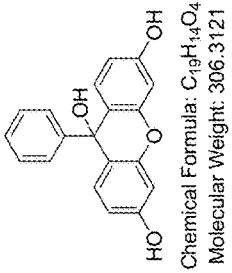 Chemical Formula: C$_{19}$H$_{14}$O$_4$<br>Molecular Weight: 306.3121 | *In vitro* inhibition | Proteins: | IC$_{50}$ (μM) | |
| | | | | | | EcSecAN68 | | |
| | | | | | | EcSecA | | |
| | | | | | | BsSecA | | |
| | | | | | | BaSecA2 | | |
| | | | | | *In vivo* inhibition | Strains: | MIC$_{50}$ (μM) | MIC (μM) |
| | | | | | | *B. anthracis* Sterne | | |
| | | | | | | *S. aureus* 6538 | | |
| | | | | | | *S. aureus* Mu50 | | |
| | | | | | | *E. coli* NR698 | | |
| | | | | | | *B. subtilis* 168 | | |

FIG. 8-24

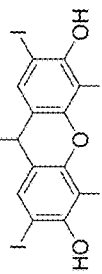

| BW-SCA-51-A | MC3-6 | Structure: Chemical Formula: $C_{19}H_{18}I_4O_3$; Molecular Weight: 801.9623 | In vitro inhibition | Proteins: | $IC_{50}$ (μM) | |
|---|---|---|---|---|---|---|
| | | | | EcSecAN68 | 3 | |
| | | | | EcSecA | >200 | |
| | | | | BsSecA | <20 | |
| | | | | BaSecA2 | | |
| | | | In vivo inhibition | Strains: | $MIC_{50}$ (μM) | MIC (μM) |
| | | | | B. anthracis Sterne | | >100 |
| | | | | S. aureus 6538 | 15 | 50/100 |
| | | | | S. aureus Mu50 | | 12.5/50/0.78 |
| | | | | E. coli NR698 | 20 | |
| | | | | B. subtilis 168 | | |
| BW-SCA-52-A | MC3-2-2 | Structure: Chemical Formula: $C_{19}H_{10}I_4O_4$; Molecular Weight: 809.8982 | In vitro inhibition | Proteins: | $IC_{50}$ (μM) | |
| | | | | EcSecAN68 | 100, 95%↓ | |
| | | | | EcSecA | | |
| | | | | BsSecA | | |
| | | | | BaSecA2 | | |
| | | | In vivo inhibition | Strains: | $MIC_{50}$ (μM) | MIC (μM) |
| | | | | B. anthracis Sterne | | |
| | | | | S. aureus 6538 | | |
| | | | | S. aureus Mu50 | | |
| | | | | E. coli NR698 | | >250 |
| | | | | B. subtilis 168 | | |

FIG. 8-26

| BW-SCA-53-A | MCIII-90 | 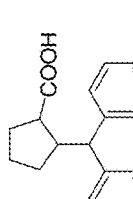 Chemical Formula: C$_{21}$H$_{22}$O$_5$<br>Molecular Weight: 354.40 | Proteins: | IC$_{50}$ (µM) | |
|---|---|---|---|---|---|
| | | | EcSecAN68 | 100, 80%↓ | |
| | | | EcSecA | >100 | |
| | | | BsSecA | >100 | |
| | | | BaSecA2 | | |
| | | *In vitro inhibition* | Strains: | MIC$_{50}$ (µM) | MIC (µM) |
| | | | B. anthracis Sterne | >10 | |
| | | | S. aureus 6538 | >10 | |
| | | | S. aureus Mu50 | | |
| | | *In vivo inhibition* | E. coli NR698 | | >250 |
| | | | B. subtilis 168 | >10 | |
| BW-SCA-54-A | MCIII-94 | 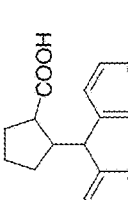 Chemical Formula: C$_{19}$H$_{18}$O$_5$<br>Molecular Weight: 326.34 | Proteins: | IC$_{50}$ (µM) | |
| | | | EcSecAN68 | 100, 74%↓/200 | |
| | | | EcSecA | >100 | |
| | | | BsSec | >100 | |
| | | | BaSecA2 | | |
| | | *In vitro inhibition* | Strains: | MIC$_{50}$ (µM) | MIC (µM) |
| | | | B. anthracis Sterne | 175 | |
| | | | S. aureus 6538 | >250 | |
| | | | S. aureus Mu50 | | |
| | | *In vivo inhibition* | E. coli NR698 | >250 | >250 |
| | | | B. subtilis 168 | >10 | |

FIG. 8-27

| | | | |
|---|---|---|---|
| BW-SCA-55-A | MCIII-95 | 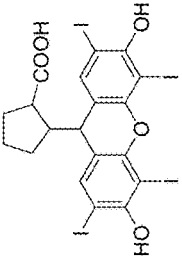 Chemical Formula: $C_{19}H_{14}I_4O_5$<br>Molecular Weight: 829.93 | *In vitro* inhibition: Proteins: EcSecAN68 IC$_{50}$ (μM) 2.5/<50; EcSecA >100; BsSecA >100; BaSecA2 —<br>*In vivo* inhibition: Strains: *B. anthracis* Sterne MIC$_{50}$ (μM) 180, MIC (μM) —; *S. aureus* 6538 >250; *S. aureus* Mu50 —; *E. coli* NR698 >250, >250; *B. subtilis* 168 >250, >250 |
| BW-SCA-56-A | MCIII-104 | 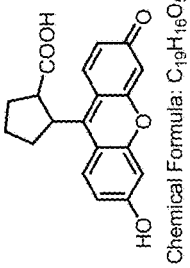 Chemical Formula: $C_{19}H_{16}O_5$<br>Molecular Weight: 324.33 | *In vitro* inhibition: Proteins: EcSecAN68 IC$_{50}$ (μM) >200; EcSecA ?; BsSecA >100; BaSecA2 —<br>*In vivo* inhibition: Strains: *B. anthracis* Sterne MIC$_{50}$ (μM) >250, MIC (μM) —; *S. aureus* 6538 —; *S. aureus* Mu50 —; *E. coli* NR698 >250, >250; *B. subtilis* 168 >250, >250 |

FIG. 8-28

| | | | Proteins: | | IC$_{50}$ (μM) | |
|---|---|---|---|---|---|---|
| BW-SCA-57-A | MCIII-110 |  Chemical Formula: C$_{19}$H$_{20}$O$_3$ Molecular Weight: 296.36 | *In vitro* inhibition | EcSecAN68 | 20 | |
| | | | | EcSecA | 100 | |
| | | | | BsSecA | 62 | |
| | | | | Strains: | MIC$_{50}$ (μ) | MIC (μM) |
| | | | *In vivo* inhibition | *B. anthracis* Sterne | | |
| | | | | *S. aureus* 6538 | 12 | 25 |
| | | | | *S. aureus* Mu50 | 12 | 25 |
| | | | | *E. coli* NR698 | 13 | 25 |
| | | | | *B. subtilis* 168 | 7 | |
| BW-SCA-58-A | MCIII-113 | 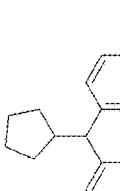 Chemical Formula: C$_{22}$H$_{28}$N$_2$O Molecular Weight: 336.47 | *In vitro* inhibition | EcSecAN68 | 64/>200 | |
| | | | | EcSecA | | |
| | | | | BsScA | >100 | |
| | | | | BaSecA2 | | |
| | | | | Strains: | MIC$_{50}$ (μM) | MIC (μM) |
| | | | *In vivo* inhibition | *B. anthracis* Sterne | >32 | |
| | | | | *S. aureus* 6538 | >32 | |
| | | | | *S. aureus* Mu50 | >32 | |
| | | | | *E. coli* NR698 | >32 | >250 |
| | | | | *B. subtilis* 168 | >32 | |

FIG. 8-29

| BW-SCA-59-A | MCII-113.2HCl | 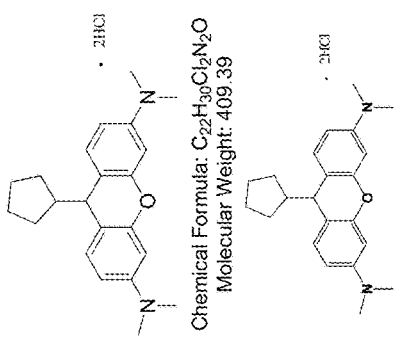 Chemical Formula: C$_{22}$H$_{30}$Cl$_2$N$_2$O  Molecular Weight: 409.39 <br> 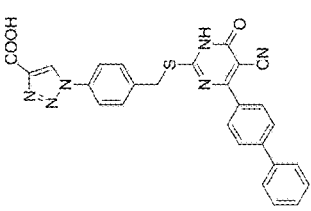 Chemical Formula: C$_{22}$H$_{30}$Cl$_2$N$_2$O Molecular Weight: 408.17 | *In vitro* inhibition | Proteins: | IC$_{50}$ (µM) | |
|---|---|---|---|---|---|---|
| | | | | EcSecAN68 | 25/70 | |
| | | | | EcSecA | | |
| | | | | BsSecA | >100 | |
| | | | | BaSecA2 | | |
| | | | *In vivo* inhibition | Strains: | MIC$_{50}$ (µM) | MIC (µM) |
| | | | | *B. anthracis* Sterne | >32 | |
| | | | | *S. aureus* 6538 | >32 | |
| | | | | *S. aureus* Mu50 | >32 | |
| | | | | *E. coli* NR698 | >32 | >250 |
| | | | | *B. subtilis* 168 | >32 | |
| BW-SCA-60-B | AS-II-134 | 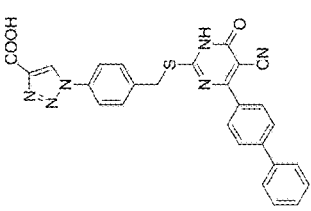 Chemical Formula: C$_{27}$H$_{18}$N$_6$O$_3$S  Molecular Weight: 506.5352 | *In vitro* inhibition | Proteins: | IC$_{50}$ (µM) | |
| | | | | EcSecAN68 | | |
| | | | | BsSecA | 100, 58%↓ | |
| | | | *In vivo* inhibition | Strains: | MIC$_{50}$ (µM) | MIC$_{95}$(µM) |
| | | | | *B. anthracis* Sterne | >20 | |
| | | | | *S. aureus* 6538 | >20 | |
| | | | | *S. aureus* Mu50 | >20 | |
| | | | | *E. coli* NR698 | >20 | |
| | | | | *B. subtilis* 168 | >20 | |

FIG. 8-30

| | | BW-SCA-61-B | AS-II-137 | Chemical Formula: C₂₉H₂₂N₆O₃S Molecular Weight: 534.5884 | In vitro inhibition | Proteins: | IC₅₀ (µM) | |
|---|---|---|---|---|---|---|---|---|
| | | | | | | EcSecAN68 | 7.5 | |
| | | | | | | BsSecA | 30 | |
| | | | | | In vivo inhibition | Strains: | MIC₅₀ (µM) | MIC₉₅ (µM) |
| | | | | | | B. anthracis Sterne | 19 | 25 |
| | | | | | | S. aureus 6538 | >100 | >100 |
| | | | | | | S. aureus Mu50 | 100 | >100 |
| | | | | | | E. coli NR698 | >100 | >100 |
| | | | |

| | | | |
|---|---|---|---|
| BW-SCA-65-B | DK-I-150 | 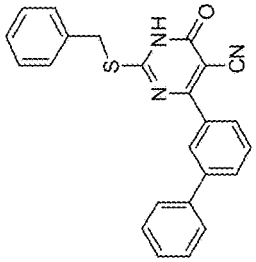Chemical Formula: C$_{24}$H$_{17}$N$_3$OS<br>Molecular Weight: 395.4763 | *In vitro* inhibition: Proteins: EcSecAN68, IC$_{50}$ (µM): 37.5<br>*In vivo* inhibition:<br>| Strains: | MIC$_{50}$(µM) | MIC$_{95}$(µM) |<br>| *B. anthracis* Sterne | >100 | >100 |

| BW-SCA-67-B | DK-II-1 | ![structure with thiouracil CN CF3 phenyl] Chemical Formula: C₁₂H₆F₃N₃OS  Molecular Weight: 297.2557 | *In vitro* inhibition | Proteins: EcSecAN68 | IC₅₀ (μM) >100 | |
|---|---|---|---|---|---|---|
| | | | *In vivo* inhibition | Strains: | MIC₅₀ (μM) | MIC₉₅ (μM) |
| | | | | *B. anthracis* Sterne | >250 | >250 |
| | | | | *S. aureus* 6538 | >100 | >100 |
| | | | | *E. coli* NR698 | >250 | >250 |
| | | | | *B. subtilis* 168 | >100 | >100 |
| BW-SCA-68-B | DK-II-2 | ![structure with SCH2COOH, CN, CF3 phenyl] Chemical Formula: C₁₄H₈F₃N₃O₃S  Molecular Weight: 355.2918 | *In vitro* inhibition | Proteins: EcSecAN68 | IC₅₀ (μM) >100 | |
| | | | *In vivo* inhibition | Strains: | MIC₅₀ (μM) | MIC₉₅ (μM) |
| | | | | *B. anthracis* Sterne | >250 | >250 |
| | | | | *S. aureus* 6538 | >100 | >100 |
| | | | | *E. coli* NR698 | >250 | >250 |
| | | | | *B. subtilis* 168 | >100 | >100 |

FIG. 8-34

| BW-SCA-69-B | DK-II-5 | Structure: biphenyl with CF3, connected to pyrimidine ring with NH, C=O, CN, C=S, NH. Chemical Formula: C₁₈H₁₀F₃N₃OS; Molecular Weight: 373.3517 | In vitro inhibition | Proteins: EcSecAN68 | IC₅₀ (μM) >100 | |
|---|---|---|---|---|---|---|
| | | | In vivo inhibition | Strains: | MIC₅₀(μM) | MIC₉₅(μM) |
| | | | | B. anthracis Sterne | 150 | 250 |
| | | | | S. aureus 6538 | >100 | >100 |
| | | | | E. coli NR698 | >250 | >250 |
| | | | | B. subtilis 168 | >100 | >100 |
| BW-SCA-70-B | DK-I-6 | Structure: biphenyl with CF3, connected to pyrimidine ring with S-CH2-COOH, NH, C=O, CN. Chemical Formula: C₂₀H₁₂F₃N₃O₃S; Molecular Weight: 431.3878 | In vitro inhibition | Proteins: EcSecAN68 | IC₅₀ (μM) | |
| | | | In vivo inhibition | Strains: | MIC₅₀(μM) | MIC₉₅(μM) |
| | | | | B. anthracis Sterne | >250 | >250 |
| | | | | S. aureus 6538 | >100 | >100 |
| | | | | E. coli NR698 | >250 | >250 |
| | | | | B. subtilis 168 | >100 | >100 |

FIG. 8-35

| | | | |
|---|---|---|---|
| BW-SCA-71-B | AS-III-51 | 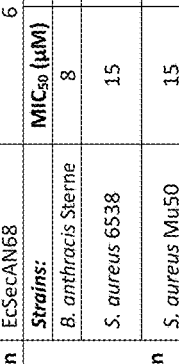Chemical Formula: C$_{26}$H$_{19}$N$_3$O$_3$S<br>Molecular Weight: 453.5124 | *In vitro* inhibition: Proteins: EcSecAN68 — IC$_{50}$ (μM) 6<br><br>*In vivo* inhibition: Strains: / MIC$_{50}$ (μM) / MIC$_{95}$ (μM)<br>B. anthracis Sterne / 8 / 10<br>S. aureus 6538 / 15 / 25, 80%↓<br>S. aureus Mu50 / 15 / 100, 90%↓<br>S. aureus Mu50 / 15 / 25, 80%↓<br>                     /   / 100, 90%↓<br>E. coli NR698

| | | | |
|---|---|---|---|
| BW-SCA-73-B | AS-II-87 | Chemical Formula: C$_{29}$H$_{26}$N$_4$O$_3$S<br>Molecular Weight: 510.6067 | *In vitro inhibition* — Proteins: EcSecAN68 —; BaSecA2 >200 IC$_{50}$ (μM)<br>*In vivo inhibition* — Strains: B. anthracis Sterne >100; S. aureus 6538 >100; S. aureus Mu50 >100; E. coli NR698 >100; B. subtilis 168 >100 MIC (μM) |
| BW-SCA-74-B | AS-II-97 | Chemical Formula: C$_{24}$H$_{17}$N$_3$O$_2$S<br>Molecular Weight: 411.4757 | *In vitro inhibition* — Proteins: EcSecAN68 >100; EcSecA >200; BaSecA1 45; Ec-F$_1$F$_0$-H$^+$-ATPase >100 IC$_{50}$ (μM)<br>*In vivo inhibition* — Strains: B. anthracis Sterne MIC$_{50}$ (μM) >20; MIC$_{95}$ (μM) — |

FIG. 8-37

| BW-SCA-75-B | AS-III-62 | ![structure with COOH, Chemical Formula: C$_{27}$H$_{19}$NO$_3$S, Molecular Weight: 437.5097] | *In vitro* inhibition — Proteins: EcSecAN68, IC$_{50}$ (μM): 30 |
|---|---|---|---|

| | | | *In vivo* inhibition | Strains: | MIC$_{50}$ (μM) | MIC$_{95}$ (μM) |
|---|---|---|---|---|---|---|
| | | | | *B. anthracis* Sterne | >100 | >100 |
| | | | | *S. aureus* 6538 | >100 | >100 |
| | | | | *S. aureus* M

| BW-SCA-77-B | DK-II-7 | <table><tr><td colspan="2">In vitro inhibition</td><td>Proteins:</td><td colspan="2">IC$_{50}$ (μM)</td></tr><tr><td colspan="2"></td><td>EcSecAN68</td><td colspan="2">30</td></tr><tr><td rowspan="5">In vivo inhibition</td><td rowspan="5"></td><td>Strains:</td><td>MIC$_{50}$ (μM)</td><td>MIC$_{95}$ (μM)</td></tr><tr><td>B. anthracis Sterne</td><td>75</td><td>>100</td></tr><tr><td>S. aureus 6538</td><td>>100</td><td>>100</td></tr><tr><td>S. aureus Mu50</td><td>>100</td><td>>100</td></tr><tr><td>E. coli NR698</td><td>>100</td><td>>100</td></tr><tr><td>B. subtilis 168</td><td>>100</td><td>>100</td></tr></table><br/>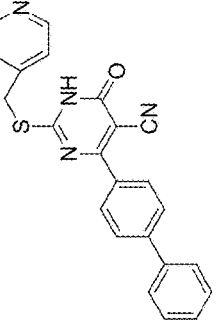<br/>Chemical Formula: C$_{23}$H$_{16}$N$_4$OS<br/>Molecular Weight: 396.4643 |
| BW-SCA-78-B | DK-II-16 | <table><tr><td colspan="2">In vitro inhibition</td><td>Proteins:</td><td colspan="2">IC$_{50}$ (μM)</td></tr><tr><td colspan="2"></td><td>EcSecAN68</td><td colspan="2">ND</td></tr><tr><td rowspan="5">In vivo inhibition</td><td rowspan="5"></td><td>Strains:</td><td>MIC$_{50}$ (μM)</td><td>MIC$_{95}$ (μM)</td></tr><tr><td>B. anthracis Sterne</td><td>>500</td><td>>500</td></tr><tr><td>S. aureus 6538</td><td>>500</td><td>>500</td></tr><tr><td>S. aureus Mu50</td><td>>500</td><td>>500</td></tr><tr><td>E. coli NR698</td><td>>500</td><td>>500</td></tr><tr><td>B. subtilis 168</td><td>>500</td><td>>500</td></tr></table><br/>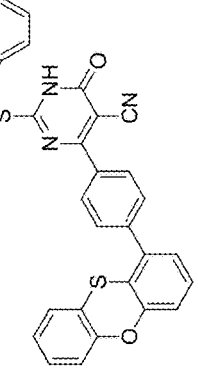<br/>Chemical Formula: C$_{30}$H$_{19}$N$_3$O$_2$S$_2$<br/>Molecular Weight: 517.6208 |

FIG. 8-39

| BW-SCA-79-B | KW-I-2 | 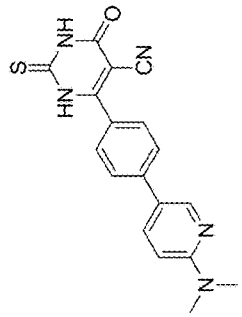 Chemical Formula: C$_{18}$H$_{15}$N$_5$OS<br>Molecular Weight: 349.4096 | *In vitro* inhibition | Proteins: | IC$_{50}$ (μM) | |
|---|---|---|---|---|---|---|
| | | | | EcSecAN68 | ND | |
| | | | *In vivo* inhibition | Strains: | MIC$_{50}$ (μM) | MIC$_{95}$ (μM) |
| | | | | *B. anthracis* Sterne | >500 | >500 |
| | | | | *S. aureus* 6538 | >500 | >500 |
| | | | | *S. aureus* Mu50 | >500 | >500 |
| | | | | *E. coli* NR698

| | | | |
|---|---|---|---|
| BW-SCA-81-B | AS-III-76a | 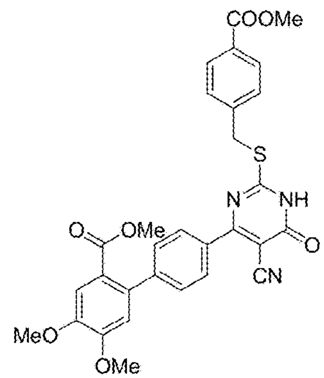 <br>Chemical Formula: $C_{30}H_{25}N_3O_7S$<br>Molecular Weight: 571.6004 | see table below |
| BW-SCA-82-B | AS-III-76c | 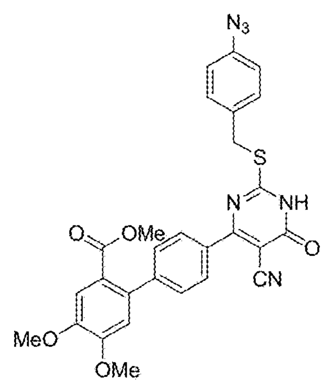 <br>Chemical Formula: $C_{28}H_{22}N_6O_5S$<br>Molecular Weight: 554.5765 | see table below |

BW-SCA-81-B / AS-III-76a:

| | | | |
|---|---|---|---|
| ***In vitro* inhibition** | Proteins: | $IC_{50}$ (μM) | |
| | EcSecAN68 | ND | |
| ***In vivo* inhibition** | *Strains:* | $MIC_{50}$ (μM) | $MIC_{95}$(μM) |
| | *B. anthracis* Sterne | 20 | 50 |
| | *S. aureus* 6538 | >100 | >100 |
| | *S. aureus* Mu50 | >100 | >100 |
| | *E. coli* NR698 | >100 | >100 |
| | *B. subtilis* 168 | >100 | >100 |

BW-SCA-82-B / AS-III-76c:

| | | | |
|---|---|---|---|
| ***In vitro* inhibition** | Proteins: | $IC_{50}$ (μM) | |
| | EcSecAN68 | 20 | |
| | BaSecA2 | 14 | |
| ***In vivo* inhibition** | *Strains:* | $MIC_{50}$ (μM) | $MIC_{95}$(μM) |
| | *B. anthracis* Sterne | 5 | 12.5 |
| | *S. aureus* 6538 | 55 | >100 |
| | *S. aureus* Mu50 | 100 | >100 |
| | *E. coli* NR698 | >100 | >100 |
| | *B. subtilis* 168 | 50 | >100 |

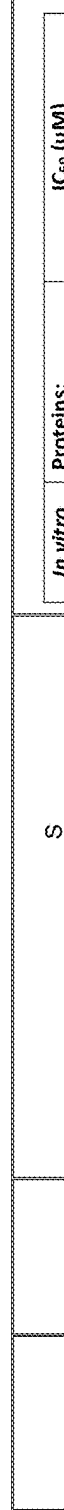
FIG. 8-42

| | | | |
|---|---|---|---|
| BW-SCA-85-B | KW-I-17 | 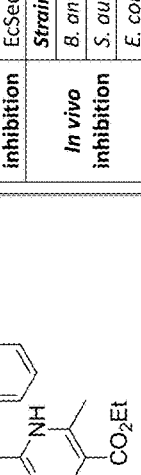  Chemical Formula: $C_{21}H_{21}BrN_2O_3$  Molecular Weight: 429.3070 | <table><tr><td colspan="2">In vitro inhibition</td><td colspan="3">Proteins:</td></tr><tr><td colspan="2"></td><td colspan="3">EcSecAN68</td></tr><tr><td colspan="2"></td><td colspan="2">$IC_{50}$ (μM)</td><td>15</td></tr><tr><td rowspan="4">In vivo inhibition</td><td>Strains:</td><td>$MIC_{50}$ (μM)</td><td colspan="2">$MIC_{95}$ (μM)</td></tr><tr><td>B. anthracis Sterne</td><td>&

| | | | |
|---|---|---|---|
| BW-SCA-87-B | DK-II-35 | 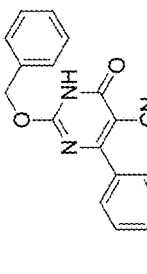Chemical Formula: C$_{19}$H$_{15}$N$_3$O$_3$<br>Molecular Weight: 333.3407 | *In vitro* inhibition: Proteins: EcSecAN68, IC$_{50}$ (µM): >100<br>*In vivo* inhibition: Strains: *B. anthracis* Sterne MIC$_{50}$ >250 MIC$_{95}$ >250; *S. aureus* 6538 MIC$_{50}$ >250 MIC$_{95}$ >250; *E. coli* NR698 MIC$_{50}$ >250 MIC$_{95}$ >250 |
| BW-SCA-88-B | DK-II-36 | 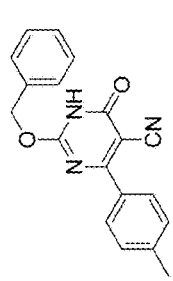Chemical Formula: C$_{19}$H$_{15}$N$_3$O$_2$<br>Molecular Weight: 317.3413 | *In vitro* inhibition: Proteins: EcSecAN68, IC$_{50}$ (µM): 65<br>*In vivo* inhibition: Strains: *B. anthracis* Sterne MIC$_{50}$ >250 MIC$_{95}$ >250; *S. aureus* 6538 MIC$_{50}$ >250 MIC$_{95}$ >250; *E. coli* NR698 MIC$_{50}$ >250 MIC$_{95}$ >250 |

FIG. 8-44

| | | In vitro inhibition | Proteins: | IC$_{50}$ (μM) | |
|---|---|---|---|---|---|
| BW-SCA-89-B | AS-III-85 | | EcSecAN68 | >200 | |
| | | | | MIC$_{50}$ (μM) | MIC$_{95}$ (μM) |
| | | In vivo inhibition | Strains: | | |
| | | | B. anthracis Sterne | >500 | >500 |
| | | | S. aureus 6538 | >500 | >500 |
| | | | E. coli NR698 | >500 | >500 |
| | | | B. subtilis 168 | >500 | >500 |

Chemical Formula: C$_{18}$H$_{13}$N$_3$OS
Molecular Weight: 319.3803

| | | In vitro inhibition | Proteins: | IC$_{50}$ (μM) | |
|---|---|---|---|---|---|
| BW-SCA-90-B | AS-III-100 | | EcSecAN68 | >200 | |
| | | | | MIC$_{50}$ (μM) | MIC$_{95}$ (μM) |
| | | In vivo inhibition | Strains: | | |
| | | | B. anthracis Sterne | >500 | >500 |
| | | | S. aureus 6538 | >500 | >500 |
| | | | E. coli NR698 | >500 | >500 |
| | | | B. subtilis 168 | >500 | >500 |

Chemical Formula: C$_{24}$H$_{16}$N$_6$OS
Molecular Weight: 436.4884

FIG. 8-45

<table>
<tr>
<td>BW-SCA-91-B</td>
<td>AS-III-110</td>
<td><br>Chemical Formula: $C_{40}H_{47}N_5O_7S$<br>Molecular Weight: 741.8955</td>
<td>
<table>
<tr><td rowspan="3">In vitro inhibition</td><td>Proteins:</td><td colspan="2">$IC_{50}$ (μM)</td></tr>
<tr><td>EcSecAN68</td><td colspan="2">25</td></tr>
<tr><td>BaSecA2</td><td colspan="2">40</td></tr>
<tr><td rowspan="5">In vivo inhibition</td><td>Strains:</td><td>$MIC_{50}$ (μM)</td><td>$MIC_{95}$(μM)</td></tr>
<tr><td>B. anthracis Sterne</td><td>75</td><td>125</td></tr>
<tr><td>S. aureus 6538</td><td>>250</td><td>>250</td></tr>
<tr><td>E. coli NR698</td><td>>250</td><td>>250</td></tr>
<tr><td>B. subtilis 168</td><td>>250</td><td>>250</td></tr>
</table>
</td>
</tr>
</table>

FIG. 8-46

| | | | |
|---|---|---|---|
| BW-SCA-92-B | AS-III-112 | <br>Chemical Formula: $C_{35}H_{39}N_5O_5S$<br>Molecular Weight: 641.7797 | see table below |

| | | | |
|---|---|---|---|
| ***In vitro* inhibition** | Proteins: | $IC_{50}$ (μM) | |
| | EcSecAN68 | 45 | |
| | BaSecA2 | 140 | |
| ***In vivo* inhibition** | *Strains:* | $MIC_{50}$ (μM) | $MIC_{95}$(μM) |
| | *B. anthracis* Sterne | >250 | >250 |
| | *S. aureus* 6538 | >250 | >250 |
| | *E. coli* NR698 | >250 | >250 |
| | *B. subtilis* 168 | >250 | >250 |

FIG. 8-47

| | BW-SCA-93-B | AS-III-119 | Structure with N₃-C₆H₄-CH₂-S-pyrimidine(CN)(biphenyl)-NH-OH<br>Chemical Formula: C₂₄H₁₇N₇OS<br>Molecular Weight: 451.5031 | In vitro inhibition | Proteins: | IC₅₀ (μM) | |
|---|---|---|---|---|---|---|---|
| | | | | | EcSecAN68 | 6 | |
| | | | | | EcSecA | 30 | |
| | | | | | EcSecA Tn | 25 | |
| | | | | | BsSecA | >100 | |
| | | | | In vivo inhibition | Strains: | MIC₅₀ (μM) | MIC₉₅ (μM) |
| | | | | | B. anthracis Sterne | 3 | 4 |
| | | | | | S. aureus 6538 | 9 | 10 |
| | | | | | S. aureus Mu50 | 9 | 10 |
| | | | | | S. aureus N315 | 9 | 18 |
| | | | | | S. aureus Mu3 | 50 | >100 |
| | | | | | E. coli NR698 | 70 | 200 (MIC₉₀) |
| | | | | | B. subtilis 168 | 4.5 | 6 |

| | BW-SCA-94-B | AS-III-115 | Structure with C₆H₅-CH₂-S-pyrimidine(CN)(biphenyl)-NH-CH₂CH₂-OH<br>Chemical Formula: C₂₆H₂₂N₄OS<br>Molecular Weight: 438.5441 | In vitro inhibition | Proteins: | IC₅₀ (μM) | |
|---|---|---|---|---|---|---|---|
| | | | | | EcSecAN68 | 55 | |
| | | | | In vivo inhibition | Strains: | MIC₅₀ (μM) | MIC₉₅ (μM) |
| | | | | | B. anthracis Sterne | >200 | >200 |
| | | | | | S. aureus 6538 | >200 | >200 |
| | | | | | E. coli NR698 | >200 | >200 |
| | | | | | B. subtilis 168 | >200 | >200 |

FIG. 8-48

| | | | |
|---|---|---|---|
| BW-SCA-97-B | AS-III-114b | 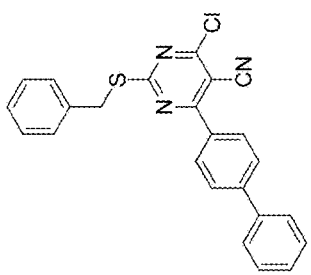Chemical Formula: $C_{24}H_{16}ClN_3S$<br>Molecular Weight: 413.9219<br>? 413.0 | *In vitro* inhibition: Proteins: EcSecAN68, $IC_{50}$ (µM): —<br><br>*In vivo* inhibition:<br><br>| Strains: | $MIC_{50}$ (µM) | $MIC_{95}$ (µM) |<br>|---|---|---|<br>| B. anthracis Sterne | 20 | 25 |<br>| S. aureus 6538 | >200 | >200 |<br>| E. coli NR698 | >200 | >200 |<br>| B. subtilis 168 | >200 | >200 | |
| BW-SCA-98-B | AS-III-120

| | | | |
|---|---|---|---|
| BW-SCA-99-B | AS-III-121 | Structure: pyrimidine derivative with 4-azidobenzylthio, biphenyl, CN, and PEG-NHBoc chain. Chemical Formula: C₃₉H₄₆N₈O₅S; Molecular Weight: 738.8981 | *In vitro inhibition* — Proteins: EcSecAN68 IC₅₀ (μM) 50; BaSecA2 >200. *In vivo inhibition* — Strains: *B. anthracis* Sterne MIC₅₀ 500, MIC₉₅ >500; *S. aureus* 6538 >500/>500; *E. coli* NR698 >500/>500; *B. subtilis* 168 >500/>500 |
| BW-SCA-100-B | AS-III-122 | Structure: pyrimidine derivative with benzylthio, biphenyl, CN, and PEG-NHBoc chain. Chemical Formula: C₃₉H₄₇N₅O₅S; Molecular Weight: 697.8860 | *In vitro inhibition* — Proteins: EcSecAN68 IC₅₀ (μM) 55; BaSecA2 >200. *In vivo inhibition* — Strains: *B. anthracis* Sterne MIC₅₀ 450, MIC₉₅ >500; *S. aureus* 6538 >500/>500; *E. coli* NR698 >500/>500; *B. subtilis* 168 >500/>500 |

FIG. 8-51

| BW-SCA-103-B | AS-IB-136 | 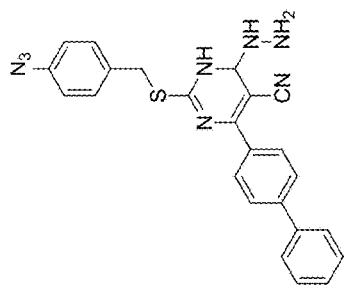 | In vitro inhibition | Proteins: | IC$_{50}$ (μM) | |
|---|---|---|---|---|---|---|
| | | | | EcSecAN68 | >100 | |
| | | | In vivo inhibition | Strains: | MIC$_{50}$ (μM) | MIC$_{95}$ (μM) |
| | | | | B. anthracis Sterne | >100 | >100 |
| | | | | S. aureus 6538 | >100 | >100 |
| | | | | S. aureus Mu50 | >100 | >100 |
| | | | | E. coli NR698 | >100 | >100 |
| | | | | B. subtilis 168 | >100 | >100 |
| BW-SCA-104-B | AS-IV-5 | 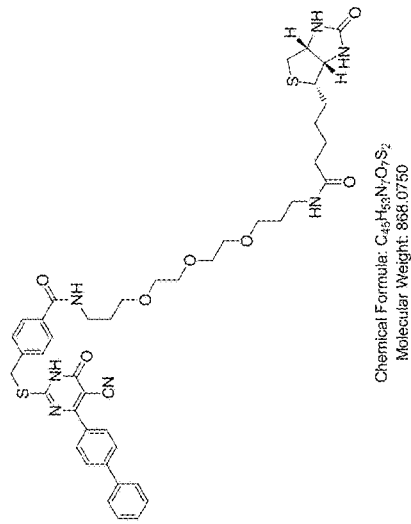 | In vitro inhibition | Proteins: | IC$_{50}$ (μM) | |
| | | | | EcSecAN68 | 20 | |
| | | | | BaSecA2 | 33 | |
FIG. 8-53

| | | | |
|---|---|---|---|
| BW-SCA-107-C | MCIV-101 | 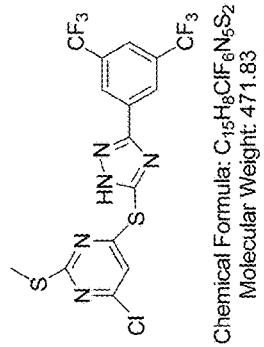<br>Chemical Formula: $C_{15}H_8ClF_6N_5S_2$<br>Molecular Weight: 471.83 | In vitro inhibition |  | Proteins: | IC$_{50}$ (µM) |
| | | | | | EcSecAN68 | 30 |
| | | | | | EcSecA | |
| | | | | | EcSecA Tn | 28 |
| | | | | | BsSecA | >200 |
| | | | | | BaSecA2 | 65 |
| | | | | | SaSecA2 | 50 |
| | | | | | Ec-F$_1$F$_0$-H$^+$-ATPase | |
| | | | Ion Channel inhibition | | Protein: | IC$_{50}$ (µM) |
| | | | | | EcSecA | 1.6 |
| | | | | | SaSecA1 | 0.6 |
| | | | | | BaSecA1 | 0.7 |
| | | | | | PaSecA | 1.3 |
| | | | | | BsSecA | 2.1 |
| | | | | | MsSecA | 2.5 |
| | | | | | MtbSecA | 2 |
| | | | | | SpSecA | 0.7 |
| | | | In vivo inhibition | | Strains: | MIC$_{50}$ (µM) | MIC (µM) |
| | | | | | B. anthracis Sterne | 0.73 | 3.125 |
| | | | | | S. aureus 6538 | 0.55 | 3.125 |
| | | | | | S. aureus Mu50 | 0.9 | 2 |
| | | | | | S. aureus N315 | 0.9 | 2 |
| | | | | | S. aureus Mu3 | 0.9 | 2 |
| | | | | | E. coli NR698 | 6.3 | 2 |
| | | | | | B. subtilis 168 | 0.33 | 1.56 |
| | | | toxicity | | Cell lines: | IC$_{50}$ (µM) |
| | | | | | HeLa cell | 38/>50/>50 |

MIC95 (µM): 1.52 for B. anthracis Sterne; 1.85 for S. aureus 6538; 1 for S. aureus Mu50; 9.5 for E. coli NR698; 0.75 for B. subtilis 168;

FIG. 8-55

| BW-SCA-108-B | AS-IV-37-a | Chemical Formula: C$_{25}$H$_{18}$N$_6$OS<br>Molecular Weight: 450.5150 | In vitro inhibition | Proteins:<br>EcSecAN68 | IC$_{50}$ (μM)<br>60 | |
|---|---|---|---|---|---|---|
| | | | In vivo inhibition | Strains: | MIC$_{50}$(μM) | MIC$_{95}$(μM) |
| | | | | B. an

| | | | |
|---|---|---|---|
| | BW-SCA-111-C | MCIv-107 | Chemical Formula: C$_{14}$H$_{12}$ClN$_5$S<br>Molecular Weight: 317.80 | |

| | Proteins: | IC$_{50}$ (µM) | |
|---|---|---|---|
| In vitro inhibition | EcSecA N68 | >200 | |
| | Strains: | MIC$_{50}$ (µM) | MIC$_{95}$ (µM) |
| In vivo inhibition | B. anthracis Sterne | 80 | >100 |
| | S. aureus 6538 | >100 | >100 |
| | S. aureus Mu50 | >100 | >100 |
| | E. coli NR698 | >100 | >100 |
| | B. subtilis 168 | >100 | >100 |

| | | | | |
|---|---|---|---|---|
| BW-SCA-113-C | MCIV-117 | [Structure: phenylthio-chloropyrimidine linked to thiazole-thiol with 3,5-dimethylphenyl]<br>Chemical Formula: C$_{20}$H$_{16}$ClN$_5$S$_2$<br>Molecular Weight: 425.96 | *In vitro* inhibition | Proteins: EcSecAN68 — IC$_{50}$ (μM): 11 |
| | | | *In vivo* inhibition | Strains: / MIC$_{50}$ (μM) / MIC$_{95}$ (μM)<br>B. anthracis Sterne: 17 / 25<br>S. aureus 6538: —<br>S. aureus Mu50: 9.5

| | | | In vitro inhibition | Proteins: EcSecAN68 | | IC₅₀ (μM) 45 |
|---|---|---|---|---|---|---|
| BW-SCA-116-C | MCIV-125-1 | 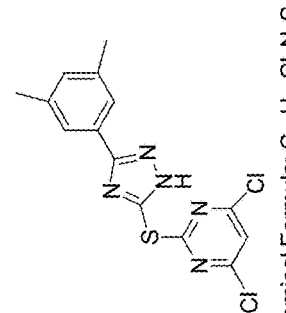Chemical Formula: C₁₄H₁₁Cl₂N₅S Molecular Weight: 352.24 | | Strains: | MIC₅₀ (μM) | MIC₉₅ (μM) |
| | | | In vivo inhibition | B. anthracis Sterne | 2 |

| | | | |
|---|---|---|---|
| BW-SCA-118-B | AS-IV-78 | Chemical Formula: C$_{52}$H$_{67}$N$_9$O$_5$SSi$_2$<br>Molecular Weight: 986.3817 | *In vitro* inhibition: Proteins: EcSecAN68, IC$_{50}$ (μM): 9 |
| BW-SCA-119-B | AS-IV-85 | Chemical Formula: C$_{25}$H$_{16}$N$_6$O$_2$S<br>Molecular Weight: 464.4985 | *In vitro* inhibition: Proteins: EcSecAN68, IC$_{50}$ (μM): 3.5<br><br>*In vivo* inhibition:<br>Strains / MIC$_{50}$(μM) / MIC$_{95}$(μM):<br>B. anthracis Sterne: 15 / 50<br>S. aureus 6538: >100 / >100<br>S. aureus Mu50: >100 / >100<br>E. coli NR698: >100 / >100<br>B. subtilis 168: >100 / >100 |

FIG. 8-61

| In vitro inhibition | Proteins: | IC$_{50}$ (µM) | |
|---|---|---|---|
| | EcSecAN68 | 6 | |
| In vivo inhibition | Strains: | MIC$_{50}$ (µM) | MIC$_{95}$ (µM) |
| | B. anthracis Sterne | >125 | >125 |
| | S. aureus 6538 | >125 | >125 |
| | S. aureus Mu50 | >125 | >125 |
| | E. coli NR698 | >125 | >125 |
| | B. subtilis 168 | >125 | >125 |

Data is for original SCA-121
>100

Chemical Formula: C$_{20}$H$_{13}$N$_3$OS
Molecular Weight: 343.4017

BW-SCA-121
MW 429.3

AS-IV-56

BW-SCA-121-B

FIG. 8-63

| | | |
|---|---|---|
| BW-SCA-122-B | AS-IV-88 | ![structure] Chemical Formula: C₂₀H₁₄N₆OS Molecular Weight: 386.4298 |

| | | |
|---|---|---|
| *In vitro* inhibition | Proteins: | IC₅₀ (μM) |
| | EcSecAN68 | >200 |
| *In vivo* inhibition | Strains: | MIC₅₀(μM) | MIC₉₅(μM) |
| | B. anthracis Sterne | >100 | >100 |
| | S. aureus 6538 | >100 | >100 |
| | S. aureus Mu50 | >100 | >100 |
| | E. coli NR698 | >100 | >100 |
| | B. subtilis 168 | >100 | >100 |

| | | |
|---|---|---|
| BW-SCA-123-C | MCIV-133 | ![structure] Chemical Formula: C₁₅H₉F₆N₅S₂ Molecular Weight: 437.39 |

| | | |
|---|---|---|
| *In vitro* inhibition | Proteins: | IC₅₀ (μM) |
| | EcSecAN68 | 95 |
| *In vivo* inhibition | Strains: | MIC₅₀(μM) | MIC₉₅(μM) |
| | B. anthracis Sterne | 2 | 12.5 |
| | S. aureus 6538 | 6.5 | 12.5 |
| | S. aureus Mu50 | 6.5 | 12.5 |
| | E. coli NR698 | 35 | 50 |
| | B. subtilis 168 | 6.5 | 12.5 |

FIG. 8-64

| | | | |
|---|---|---|---|
| BW-SCA-126-C | MCIV-100 | Structure: thiol-imidazole with 3,5-bis(CF$_3$)phenyl. Chemical Formula: C$_{10}$H$_5$F$_6$N$_3$S; Molecular Weight: 313.22 | *In vitro inhibition* — Proteins: EcSecAN68, IC$_{50}$ (µM): 60<br>*In vivo inhibition* — Strains / MIC$_{50}$ (µM) / MIC$_{95}$ (µM): B. anthracis Sterne 72.05 / 163.75, MIC90; S. aureus 6538 163.75 / 163.75; S. aureus

| | | | |
|---|---|---|---|
| BW-SCA-129-C | MCIV-155 | 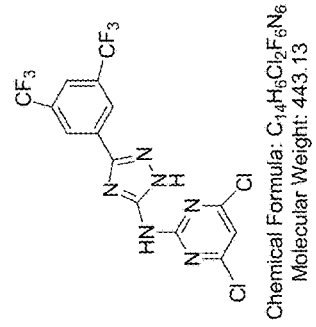<br>Chemical Formula: C_{14}H_6Cl_2F_6N_6<br>Molecular Weight: 443.13 | *In vitro* inhibition: Proteins: EcSecAN68, IC_{50} (μM): 60<br><br>*In vivo* inhibition:<br>Strains: B. anthracis Sterne — MIC_{50}(μM): 6.5, MIC_{95}(μM): —<br>S. aureus

| | | | In vitro inhibition | Proteins: EcSecAN68 | IC₅₀ (µM) | |
|---|---|---|---|---|---|---|
| BW-SCA-131-C | MCV-3 | [Structure: CF₃-phenyl-CF₃, pyrazole, thiopyrimidine with Cl, HN-CH₂-phenyl. Chemical Formula: C₂₁H₁₃ClF₆N₆S; Molecular Weight: 530.88] | In vivo inhibition | Strains: | MIC₅₀ (µM) | MIC₉₅ (µM) |
| | | | | B. anthracis Sterne | 30 | 50 |
| | | | | S. aureus 6538 | 35 | 50 |
| | | | | S. aureus Mu50 | 60 | 100 |
| | | | | E. coli NR698 | >100 | >100 |
| | | | | B. subtilis 168 | 75 | 100 |

| | | | In vitro inhibition | Proteins: EcSecAN68 | IC₅₀ (µM) 25 | |
|---|---|---|---|---|---|---|
| BW-SCA-132-C | MCV-7 | [Structure: 3,5-di-CF₃-phenyl, imidazole-thio-pyrimidine with Cl, HN-CH₂Ph. Chemical Formula: C₂₁H₁₃ClF₆N₆S; Molecular Weight: 530.88] | In vivo inhibition | Strains: | MIC(µM) | |
| | | | | B. anthracis Sterne | 3.125 14 hour/6.25 20 hour | |
| | | | | S. aureus 6538 | 3.125 | |
| | | | | S. aureus Mu50 | 3.125 | |
| | | | | E. coli NR698 | >100 | |
| | | | | B. subtilis 168 | 3.125 | |

| | | | In vitro inhibition | Proteins: EcSecAN68 | IC₅₀ (µM) 200 | |
|---|---|---|---|---|---|---|
| BW-SCA-133-C | MCV-19 | [Structure: 3,5-di-CF₃-phenyl, oxazole, S-pyrimidine with Cl and SMe. Chemical Formula: C₁₅H₇ClF₆N₄OS₂; Molecular Weight: 472.82] | In vivo inhibition | Strains: | MIC (µM) | |
| | | | | B. anthracis Sterne | >100 | |
| | | | | S. aureus 6538 | >100 | |
| | | | | S. aureus Mu50 | >100 | |
| | | | | E. coli NR698 | >100 | |
| | | | | B. subtilis 168 | >100 | |

FIG. 8-68

| | | |
|---|---|---|
| BW-SCA-134-C | MCV-15 | *In vitro* inhibition: Proteins: EcSecAN68, IC$_{50}$ (µM): 12.5 14h/25 20h<br>*In vivo* inhibition: Strains: *B. anthracis* Sterne MIC (µM): >100; *S. aureus* 6538: >100; *S. aureus* Mu50: 100; *E. coli* NR698: >100; *B. subtilis* 168: >100 |
| BW-SCA-135-C | MCV-21 | *In vitro* inhibition: Proteins: EcSecAN68, IC$_{50}$ (µM): 6.25 14h<br>*In vivo* inhibition: Strains: *B. anthracis* Sterne MIC (µM): 25 14h; *S. aureus* 6538: 50; *S. aureus* Mu50: 14h/>100; *E. coli* NR698: >100; *B. subtilis* 168: 25 14h |
| BW-SCA-136-B Prev ID-BW-SCA-113 | AS-III-118 | |

FIG. 8-69

| | | | In vitro inhibition | Proteins: | IC$_{50}$ (μM) |
|---|---|---|---|---|---|
| | | | | EcSecAN68 | |
| | | | In vivo inhibition | Strains: | MIC (μM) |
| | | | | B. anthracis Sterne | >100 |
| | | | | S. aureus 6538 | >100 |
| | | | | S. aureus Mu50 | >100 |
| | | | | E. coli NR698 | |
| | | | | B. subtilis 168 | >100 |

BW-SCA-137-C — MCV-12-3

Chemical Formula: C$_{17}$H$_{11}$Cl$_2$N$_5$OS
Molecular Weight: 404.27

| | In vitro inhibition | Proteins: | IC$_{50}$ (μM) |
|---|---|---|---|
| | | EcSecAN68 | 25 |
| | In vivo inhibition | Strains: | MIC (μM) |
| | | B. anthracis Sterne | 25 14h |
| | | S. aureus 6538 | 25 14h |
| | | S. aureus Mu50 | 12.5 14h |
| | | E. coli NR698 | 50 14h |
| | | B. subtilis 168 | 25 14h |

BW-SCA-138-C — MCV-31

Chemical Formula: C$_{18}$H$_{14}$ClF$_6$N$_5$OS$_2$
Molecular Weight: 529.91

| | In vitro inhibition | Proteins: | IC$_{50}$ (μM) |
|---|---|---|---|
| | | EcSecAN68 | |
| | In vivo inhibition | Strains: | MIC (μM) |
| | | B. anthracis Sterne | 12.5 14h |
| | | S. aureus 6538 | 12.5 14h |
| | | S. aureus Mu50 | 50 14h |
| | | E. coli NR698 | >100 |
| | | B. subtilis 168 | 25 14h |

BW-SCA-139-C — MCV-32-1

Chemical Formula: C$_{14}$H$_5$Cl$_2$F$_6$N$_5$O
Molecular Weight: 444.12

FIG. 8-70

| | | |
|---|---|---|
| BW-SCA-143-A | MCH-126 | ![structure with hexyl chain, MeO and OMe groups on xanthene]<br>Chemical Formula: C₂₁H₂₆O₃<br>Molecular Weight: 326.43 | *In vitro* inhibition: Proteins: EcSecAN68 = 100, BsSecA >200; MIC (μM): >126; *In vivo* inhibition: Strains: E. coli NR698, B. subtilis 168 >100 |
| BW-SCA-144-A | MCH-109 | ![structure with cyclohexyl, MeO and OMe groups on xanthene]<br>Chemical Formula: C₂₁H₂₄O₃<br>Molecular Weight: 324.41 | *In vitro* inhibition: Proteins: EcSecAN68 = 120, BsSecA >200; MIC (μM): >250; *In vivo* inhibition: Strains: E. coli NR698, B. subtilis 168 >100 |
| BW-SCA-145-A | MCH-125 | ![structure with cyclopentyl, NaO and ONa groups on xanthene]<br>Chemical Formula: C₁₈H₁₆Na₂O₃<br>Molecular Weight: 326.30 | *In vitro* inhibition: Proteins: EcSecAN68; MIC₅₀ (μM): ; *In vivo* inhibition: Strains: B. anthracis Sterne >30, S. aureus 6538 >30, S. aureus Mu50 = 26, E. coli NR698 = 29, B. subtilis 168 >30 |

Table (reconstructed):

| | | | In vitro inhibition | | In vivo inhibition | |
|---|---|---|---|---|---|---|
| | | | Proteins: | IC₅₀ (μM) | Strains: | MIC (μM) |
| BW-SCA-143-A | MCH-126 | C₂₁H₂₆O₃; MW 326.43 | EcSecAN68 / BsSecA | 100 / >200 | E. coli NR698 / B. subtilis 168 | >126 / >100 |
| BW-SCA-144-A | MCH-109 | C₂₁H₂₄O₃; MW 324.41 | EcSecAN68 / BsSecA | 120 / >200 | E. coli NR698 / B. subtilis 168 | >250 / >100 |
| BW-SCA-145-A | MCH-125 | C₁₈H₁₆Na₂O₃; MW 326.30 | EcSecAN68 | — | B. anthracis Sterne / S. aureus 6538 / S. aureus Mu50 / E. coli NR698 / B. subtilis 168 | >30 / >30 / 26 / 29 / >30 (MIC₅₀) |

FIG. 8-72

| BW-SCA-146-A | MCI-40 | Structure: imino-isobenzofuran fused with iodo-methoxy chromane. Chemical Formula: $C_{17}H_{14}INO_3$; Molecular Weight: 407.20 | *In vitro* inhibition | Proteins | $IC_{50}$ (μM) |
|---|---|---|---|---|---|
| | | | | EcSecAN68 | >100 |
| | | | | BaSecA2 | >200 |
| | | | | | $MIC_{50}$ (μM) | MIC (μM) |
| | | | *In vivo* inhibition | Strains: | |
| | | | | *E. coli* NR698 | >250 |
| BW-SCA-147-A | MCI-52 | Structure: isoindolinone fused with methoxy chromane. Chemical Formula: $C_{17}H_{15}NO_3$; Molecular Weight: 281.31 | *In vitro* inhibition | Proteins | $IC_{50}$ (μM) |
| | | | | EcSecAN68 | >100 |
| | | | | BaSecA2 | >200 |
| | | | | | $MIC_{50}$ (μM) | MIC (μM) |
| | | | *In vivo* inhibition | Strains: | |
| | | | | *E. coli* NR698 | >250 |
| BW-SCA-148-A | MCI-53 | Structure: isobenzofuranone fused with methoxy chromane. Chemical Formula: $C_{17}H_{14}O_4$; Molecular Weight: 282.29 | *In vitro* inhibition | Proteins | $IC_{50}$ (μM) |
| | | | | EcSecAN68 | >100 |
| | | | | BsSecA | >200 |
| | | | | BaSecA2 | >200 |
| | | | | | $MIC_{50}$ (μM) | MIC (μM) |
| | | | *In vivo* inhibition | Strains: | |
| | | | | *E. coli* NR698 | >100 | >250* |
| | | | | *B. subtilis* 168 | >100 | |

FIG. 8-73

| | | | |
|---|---|---|---|
| BW-SCA-149-A | MCI-58 | Chemical Formula: $C_{17}H_{16}O_4$<br>Molecular Weight: 284.31 | *In vitro inhibition* — Proteins: EcSecAN68 $IC_{50}$ >100/>200 μM; BsSecA >200; BaSecA2 >200. *In vivo inhibition* — Strains: E. coli NR698 $MIC_{50}$ >100, MIC >250*; B. subtilis 168 $MIC_{50}$ >100, MIC >100 |
| BW-SCA-150-A | MCI-65 | Chemical Formula: $C_{17}H_{12}Br_2O_4$<br>Molecular Weight: 437.91 | *In vitro inhibition* — Proteins: EcSecAN68 $IC_{50}$ >100/200 μM; BsSecA >200; BaSecA2 >200. *In vivo inhibition* — Strains: E. coli NR698 $MIC_{50}$ >100, MIC >250; B. subtilis 168 $MIC_{50}$ >100 |
| BW-SCA-151-A | MCI-70 | Chemical Formula: $C_{17}H_{14}Br_2O_4$<br>Molecular Weight: 442.10 | *In vitro inhibition* — Proteins: EcSecAN68 $IC_{50}$ >100/>200 μM; BaSecA2 >200. *In vivo inhibition* — Strains: E. coli NR698 $MIC_{50}$ —, MIC >250 |

FIG. 8-74

| | | | |
|---|---|---|---|
| BW-SCA-152-C | MCV-34 | ![structure: 4-(3-fluorophenyl)-2-((4,6-dichloropyridin-2-yl)thio)-1H-imidazole] Chemical Formula: $C_{12}H_6Cl_2FN_5S$ Molecular Weight: 342.18 | *In vitro* inhibition — Proteins: EcSecAN68 — IC$_{50}$ (μM): <br>*In vivo* inhibition — Strains / MIC (μM) 16h:<br>B. anthracis Sterne: >100<br>S. aureus 6538: >100<br>S. aureus Mu50: >100<br>E. coli NR698: >100<br>B. subtilis 168: >100 |
| BW-SCA-153-C | MCV-35 | ![structure] Chemical Formula: $C_{13}H_9ClFN_5S_2$ Molecular Weight: 353.83 | *In vitro* inhibition — Proteins: EcSecAN68 — IC$_{50}$ (μM):<br>*In vivo* inhibition — Strains / MIC (μM) 16h:<br>B. anthracis Sterne: >100<br>S. aureus 6538: >100<br>S. aureus Mu50: >100<br>E. coli NR698: >100<br>B. subtilis 168: >100 |
| BW-SCA-154-C | MCV-36 | ![structure] Chemical Formula: $C_{18}H_{11}ClFN_5S_2$ Molecular Weight: 415.89 | *In vitro* inhibition — Proteins: EcSecAN68 — IC$_{50}$ (μM):<br>*In vivo* inhibition — Strains / MIC (μM) 16h:<br>B. anthracis Sterne: 100<br>S. aureus 6538: >100<br>S. aureus Mu50: 100<br>E. coli NR698: 100<br>B. subtilis 168: 100 |

FIG. 8-75

| | | Proteins: | IC$_{50}$ (μM) |
|---|---|---|---|
| | *In vitro* inhibition | EcSecAN68 | |
| BW-SCA-155-C | MCV-44 | Strains: | MIC (μM) 16h |
| | | *B. anthracis* Sterne | 25 |
| | *

| BW-SCA-158-C | MCV-49 | ![structure with SPh, Cl, CF3, C19H11ClF3N5S2, MW 465.90] | *In vitro* inhibition | Proteins:<br>EcSecAN68 | IC50 (µM) | |
|---|---|---|---|---|---|---|
| | | | | Strains: | MIC (µM) 16h | |
| | | | *In vivo* inhibition | B. anthracis Sterne | 12.5 | |
| | | | | S. aureus 6538 | 25 | |
| | | | | S. aureus Mu50 | 25 | |
| | | | | E. coli NR698 | 25 | |
| | | | | B. subtilis 168 | 12.5 | |
| BW-SCA-159-C | MCV-52 | ![structure with SMe, Cl, OMe, OMe, C15H14ClN5O2S2, MW 395.89] | *In vitro* inhibition | Proteins:<br>EcSecAN68 | IC50 (µM) | |
| | | | | Strains: | MIC (µM) 16h | MIC (µM) 24h |
| | | | *In vivo* inhibition | B. anthracis Sterne | >100 | >100 |
| | | | | S. aureus 6538 | >100 | >100 |
| | | | | S. aureus Mu50 | >100 | >100 |
| | | | | E. coli NR698 | >100 | >100 |
| | | | | B. subtilis 168 | >100 | >100 |
| | | | *In vitro* inhibition | Proteins:<br>EcSecAN68 | IC50 (µM) | |
| | | | | Strains: | MIC (µM) 16h | |
| | | | *In vivo* inhibition | B. anthracis Sterne | >100 | |
| | | | | S. aureus 6538 | >100 | |
| | | | | S. aureus Mu50 | >100 | |
| | | | | E. coli NR698 | >100 | |
| | | | | B. subtilis 168 | >100 | |

FIG. 8-77

| | | |
|---|---|---|
| BW-SCA-160-C | MCV-53 | 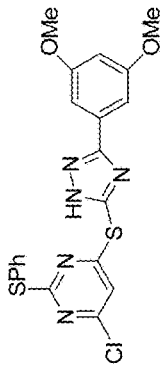 Chemical Formula: $C_{20}H_{16}ClN_5O_2S_2$<br>Molecular Weight: 457.96 | *In vitro* inhibition | Proteins:<br>EcSecAN68 | $IC_{50}$ (µM) | |
| | | | | Strains: | MIC (µM) 16h | MIC (µM) 24h |
| | | | *In vivo* inhibition | *B. anthracis* Sterne | 100 | >100 |
| | | | |

| BW-SCA-162-C | MCV-55 | 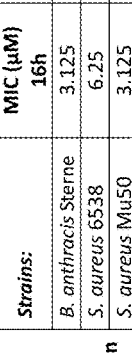 Chemical Formula: C<sub>19</sub>H<sub>11</sub>ClF<sub>3</sub>N<sub>5</sub>S<sub>2</sub><br>Molecular Weight: 465.90 | In vitro inhibition | Proteins:<br>EcSecAN68 | IC$_{50}$ (µM) | |
|---|---|---|---|---|---|---|
| | | | | | MIC (µM) 16h | MIC (µM) 24h |
| | | | In vivo inhibition | Strains: | | |
| | | | | B. anthracis Sterne | 3.125

| | | |
|---|---|---|
| BW-SCA-164-C | MCV-58-2 | 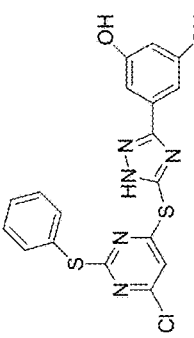<br>Chemical Formula: $C_{18}H_{12}ClN_5O_2S_2$<br>Molecular Weight: 429.90 |
| BW-SCA-165-C | AS-IV-151 | 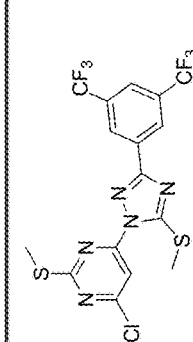<br>Chemical Formula: $C_{16}H_{10}ClF_6N_5S_2$<br>Molecular Weight: 485.8575 | *In vitro* inhibition — Proteins: EcSecAN68 — IC$_{50}$ (µM): <br>*In vivo* inhibition — Strains / MIC (µM) 16h / MIC (µM) 24h:<br>B. anthracis Sterne: >100 / >100<br>S. aureus 6538: >100 / >100<br>S. aureus Mu50: >100 / >100<br>E. coli NR698: >100 / >100<br>B. subtilis 168: >100 / >100 |
| BW-SCA-166-C | AS-IV-142 | 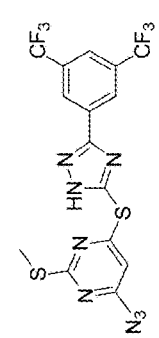<br>Chemical Formula: $

| | | | |
|---|---|---|---|
| BW-SCA-167-C | AS-IV-148 | 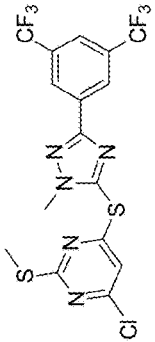 Chemical Formula: $C_{16}H_{10}ClF_6N_5S_2$ Molecular Weight: 485.8575 | *In vitro* inhibition: Proteins: EcSecAN68 IC$_{50}$ (µM): — *In vivo* inhibition: Strains / MIC (µM) 16h / MIC (µM) 24h: B. anthracis Sterne: >100 / >100; S. aureus 6538: >100 / >100; S. aureus Mu50: >100 / >100; E. coli NR698: >100 / >100; B. subtilis 168: >100 / >100 |
| BW-SCA-168-B | AS-IV-146a | 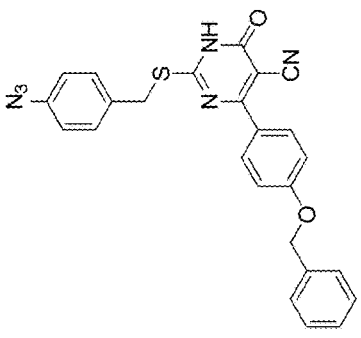 Chemical Formula: $C_{25}H_{18}N_6O_2S$ Molecular Weight: 466.5144 | *In vitro* inhibition: Proteins: EcSecAN68 IC$_{50}$ (µM): — *In vivo* inhibition: Strains / MIC (µM) 16h / MIC (µM) 24h: B. anthracis Sterne: 3.125 / 3.125; S. aureus 6538: 50 / 50; S. aureus Mu50: 6.25 / 50; E. coli NR698: 6.25 / 6.25; B. subtilis 168: 6.25 / 6.25 |

FIG. 8-81

| | BW-SCA-169-B | AS-IV-146b | 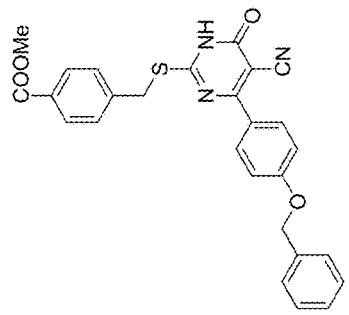 Chemical Formula: $C_{27}H_{21}N_3O_4S$<br>Molecular Weight: 483.5383 | In vitro inhibition | Proteins:<br>EcSecAN68 | IC$_{50}$ (µM) | |
|---|---|---|---|---|---|---|---|
| | | | | In vivo inhibition | Strains: | MIC (µM)<br>16h | MIC (µM)<br>24h |
| | | | | | B. anthracis Sterne | 6.25 |

| | Proteins: | $IC_{50}$ (μM) | |
|---|---|---|---|
| In vitro inhibition | EcSecAN68 | | |
| | Strains: | MIC (μM) 16h | MIC (μM) 24h |
| In vivo inhibition | B. anthracis Sterne | 3.125 | 3.125 |
| | S. aureus 6538 | 12.5 | 25 |
| | S. aureus Mu50 | 12.5 | 25 |
| | E. coli NR698 | 12.5 | 12.5 |
| | B. subtilis 168 | 6.25 | 12.5 |

BW-SCA-171-B  AS-IV-150b

Chemical Formula: $C_{26}H_{19}N_3O_4S$
Molecular Weight: 469.5118

FIG. 8-83

| BW-SCA-173-C | WLF-V-069 | (structure: pyrazole with SH, NH2, and 3,5-bis(trifluoromethyl)phenyl) C₁₀H₆F₆N₄S Mol. Wt.: 328.24 | *In vitro* inhibition | Proteins: EcSecAN68 | IC₅₀ (μM) | |
|---|---|---|---|---|---|---|
| | | | | Strains: | MIC (μM) 16h | MIC (μM) 24h |
| | | | *In vivo* inhibition | B. anthrac

| BW-SCA-175-C | dcf-V-1 | 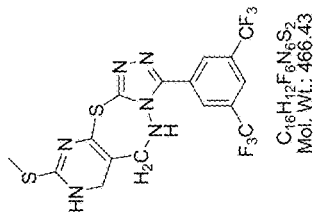 C₁₆H₁₂F₆N₆S₂ Mol. Wt.: 466.43 | In vitro inhibition | Proteins: EcSecAN68 | IC₅₀ (µM) | |
|---|---|---|---|---|---|---|
| | | | | | MIC (µM) 16h | MIC (µM) 24h |
| | | | In vivo inhibition | Strains: | | |
| | | | | B. anthracis Sterne | >100 | >100 |
|

| | | | |
|---|---|---|---|
| BW-SCA-177-C | dcf-V-12 | <br>$C_{16}H_9ClF_6N_6S_2$<br>Molecular Weight: 498.86 | see table below |

| *In vitro* inhibition | Proteins: | IC₅₀ (μM) | |
|---|---|---|---|
| | EcSecAN68 | | |
| *In vivo* inhibition | *Strains:* | MIC (μM) 16h | MIC (μM) 24h |
| | *B. anthracis* Sterne | >250 | >250 |
| | *S. aureus* 6538 | >250 | >250 |
| | *S. aureus* Mu50 | >250 | >250 |
| | *E. coli* NR698 | >250 | >250 |
| | *B. subtilis* 168 | >250 | >250 |

| | | | |
|---|---|---|---|
| BW-SCA-178-C | dcf-V-9 | <br>$C_{13}H_{10}F_6N_4S$<br>Molecular Weight: 368.30 | see table below |

| *In vitro* inhibition | Proteins: | $IC_{50}$ (μM) | |
|---|---|---|---|
| | EcSecAN68 | | |
| *In vivo* inhibition | *Strains:* | MIC (μM) 16h | MIC (μM) 24h |
| | *B. anthracis* Sterne | >250 | >250 |
| | *S. aureus* 6538 | >250 | >250 |
| | *S. aureus* Mu50 | >250 | >250 |
| | *E. coli* NR698 | >250 | >250 |
| | *B. subtilis* 168 | >250 | >250 |

FIG. 8-87

| BW-SCA-179-C | dcf-V-10 | 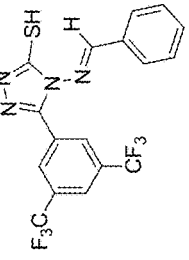 C₁₇H₁₀F₆N₄S Molecular Weight: 416.34 | In vitro inhibition | Proteins: EcSecAN68 | IC₅₀ (µM) | |
|---|---|---|---|---|---|---|
| | | | | Strains: | MIC (µM) 16h | MIC (µM) 24h |
| | | | In vivo inhibition | B. anthracis Sterne | >250 | >250 |
| | | | | S. aureus 6538 | >250 | >250 |
| | | | | S. aureus Mu50 | >250 | >250 |
| | | | | E. coli NR698 | >250 | >250 |
| | | | | B. subtilis 168 | >250 | >250 |

| BW-SCA-180-C | AS-IV-154a | 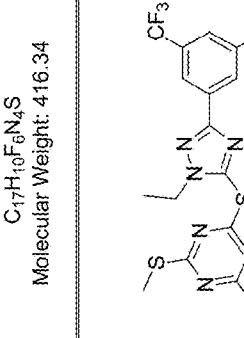 Molecular Weight: 499.8841 | In vitro inhibition | Proteins: EcSecAN68 | IC₅₀ (µM) | |
|---|---|---|---|---|---|---|
| | | | | Strains: | MIC (µM) 16h | MIC (µM) 24h |
| | | | In vivo inhibition | B. anthracis Sterne | >250 | >250 |
| | | | | S. aureus 6538 | >250 | >250 |
| | | | | S. aureus Mu50 | >250 | >250 |
| | | | | E. coli NR698 | >250 | >250 |
| | | | | B. subtilis 168 | >250 | >250 |

| BW-SCA-181-C | AS-IV-154b | 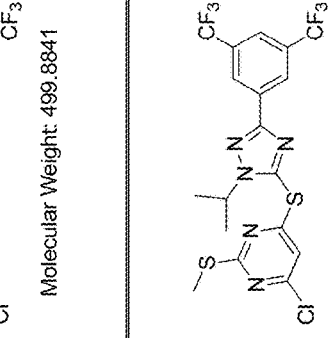 Molecular Weight: 513.9107 | In vitro inhibition | Proteins: EcSecAN68 | IC₅₀ (µM) | |
|---|---|---|---|---|---|---|
| | | | | Strains: | MIC (µM) 16h | |
| | | | In vivo inhibition | B. anthracis Sterne | >250 | |
| | | | | S. aureus 6538 | >250 | |
| | | | | S. aureus Mu50 | >250 | |
| | | | | E. coli NR698 | >250 | |
| | | | | B. subtilis 168 | >250 | |

FIG. 8-88

| | | | |
|---|---|---|---|
| BW-SCA-182-C | AS-IV-154c | (structure: 3,5-bis(CF₃)phenyl imidazole with cyclopropylmethyl, linked via S to 2-methylthio-6-chloropyridine) Molecular Weight: 525.9214 | *In vitro* inhibition — Proteins: EcSecAN68 — IC₅₀ (μM): <br> *In vivo* inhibition — Strains: <br> *B. anthracis* Sterne — MIC (μM) 16h: >250 <br> *S. aureus* 6538: >250 <br> *S. aureus* Mu50: >250 <br> *E. coli* NR698: >250 <br> *B. subtilis* 168: >250 |
| BW-SCA-183-C | AS-V-25-b | (structure: 3,5-bis(CF₃)phenyl imidazole NH, linked via S to 2-methylthio-6-methylaminopyridine) Molecular Weight: 466.4271 | *In vitro* inhibition — Proteins: EcSecAN68 — IC₅₀ (μM): <br> *In vivo* inhibition — Strains: <br> *B. anthracis* Sterne — MIC (μM) 16h: >250 <br> *S. aureus* 6538: >250 <br> *S. aureus* Mu50: >250 <br> *E. coli* NR698: >250 <br> *B. subtilis* 168: >250 |
| BW-SCA-184-C | AS-IV-155 | (structure: 3,5-bis(CF₃)phenyl imidazole NH, linked via S to 2-methylthio-6-ethylaminopyridine) Molecular Weight: 480.4537 | *In vitro* inhibition — Proteins: EcSecAN68 — IC₅₀ (μM): <br> *In vivo* inhibition — Strains: <br> *B. anthracis* Sterne — MIC (μM) 16h: <br> *S. aureus* 6538: <br> *S. aureus* Mu50: <br> *E. coli* NR698: <br> *B. subtilis* 168: |

FIG. 8-89

| | | |
|---|---|---|
| BW-SCA-190-B | AS-V-33-b |  Molecular Weight: 431.5499 <br><br> *In vitro* inhibition: Proteins: EcSecAN68, IC$_{50}$ (µM): 3.125 <br> *In vivo* inhibition: Strains — B. anthracis Sterne MIC (µM) 16h: 15.6; S. aureus 6538: 12.5; S. aureus Mu50: 16.67; E. coli NR698: 10.4; B. subtilis 168: — |
| BW-SCA-191-B | AS-V-33-a |  Molecular Weight: 504.3983 <br><br> *In vitro* inhibition: Proteins: EcSecAN68, IC$_{50}$ (µM): 3.125 <br> *In vivo* inhibition: Strains — B. anthracis Sterne MIC (µM) 16h: >250; S. aureus 6538: >250; S. aureus Mu50: 12.5; E. coli NR698: 31.25; B. subtilis 168: — |

| | | | In vitro inhibition | Proteins: | IC$_{50}$ (μM) |
|---|---|---|---|---|---|
| BW-SCA-192-C | AS-V-28-1 | [Chemical structure with CF$_3$ groups, pyrimidine, morpholine, SMe. Molecular Weight: 522.4904] | | EcSecAN68 | |
| | | | In vivo inhibition | Strains: | MIC (μM) 16h |
| | | | | B. anthracis Sterne | 16.67 |
| | | | | S. aureus 6538 | 25 |

| BW-SCA-194-B | AS-V-36-1 | [Structure: azide-phenyl-CH2-S-pyrimidinone(NH)(CN)-phenyl-C≡C-phenyl] Molecular Weight: 460.5098 | *In vitro* inhibition | Proteins: EcSecAN68 | IC$_{50}$ (μM) |
|---|---|---|---|---|---|
| | | | | | |
| | | | *In vivo* inhibition | Strains: | MIC (μM) 16h |
| | | | | *B. anthracis* Sterne |

| | | |
|---|---|---|
| BW-SCA-196-B | AS-V-36-3 | MeO, OMe, structure with S, NH, O, CN, phenyl-alkyne-phenyl. Molecular Weight: 479.5496 | *In vitro* inhibition — Proteins: EcSecAN68, IC$_{50}$ (μM): 10.4 <br> *In vivo* inhibition — Strains: B. anthracis Sterne MI

| | | | |
|---|---|---|---|
| BW-SCA-198-B | AS-V-33-5 | Structure with MeO, OMe, S, NH, O, CN, phenyl-O-benzyl groups. Molecular Weight: 485.5542 | *In vitro* inhibition: Proteins: EcSecAN68, IC$_{50}$ (μM): —<br>*In vivo* inhibition: Strains: MIC (μM) 16h:<br>B. anthracis Sterne: 43.75<br>S. aureus 6538: >250<br>S. aureus Mu50: >250<br>E. coli NR698: >250<br>B. subtilis 168: >250 |
| BW-SCA-199-C | AS-V-36-4 | Structure with two CF$_3$ groups, pyrazole, Cl, pyrimidine, S, HN, MeO-benzyl. Molecular Weight: 560.9025 | *In vitro* inhibition: Proteins: EcSecAN68, IC$_{50}$ (μM): —<br>*In vivo* inhibition: Strains: MIC (μM) 16h:<br>B. anthracis Sterne: 6.25<br>S. aureus 6538: 20.31<br>S. aureus Mu50: 4.68<br>E. coli NR698: >250<br>B. subtilis 168: 6.25 |
| BW-SCA-200-C | AS-V-48-cycPentl | Structure with two CF$_3$ groups, pyrazole, Cl, pyrimidine, S, HN-cyclopentyl. Molecular Weight: 508.8710 | |

FIG. 8-96

| | | | |
|---|---|---|---|
| BW-SCA-201-C | AS-V-52-Isopent | 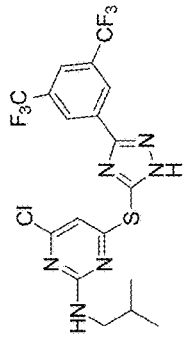<br>Molecular Weight: 496.86 | *In vitro* inhibition | Proteins: EcSecAN68 | IC$_{50}$ (μM) | |
| | | | *In vivo* inhibition | Strains: | MIC (μM) 16h | |
| | | | | *B. anthracis* Sterne | >250 | |
| | | | | *S. aureus* 6538 | >250 | |
| | | | | *S.

| | | |
|---|---|---|
| BW-SCA-204-C | AS-V-50-Morph-Top | 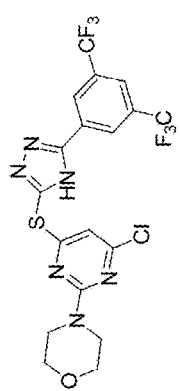<br>Molecular Weight: 510.8438 | *In vitro* inhibition | Proteins:<br>EcSecAN68 | IC$_{50}$ (μM) |
| | | | *In vivo* inhibition | Strains:<br>B. anthracis Sterne<br>S. aureus 6538<br>S. aureus Mu50<br>E. coli NR698<br>B. subtilis 168 | MIC (μM) 16h<br>6.25<br>7.81<br>6.25<br>15.63<br>4.69 |
| BW-SCA-205-C | AS-V-50-Morp-Bottom | 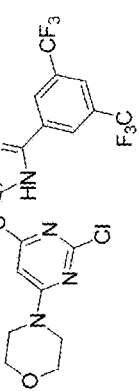<br>Molecular Weight: 510.84 | *In vitro* inhibition | Proteins:<br>EcSecAN68 | IC$_{50}$ (μM) |
| | | | *In vivo* inhibition | Strains:<br>B. anthracis Sterne<br>S. aureus 6538<br>S. aureus Mu50<br>E. coli NR698<br>B. subtilis 168 | MIC (μM) 16h<br>12.5<br>18.75<br>12.5<br>50<br>7.81 |
| BW-SCA-206-C | AS-V-48-CycButyl | 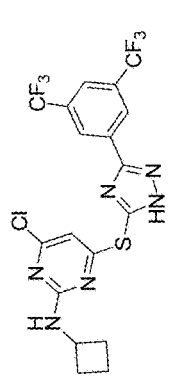<br>Exact Mass: 494.05 | *In vitro* inhibition | Proteins:<br>EcSecAN68 | IC$_{50}$ (μM) |
| | | | *In vivo* inhibition | Strains:<br>B. anthracis Sterne<br>S. aureus 6538<br>S. aureus Mu50<br>E. coli NR698<br>B. subtilis 168 | MIC (μM) 16h<br>>250<br>>250<br>>250<br>>250<br>>250 |

FIG. 8-98

| BW-SCA-207-C | AS-V-49-Pyrolidine | 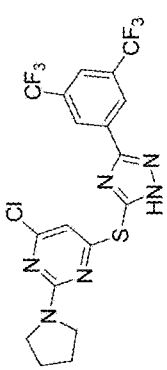 Molecular Weight: 494.84 | *In vitro* inhibition | Proteins: | IC₅₀ (µM) |
| | | | | EcSecAN68 | |
| | | | *In vivo* inhibition | Strains: | MIC (µM) 16h |
| | | | | B. anthracis Sterne | 3.125 |
| | | | | S. aureus 6538 | 6.25 |
| | | | | S. aureus Mu50 | 4.7 |
| | | | | E. coli NR698 | 10.94 |
| | | | | B. subtilis 168 | 2.08 |
| BW-SCA-208-C | AS-V-48-cyclohexyl | 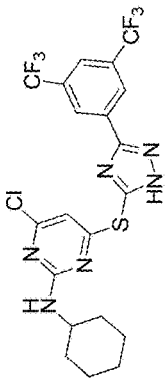 Molecular Weight: 522.90 | *In vitro* inhibition | Proteins: | IC₅₀ (µM) |
| | | | | EcSecAN68 | |
| | | | *In vivo* inhibition | Strains: | MIC (µM) 16h |
| | | | | B. anthracis Sterne | 5.08 |
| | | | | S. aureus 6538 | 13.28 |
| | | | | S. aureus Mu50 | 3.9 |
| | | | | E. coli NR698 | >250 |
| | | | | B. subtilis 168 | 5.08 |
| BW-SCA-209-C | AS-V-39-Propargyl-amine | 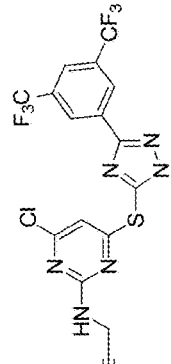 Molecular Weight: 478.80 | *In vitro* inhibition | Proteins: | IC₅₀ (µM) |
| | | | | EcSecAN68 | |
| | | | *In vivo* inhibition | Strains: | MIC (µM) 16h |
| | | | | B. anthracis Sterne | >250 |
| | | | | S. aureus 6538 | >250 |
| | | | | S. aureus Mu50 | >250 |
| | | | | E. coli NR698 | >250 |
| | | | | B. subtilis 168 | >250 |

FIG. 8-99

| | | |
|---|---|---|
| BW-SCA-210-C | AS-V-55-Me | Structure with Molecular Weight: 547.93 |

| In vitro inhibition | Proteins: EcSecAN68 | IC₅₀ (μM) |
|---|---|---|
| In vivo inhibition | Strains: | MIC (μM) 16h |
| | B. anthracis Sterne | 2.73 |
| | S. aureus 6538 | 1.56 |
| | S. aureus Mu50 | 1.365 |
| | E. coli NR698 | 5.47 |
| | B. subtilis 168 | 1.56 |

| | | |
|---|---|---|
| BW-SCA-211-C | AS-V-58/54-Ome | Structure with Molecular Weight: 563.93 |

| In vitro inhibition | Proteins: EcSecAN68 | IC₅₀ (μM) |
|---|---|---|
| In vivo inhibition | Strains: | MIC (μM) 16h |
| | B. anthracis Sterne | 3.91 |
| | S. aureus 6538 | 3.125 |
| | S. aureus Mu50 | 2.34 |
| | E. coli NR698 | 9.375 |
| | B. subtilis 168 | 3.125 |

| | | |
|---|---|---|
| BW-SCA-212-C | AS-V-42-CF3 | Structure with Molecular Weight: 598.87 |

| In vitro inhibition | Proteins: EcSecAN68 | IC₅₀ (μM) |
|---|---|---|
| In vivo inhibition | Strains: | MIC (μM) 16h |
| | B. anthracis Sterne | 2.08 |
| | S. aureus 6538 | 2.34 |
| | S. aureus Mu50 | 1.95 |
| | E. coli NR698 | 12.5 |
| | B. subtilis 168 | 1.56 |

FIG. 8-100

| | | | In vitro inhibition | Proteins:<br>EcSecAN68 | IC$_{50}$ (μM) |
|---|---|---|---|---|---|
| BW-SCA-213-C | AS-V-57-top | [structure with CF$_3$ groups, Cl, NH, S, imidazole]<br>Molecular Weight: 539.91 | In vivo inhibition | Strains:<br>B. anthracis Sterne<br>S. aureus 6538<br>S. aureus Mu50<br>E. coli NR698<br>B. subtilis 168 | MIC (μM) 16h<br>18.75<br>43.75<br>43.75<br>43.75<br>31.25 |
| BW-SCA-214-C | AS-V-57-Bottom | [structure with CF$_3$ groups, Cl, NH, O, imidazole]<br>Molecular Weight: 523.84 | In vitro inhibition | Proteins:<br>EcSecAN68 | IC$_{50}$ (μM) |
| | | | In vivo inhibition | Strains:<br>B. anthracis Sterne<br>S. aureus 6538<br>S. aureus Mu50<br>E. coli NR698<br>B. subtilis 168 | MIC (μM) 16h<br>250<br>>250<br>>250<br>>250<br>>250 |
| BW-SCA-215-B | AS-IV-146-top | [structure with N$_3$ groups, CN, O, S]<br>Molecular Weight: 597.65 | In vitro inhibition | Proteins:<br>EcSecAN68 | IC$_{50}$ (μM) |
| | | | In vivo inhibition | Strains:<br>B. anthracis Sterne<br>S. aureus 6538<br>S. aureus Mu50<br>E. coli NR698<br>B. subtilis 168 | MIC (μM) 16h<br>>250<br>>250<br>>250<br>>250<br>>250 |

FIG. 8-101

| | | | |
|---|---|---|---|
| BW-SCA-216- | AS-V-62-Pyrimdine | 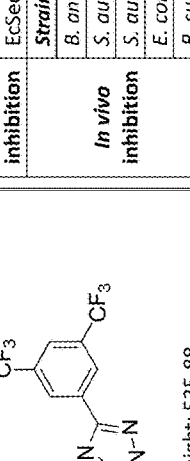Molecular Weight: 535.88 | *In vitro* inhibition | Proteins: | IC₅₀ (µM) |
|   |   |   |   | EcSecAN68 |   |
|   |   |   | *In vivo* inhibition | Strains: | MIC (µM) 16h |
|   |   |   |   | B. anthracis Sterne | 25 |
|   |   |   |   | S. aureus 6538 | 25 |

| BW-SCA-218 | AS-V-65-Disub-b2 |  Molecular Weight: 745.59 | *In vitro* inhibition | Proteins: EcSecAN68 | IC$_{50}$ (μM) |
|---|---|---|---|---|---|
| | | | | Strains: | MIC (μM) 16h |
| | | | *In vivo* inhibition | *B. anthracis* Sterne | 8.33 |
| | | | | *S. aureus* 6538 | 3.91 |
| | | | | *S. aureus* Mu50 | 1.95 |
| | | | | *E. coli* NR698 | 37.5 |
| | | | | *B. subtilis* 168 | 1.95 |
| BW-SCA-219-C | AS-V-65-Mono-b1 |  Molecular Weight: 602.89 | *In vitro* inhibition | Proteins: EcSecAN68 | IC$_{50}$ (μM) |
| | | | | Strains: | MIC (μM) 16h |
| | | | *In vivo* inhibition | *B. anthracis* Sterne | 4.17 |
| | | | | *S. aureus* 6538 | 3.91 |
| | | | | *S. aureus* Mu50 | 1.95 |
| | | | | *E. coli* NR698 | 9.375 |
| | | | | *B. subtilis* 168 | 2.34 |

| | | |
|---|---|---|
| BW-SCA-220-C | AS-V-67-bottom | Molecular Weight: 617.01 | *In vitro* inhibition | Proteins: EcSecAN68 | IC$_{50}$ (µM) |
| | | | *In vivo* inhibition | Strains: B. anthracis Sterne | M

| | | In vitro inhibition | Proteins: | IC$_{50}$ (µM) |
|---|---|---|---|---|
| BW-SCA-222-C | As-V-41-2OME | | EcSecAN68 | |
| | | In vivo inhibition | Strains: | MIC (µM) 16h |
| | | | B. anthracis Sterne | >250 |
| | | | S. aureus 6538 | >250 |
| | | | S. aureus Mu50 | >250 |
| | | | E. coli NR698 | >250 |
| | | | B. subtilis 168 | >250 |
| BW-SCA-223-C | AS-V-67-top | In vitro inhibition | Proteins: | IC$_{50}$ (µM) |
| | | | EcSecAN68 | |
| | | In vivo inhibition | Strains: | MIC (µM) 16h |
| | | | B. anthracis Sterne | >250 |
| | | | S. aureus 6538 | |
| | | | S. aureus Mu50 | |
| | | | E. coli NR698 | |
| | | | B. subtilis 168 | |

Molecular Weight: 622.01

Molecular weight: 617.02

| | |
|---|---|
| BW-SCA-230-B | FB-1-31 | Structure with CO2Me, S, NH, N, CN, O, S-benzyl groups. Molecular Weight: 499.60, 20.2 mg |
| BW-SCA-231-B | Fb-1-38 | Structure with N3, S, NH, N, CN, O, O-CH2-C6H4-CF3 groups. Molecular Weight: 480.54, 16.4 mg |

FIG. 8-109

| | | |
|---|---|---|
| BW-SCA-248 | DCF-V-39b-C |  Chemical Formula: C₁₅H₇ClF₆N₅NaS₂<br>Molecular Weight: 493.81 |
| BW-SCA-249 | DCF-V-39c-C | 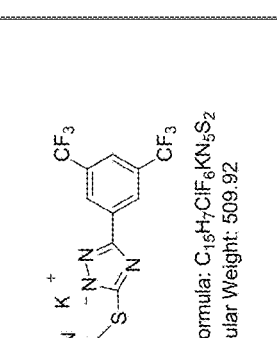 Chemical Formula: C₁₅H₇ClF₆KN₅S₂<br>Molecular Weight: 509.92 |
| BW-SCA-250 | DCF-V-42-C | 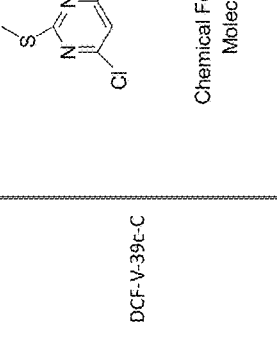 Chemical Formula: C₁₆H₁₁F₆N₅OS₂<br>Molecular Weight: 467.41 |
FIG. 8-118

| BW-SCA-251 | DCF-V-43-C |  Chemical Formula: C₁₇H₁₃F₆N₅OS₂<br>Molecular Weight: 481.44 | | |
|---|---|---|---|---|
| BW-SCA-252 | DCF-V-44-C |  Chemical Formula: C₁₅H₉F₆N₅OS₂<br>Molecular Weight: 453.39 | | |
| BW-SCA-253 | DK-V-108 |  Chemical Formula: C₁₉H₄Cl₄I₄O₃<br>Molecular Weight: 929.66<br>3.2 mg | | |
FIG. 8-119

SECA INHIBITORS AND METHODS OF MAKING AND USING THEREOF

STATEMENT REGARDING FEDERALLY SPONSORED RESEARCH OR DEVELOPMENT

This invention was made with government support under Agreement Nos. CA123329, CA 883343, GM34766, and GM 084933 awarded by the National Institutes of Health. The government has certain rights in the invention.

FIELD OF THE INVENTION

This invention is in the field of inhibitors of SecA, and methods of making and using thereof.

BACKGROUND OF THE INVENTION

Due to the widespread emergence of drug-resistance, diseases caused by bacterial pathogens have become a major public health concern in recent years. There is an urgent need for the development of new antimicrobials, especially those that have a new target, in order to overcome drug resistance. Bacteria generally develop drug resistance in three ways: production of metabolizing enzymes for the degradation of the drugs, modification of their targets to render the drugs ineffective, and expression of high levels of efflux proteins that "pump" the drug out of cells resulting in the lowering of drug concentration inside. Therefore, the most promising approaches to finding new antimicrobials include (1) searching for new targets, (2) inhibiting or overcoming efflux, and (3) inhibiting metabolic enzymes.

SecA, an indispensable ATPase of the protein translocation machinery is present in all bacteria. SecA is responsible for the secretion of many vital proteins, important toxins and other virulence factors, and is essential for bacterial survival. SecA has no counterpart in mammalian cells, thus providing an ideal target for developing antimicrobial agents. SecA functions as a membrane protein, forming a transmembrane channel and thus provides the possibility for antimicrobial agents to reach this target without entering into the cells. In such a case, the drug efflux pump would have less negative effects on the inhibitor's ability to exert antimicrobial activity. In addition, because SecA is present in all bacteria, this is a target for the development of broad-spectrum antimicrobials.

Inhibitors of SecA can be potential antimicrobial agents. However, inhibitor development for SecA had not been an active area of research until recently, presumably due to the difficulty in working with this membrane protein and the active translocation complex. To date, inorganic azide was the only known SecA inhibitor with an $IC_{50}$ at the mM range. However, azide is also an inhibitor of many other enzymes such as cytochrome c oxidase, superoxide dismutase, alcohol dehydrogenase, and ceruloplasmin. Additional SecA inhibitors with potencies in the high µM to low mM range have been reported.

There exists a need for new SecA inhibitors which have activity in the low or high nanomolar to low micromolar range.

Therefore, it is an object of the invention to provide SecA inhibitors which have activity in the low or high nanomolar to low micromolar range and methods of making and using thereof.

BRIEF DESCRIPTION OF THE DRAWINGS

FIG. 3A shows non-competitive inhibition of EcSecA translocation ATPase by Rose Bengal. FIGS. 3B-3D shows non-competitive inhibition of channel activity in the oocytes with EcSecA-liposomes (FIG. 3B), PaSecA-liposomes (FIG. 3C), and SaSecA1-liposomes (FIG. 3D).

FIG. 7 shows the structure of selected Rose Bengal analogs.

FIG. 8-1 through 8-120 is a table showing compounds within the genus described herein that were synthesized or will be synthesized. Some of the compounds were evaluated in vitro for inhibition activity and/or toxicity.

SUMMARY OF THE INVENTION

Figure 1:
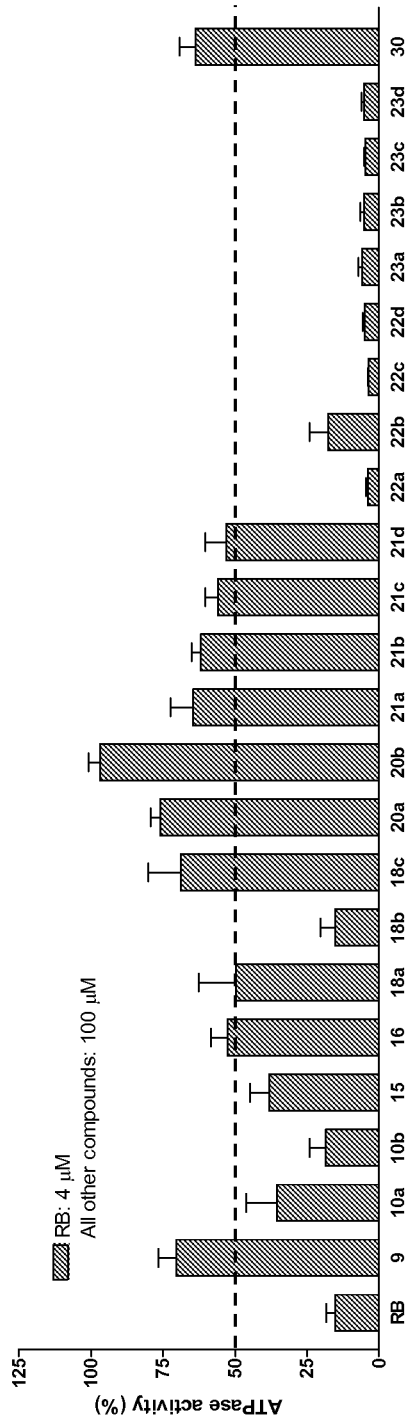
FIG. 1 is a bar graph showing the inhibition of ATPase in *E. Coli* NR68 for Rose Bengal and selected Rose Bengal analogs.

Compounds having Formula I-X, and methods of making and using are described herein.

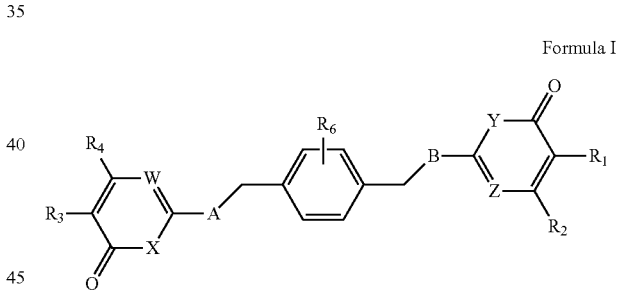

Formula I wherein
A and B are independently S, $SO_2$, SO, O, $NR_6$, or $CR_7R_8$;
W and Z are independently N or $CR_9$;
X and Y are independently S, O, or $CR_{10}R_{11}$; and
$R_1$-$R_{11}$ are independently absent or selected from hydrogen, substituted or unsubstituted, linear, branched, hetero, or cyclic alkyl, alkenyl, or alkynyl; substituted or unsubstituted aryl or heteroaryl, halogen, substituted or unsubstituted alkoxy; hydroxy, cyano, formyl, acyl, carboxylic acid (—COOH), carboxylate (—COO⁻), primary amide (e.g., —$CONH_2$), secondary amide (e.g., —$CONHR_{12}$), tertiary amide (e.g., —$CONR_{12}R_{12}$), secondary carbamate (e.g., —$OCONHR_{12}$; —$NHCOOR_{12}$), tertiary carbamate (e.g., —$OCONR_{12}R_{12}$; —$NR_{12}COOR_{12}$), urea (e.g., $NHCONHR_{12}$; —$NR_{12}CONHR_{12}$; —$NHCONR_{12}R_{12}$, —$NR_{12}CONR_{12}R_{12}$), carbinol (e.g., —$CH_2OH$; —$CHR_{12}OH$, —$CR_{12}R_{12}OH$), ester (e.g., —$COOR_{12}$), thiol (—SH), primary amine (—$NH_2$), secondary amine (e.g., —$NHR_{12}$), tertiary amine (e.g., —$NR_{12}R_{12}$), thioether (e.g., —SR$_{12}$), sulfinyl group (e.g., —SOR$_{12}$), and sulfonyl group (e.g., —SOOR$_{12}$), wherein R$_{12}$ is defined the same as R$_1$-R$_{11}$.

In some embodiments, A and B are S.

In some embodiments, A and B are S and W and Z are N.

In some embodiments, A and B are S, W and Z are N, and X and Y are NR, wherein R is hydrogen or lower alkyl.

In some embodiments, A and B are S, W and Z are N, X and Y are NR, wherein R is hydrogen or lower alkyl, and R$_1$ and R$_3$ are C≡N.

In some embodiments, A and B are S, W and Z are N, X and Y are NR, wherein R is hydrogen or lower alkyl, R$_1$ and R$_3$ are C≡N, and R$_2$ and R$_4$ are aryl, such as substituted or unsubstituted phenyl or naphthyl. In some embodiments, the phenyl ring is substituted with a lower alkyl, such as methyl, ethyl, n-propyl, or isopropyl, at the ortho, meta, or para position. In other embodiments, the phenyl ring is substituted with a lower alkoxy, such as methoxy, at the ortho, meta, or para position. In still other embodiments, the phenyl ring is substituted with a halogen, such as chloro, bromo, or iodo at the ortho, meta, or para position. In still other embodiments, the phenyl ring is substituted with an aryl group, such as a substituted or unsubstituted phenyl.

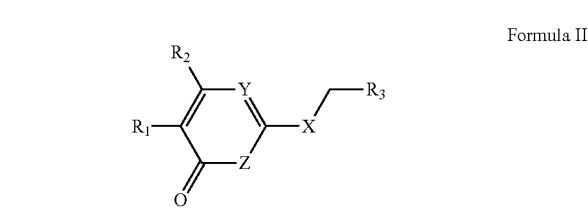

Formula II wherein
X is S, SO, SO$_2$, NHR$_4$, O, or CR$_5$R$_6$;
Y is N or CR$_7$;
Z is S, O, NR$_8$, or CR$_9$R$_{10}$; and
R$_1$-R$_{10}$ is independently absent or selected from hydrogen, substituted or unsubstituted, linear, branched, hetero, or cyclic alkyl, alkenyl, or alkynyl; substituted or unsubstituted aryl or heteroaryl; halogen, substituted or unsubstituted alkoxy; hydroxy, cyano, formyl, acyl, carboxylic acid (—COOH), carboxylate (—COO$^-$), primary amide (e.g., —CONH$_2$), secondary amide (e.g., —CONHR$_{11}$), tertiary amide (e.g., —CONR$_{11}$R$_{11}$), secondary carbamate (e.g., —OCONHR$_{11}$; —NHCOOR$_{11}$), tertiary carbamate (e.g., —OCONR$_{11}$R$_{11}$; —NR$_{11}$COOR$_{11}$), urea (e.g., NHCONHR$_{11}$; —NR$_{10}$CONHR$_{11}$; —NHCONR$_{11}$R$_{11}$, —NR$_{11}$CONR$_{11}$R$_{11}$), carbinol (e.g., —CH$_2$OH; —CHR$_{11}$OH, —CR$_{11}$R$_{11}$OH), ester (e.g., —COOR$_{11}$), thiol (—SH), primary amine (—NH$_2$), secondary amine (e.g., —NHR$_{11}$), tertiary amine (e.g., —NR$_{11}$R$_{11}$), thioether (e.g., —SR$_{11}$), sulfinyl group (e.g., —SOR$_{11}$), and sulfonyl group (e.g., —SOOR$_{11}$), wherein R$_{11}$ is defined the same as R$_1$-R$_{10}$.

In some embodiments, X is S.

In some embodiments, X is S and Y is N.

In some embodiments, X is S, Y is N, and Z is NR, wherein R is hydrogen or lower alkyl.

In some embodiments, X is S, Y is N, Z is NR, wherein R is hydrogen or lower alkyl, and R$_3$ is substituted or unsubstituted aryl, such as phenyl. In some embodiments, R$_3$ is unsubstituted phenyl. In other embodiments, R$_3$ is phenyl substituted with amino or azide at the ortho, meta, or para position. In still other embodiments, R$_3$ is phenyl, substituted at the para position by

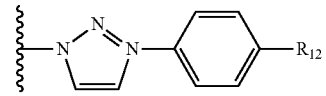

wherein R$_{12}$ is as defined above. In some embodiments, R$_{12}$ is amino.

In some embodiments, X is S, Y is N, Z is NR, wherein R is hydrogen or lower alkyl, and R$_3$ is substituted or unsubstituted aryl as described above, and R$_2$ is substituted or unsubstituted aryl, such as phenyl or naphthyl. In some embodiments R$_2$ is phenyl substituted with lower alkyl, such as methyl, ethyl, n-propyl, or isopropyl at the ortho, meta, or para position. In other embodiments, R$_2$ is phenyl substituted with a halogen, such as chloro, bromo, or iodo, at the ortho, meta, or para position. In still other embodiments, the phenyl ring is substituted with an aryl group, such as a substituted or unsubstituted phenyl.

In some embodiments, X is S, Y is N, Z is NR, wherein R is hydrogen or lower alkyl, and R$_3$ is substituted or unsubstituted aryl as described above, R$_2$ is substituted or unsubstituted aryl as described above, and R$_1$ is C≡N.

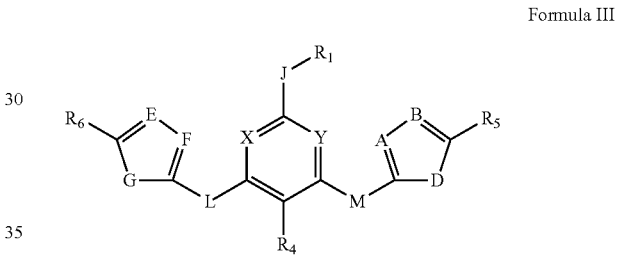

Formula III wherein
X and Y are independently N or C;
D and G are independently NR$_7$, CR$_8$R$_9$, O, or S;
A, B, E, and F are independently N or CR$_{10}$;
L and M are independently S, SO, SO$_2$, O, NR$_{11}$, or CR$_{12}$R$_{13}$;
J is O, S, SO, SO$_2$, NR$_{14}$, or CR$_{15}$R$_{16}$; and
R$_1$-R$_{16}$ are independently absent or selected from hydrogen, substituted or unsubstituted, linear, branched, hetero, or cyclic alkyl, alkenyl, or alkynyl; substituted or unsubstituted aryl or heteroaryl; halogen, substituted or unsubstituted alkoxy; hydroxy, cyano, formyl, acyl, carboxylic acid (—COOH), carboxylate (—COO$^-$), primary amide (e.g., —CONH$_2$), secondary amide (e.g., —CONHR$_{17}$), tertiary amide (e.g., —CONR$_{17}$R$_{17}$), secondary carbamate (e.g., —OCONHR$_{17}$; —NHCOOR$_{17}$), tertiary carbamate (e.g., —OCONR$_{17}$R$_{17}$; —NR$_{14}$COOR$_{17}$), urea (e.g., NHCONHR$_{17}$; —NR$_{14}$CONHR$_{17}$; —NHCONR$_{17}$R$_{17}$, —NR$_{17}$CONR$_{17}$R$_{17}$), carbinol (e.g., —CH$_2$OH; —CHR$_{17}$OH, —CR$_{17}$R$_{17}$OH), ester (e.g., —COOR$_{17}$), thiol (—SH), primary amine (—NH$_2$), secondary amine (e.g., —NHR$_{17}$), tertiary amine (e.g., —NR$_{17}$R$_{17}$), thioether (e.g., —SR$_{17}$), sulfinyl group (e.g., —SOR$_{17}$), and sulfonyl group (e.g., —SOOR$_{17}$), wherein R$_{17}$ is defined the same as R$_1$-R$_{16}$.

In some embodiments, J is S.

In some embodiments, J is S and X and Y are N.

In some embodiments, J is S, X and Y are N, and L and M are S.

In some embodiments, J is S, X and Y are N, L and M are S, and D and G are NR, where R is hydrogen or lower alkyl.

In some embodiments, J is S, X and Y are N, L and M are S, D and G are NR, where R is hydrogen or lower alkyl, and A, B, E, and F are N.

In some embodiments, J is S, X and Y are N, L and M are S, D and G are NR, where R is hydrogen or lower alkyl, A, B, E, and F are N, and $R_1$ is lower alkyl, such as methyl.

In some embodiments, J is S, X and Y are N, L and M are S, D and G are NR, where R is hydrogen or lower alkyl, A, B, E, and F are N, and $R_1$ is lower alkyl, such as methyl.

In some embodiments, J is S, X and Y are N, L and M are S, D and G are NR, where R is hydrogen or lower alkyl, A, B, E, and F are N, $R_1$ is lower alkyl, such as methyl, and $R_5$ and $R_6$ are substituted or unsubstituted aryl, such as phenyl. In some embodiments, $R_5$ and $R_6$ are phenyl, substituted with chloro or trifluoromethyl at the two meta positions.

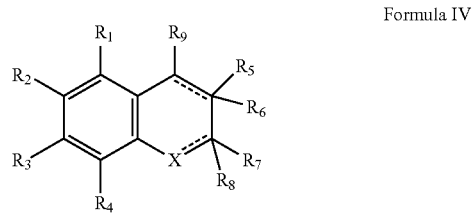

Formula IV wherein

X is O, S, $NR_{10}$, or $CR_{11}R_{12}$;

$R_1$-$R_{12}$ are independently absent or selected from hydrogen, substituted or unsubstituted, linear, branched, hetero, or cyclic alkyl, alkenyl, or alkynyl; substituted or unsubstituted aryl or heteroaryl; halogen, substituted or unsubstituted alkoxy; hydroxy, cyano, formyl, acyl, carboxylic acid (—COOH), carboxylate (—COO⁻), primary amide (e.g., —CONH$_2$), secondary amide (e.g., —CONHR$_{13}$), tertiary amide (e.g., —CONR$_{13}$R$_{13}$), secondary carbamate (e.g., —OCONHR$_{13}$; —NHCOOR$_{13}$), tertiary carbamate (e.g., —OCONR$_{13}$R$_{13}$; —NR$_{14}$COOR$_{13}$), urea (e.g., NHCONHR$_{13}$; —NR$_{14}$CONHR$_{13}$; —NHCONR$_{13}$R$_{13}$, —NR$_{12}$CONR$_{13}$R$_{13}$), carbinol (e.g., —CH$_2$OH; —CHR$_{13}$OH, —CR$_{13}$R$_{13}$OH), ester (e.g., —COOR$_{13}$), thiol (—SH), primary amine (—NH$_2$), secondary amine (e.g., —NHR$_{13}$), tertiary amine (e.g., —NR$_{13}$R$_{13}$), thioether (e.g., —SR$_{13}$), sulfinyl group (e.g., —SOR$_{13}$), and sulfonyl group (e.g., —SOOR$_{13}$), wherein $R_{13}$ is defined the same as $R_1$-$R_{12}$.

The dotted lines represent optional double bonds.

In some embodiments, X is O or CR, wherein R is defined as above for $R_1$-$R_{13}$ and wherein the bond between X and the carbon containing $R_7$ and $R_8$ is a double bond and the bond between the carbons containing $R_5$ and $R_6$ and $R_9$ is a double bond.

In some embodiments, X is O or CR, wherein R is defined as above for $R_1$-$R_{13}$ and wherein the bond between X and the carbon containing $R_7$ and $R_8$ is a double bond and the bond between the carbons containing $R_5$ and $R_6$ and $R_9$ is a double bond, $R_9$ is substituted or unsubstituted aryl, such as phenyl. In some embodiments, $R_9$ is phenyl substituted with a carboxylic acid group at the meta, ortho or para position.

In some embodiments, X is O or CR, wherein R is defined as above for $R_1$-$R_{13}$ and wherein the bond between X and the carbon containing $R_7$ and $R_8$ is a double bond and the bond between the carbons containing $R_5$ and $R_6$ and $R_9$ is a double bond, $R_9$ is substituted or unsubstituted aryl as described above, and $R_3$ is hydroxy.

In some embodiments, X is O or CR, wherein R is defined as above for $R_1$-$R_{13}$ and wherein the bond between X and the carbon containing $R_7$ and $R_8$ is a double bond and the bond between the carbons containing $R_5$ and $R_6$ and $R_9$ is a double bond, $R_9$ is substituted or unsubstituted aryl as described above, and $R_3$ is hydroxy.

In some embodiments, X is O or CR, wherein R is defined as above for $R_1$-$R_{13}$ and wherein the bond between X and the carbon containing $R_7$ and $R_8$ is a double bond and the bond between the carbons containing $R_5$ and $R_6$ and $R_9$ is a double bond, $R_9$ is substituted or unsubstituted aryl as described above, $R_3$ is hydroxy, and $R_2$ and/or $R_4$ are halogen, such as chloro, bromo, or iodo.

In some embodiments, X is O or CR, wherein R is defined as above for $R_1$-$R_{13}$ and wherein the bond between X and the carbon containing $R_7$ and $R_8$ is a double bond and the bond between the carbons containing $R_5$ and $R_6$ and $R_9$ is a double bond, $R_9$ is substituted or unsubstituted aryl as described above, $R_3$ is hydroxy, $R_2$ and/or $R_4$ are halogen, such as chloro, bromo, or iodo, and $R_1$ is hydrogen.

In some embodiments, X is O or CR, wherein R is defined as above for $R_1$-$R_{13}$ and wherein the bond between X and the carbon containing $R_7$ and $R_8$ is a double bond and the bond between the carbons containing $R_5$ and $R_6$ and $R_9$ is a double bond, $R_9$ is substituted or unsubstituted aryl as described above, $R_3$ is hydroxy, $R_2$ and/or $R_4$ are halogen, such as chloro, bromo, or iodo, $R_1$ is hydrogen, and $R_5$ is halogen, such as chloro, bromo, or iodo.

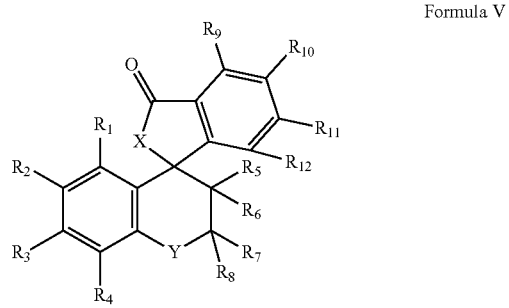

Formula V wherein

X and Y are independently O, S, $NR_{13}$, or $CR_{14}R_{15}$; and $R_1$-$R_{15}$ are independently absent or selected from hydrogen, substituted or unsubstituted, linear, branched, hetero, or cyclic alkyl, alkenyl, or alkynyl; substituted or unsubstituted aryl or heteroaryl; halogen, substituted or unsubstituted alkoxy; hydroxy, cyano, formyl, acyl, carboxylic acid (—COOH), carboxylate (—COO⁻), primary amide (e.g., —CONH$_2$), secondary amide (e.g., —CONHR$_{16}$), tertiary amide (e.g., —CONR$_{16}$R$_{16}$), secondary carbamate (e.g., —OCONHR$_{16}$; —NHCOOR$_{16}$), tertiary carbamate (e.g., —OCONR$_{16}$R$_{16}$; —NR$_{16}$COOR$_{16}$), urea (e.g., NHCONHR$_{16}$; —NR$_{16}$CONHR$_{16}$; —NHCONR$_{16}$R$_{16}$, —NR$_{16}$CONR$_{16}$R$_{16}$), carbinol (e.g., —CH$_2$OH; —CHR$_{16}$OH, —CR$_{16}$R$_{16}$OH), ester (e.g., —COOR$_{16}$), thiol (—SH), primary amine (—NH$_2$), secondary amine (e.g., —NHR$_{16}$), tertiary amine (e.g., —NR$_{16}$R$_{16}$), thioether (e.g., —SR$_{16}$), sulfinyl group (e.g., —SOR$_{16}$), and sulfonyl group (e.g., —SOOR$_{16}$), wherein $R_{16}$ is defined the same as $R_1$-$R_{15}$. In some embodiments, X is O.

In some embodiments, X is O and Y is O.

In some embodiments, X is O, Y is O, and $R_2$ and/or $R_4$ are halogen, such as chloro, bromo, and/or iodo.

In some embodiments, X is O, Y is O, $R_2$ and/or $R_4$ are halogen, such as chloro, bromo, and/or iodo, and $R_3$ is hydroxy.

In some embodiments, X is O, Y is O, $R_2$ and/or $R_4$ are halogen, such as chloro, bromo, and/or iodo, $R_3$ is hydroxy, and $R_9$-$R_{12}$ are hydrogen.

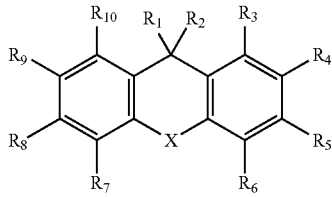

Formula VI wherein

X is O, S, SO, $SO_2$, $NR_{11}$, or $CR_{12}R_{13}$; and $R_1$-$R_{13}$ are independently absent or selected from hydrogen, substituted or unsubstituted, linear, branched, hetero, or cyclic alkyl, alkenyl, or alkynyl; substituted or unsubstituted aryl or heteroaryl; halogen, substituted or unsubstituted alkoxy; hydroxy, cyano, formyl, acyl, carboxylic acid (—COOH), carboxylate (—COO$^-$), primary amide (e.g., —$CONH_2$), secondary amide (e.g., —$CONHR_{14}$), tertiary amide (e.g., —$CONR_{14}R_{14}$), secondary carbamate (e.g., —$OCONHR_{14}$; —$NHCOOR_{14}$), tertiary carbamate (e.g., —$OCONR_{14}R_{14}$; —$NR_{14}COOR_{14}$), urea (e.g., $NHCONHR_{14}$; —$NR_{14}CONHR_{14}$; —$NHCONR_{14}R_{14}$; —$NR_{14}CONR_{14}R_{14}$), carbinol (e.g., —$CH_2OH$; —$CHR_{14}OH$, —$CR_{14}R_{14}OH$), ester (e.g., —$COOR_{14}$), thiol (—SH), primary amine (—$NH_2$), secondary amine (e.g., —$NHR_{14}$), tertiary amine (e.g., —$NR_{14}R_{14}$), thioether (e.g., —$SR_{14}$), sulfinyl group (e.g., —$SOR_{14}$), and sulfonyl group (e.g., —$SOOR_{14}$), wherein $R_{14}$ is defined the same as $R_1$-$R_{13}$.

In some embodiments, X is O.

In some embodiments, X is O and $R_1$ is lower alkyl, such as methyl, ethyl, n-propyl, or isopropyl.

In some embodiments, X is O, $R_1$ is lower alkyl, such as methyl, ethyl, n-propyl, or isopropyl, and one or more of $R_4$, $R_6$, $R_7$, and $R_{11}$ are halogen, such as chloro, bromo, iodo, or combinations thereof.

In some embodiments, X is O, $R_1$ is lower alkyl, such as methyl, ethyl, n-propyl, or isopropyl, one or more of $R_4$, $R_6$, $R_7$, and $R_{11}$ are halogen, such as chloro, bromo, iodo, or combinations thereof, and one or more of $R_5$ and $R_8$ are hydroxy.

In some embodiments, X is O, $R_1$ is substituted or unsubstituted aryl, such as phenyl, $R_2$, $R_5$, and $R_8$ are hydroxy and $R_3$-$R_{10}$ are hydrogen or as defined in the various embodiments above.

In some embodiments, $R_1$ is substituted or unsubstituted cycloalkyl, such as cyclopentyl or cyclohexyl, $R_5$ and $R_8$ are hydroxy or lower alkoxy, such methoxy or ethoxy, and one or more of $R_2$-$R_4$, $R_6$, $R_7$, and $R_8$-$R_{10}$ are hydrogen, halogen (chloro, bromo, iodo), hydroxy, or combinations thereof.

In some embodiments, $R_1$ is substituted or unsubstituted cycloalkyl, such as cyclopentyl or cyclohexyl or alkyl, such as methyl, ethyl, n-propyl, isopropyl, butyl (n-, sec-, iso-, t-), pentyl, hexyl, or heptyl, $R_5$ and $R_8$ are hydroxy, lower alkoxy, such methoxy or ethoxy, or primary, secondary, or tertiary amino, one or more of $R_4$, $R_6$, $R_7$, and $R_9$ are halogen, such as chloro, bromo, iodo, or combinations thereof, and one or more of $R_2$, $R_3$, $R_4$, $R_6$, $R_7$, $R_9$, and $R_{10}$ are hydrogen. In some embodiments, $R_1$ is cyclopentyl substituted with a carboxylic acid group at the 2 position.

In some embodiments, $R_1$ and $R_2$ together are =O or =$CR_{12}R_{13}$, X is O, and $R_3$-$R_{10}$ are defined in the various embodiments above. In some embodiments, $R_1$ is a substituted or unsubstituted cycloalkyl, such as cyclopentyl or cyclohexyl, and $R_2$ and the valence on C1 of the cycloalkyl ring is a double bond, X is O, and $R_3$-$R_{10}$ are as defined in the various embodiments above.

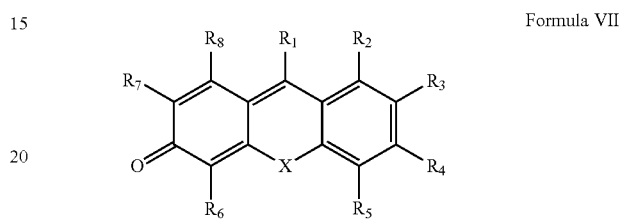

Formula VII wherein X is O, S, SO, $SO_2$, $NR_9$, $CR_{10}R_{11}$; and $R_1$-$R_{11}$ are independently absent or selected from hydrogen, substituted or unsubstituted, linear, branched, hetero, or cyclic alkyl, alkenyl, or alkynyl; substituted or unsubstituted aryl or heteroaryl; halogen, substituted or unsubstituted alkoxy; hydroxy, cyano, formyl, acyl, carboxylic acid (—COOH), carboxylate (—COO$^-$), primary amide (e.g., —$CONH_2$), secondary amide (e.g., —$CONHR_{12}$), tertiary amide (e.g., —$CONR_{12}R_{12}$), secondary carbamate (e.g., —$OCONHR_{12}$; —$NHCOOR_{12}$), tertiary carbamate (e.g., —$OCONR_{12}R_{12}$; —$NR_{14}COOR_{12}$), urea (e.g., $NHCONHR_{12}$; —$NR_{12}CONHR_{12}$; —$NHCONR_{12}R_{12}$, —$NR_{14}CONR_{12}R_{12}$), carbinol (e.g., —$CH_2OH$; —$CHR_{12}OH$, —$CR_{12}R_{12}OH$), ester (e.g., —$COOR_{12}$), thiol (—SH), primary amine (—$NH_2$), secondary amine (e.g., —$NHR_{12}$), tertiary amine (e.g., —$NR_{12}R_{12}$), thioether (e.g., —$SR_{12}$), sulfinyl group (e.g., —$SOR_{12}$), and sulfonyl group (e.g., —$SOOR_{12}$), wherein $R_{12}$ is defined the same as $R_1$-$R_{11}$ wherein the compound of formula VII is not Rose Bengal.

In some embodiments, X=O, $R_1$ is substituted or unsubstituted cycloalkyl, such as cyclopentyl or cyclohexyl, and one or more of $R_2$-$R_7$ are hydrogen, hydroxy, halogen (chloro, bromo, iodo), or combinations thereof.

In some embodiments, $R_1$ is substituted or unsubstituted aryl, such as phenyl. In some embodiments, $R_1$ is 2,3,4,5-tetrachloro-2-benzoic acid.

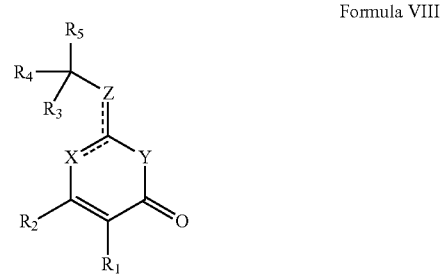

Formula VIII wherein Z is O, S, SO, SO$_2$, NR$_6$, or CR$_7$R$_8$;

X and Y are independently N, NR$_9$, or CR$_{10}$R$_{11}$;

R$_1$-R$_{11}$ are independently absent or selected from hydrogen, substituted or unsubstituted, linear, branched, hetero, or cyclic alkyl, alkenyl, or alkynyl; substituted or unsubstituted aryl or heteroaryl; halogen, substituted or unsubstituted alkoxy; hydroxy, cyano, formyl, acyl, carboxylic acid (—COOH), carboxylate (—COO⁻), primary amide (e.g., —CONH$_2$), secondary amide (e.g., —CONHR$_{12}$), tertiary amide (e.g., —CONR$_{12}$R$_{12}$), secondary carbamate (e.g., —OCONHR$_{12}$; —NHCOOR$_{12}$), tertiary carbamate (e.g., —OCONR$_{12}$R$_{12}$; —NR$_{14}$COOR$_{12}$), urea (e.g., NHCONHR$_{12}$; —NR$_{12}$CONHR$_{12}$; —NHCONR$_{12}$R$_{12}$, —NR$_{14}$CONR$_{12}$R$_{12}$), carbinol (e.g., —CH$_2$OH; —CHR$_{12}$OH, —CR$_{12}$R$_{12}$OH), ester (e.g., —COOR$_{12}$), thiol (—SH), primary amine (—NH$_2$), secondary amine (e.g., —NHR$_{12}$), tertiary amine (e.g., —NR$_{12}$R$_{12}$), thioether (e.g., —SR$_{12}$), sulfinyl group (e.g., —SOR$_{12}$), and sulfonyl group (e.g., —SOOR$_{12}$), wherein R$_{12}$ is defined the same as R$_1$-R$_{11}$; and the dotted lines represent optional double bonds.

In some embodiments, Z is S.

In some embodiments, Z is S, X is N, and Y is NR, where R is hydrogen or lower alkyl, such as methyl, ethyl, or propyl.

In some embodiments, Z is S, X is N, Y is NR, where R is hydrogen or lower alkyl, such as methyl, ethyl, or propyl, and R$_1$ is C≡N.

In some embodiments, Z is S, X is N, Y is NR, where R is hydrogen or lower alkyl, such as methyl, ethyl, or propyl, R$_1$ is C≡N, and R$_2$ and R$_5$ are aryl, such as phenyl.

In some embodiments, Z is S, X is N, Y is NR, where R is hydrogen or lower alkyl, such as methyl, ethyl, or propyl, R$_1$ is C≡N, R$_2$ and R$_5$ are aryl, such as phenyl, wherein R$_2$ is phenyl substituted with a phenyl ring at the 3 or 4 position and the phenyl ring at the 3 or 4 position is optionally substituted with OH at any position or —NH—COOalkyl, such as methyl, ethyl, propyl, butyl (e.g., t-butyl) at any position.

In some embodiments, Z is S, X is N, Y is NR, where R is hydrogen or lower alkyl, such as methyl, ethyl, or propyl, R$_1$ is C≡N, R$_2$ and R$_5$ are aryl, such as phenyl, wherein R$_2$ is phenyl substituted with a phenyl ring at the 3 or 4 position and the phenyl ring at the 3 or 4 position and R$_5$ is phenyl substituted with —COOH or B(OH)$_2$. In other embodiments, R$_5$ is pyridinyl.

In some embodiments, Z is S, X is N, Y is NR, where R is hydrogen or lower alkyl, such as methyl, ethyl, or propyl, R$_1$ is C≡N, R$_2$ and R$_5$ are aryl, such as phenyl, wherein R$_2$ is phenyl substituted with a phenyl ring at the 4 position, and R$_5$ is phenyl substituted at the 4 position with

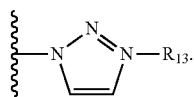

In some embodiments, Z is S, X is N, Y is NR, where R is hydrogen or lower alkyl, such as methyl, ethyl, or propyl, R$_1$ is C≡N, R$_2$ and R$_5$ are aryl, such as phenyl, wherein R$_2$ is phenyl substituted with a phenyl ring at the 4 position, and R$_5$ is phenyl substituted at the 4 position with

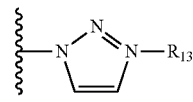

wherein R$_{13}$ is —(CH$_2$)$_n$—OCOalkyl, where alkyl is a lower alkyl, —(CH$_2$)$_n$—COOH, —(CH$_2$)$_n$—OH, wherein n is at least 1, such as 1, 2, 3, 4, 5, or 6.

In still other embodiments, In some embodiments, Z is S, X is N, Y is NR, where R is hydrogen or lower alkyl, such as methyl, ethyl, or propyl, R$_1$ is C≡N, R$_2$ is aryl, such as phenyl, wherein R$_2$ is phenyl substituted with a phenyl ring at the 3 or 4 position, and R$_5$ is —(CH$_2$)$_n$—OCOalkyl, where alkyl is a lower alkyl, —(CH$_2$)$_n$—COOH, —(CH$_2$)$_n$—OH, wherein n is at least 1, such as 1, 2, 3, 4, 5, or 6.

In still other embodiments, In some embodiments, Z is S, X is N, Y is NR, where R is hydrogen or lower alkyl, such as methyl, ethyl, or propyl, R$_1$ is C≡N, R$_2$ is aryl, such as phenyl, substituted with trifluoromethyl at the 4 position or wherein R$_2$ is phenyl substituted with a phenyl ring at the 3 or 4 position which is optionally subsitituted with trifluoromethyl, and R$_5$ is —(CH$_2$)$_n$—OCOalkyl, where alkyl is a lower alkyl, —(CH$_2$)$_n$—COOH, —(CH$_2$)$_n$—OH, wherein n is at least 1, such as 1, 2, 3, 4, 5, or 6.

In some embodiments, Z is S, X is N, Y is NR, where R is hydrogen or lower alkyl, such as methyl, ethyl, or propyl, R$_1$ is C≡N, R$_2$ and R$_5$ are aryl, such as phenyl, wherein R$_2$ is phenyl substituted with a phenyl ring at the 3 or 4 position and R$_5$ is phenyl substituted with —COOalkyl, where alkyl is lower alkyl, at the 4 position.

In still other embodiments, Z is S, R$_3$-R$_5$ are hydrogen, and the remaining variables are defined as in the embodiments above.

In still other embodiments, Z is S, the bond between the ring and Z is a double bond, the bond between N and the carbon bound to Z is a single bond, and the remaining variables are defined as in the embodiments above.

In still other embodiments, Z is O, and the remaining variables are defined as in the embodiments above.

Formula IX

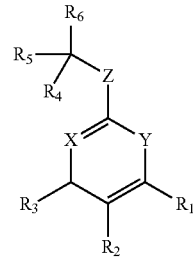

wherein Z is O, S, SO, SO$_2$, NR$_7$, or CR$_8$R$_9$;

X and Y are independently N, NR$_{10}$, or CR$_{11}$R$_{12}$;

R$_1$-R$_{12}$ are independently absent or selected from hydrogen, substituted or unsubstituted, linear, branched, hetero, or cyclic alkyl, alkenyl, or alkynyl; substituted or unsubstituted aryl or heteroaryl; halogen, substituted or unsubstituted alkoxy; hydroxy, cyano, formyl, acyl, carboxylic acid (—COOH), carboxylate (—COO⁻), primary amide (e.g., —CONH$_2$), secondary amide (e.g., —CONHR$_{13}$), tertiary amide (e.g., —CONR$_{13}$R$_{13}$), secondary carbamate (e.g., —OCONHR$_{13}$; —NHCOOR$_{13}$), tertiary carbamate (e.g., —OCONR$_{13}$R$_{13}$; —NR$_{13}$COOR$_{13}$), urea (e.g., NHCONHR$_{13}$; —NR$_{13}$CONHR$_{13}$; —NHCONR$_{13}$R$_{13}$, —NR$_{13}$CONR$_{13}$R$_{13}$), carbinol (e.g., —CH$_2$OH; —CHR$_{13}$OH, —CR$_{13}$R$_{13}$OH), ester (e.g., —COOR$_{13}$), thiol (—SH), primary amine (—NH$_2$), secondary amine (e.g., —NHR$_{13}$), tertiary amine (e.g., —NR$_{13}$R$_{13}$), thioether (e.g., —SR$_{13}$), sulfinyl group (e.g., —SOR$_{13}$), and sulfonyl group (e.g., —SOOR$_{13}$), wherein R$_{13}$ is defined the same as R$_1$-R$_{12}$.

In some embodiments, Z is O or S, X is N, Y is NH, R$_2$ is CN or COOalkyl, R$_1$ is —NH—OH, NH(CH$_2$)$_n$OH, where n is 1, 2, 3, 4, 5, or 6, halogen (Cl, Br, or I), alkoxy (e.g., methoxy), —NHR, where R is alkyl, or oligo- or polyethylglycol, or —NH—NH$_2$, and the remaining variables are defined as in the embodiments above.

In still other embodiments, the compound has the formula

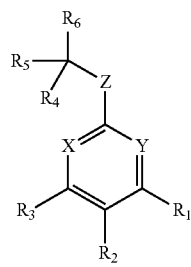

wherein the variable positions are as defined above for Formula IX.

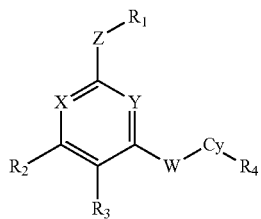

Formula X wherein
Z and W are O, S, SO, SO$_2$, NR$_5$, or CR$_6$R$_7$;
X and Y are independently N, NR$_B$, or CR$_9$R$_{10}$;
Cy is substituted or unsubstituted aryl, heteroaryl, cycloalkyl, or heterocycloalkyl group; and
R$_1$-R$_{10}$ are independently absent or selected from hydrogen, substituted or unsubstituted, linear, branched, hetero, or cyclic alkyl, alkenyl, or alkynyl; substituted or unsubstituted aryl or heteroaryl; halogen, substituted or unsubstituted alkoxy; hydroxy, cyano, formyl, acyl, carboxylic acid (—COOH), carboxylate (—COO$^-$), primary amide (e.g., —CONH$_2$), secondary amide (e.g., —CONHR$_{11}$), tertiary amide (e.g., —CONR$_{11}$R$_{11}$), secondary carbamate (e.g., —OCONHR$_{11}$; —NHCOOR$_{11}$), tertiary carbamate (e.g., —OCONR$_{11}$R$_{11}$; —NR$_{14}$COOR$_{11}$), urea (e.g., NHCONHR$_{11}$; —NR$_{11}$CONHR$_{11}$; —NHCONR$_{11}$R$_{11}$, —NR$_{14}$CONR$_{11}$R$_{11}$), carbinol (e.g., —CH$_2$OH; —CHR$_{11}$OH, —CR$_{11}$R$_{11}$OH), ester (e.g., —COOR$_{11}$), thiol (—SH), primary amine (—NH$_2$), secondary amine (e.g., —NHR$_{11}$), tertiary amine (e.g., —NR$_{11}$R$_{11}$), thioether (e.g., —SR$_{11}$), sulfinyl group (e.g., —SOR$_{11}$), and sulfonyl group (e.g., —SOOR$_{11}$), wherein R$_{11}$ is defined the same as R$_1$-R$_{10}$.

In some embodiments, Z and W are O or S, X and Y are N, Cy is a triazole ring, substituted at the two position with a substituted or unsubstituted aryl, such as phenyl (e.g., 3,5-dimethylphenyl, 3,5-di(trifluoromethyl)), and R$_2$ is halogen.

In some embodiments, Z and W are O or S, X and Y are N, Cy is a triazole or oxadiazole ring, substituted at the two position with a substituted or unsubstituted aryl, such as phenyl (e.g., 3,5-dimethylphenyl, 3,5-di(trifluoromethyl)), R$_2$ is halogen, and R$_1$ is aryl, such as phenyl.

In some embodiments, Z and R$_1$ and/or W are absent and the remaining variables are as defined above.

In some embodiments, the compound has the formula below, wherein the variables are as defined above for Formula X.

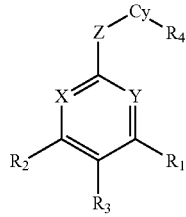

The compounds can be combined with one or more pharmaceutically acceptable excipients to prepare pharmaceutical compositions. The compositions can be administered by any route of administration, such as enteral, parenteral, topical, or transmucosal. The compositions may be useful for treating or preventing infections, such as microbial (bacteria, fungi, etc.) infections.

DETAILED DESCRIPTION OF THE INVENTION

I. Definitions

"Analog" and "Derivative", are used herein interchangeably, and refer to a compound that possesses the same core as a parent compound, but differs from the parent compound in bond order, in the absence or presence of one or more atoms and/or groups of atoms, and combinations thereof. The derivative can differ from the parent compound, for example, in one or more substituents present on the core, which may include one or more atoms, functional groups, or substructures. The derivative can also differ from the parent compound in the bond order between atoms within the core. In general, a derivative can be imagined to be formed, at least theoretically, from the parent compound via chemical and/or physical processes. For example, derivatives of celastrol include compounds possessing one or more substituents affixed to the core.

"Co-administration", as used herein, includes simultaneous and sequential administration. An appropriate time course for sequential administration may be chosen by the physician, according to such factors as the nature of a patient's illness, and the patient's condition.

"Pharmaceutically acceptable", as used herein, refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

"Prodrug", as used herein, refers to a pharmacological substance (drug) that is administered to a subject in an inactive (or significantly less active) form. Once administered, the prodrug is metabolized in the body (in vivo) into a compound having the desired pharmacological activity.

"Alkyl", as used herein, refers to the radical of saturated or unsaturated aliphatic groups, including straight-chain alkyl, heteroalkyl, alkenyl, or alkynyl groups, branched-chain alkyl, alkenyl, or alkynyl groups, cycloalkyl, cycloalkenyl, or cycloalkynyl (alicyclic) groups, alkyl substituted cycloalkyl, cycloalkenyl, or cycloalkynyl groups, and cycloalkyl substituted alkyl, alkenyl, or alkynyl groups. Unless otherwise indicated, a straight chain or branched chain alkyl has 30 or fewer carbon atoms in its backbone (e.g., $C_1$-$C_{30}$ for straight chain, $C_3$-$C_{30}$ for branched chain), more preferably 20 or fewer carbon atoms, more preferably 12 or fewer carbon atoms, and most preferably 8 or fewer carbon atoms. Likewise, preferred cycloalkyls have from 3-10 carbon atoms in their ring structure, and more preferably have 5, 6 or 7 carbons in the ring structure. The ranges provided above are inclusive of all values between the minimum value and the maximum value.

The term "alkyl" includes "heteroalkyls", "unsubstituted alkyls", and "substituted alkyls", the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls.

The alkyl groups may also contain one or more heteroatoms within the carbon backbone. Preferably the heteroatoms incorporated into the carbon backbone are oxygen, nitrogen, sulfur, and combinations thereof. In certain embodiments, the alkyl group contains between one and four heteroatoms.

"Alkenyl" and "Alkynyl", as used herein, refer to unsaturated aliphatic groups containing one or more double or triple bonds analogous in length (e.g., $C_2$-$C_{30}$) and possible substitution to the alkyl groups described above.

"Aryl", as used herein, refers to 5-, 6- and 7-membered aromatic ring. The ring may be a carbocyclic, heterocyclic, fused carbocyclic, fused heterocyclic, bicarbocyclic, or biheterocyclic ring system, optionally substituted by halogens, alkyl-, alkenyl-, and alkynyl-groups. Broadly defined, "Ar", as used herein, includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "heteroaryl", "aryl heterocycles", or "heteroaromatics". The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "Ar" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocycles. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Alkylaryl", as used herein, refers to an alkyl group substituted with an aryl group (e.g., an aromatic or hetero aromatic group).

"Heterocycle" or "heterocyclic", as used herein, refers to a cyclic radical attached via a ring carbon or nitrogen of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, ($C_{1-4}$) alkyl, phenyl or benzyl, and optionally containing one or more double or triple bonds, and optionally substituted with one or more substituents. The term "heterocycle" also encompasses substituted and unsubstituted heteroaryl rings. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Heteroaryl", as used herein, refers to a monocyclic aromatic ring containing five or six ring atoms consisting of carbon and 1, 2, 3, or 4 heteroatoms each selected from the group consisting of non-peroxide oxygen, sulfur, and N(Y) where Y is absent or is H, O, ($C_1$-$C_8$) alkyl, phenyl or benzyl. Non-limiting examples of heteroaryl groups include furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide), quinolyl (or its N-oxide) and the like. The term "heteroaryl" can include radicals of an ortho-fused bicyclic heterocycle of about eight to ten ring atoms derived therefrom, particularly a benz-derivative or one derived by fusing a propylene, trimethylene, or tetramethylene diradical thereto. Examples of heteroaryl can be furyl, imidazolyl, triazolyl, triazinyl, oxazoyl, isoxazoyl, thiazolyl, isothiazoyl, pyraxolyl, pyrrolyl, pyrazinyl, tetrazolyl, pyridyl (or its N-oxide), thientyl, pyrimidinyl (or its N-oxide), indolyl, isoquinolyl (or its N-oxide), quinolyl (or its N-oxide), and the like.

"Halogen", as used herein, refers to fluorine, chlorine, bromine, or iodine.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, peptide, and polypeptide groups.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

II. Compounds

Compounds having Formula I-X, and methods of making and using are described herein.

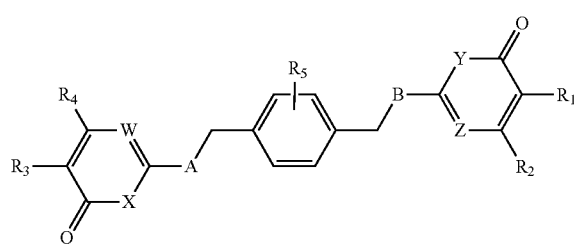

Formula I wherein

A and B are independently S, $SO_2$, SO, O, $NR_6$, or $CR_7R_8$;

W and Z are independently N or $CR_9$;

X and Y are independently S, O, or $CR_{10}R_{11}$; and $R_1$-$R_{11}$ are independently absent or selected from hydrogen, substituted or unsubstituted, linear, branched, hetero, or cyclic alkyl, alkenyl, or alkynyl; substituted or unsubstituted aryl or heteroaryl; halogen, substituted or unsubstituted alkoxy; hydroxy, cyano, formyl, acyl, carboxylic acid (—COOH), carboxylate (—COO⁻), primary amide (e.g., —CONH$_2$), secondary amide (e.g., —CONHR$_{12}$), tertiary amide (e.g., —CONR$_{12}$R$_{12}$), secondary carbamate (e.g., —OCONHR$_{12}$; —NHCOOR$_{12}$), tertiary carbamate (e.g., —OCONR$_{12}$R$_{12}$; —NR$_{12}$COOR$_{12}$), urea (e.g., NHCONHR$_{12}$; —NR$_{12}$CONHR$_{12}$; —NHCONR$_{12}$R$_{12}$, —NR$_{12}$CONR$_{12}$R$_{12}$), carbinol (e.g., —CH$_2$OH; —CHR$_{12}$OH, —CR$_{12}$R$_{12}$OH), ester (e.g., —COOR$_{12}$), thiol (—SH), primary amine (—NH$_2$), secondary amine (e.g., —NHR$_{12}$), tertiary amine (e.g., —NR$_{12}$R$_{12}$), thioether (e.g., —SR$_{12}$), sulfinyl group (e.g., —SOR$_{12}$), and sulfonyl group (e.g., —SOOR$_{12}$), wherein R$_{12}$ is defined the same as R$_1$-R$_{11}$.

In some embodiments, A and B are S.

In some embodiments, A and B are S and W and Z are N.

In some embodiments, A and B are S, W and Z are N, and X and Y are NR, wherein R is hydrogen or lower alkyl.

In some embodiments, A and B are S, W and Z are N, X and Y are NR, wherein R is hydrogen or lower alkyl, and R$_1$ and R$_3$ are C≡N.

In some embodiments, A and B are S, W and Z are N, X and Y are NR, wherein R is hydrogen or lower alkyl, R$_1$ and R$_3$ are C≡N, and R$_2$ and R$_4$ are aryl, such as substituted or unsubstituted phenyl or naphthyl. In some embodiments, the phenyl ring is substituted with a lower alkyl, such as methyl, ethyl, n-propyl, or isopropyl, at the ortho, meta, or para position. In other embodiments, the phenyl ring is substituted with a lower alkoxy, such as methoxy, at the ortho, meta, or para position. In still other embodiments, the phenyl ring is substituted with a halogen, such as chloro, bromo, or iodo at the ortho, meta, or para position. In still other embodiments, the phenyl ring is substituted with an aryl group, such as a substituted or unsubstituted phenyl.

Formula II

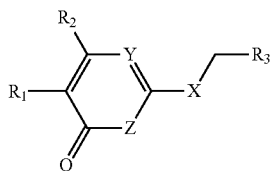

wherein
X is S, SO, SO$_2$, NHR$_4$, O, or CR$_5$R$_6$;
Y is N or CR$_7$;
Z is S, O, NR$_8$, or CR$_9$R$_{10}$; and
R$_1$-R$_{10}$ is independently absent or selected from hydrogen, substituted or unsubstituted, linear, branched, hetero, or cyclic alkyl, alkenyl, or alkynyl; substituted or unsubstituted aryl or heteroaryl; halogen, substituted or unsubstituted alkoxy; hydroxy, cyano, formyl, acyl, carboxylic acid (—COOH), carboxylate (—COO$^-$), primary amide (e.g., —CONH$_2$), secondary amide (e.g., —CONHR$_{11}$), tertiary amide (e.g., —CONR$_{11}$R$_{11}$), secondary carbamate (e.g., —OCONHR$_{11}$; —NHCOOR$_{11}$), tertiary carbamate (e.g., —OCONR$_{11}$R$_{11}$; —NR$_{11}$COOR$_{11}$), urea (e.g., NHCONHR$_{11}$; —NH$_{10}$CONHR$_{11}$; —NHCONR$_{11}$R$_{11}$; —NR$_{11}$CONR$_{11}$R$_{11}$), carbinol (e.g., —CH$_2$OH; —CHR$_{11}$OH, —CR$_{11}$R$_{11}$OH), ester (e.g., —COOR$_{11}$), thiol (—SH), primary amine (—NH$_2$), secondary amine (e.g., —NHR$_{11}$), tertiary amine (e.g., —NR$_{11}$R$_{11}$), thioether (e.g., —SR$_{11}$), sulfinyl group (e.g., —SOR$_{11}$), and sulfonyl group (e.g., —SOOR$_{11}$), wherein R$_{11}$ is defined the same as R$_1$-R$_{10}$.

In some embodiments, X is S.

In some embodiments, X is S and Y is N.

In some embodiments, X is S, Y is N, and Z is NR, wherein R is hydrogen or lower alkyl.

In some embodiments, X is S, Y is N, Z is NR, wherein R is hydrogen or lower alkyl, and R$_3$ is substituted or unsubstituted aryl, such as phenyl. In some embodiments, R$_3$ is unsubstituted phenyl. In other embodiments, R$_3$ is phenyl substituted with amino or azide at the ortho, meta, or para position. In still other embodiments, R$_3$ is phenyl, substituted at the para position by

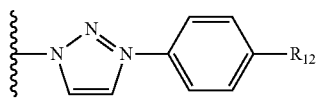

wherein R$_{12}$ is as defined above. In some embodiments, R$_{12}$ is amino.

In some embodiments, X is S, Y is N, Z is NR, wherein R is hydrogen or lower alkyl, and R$_3$ is substituted or unsubstituted aryl as described above, and R$_2$ is substituted or unsubstituted aryl, such as phenyl or naphthyl. In some embodiments R$_2$ is phenyl substituted with lower alkyl, such as methyl, ethyl, n-propyl, or isopropyl at the ortho, meta, or para position. In other embodiments, R$_2$ is phenyl substituted with a halogen, such as chloro, bromo, or iodo, at the ortho, meta, or para position. In still other embodiments, the phenyl ring is substituted with an aryl group, such as a substituted or unsubstituted phenyl.

In some embodiments, X is S, Y is N, Z is NR, wherein R is hydrogen or lower alkyl, and R$_3$ is substituted or unsubstituted aryl as described above, R$_2$ is substituted or unsubstituted aryl as described above, and R$_1$ is C≡N.

Formula III

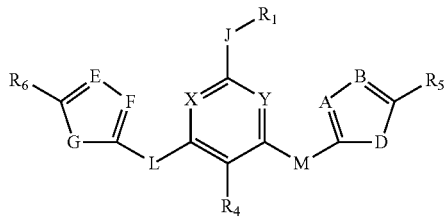

wherein
X and Y are independently N or C;
D and G are independently NR$_7$, CR$_8$R$_9$, O, or S;
A, B, E, and F are independently N or CR$_{10}$;
L and M are independently S, SO, SO$_2$, O, NR$_{11}$, or CR$_{12}$R$_{13}$
J is O, S, SO, SO$_2$, NR$_{14}$, or CR$_{15}$R$_{16}$; and
R$_1$-R$_{16}$ are independently absent or selected from hydrogen, substituted or unsubstituted, linear, branched, or cyclic alkyl, alkenyl, or alkynyl; substituted or unsubstituted aryl or heteroaryl; halogen, substituted or unsubstituted alkoxy; hydroxy, cyano, formyl, acyl, carboxylic acid (—COOH), carboxylate (—COO$^-$), primary amide (e.g., —CONH$_2$), secondary amide (e.g., —CONHR$_{17}$), tertiary amide (e.g., —CONR$_{17}$R$_{17}$), secondary carbamate (e.g., —OCONHR$_{17}$; —NHCOOR$_{17}$), tertiary carbamate (e.g., —OCONR$_{17}$R$_{17}$; —NR$_{14}$COOR$_{17}$), urea (e.g., NHCONHR$_{17}$; —NR$_{14}$CONHR$_{17}$; —NHCONR$_{12}$R$_{17}$; —NR$_{12}$CONR$_{17}$R$_{17}$), carbinol (e.g., —CH$_2$OH; —CHR$_{17}$OH, —CR$_{17}$R$_{17}$OH), ester (e.g., —COOR$_{17}$), thiol (—SH), primary amine (—NH$_2$), secondary amine (e.g., —NHR$_{17}$), tertiary amine (e.g., —NR$_{17}$R$_{17}$), thioether (e.g., —SR$_{17}$), sulfinyl group (e.g., —SOR$_{17}$), and sulfonyl group (e.g., —SOOR$_{17}$), wherein R$_{17}$ is defined the same as R$_1$-R$_{16}$.

In some embodiments, J is S.

In some embodiments, J is S and X and Y are N.

In some embodiments, J is S, X and Y are N, and L and M are S.

In some embodiments, J is S, X and Y are N, L and M are S, and D and G are NR, where R is hydrogen or lower alkyl.

In some embodiments, J is S, X and Y are N, L and M are S, D and G are NR, where R is hydrogen or lower alkyl, and A, B, E, and F are N.

In some embodiments, J is S, X and Y are N, L and M are S, D and G are NR, where R is hydrogen or lower alkyl, A, B, E, and F are N, and R$_1$ is lower alkyl, such as methyl.

In some embodiments, J is S, X and Y are N, L and M are S, D and G are NR, where R is hydrogen or lower alkyl, A, B, E, and F are N, and R$_1$ is lower alkyl, such as methyl.

In some embodiments, J is S, X and Y are N, L and M are S, D and G are NR, where R is hydrogen or lower alkyl, A, B, E, and F are N, R$_1$ is lower alkyl, such as methyl, and R$_5$ and R$_6$ are substituted or unsubstituted aryl, such as phenyl. In some embodiments, R$_5$ and R$_6$ are phenyl, substituted with chloro or trifluoromethyl at the two meta positions.

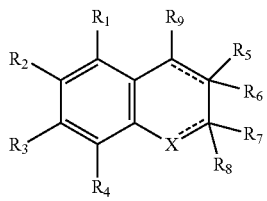

Formula IV wherein

X is O, S, $NR_{10}$, or $CR_{11}R_{12}$;

$R_1$-$R_{12}$ are independently absent or selected from hydrogen, substituted or unsubstituted, linear, branched, hetero, or cyclic alkyl, alkenyl, or alkynyl; substituted or unsubstituted aryl or heteroaryl; halogen, substituted or unsubstituted alkoxy; hydroxy, cyano, formyl, acyl, carboxylic acid (—COOH), carboxylate (—COO⁻), primary amide (e.g., —$CONH_2$), secondary amide (e.g., —$CONHR_{13}$), tertiary amide (e.g., —$CONR_{13}R_{13}$), secondary carbamate (e.g., —$OCONHR_{13}$; —$NHCOOR_{13}$), tertiary carbamate (e.g., —$OCONR_{13}R_{13}$; —$NR_{14}COOR_{13}$), urea (e.g., $NHCONHR_{13}$; —$NR_{14}CONHR_{13}$; —$NHCONR_{13}R_{13}$, —$NR_{17}CONR_{13}R_{13}$), carbinol (e.g., —$CH_2OH$; —$CHR_{13}OH$, —$CR_{13}R_{13}OH$), ester (e.g., —$COOR_{13}$), thiol (—SH), primary amine (—$NH_2$), secondary amine (e.g., —$NHR_{13}$), tertiary amine (e.g., —$NR_{13}R_{13}$), thioether (e.g., —$SR_{13}$), sulfinyl group (e.g., —$SOR_{13}$), and sulfonyl group (e.g., —$SOOR_{13}$), wherein $R_{13}$ is defined the same as $R_1$-$R_{12}$.

The dotted lines represent optional double bonds.

In some embodiments, X is O or CR, wherein R is defined as above for $R_1$-$R_{13}$ and wherein the bond between X and the carbon containing $R_7$ and $R_8$ is a double bond and the bond between the carbons containing $R_5$ and $R_6$ and $R_9$ is a double bond.

In some embodiments, X is O or CR, wherein R is defined as above for $R_1$-$R_{13}$ and wherein the bond between X and the carbon containing $R_7$ and $R_8$ is a double bond and the bond between the carbons containing $R_5$ and $R_6$ and $R_9$ is a double bond, $R_9$ is substituted or unsubstituted aryl, such as phenyl. In some embodiments, $R_9$ is phenyl substituted with a carboxylic acid group at the meta, ortho or para position.

In some embodiments, X is O or CR, wherein R is defined as above for $R_1$-$R_{13}$ and wherein the bond between X and the carbon containing $R_7$ and $R_8$ is a double bond and the bond between the carbons containing $R_5$ and $R_6$ and $R_9$ is a double bond, $R_9$ is substituted or unsubstituted aryl as described above, and $R_3$ is hydroxy.

In some embodiments, X is O or CR, wherein R is defined as above for $R_1$-$R_{13}$ and wherein the bond between X and the carbon containing $R_7$ and $R_8$ is a double bond and the bond between the carbons containing $R_5$ and $R_6$ and $R_9$ is a double bond, $R_9$ is substituted or unsubstituted aryl as described above, and $R_3$ is hydroxy.

In some embodiments, X is O or CR, wherein R is defined as above for $R_1$-$R_{13}$ and wherein the bond between X and the carbon containing $R_7$ and $R_8$ is a double bond and the bond between the carbons containing $R_5$ and $R_6$ and $R_9$ is a double bond, $R_9$ is substituted or unsubstituted aryl as described above, $R_3$ is hydroxy, and $R_2$ and/or $R_4$ are halogen, such as chloro, bromo, or iodo.

In some embodiments, X is O or CR, wherein R is defined as above for $R_1$-$R_{13}$ and wherein the bond between X and the carbon containing $R_7$ and $R_8$ is a double bond and the bond between the carbons containing $R_5$ and $R_6$ and $R_9$ is a double bond, $R_9$ is substituted or unsubstituted aryl as described above, $R_3$ is hydroxy, $R_2$ and/or $R_4$ are halogen, such as chloro, bromo, or iodo, and $R_1$ is hydrogen.

In some embodiments, X is O or CR, wherein R is defined as above for $R_1$-$R_{13}$ and wherein the bond between X and the carbon containing $R_7$ and $R_8$ is a double bond and the bond between the carbons containing $R_5$ and $R_6$ and $R_9$ is a double bond, $R_9$ is substituted or unsubstituted aryl as described above, $R_3$ is hydroxy, $R_2$ and/or $R_4$ are halogen, such as chloro, bromo, or iodo, $R_1$ is hydrogen, and $R_5$ is halogen, such as chloro, bromo, or iodo.

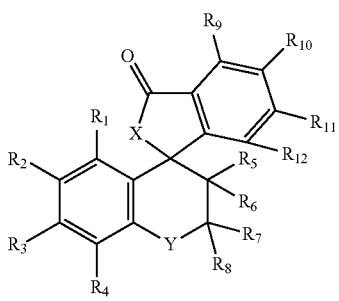

Formula V wherein

X and Y are independently O, S, $NR_{13}$, or $CR_{14}R_{15}$; and $R_1$-$R_{15}$ are independently absent or selected from hydrogen, substituted or unsubstituted, linear, branched, hetero, or cyclic alkyl, alkenyl, or alkynyl; substituted or unsubstituted aryl or heteroaryl; halogen, substituted or unsubstituted alkoxy; hydroxy, cyano, formyl, acyl, carboxylic acid (—COOH), carboxylate (—COO⁻), primary amide (e.g., —$CONH_2$), secondary amide (e.g., —$CONHR_{16}$), tertiary amide (e.g., —$CONR_{16}R_{16}$), secondary carbamate (e.g., —$OCONHR_{16}$; —$NHCOOR_{16}$), tertiary carbamate (e.g., —$OCONR_{16}R_{16}$; —$NR_{16}COOR_{16}$), urea (e.g., $NHCONHR_{16}$; —$NR_{16}CONHR_{16}$; —$NHCONR_{16}R_{16}$, —$NR_{16}CONR_{16}R_{16}$), carbinol (e.g., —$CH_2OH$; —$CHR_{16}OH$, —$CR_{16}R_{16}OH$), ester (e.g., —$COOR_{16}$), thiol (—SH), primary amine (—$NH_2$), secondary amine (e.g., —$NHR_{16}$), tertiary amine (e.g., —$NR_{16}R_{16}$), thioether (e.g., —$SR_{16}$), sulfinyl group (e.g., —$SOR_{16}$), and sulfonyl group (e.g., —$SOOR_{16}$), wherein $R_{16}$ is defined the same as $R_1$-$R_{15}$. In some embodiments, X is O.

In some embodiments, X is O and Y is O.

In some embodiments, X is O, Y is O, and $R_2$ and/or $R_4$ are halogen, such as chloro, bromo, and/or iodo.

In some embodiments, X is O, Y is O, $R_2$ and/or $R_4$ are halogen, such as chloro, bromo, and/or iodo, and $R_3$ is hydroxy.

In some embodiments, X is O, Y is O, $R_2$ and/or $R_4$ are halogen, such as chloro, bromo, and/or iodo, $R_3$ is hydroxy, and $R_9$-$R_{12}$ are hydrogen.

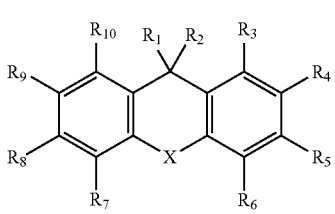

Formula VI wherein

X is O, S, SO, SO$_2$, NR$_{11}$, or CR$_{12}$R$_{13}$; and

R$_1$-R$_{13}$ are independently absent or selected from hydrogen, substituted or unsubstituted, linear, branched, hetero, or cyclic alkyl, alkenyl, or alkynyl; substituted or unsubstituted aryl or heteroaryl; halogen, substituted or unsubstituted alkoxy; hydroxy, cyano, formyl, acyl, carboxylic acid (—COOH), carboxylate (—COO$^-$), primary amide (e.g., —CONH$_2$), secondary amide (e.g., —CONHR$_{14}$), tertiary amide (e.g., —CONR$_{14}$R$_{14}$), secondary carbamate (e.g., —OCONHR$_{14}$; —NHCOOR$_{14}$), tertiary carbamate (e.g., —OCONR$_{14}$R$_{14}$;  —NR$_{14}$COOR$_{14}$), urea (e.g., NHCONHR$_{14}$; —NR$_{14}$CONHR$_{14}$; —NHCONR$_{14}$R$_{14}$, —NR$_{14}$CONR$_{14}$R$_{14}$), carbinol (e.g., —CH$_2$OH; —CHR$_{14}$OH, —CR$_{14}$R$_{14}$OH), ester (e.g., —COOR$_{14}$), thiol (—SH), primary amine (—NH$_2$), secondary amine (e.g., —NHR$_{14}$), tertiary amine (e.g., —NR$_{14}$R$_{14}$), thioether (e.g., —SR$_{14}$), sulfinyl group (e.g., —SOR$_{14}$), and sulfonyl group (e.g., —SOOR$_{14}$), wherein R$_{14}$ is defined the same as R$_1$-R$_{13}$.

In some embodiments, X is O.

In some embodiments, X is O and R$_1$ is lower alkyl, such as methyl, ethyl, n-propyl, or isopropyl.

In some embodiments, X is O, R$_1$ is lower alkyl, such as methyl, ethyl, n-propyl, or isopropyl, and one or more of R$_4$, R$_6$, R$_7$, and R$_{11}$ are halogen, such as chloro, bromo, iodo, or combinations thereof.

In some embodiments, X is O, R$_1$ is lower alkyl, such as methyl, ethyl, n-propyl, or isopropyl, one or more of R$_4$, R$_6$, R$_7$, and R$_{11}$ are halogen, such as chloro, bromo, iodo, or combinations thereof, and one or more of R$_5$ and R$_8$ are hydroxy.

In some embodiments, X is O, R$_1$ is substituted or unsubstituted aryl, such as phenyl, R$_2$, R$_5$, and R$_8$ are hydroxy and R$_3$-R$_{10}$ are hydrogen or as defined in the various embodiments above.

In some embodiments, R$_1$ is substituted or unsubstituted cycloalkyl, such as cyclopentyl or cyclohexyl, R$_5$ and R$_8$ are hydroxy or lower alkoxy, such methoxy or ethoxy, and one or more of R$_2$-R$_4$, R$_6$, R$_7$, and R$_8$-R$_{10}$ are hydrogen, halogen (chloro, bromo, iodo), hydroxy, or combinations thereof.

In some embodiments, R$_1$ is substituted or unsubstituted cycloalkyl, such as cyclopentyl or cyclohexyl or alkyl, such as methyl, ethyl, n-propyl, isopropyl, butyl (n-, sec-, iso-, t-), pentyl, hexyl, or heptyl, R$_5$ and R$_8$ are hydroxy, lower alkoxy, such methoxy or ethoxy, or primary, secondary, or tertiary amino, one or more of R$_4$, R$_6$, R$_7$, and R$_9$ are halogen, such as chloro, bromo, iodo, or combinations thereof, and one or more of R$_2$, R$_3$, R$_4$, R$_6$, R$_7$, R$_9$, and R$_{10}$ are hydrogen. In some embodiments, R$_1$ is cyclopentyl substituted with a carboxylic acid group at the 2 position.

In some embodiments, R$_1$ and R$_2$ together are =O or =CR$_{12}$R$_{13}$, X is O, and R$_3$-R$_{10}$ are defined in the various embodiments above. In some embodiments, R$_1$ is a substituted or unsubstituted cycloalkyl, such as cyclopentyl or cyclohexyl, and R$_2$ and the valence on C1 of the cycloalkyl ring is a double bond, X is O, and R$_3$-R$_{10}$ are as defined in the various embodiments above.

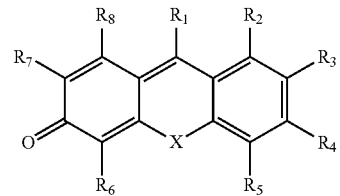

Formula VII wherein X is O, S, SO, SO$_2$, NR$_9$, CR$_{10}$R$_{11}$; and

R$_1$-R$_{11}$ are independently absent or selected from hydrogen, substituted or unsubstituted, linear, branched, hetero, or cyclic alkyl, alkenyl, or alkynyl; substituted or unsubstituted aryl or heteroaryl; halogen, substituted or unsubstituted alkoxy; hydroxy, cyano, formyl, acyl, carboxylic acid (—COOH), carboxylate (—COO$^-$), primary amide (e.g., —CONH$_2$), secondary amide (e.g., —CONHR$_{12}$), tertiary amide (e.g., —CONR$_{12}$R$_{12}$), secondary carbamate (e.g., —OCONHR$_{12}$; —NHCOOR$_{12}$), tertiary carbamate (e.g., —OCONR$_{12}$R$_{12}$; —NR$_{14}$COOR$_{12}$), urea (e.g., NHCONHR$_{12}$; —NR$_{12}$CONHR$_{12}$; —NHCONR$_{12}$R$_{12}$, —NR$_{14}$CONR$_{12}$R$_{12}$), carbinol (e.g., —CH$_2$OH; —CHR$_{12}$OH, —CR$_{12}$R$_{12}$OH), ester (e.g., —COOR$_{12}$), thiol (—SH), primary amine (—NH$_2$), secondary amine (e.g., —NHR$_{12}$), tertiary amine (e.g., —NR$_{12}$R$_{12}$), thioether (e.g., —SR$_{12}$), sulfinyl group (e.g., —SOR$_{12}$), and sulfonyl group (e.g., —SOOR$_{12}$), wherein R$_{12}$ is defined the same as R$_1$-R$_{11}$;

wherein the compound of formula VII is not Rose Bengal.

In some embodiments, X=O, R$_1$ is substituted or unsubstituted cycloalkyl, such as cyclopentyl or cyclohexyl, and one or more of R$_2$-R$_7$ are hydrogen, hydroxy, halogen (chloro, bromo, iodo), or combinations thereof.

In some embodiments, R$_1$ is substituted or unsubstituted aryl, such as phenyl. In some embodiments R, is 2,3,4,5-tetrachloro-2-benzoic acid.

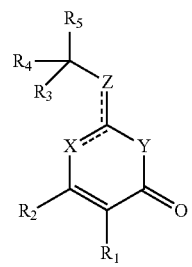

Formula VIII wherein Z is O, S, SO, SO$_2$, NR$_6$, or CR$_7$R$_8$;

X and Y are independently N, NR$_9$, or CR$_{10}$R$_{11}$;

R$_1$-R$_{11}$ are independently absent or selected from hydrogen, substituted or unsubstituted, linear, branched, hetero, or cyclic alkyl, alkenyl, or alkynyl; substituted or unsubstituted aryl or heteroaryl; halogen, substituted or unsubstituted alkoxy; hydroxy, cyano, formyl, acyl, carboxylic acid (—COOH), carboxylate (—COO$^-$), primary amide (e.g., —CONH$_2$), secondary amide (e.g., —CONHR$_{12}$), tertiary amide (e.g., —CONR$_{12}$R$_{12}$), secondary carbamate (e.g., —OCONHR$_{12}$; —NHCOOR$_{12}$), tertiary carbamate (e.g., —OCONR$_{12}$R$_{12}$; —NR$_{14}$COOR$_{12}$), urea (e.g., NHCONHR$_{12}$; —NR$_{12}$CONHR$_{12}$; —NHCONR$_{12}$R$_{12}$, —NR$_{14}$CONR$_{12}$R$_{12}$), carbinol (e.g., —CH$_2$OH; —CHR$_{12}$OH, —CR$_{12}$R$_{12}$OH), ester (e.g., —COOR$_{12}$), thiol (—SH), primary amine (—NH$_2$), secondary amine (e.g., —NHR$_{12}$), tertiary amine (e.g., —NR$_{12}$R$_{12}$), thioether (e.g., —SR$_{12}$), sulfinyl group (e.g., —SOR$_{12}$), and sulfonyl group (e.g., —SOOR$_{12}$), wherein R$_{12}$ is defined the same as R$_1$-R$_{11}$; and the dotted lines represent optional double bonds.

In some embodiments, Z is S.

In some embodiments, Z is S, X is N, and Y is NR, where R is hydrogen or lower alkyl, such as methyl, ethyl, or propyl.

In some embodiments, Z is S, X is N, Y is NR, where R is hydrogen or lower alkyl, such as methyl, ethyl, or propyl, and R$_1$ is C≡N.

In some embodiments, Z is S, X is N, Y is NR, where R is hydrogen or lower alkyl, such as methyl, ethyl, or propyl, R$_1$ is C≡N, and R$_2$ and R$_5$ are aryl, such as phenyl.

In some embodiments, Z is S, X is N, Y is NR, where R is hydrogen or lower alkyl, such as methyl, ethyl, or propyl, R$_1$ is C≡N, R$_2$ and R$_5$ are aryl, such as phenyl, wherein R$_2$ is phenyl substituted with a phenyl ring at the 3 or 4 position and the phenyl ring at the 3 or 4 position is optionally substituted with OH at any position or —NH—COOalkyl, such as methyl, ethyl, propyl, butyl (e.g., t-butyl) at any position.

In some embodiments, Z is S, X is N, Y is NR, where R is hydrogen or lower alkyl, such as methyl, ethyl, or propyl, R$_1$ is C≡N, R$_2$ and R$_5$ are aryl, such as phenyl, wherein R$_2$ is phenyl substituted with a phenyl ring at the 3 or 4 position and the phenyl ring at the 3 or 4 position and R$_5$ is phenyl substituted with —COOH or B(OH)$_2$. In other embodiments, R$_5$ is pyridinyl.

In some embodiments, Z is S, X is N, Y is NR, where R is hydrogen or lower alkyl, such as methyl, ethyl, or propyl, R$_1$ is C≡N, R$_2$ and R$_5$ are aryl, such as phenyl, wherein R$_2$ is phenyl substituted with a phenyl ring at the 4 position, and R$_5$ is phenyl substituted at the 4 position with

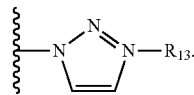

In some embodiments, Z is S, X is N, Y is NR, where R is hydrogen or lower alkyl, such as methyl, ethyl, or propyl, R$_1$ is C≡N, R$_2$ and R$_5$ are aryl, such as phenyl, wherein R$_2$ is phenyl substituted with a phenyl ring at the 4 position, and R$_5$ is phenyl substituted at the 4 position with

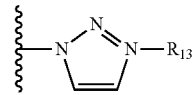

wherein R$_{13}$ is —(CH$_2$)$_n$—OCOalkyl, where alkyl is a lower alkyl, —(CH$_2$)$_n$—COOH, —(CH$_2$)$_n$—OH, wherein n is at least 1, such as 1, 2, 3, 4, 5, or 6.

In still other embodiments, In some embodiments, Z is S, X is N, Y is NR, where R is hydrogen or lower alkyl, such as methyl, ethyl, or propyl, R$_1$ is C≡N, R$_2$ is aryl, such as phenyl, wherein R$_2$ is phenyl substituted with a phenyl ring at the 3 or 4 position, and R$_5$ is —(CH$_2$)$_n$—OCOalkyl, where alkyl is a lower alkyl, —(CH$_2$)$_n$—COOH, —(CH$_2$)$_n$—OH, wherein n is at least 1, such as 1, 2, 3, 4, 5, or 6.

In still other embodiments, In some embodiments, Z is S, X is N, Y is NR, where R is hydrogen or lower alkyl, such as methyl, ethyl, or propyl, R$_1$ is C≡N, R$_2$ is aryl, such as phenyl, substituted with trifluoromethyl at the 4 position or wherein R$_2$ is phenyl substituted with a phenyl ring at the 3 or 4 position which is optionally subsitituted with trifluoromethyl, and R$_5$ is —(CH$_2$)$_n$—COOalkyl, where alkyl is a lower alkyl, —(CH$_2$)$_n$—COOH, —(CH$_2$)$_n$—OH, wherein n is at least 1, such as 1, 2, 3, 4, 5, or 6.

In some embodiments, Z is S, X is N, Y is NR, where R is hydrogen or lower alkyl, such as methyl, ethyl, or propyl, R$_1$ is C≡N, R$_2$ and R$_5$ are aryl, such as phenyl, wherein R$_2$ is phenyl substituted with a phenyl ring at the 3 or 4 position and R$_5$ is phenyl substituted with —COOalkyl, where alkyl is lower alkyl, at the 4 position.

In still other embodiments, Z is S, R$_3$-R$_5$ are hydrogen, and the remaining variables are defined as in the embodiments above.

In still other embodiments, Z is S, the bond between the ring and Z is a double bond, the bond between N and the carbon bound to Z is a single bond, and the remaining variables are defined as in the embodiments above.

In still other embodiments, Z is O, and the remaining variables are defined as in the embodiments above.

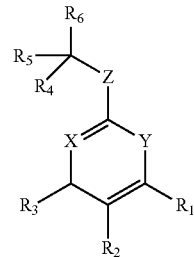

Formula IX wherein Z is O, S, SO, SO$_2$, NR$_7$, or CR$_8$R$_9$;

X and Y are independently N, NR$_{10}$, or CR$_{11}$R$_{12}$;

R$_1$-R$_{12}$ are independently absent or selected from hydrogen, substituted or unsubstituted, linear, branched, hetero, or cyclic alkyl, alkenyl, or alkynyl; substituted or unsubstituted aryl or heteroaryl; halogen, substituted or unsubstituted alkoxy; hydroxy, cyano, formyl, acyl, carboxylic acid (—COOH), carboxylate (—COO$^-$), primary amide (e.g., —CONH$_2$), secondary amide (e.g., —CONHR$_{13}$), tertiary amide (e.g., —CONR$_{13}$R$_{13}$), secondary carbamate (e.g., —OCONHR$_{13}$; —NHCOOR$_{13}$), tertiary carbamate (e.g., —OCONR$_{13}$R$_{13}$; —NR$_{13}$COOR$_{13}$), urea (e.g., NHCONHR$_{13}$; —NR$_{13}$CONHR$_{13}$; —NHCONR$_{13}$R$_{13}$, —NR$_{13}$CONR$_{13}$R$_{13}$), carbinol (e.g., —CH$_2$OH; —CHR$_{13}$OH, —CR$_{13}$R$_{13}$OH), ester (e.g., —COOR$_{13}$), thiol (—SH), primary amine (—NH$_2$), secondary amine (e.g., —NHR$_{13}$), tertiary amine (e.g., —NR$_{13}$R$_{13}$), thioether (e.g., —SR$_{13}$), sulfinyl group (e.g., —SOR$_{13}$), and sulfonyl group (e.g., —SOOR$_{13}$), wherein R$_{13}$ is defined the same as R$_1$-R$_{12}$.

In some embodiments, Z is O or S, X is N, Y is NH, R$_2$ is CN or COOalkyl, R$_1$ is —NH—OH, NH(CH$_2$)—OH, where n is 1, 2, 3, 4, 5, or 6, halogen (Cl, Br, or I), alkoxy (e.g., methoxy), —NHR, where R is alkyl, or oligo- or polyethylglycol, or —NH—NH$_2$, and the remaining variables are defined as in the embodiments above.

In still other embodiments, the compound has the formula

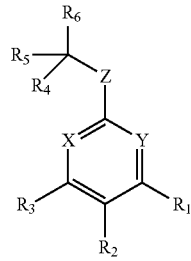

wherein the variable positions are as defined above for Formula IX.

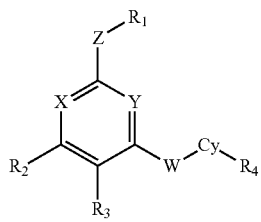

Formula X wherein

Z and W are O, S, SO, SO$_2$, NR$_5$, or CR$_6$R$_7$;

X and Y are independently N, NR$_B$, or CR$_9$R$_{10}$;

Cy is substituted or unsubstituted aryl, heteroaryl, cycloalkyl, or heterocycloalkyl group; and R$_1$-R$_{10}$ are independently absent or selected from hydrogen, substituted or unsubstituted, linear, branched, hetero, or cyclic alkyl, alkenyl, or alkynyl; substituted or unsubstituted aryl or heteroaryl; halogen, substituted or unsubstituted alkoxy; hydroxy, cyano, formyl, acyl, carboxylic acid (—COOH), carboxylate (—COO$^-$), primary amide (e.g., —CONH$_2$), secondary amide (e.g., —CONHR$_{11}$), tertiary amide (e.g., —CONR$_{11}$R$_{11}$), secondary carbamate (e.g., —OCONHR$_{11}$; —NHCOOR$_{11}$), tertiary carbamate (e.g., —OCONR$_{11}$R$_{11}$; —NR$_{14}$COOR$_{11}$), urea (e.g., NHCONHR$_{11}$; —NR$_{11}$CONHR$_{11}$; —NHCONR$_{11}$R$_{11}$; —NR$_{14}$CONR$_{11}$R$_{11}$), carbinol (e.g., —CH$_2$OH; —CHR$_{11}$OH, —CR$_{11}$R$_{11}$OH), ester (e.g., —COOR$_{11}$), thiol (—SH), primary amine (—NH$_2$), secondary amine (e.g., —NHR$_{11}$), tertiary amine (e.g., —NR$_{11}$R$_{11}$), thioether (e.g., —SR$_{11}$), sulfinyl group (e.g., —SOR$_{11}$), and sulfonyl group (e.g., —SOOR$_{11}$), wherein R$_{11}$ is defined the same as R$_1$-R$_{10}$.

In some embodiments, Z and W are O or S, X and Y are N, Cy is a triazole ring, substituted at the two position with a substituted or unsubstituted aryl, such as phenyl (e.g., 3,5-dimethylphenyl, 3,5-di(trifluoromethyl)), and R$_2$ is halogen.

In some embodiments, Z and W are O or S, X and Y are N, Cy is a triazole or oxadiazole ring, substituted at the two position with a substituted or unsubstituted aryl, such as phenyl (e.g., 3,5-dimethylphenyl, 3,5-di(trifluoromethyl)), R$_2$ is halogen, and R$_1$ is aryl, such as phenyl.

In some embodiments, Z and R$_1$ and/or W are absent and the remaining variables are as defined above.

In some embodiments, the compound has the formula below, wherein the variables are as defined above for Formula X.

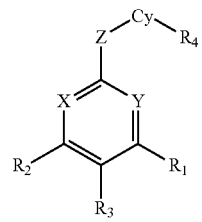

In another embodiment, the compounds of formula I, or a pharmaceutically acceptable salt or a prodrug thereof, is a compound selected from the group consisting of:

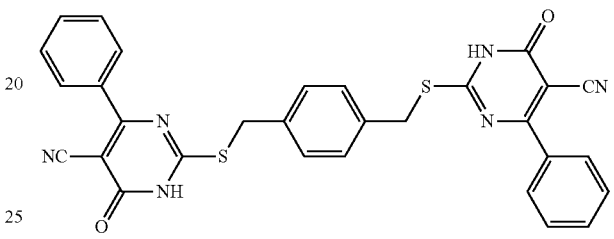

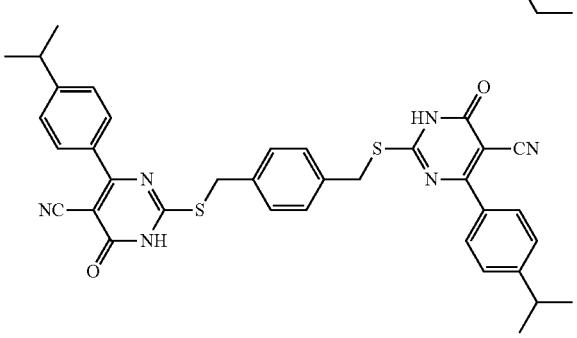

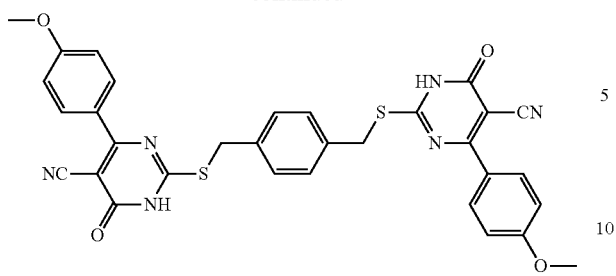
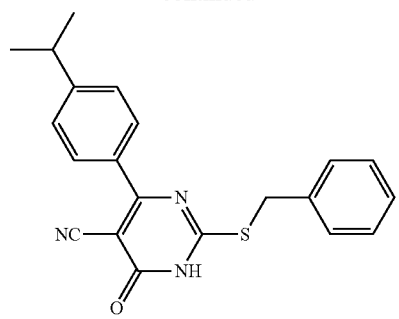
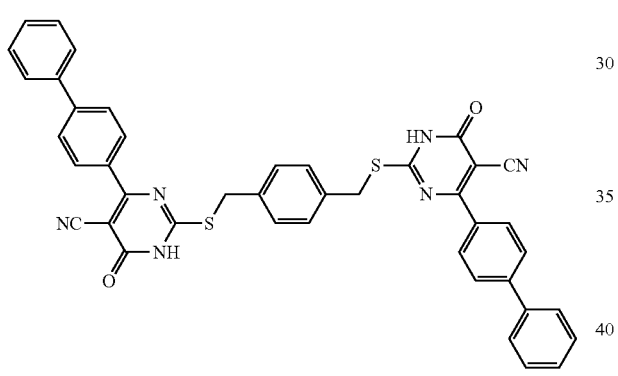
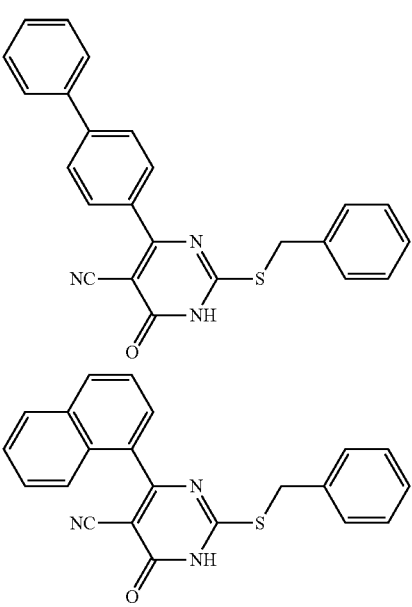
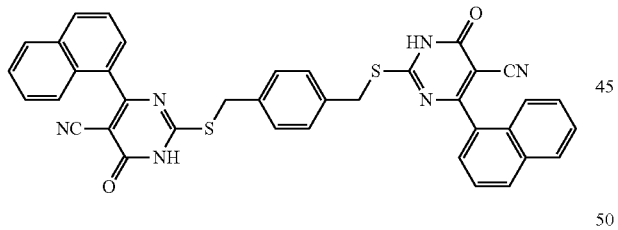
In another embodiment, the compounds of formula II, or a pharmaceutically acceptable salt or a prodrug thereof, is a compound selected from the group consisting of:
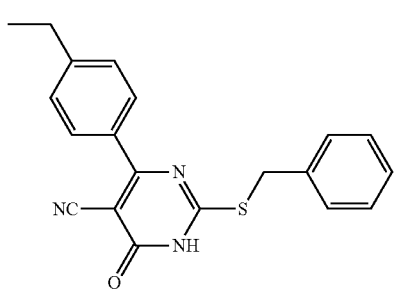
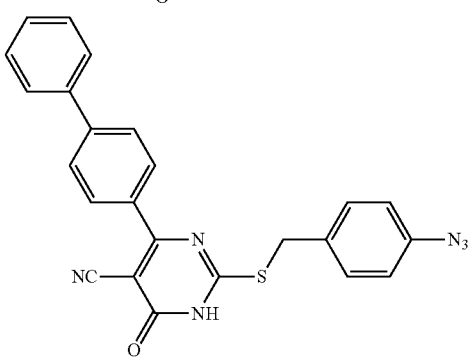

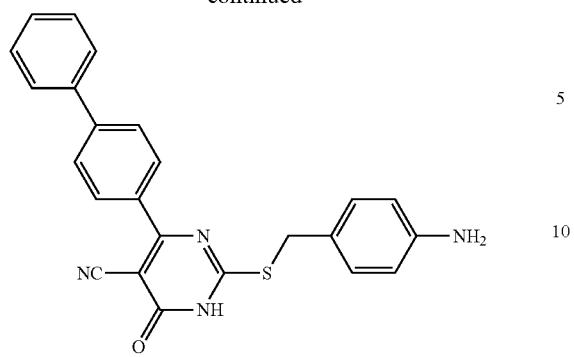
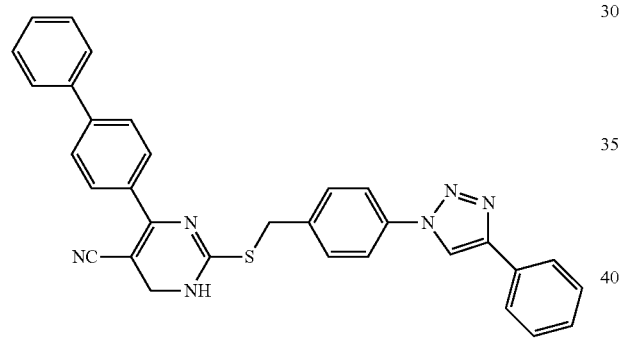
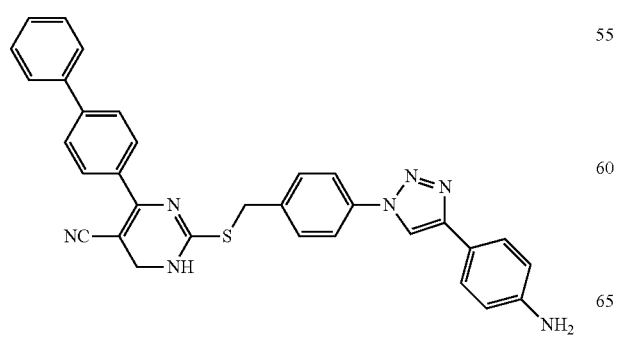
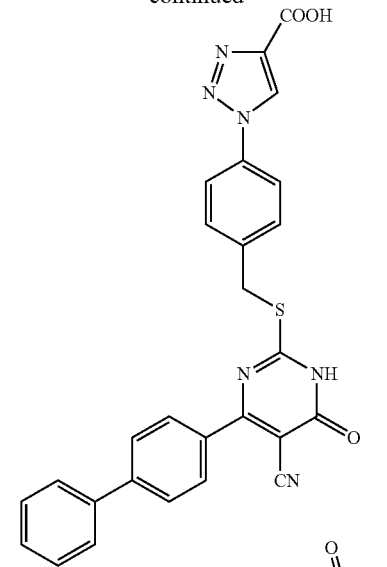
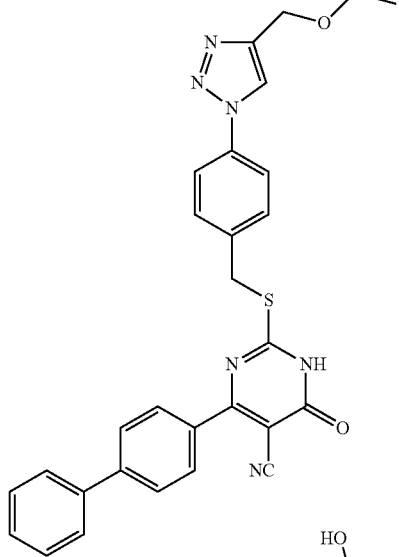
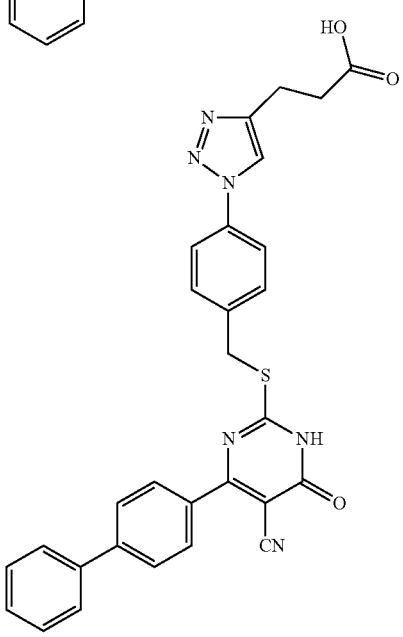

31
-continued
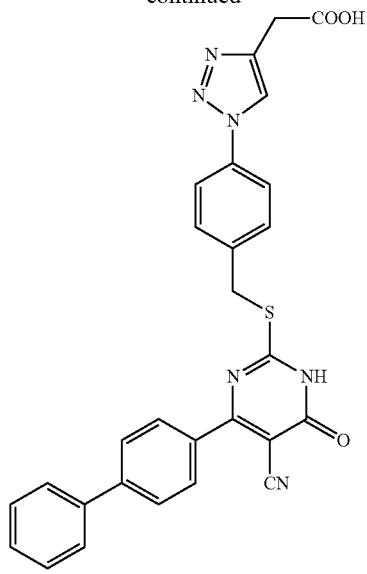
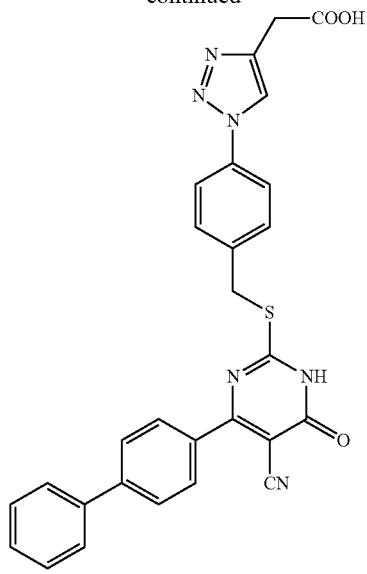
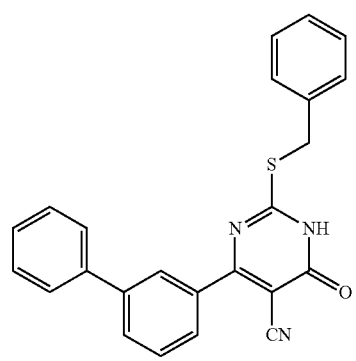
32
-continued
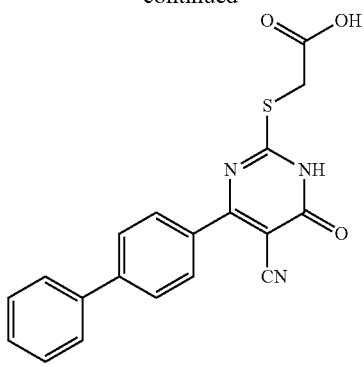
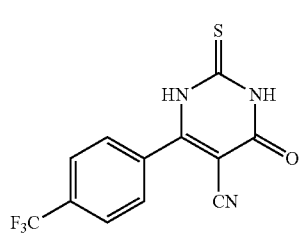
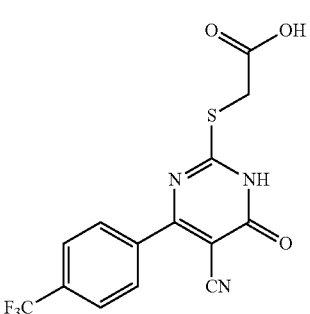
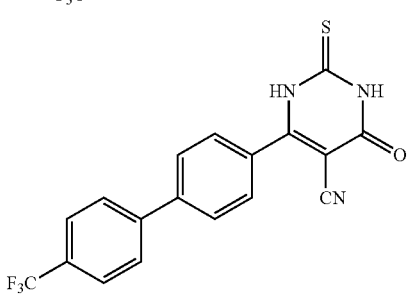
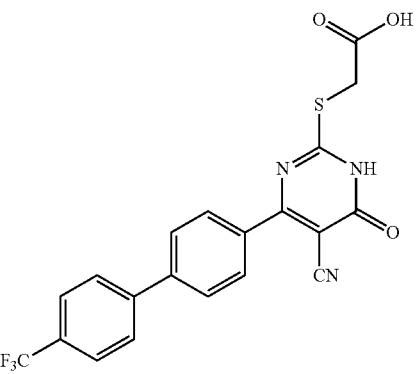

33
-continued

34
-continued

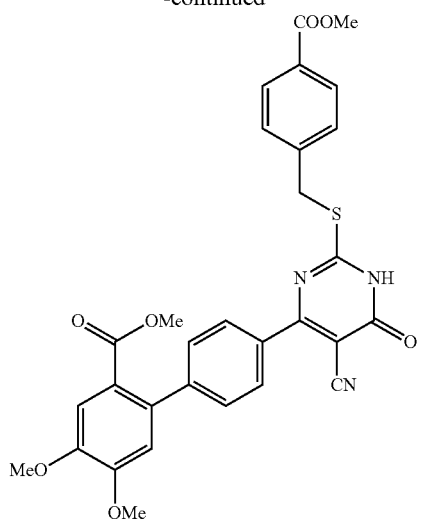
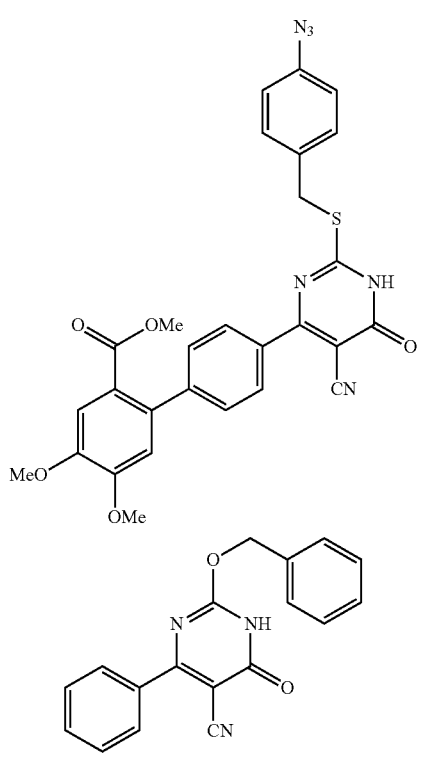
In another embodiment, the compounds of formula III, or a pharmaceutically acceptable salt or a prodrug thereof, is a compound selected from the group consisting of:
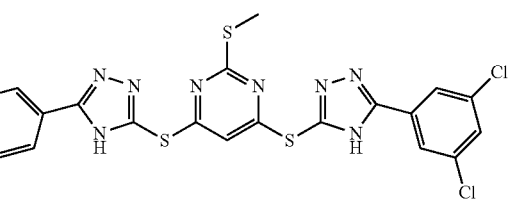
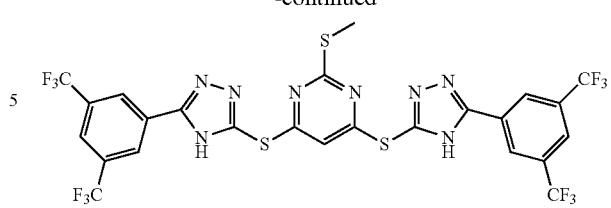
In another embodiment, the compounds of formula IV, or a pharmaceutically acceptable salt or a prodrug thereof, is a compound selected from the group consisting of:
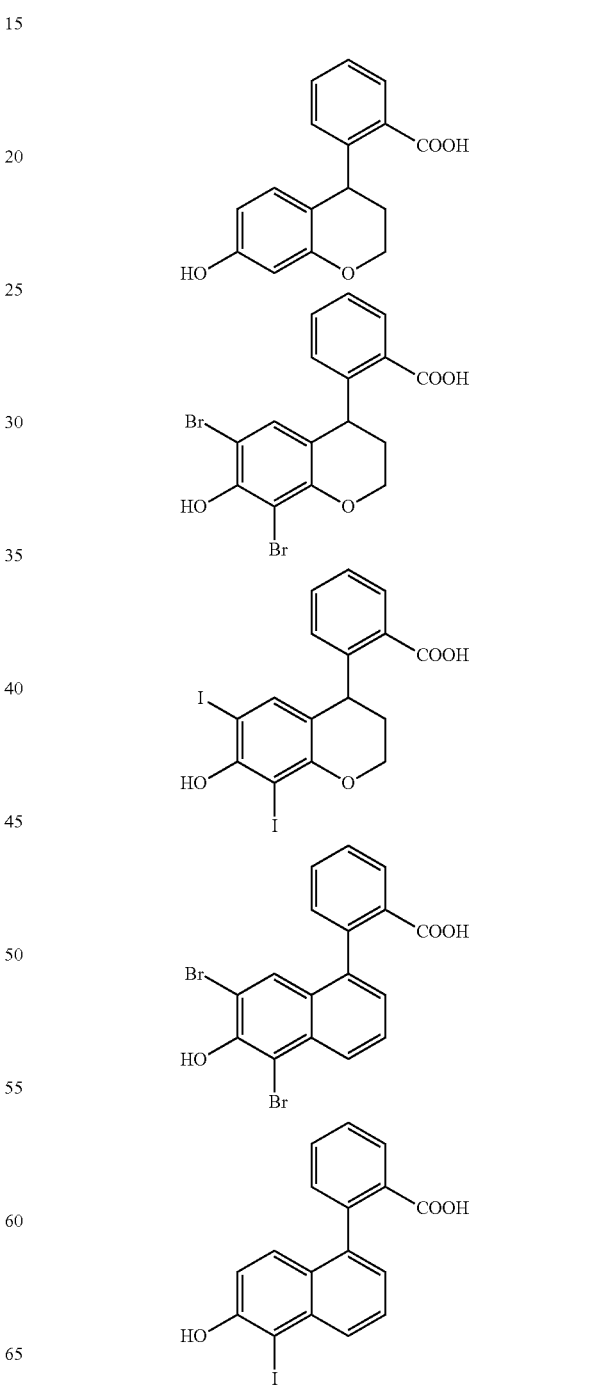

-continued
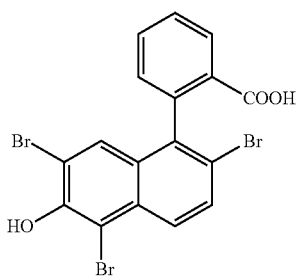
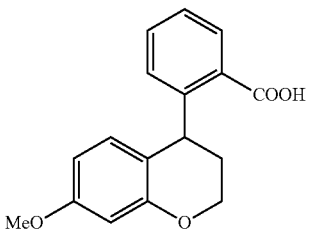
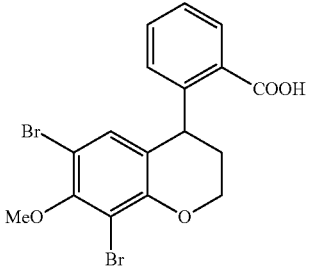
In another embodiment, the compounds of formula V, or a pharmaceutically acceptable salt or a prodrug thereof, is a compound selected from the group consisting of:
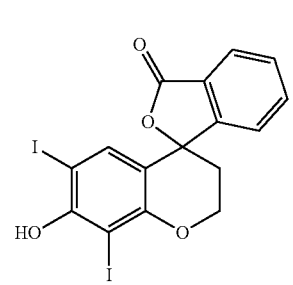
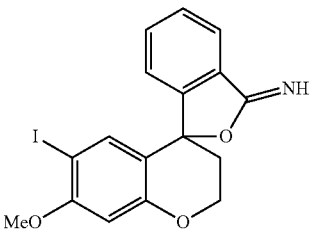
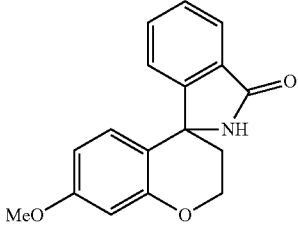
-continued
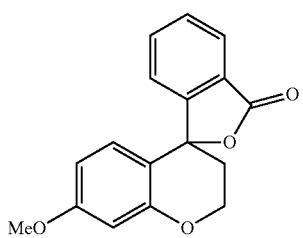
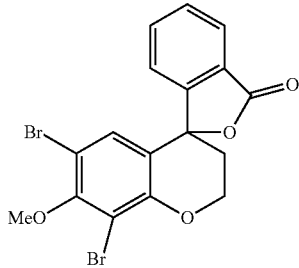
In another embodiment, the compounds of formula VI, or a pharmaceutically acceptable salt or a prodrug thereof, is a compound selected from the group consisting of:
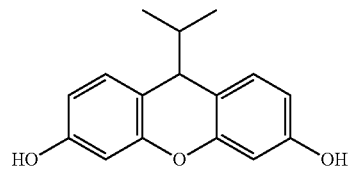
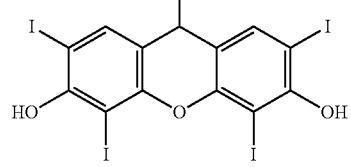
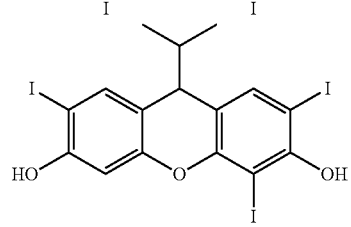
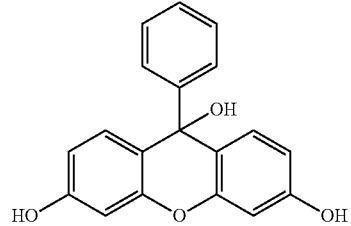
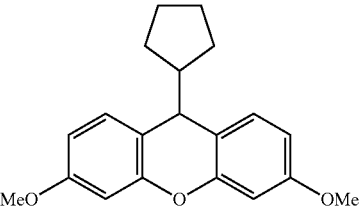

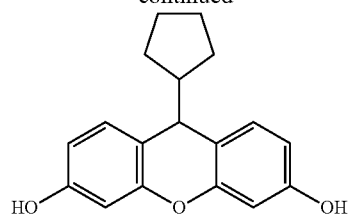
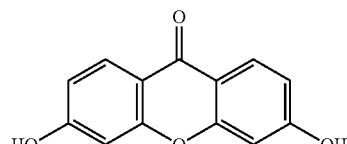
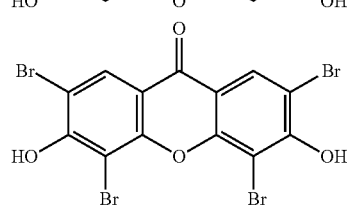
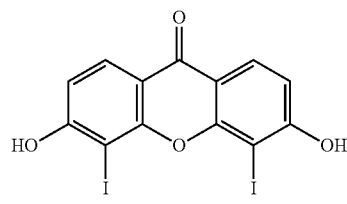
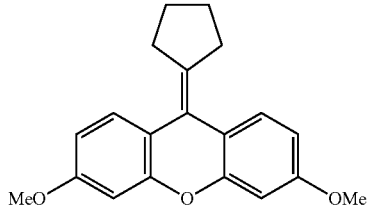
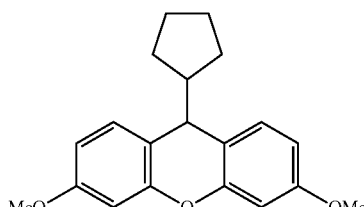
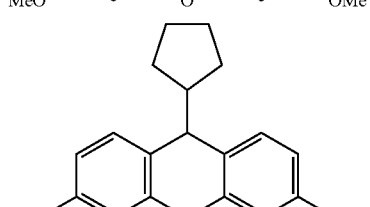
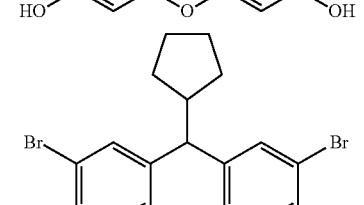
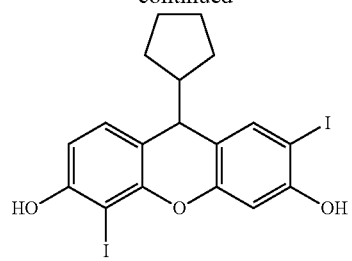
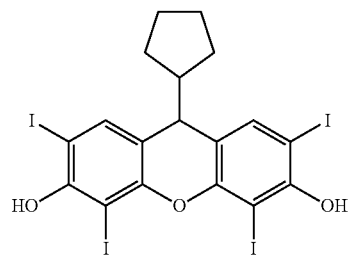
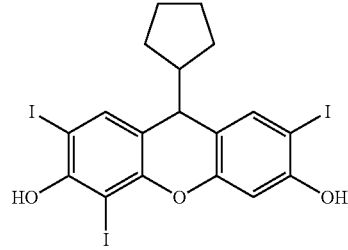
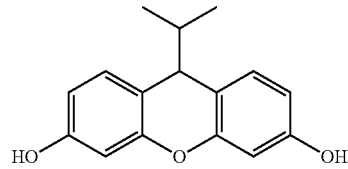
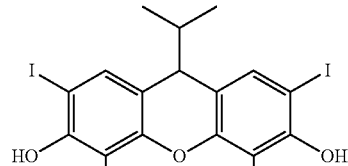
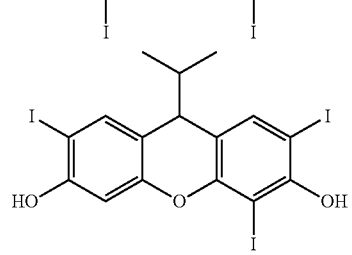
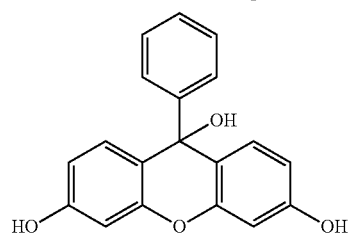

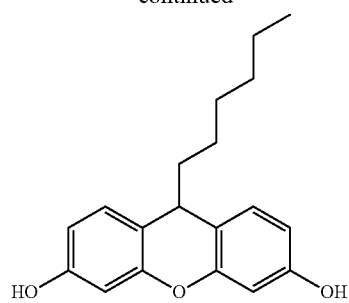
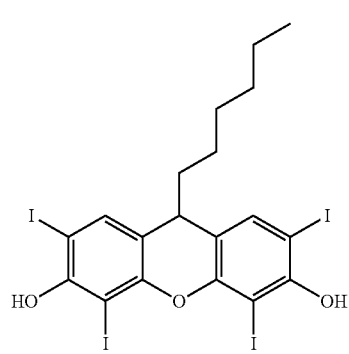
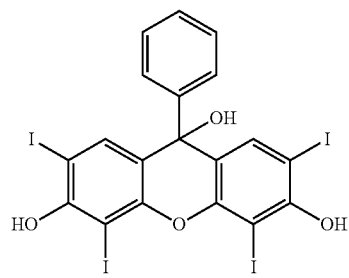
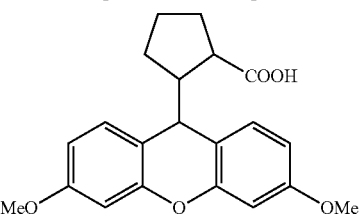
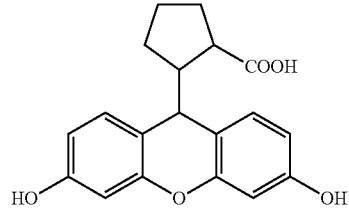
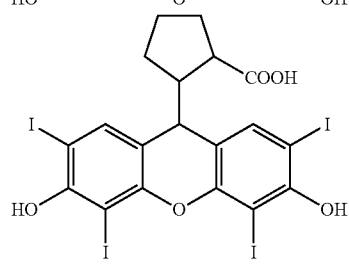
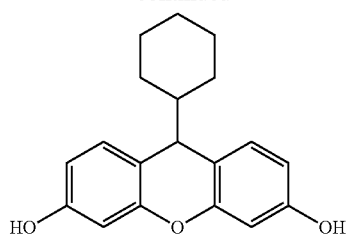
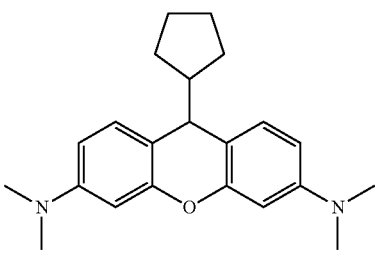
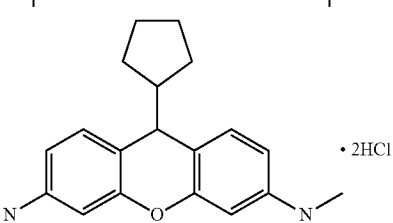
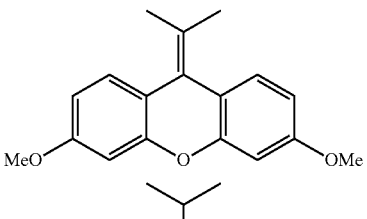
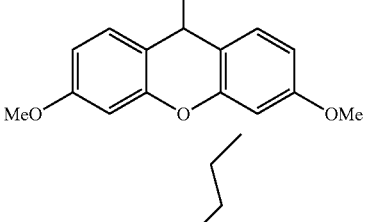
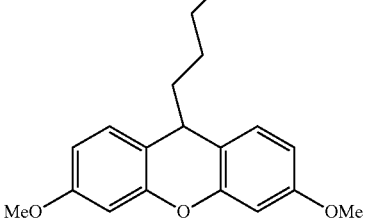
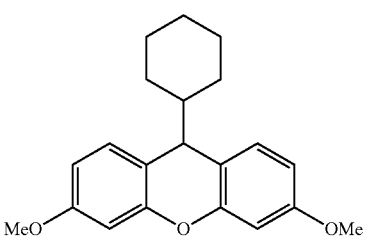

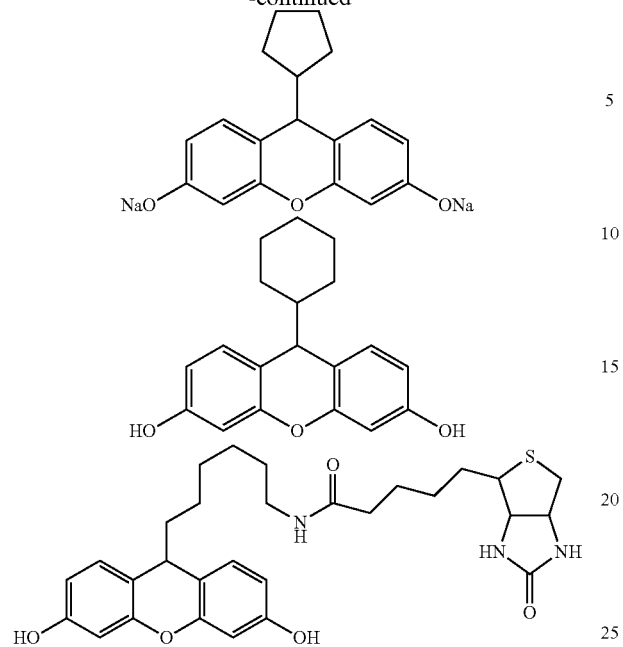
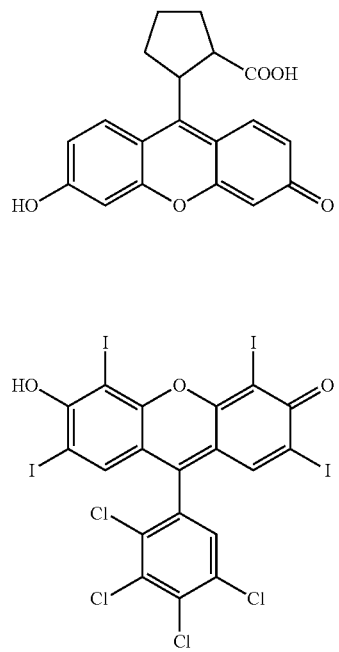
In another embodiment, the compounds of formula VII, or a pharmaceutically acceptable salt or a prodrug thereof, is a compound selected from the group consisting of:
In another embodiment, the compounds of formula VIII, or a pharmaceutically acceptable salt or a prodrug thereof, is a compound selected from the group consisting of:
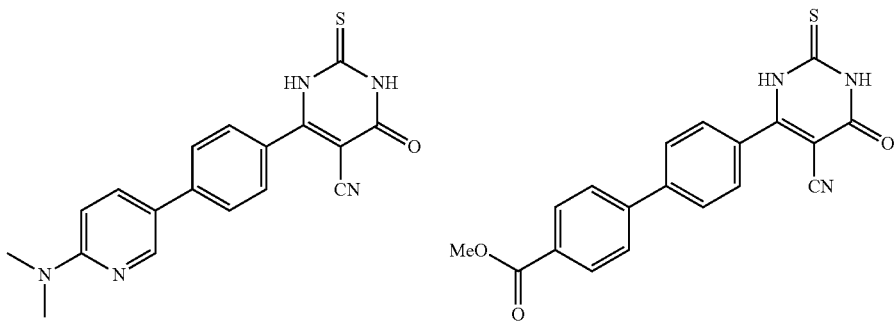
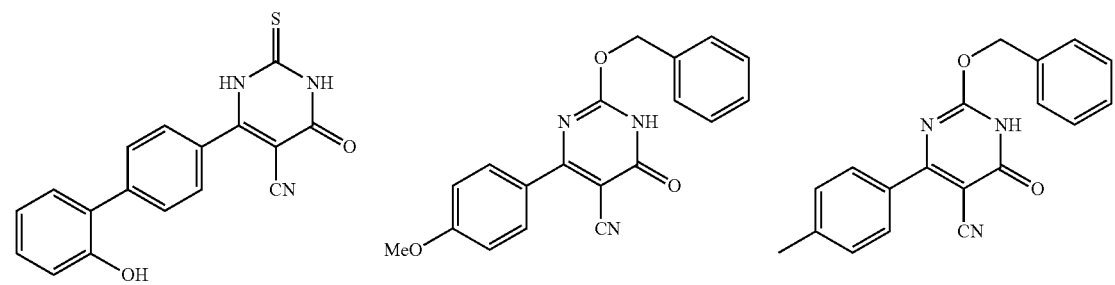

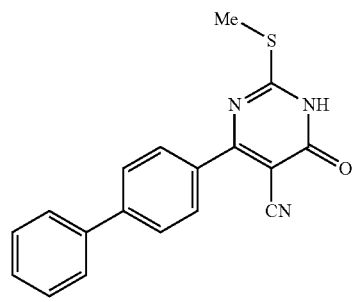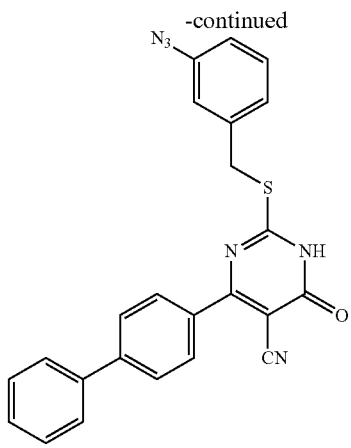
-continued
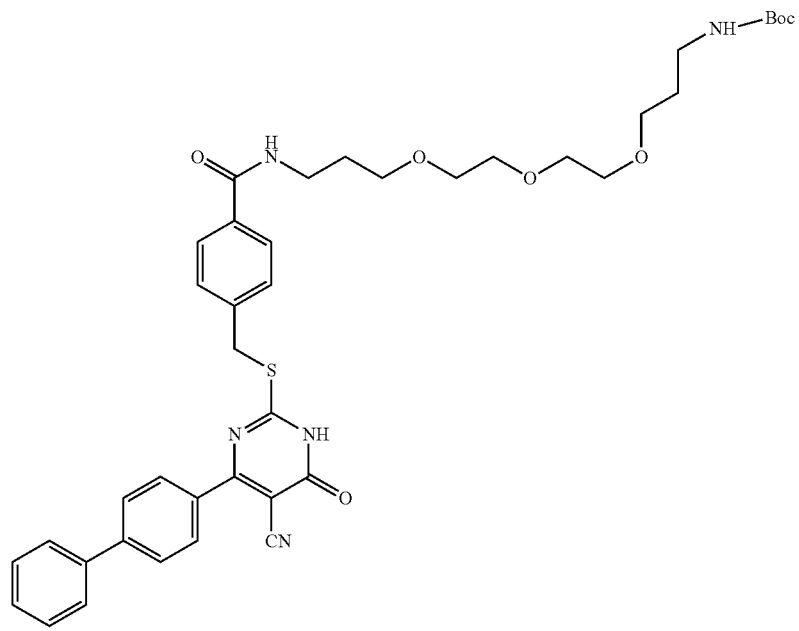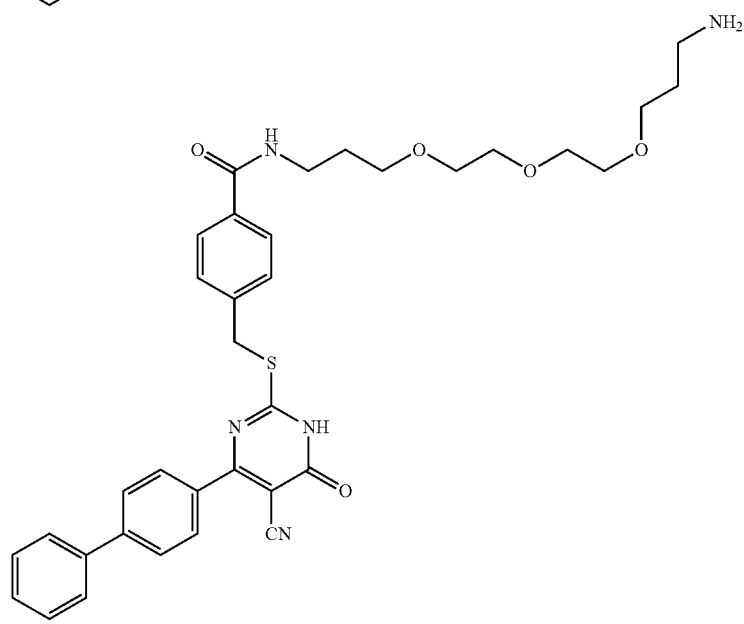

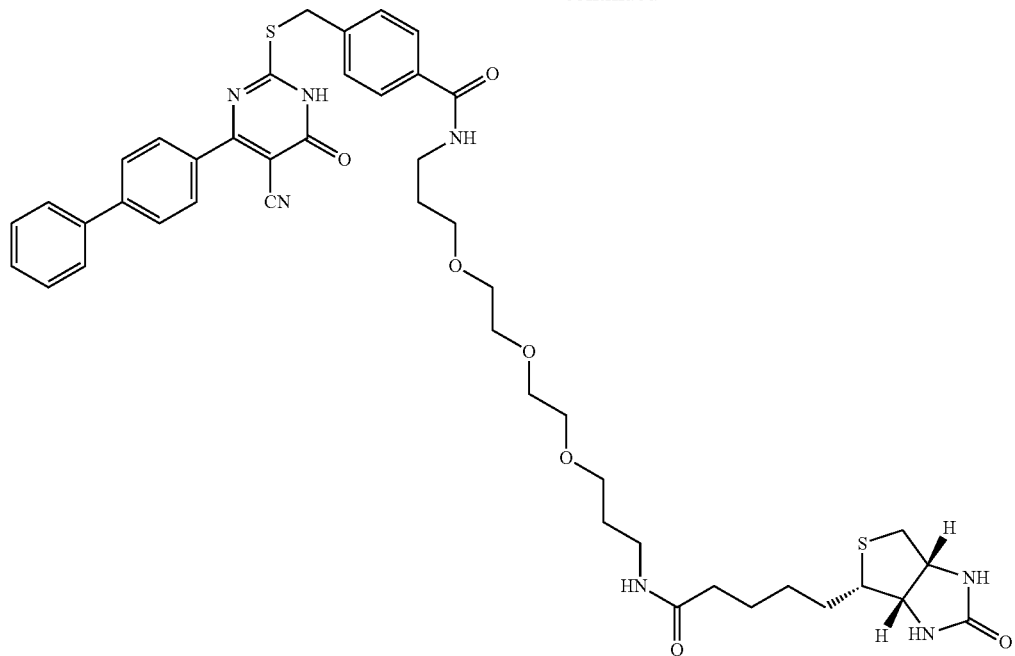
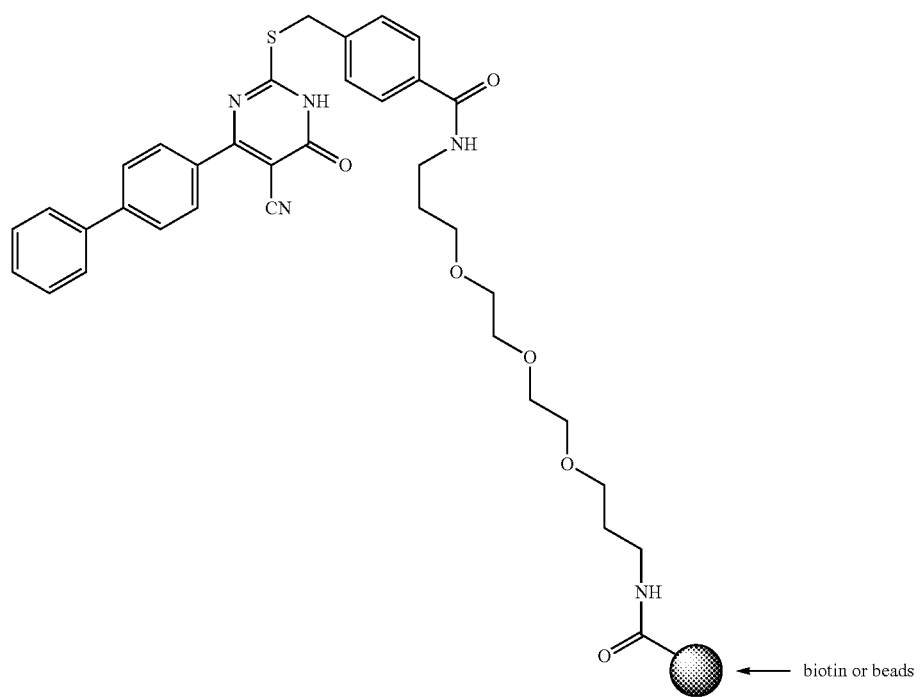

-continued
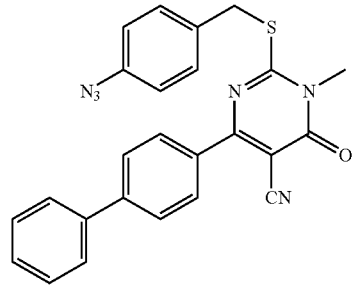
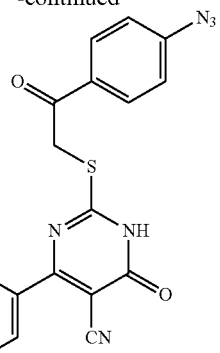
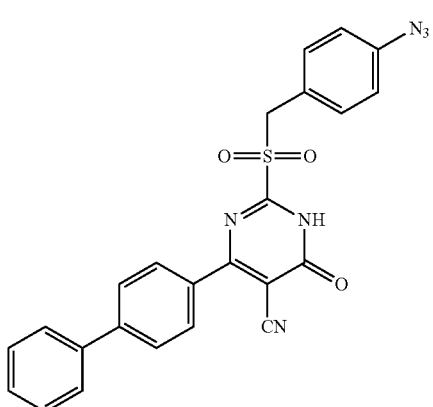
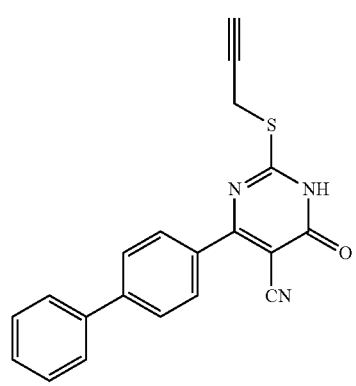
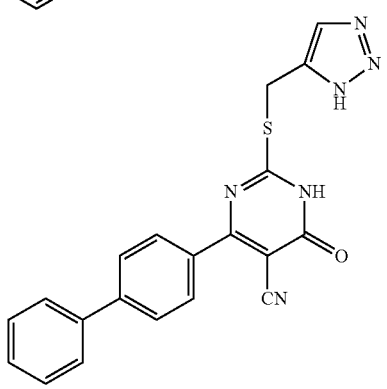
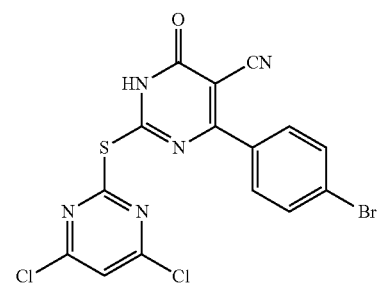
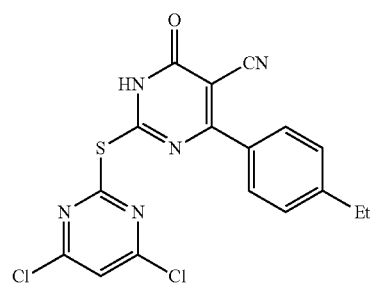
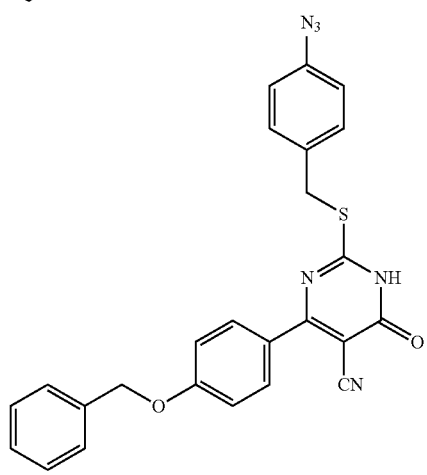
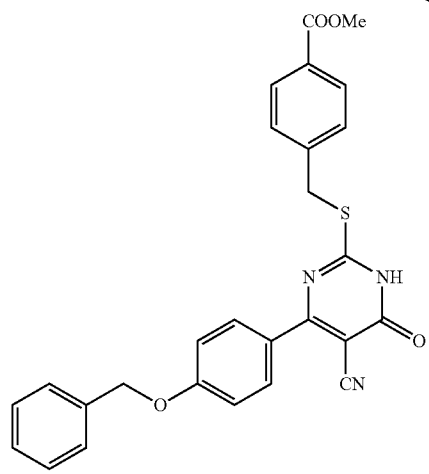
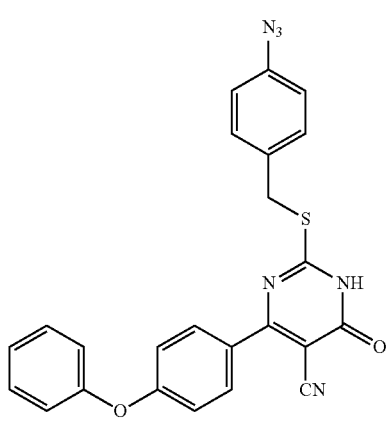

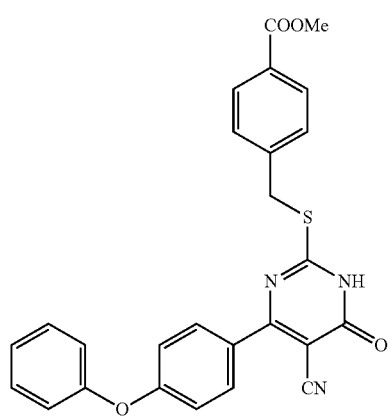
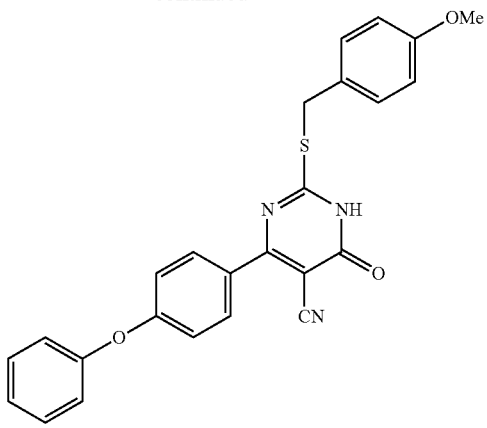
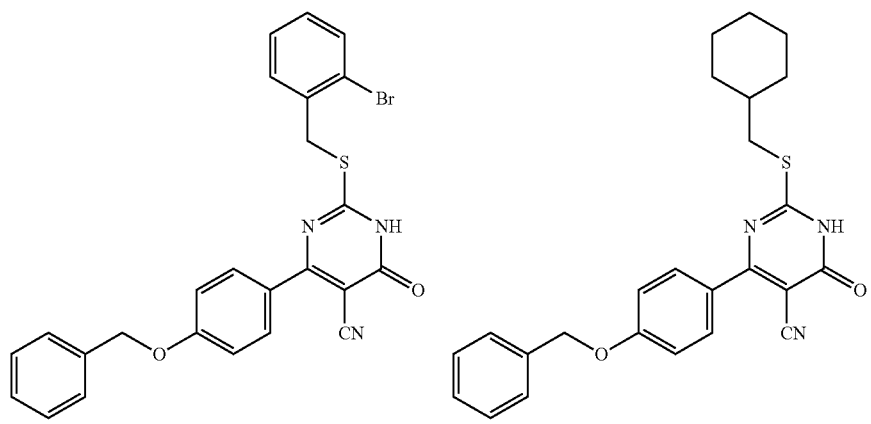
Molecular Weight: 431.5499
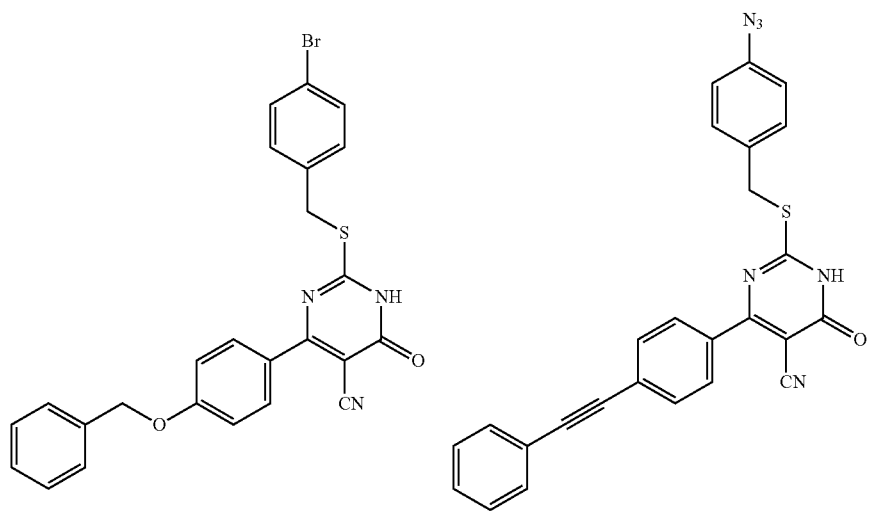

-continued
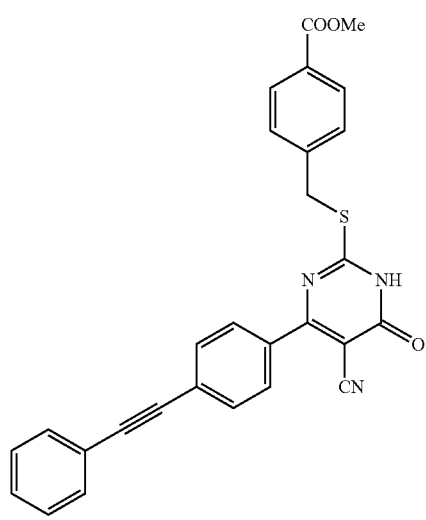
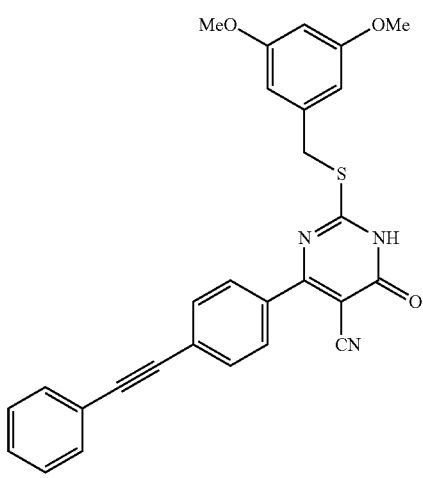
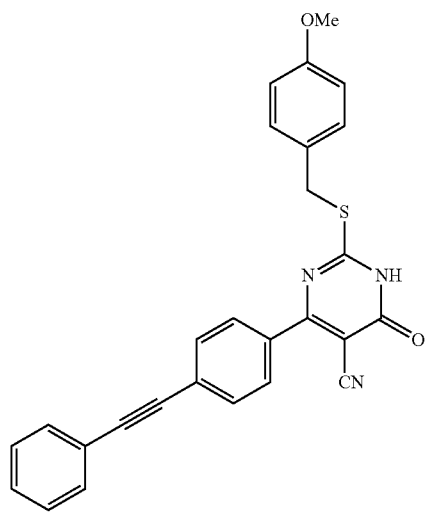
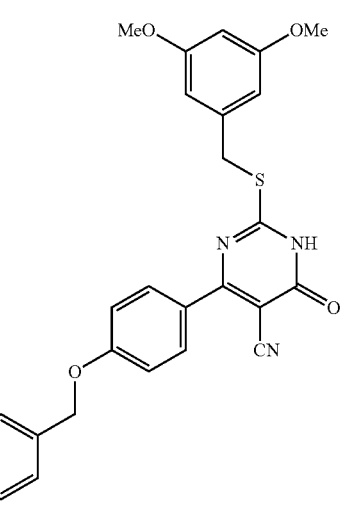
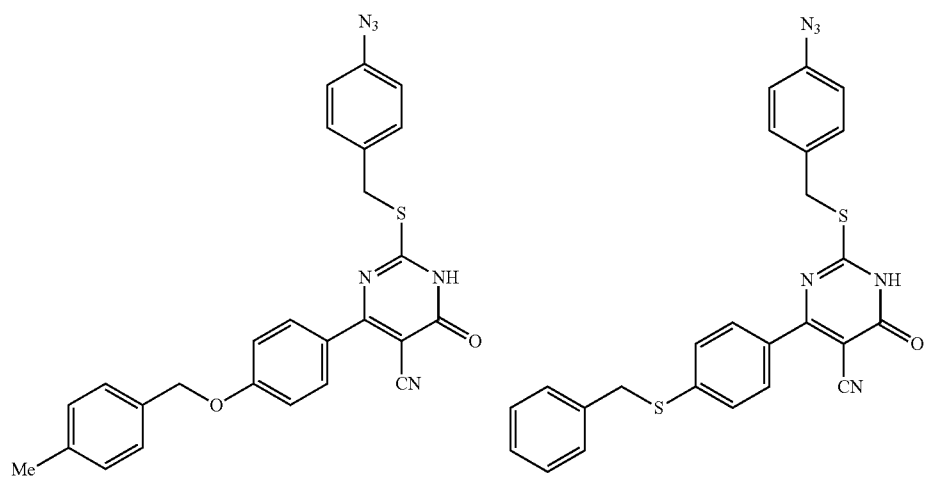

-continued
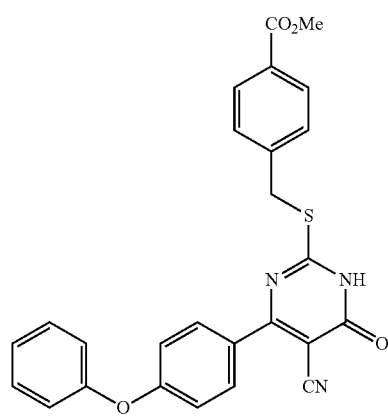
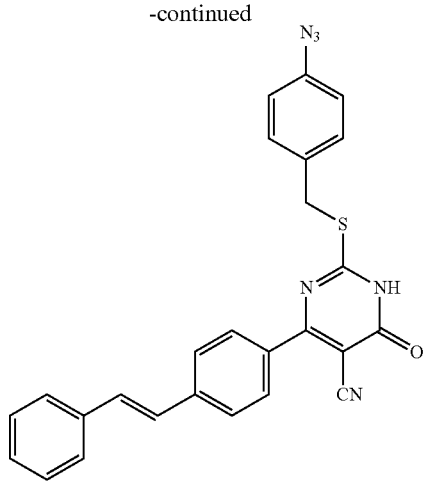
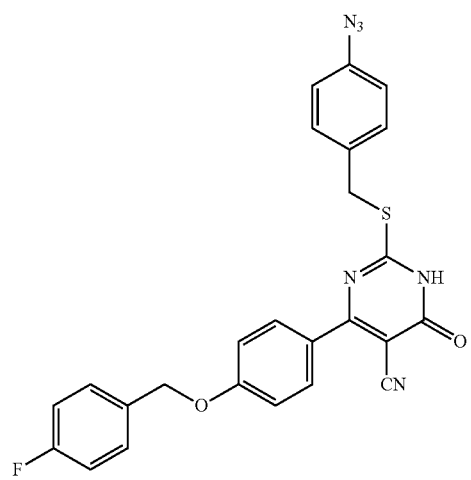
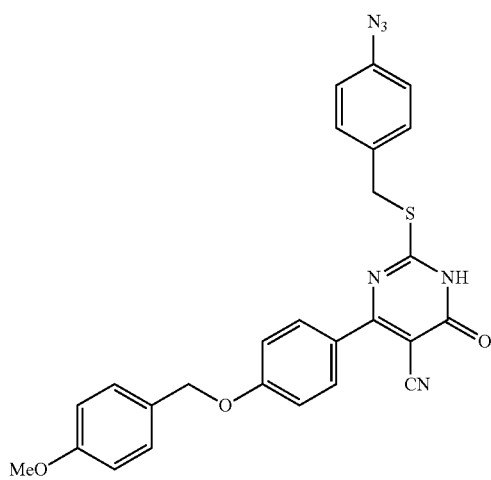
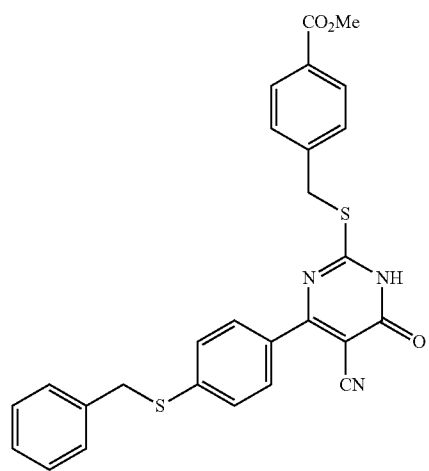
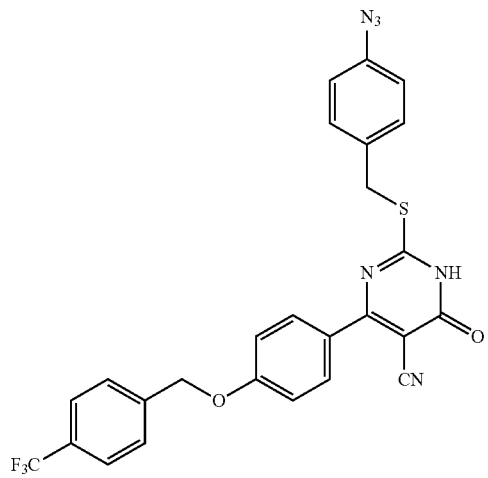

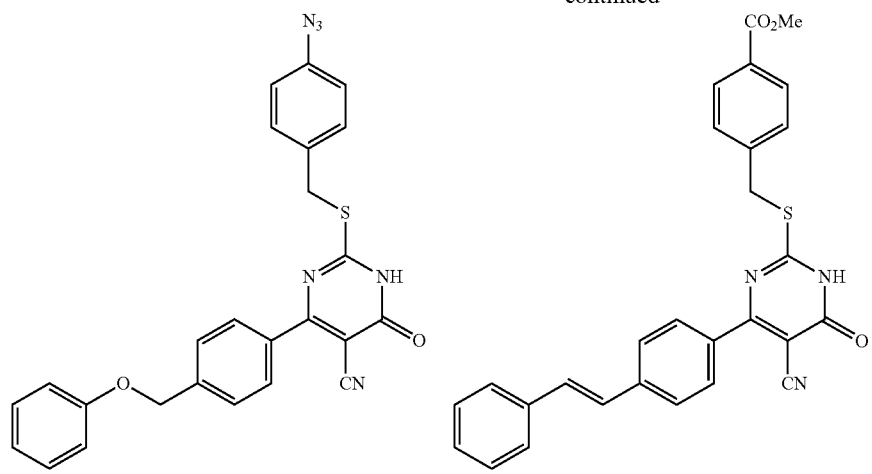
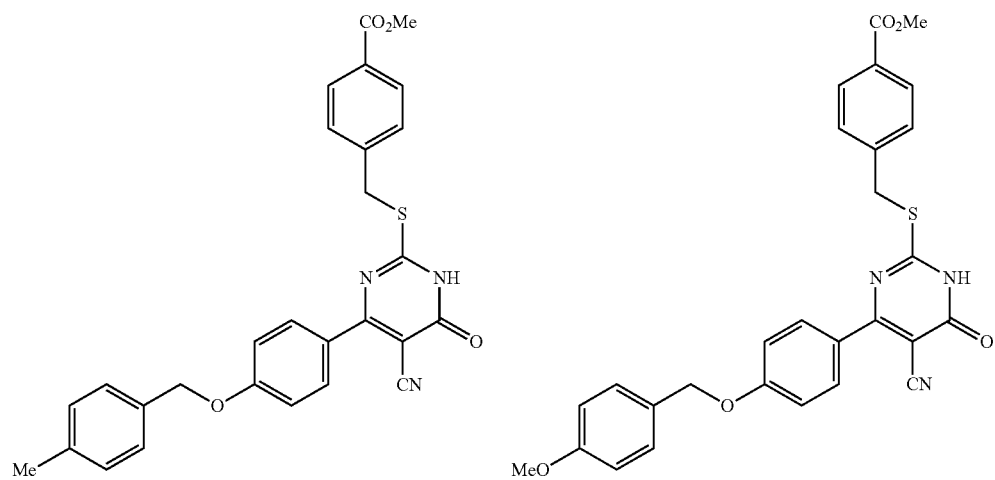
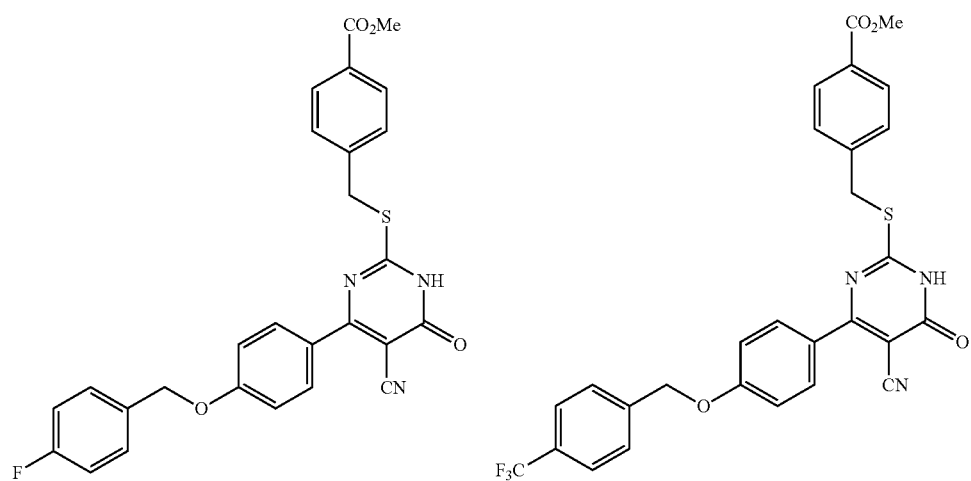

-continued
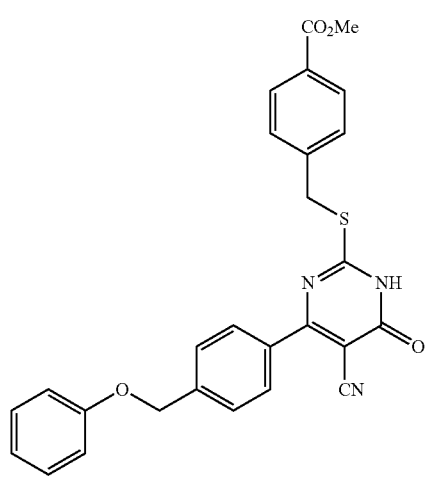
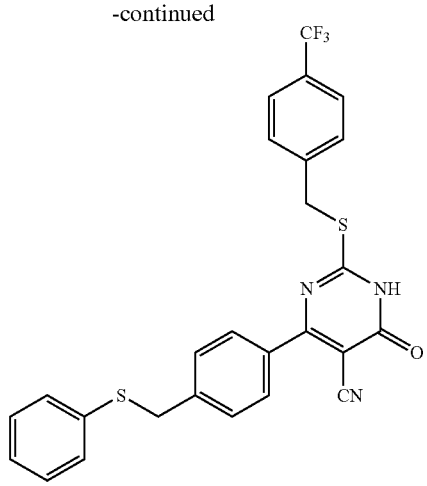
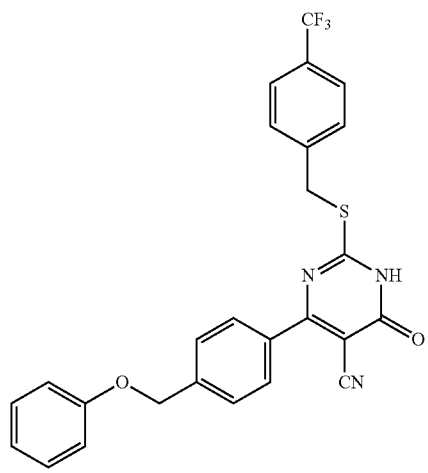
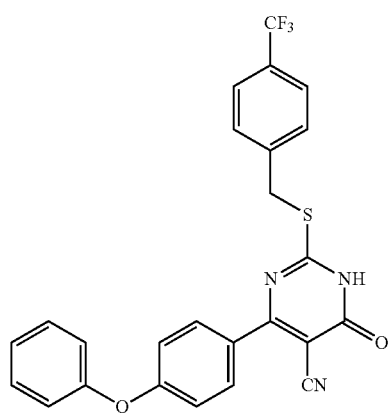
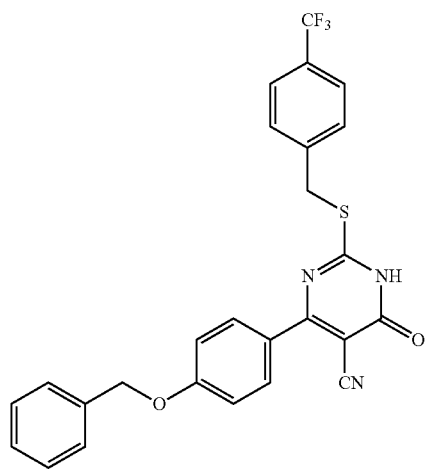
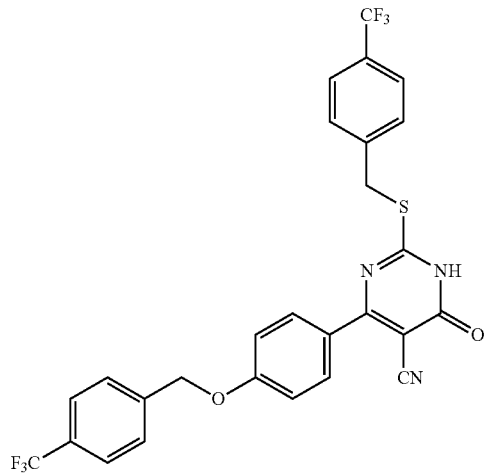

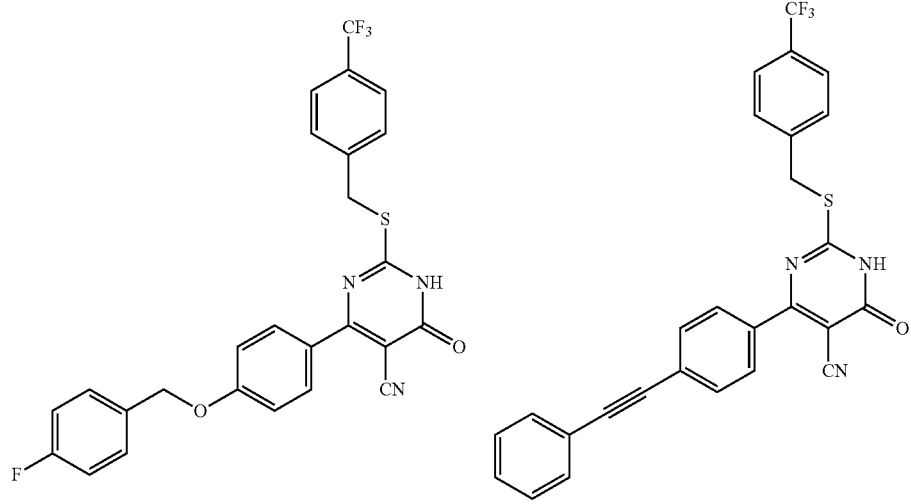
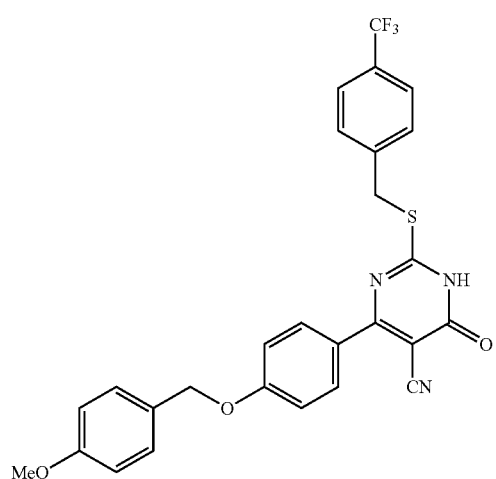
In another embodiment, the compounds of formula IX, or a pharmaceutically acceptable salt or a prodrug thereof, is a compound selected from the group consisting of:
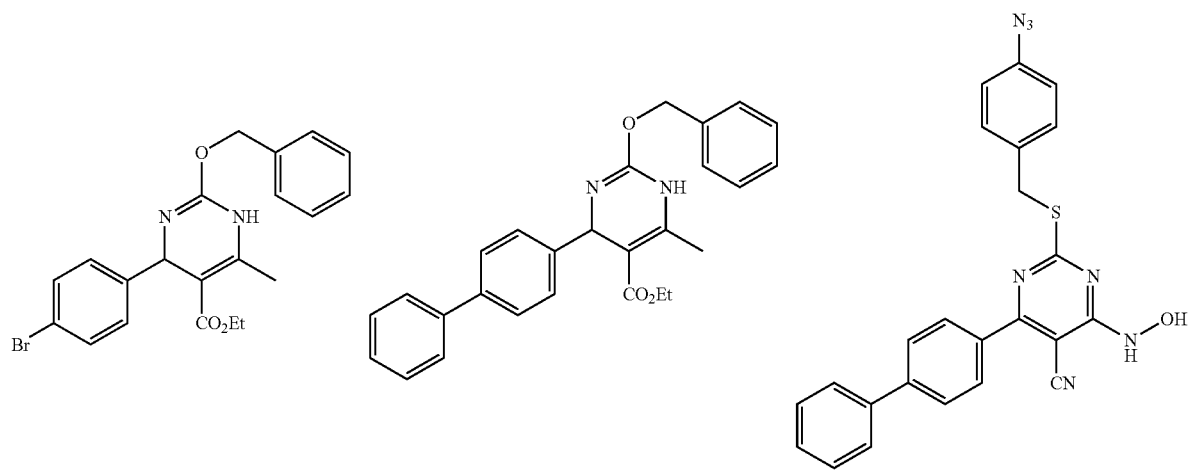

63
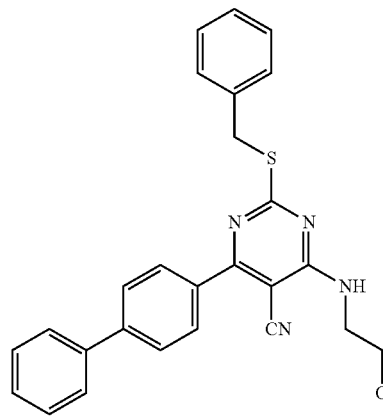
-continued
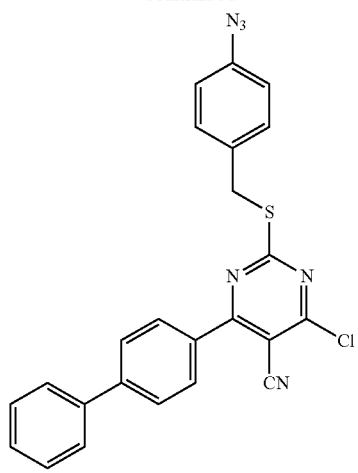
64
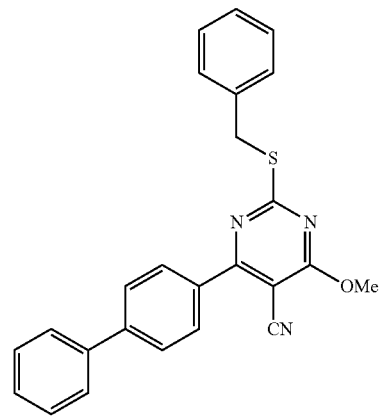
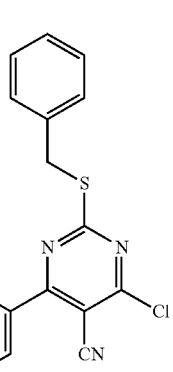
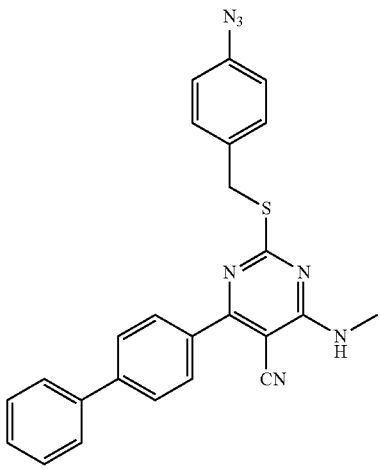
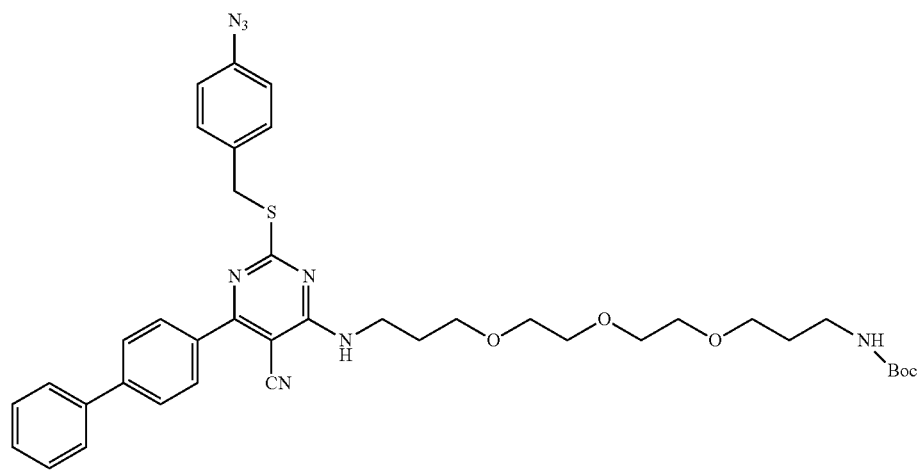

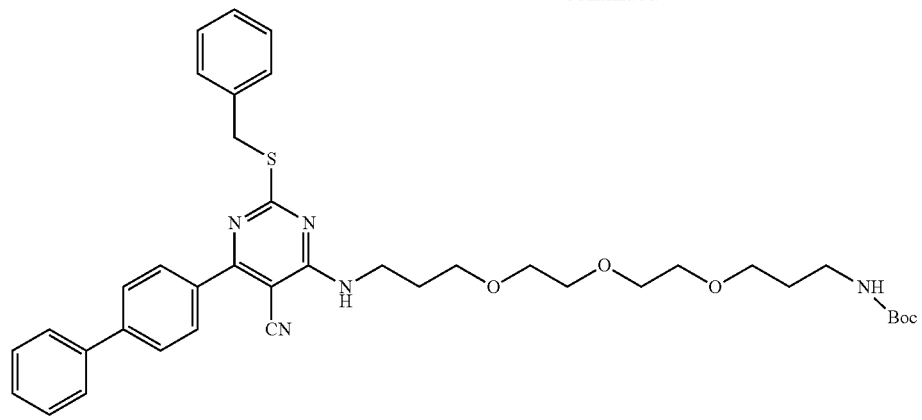
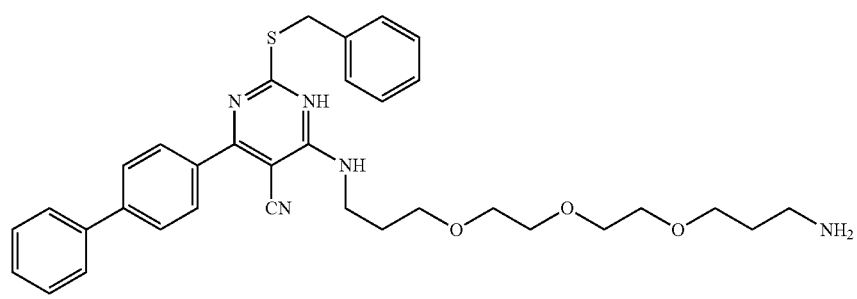
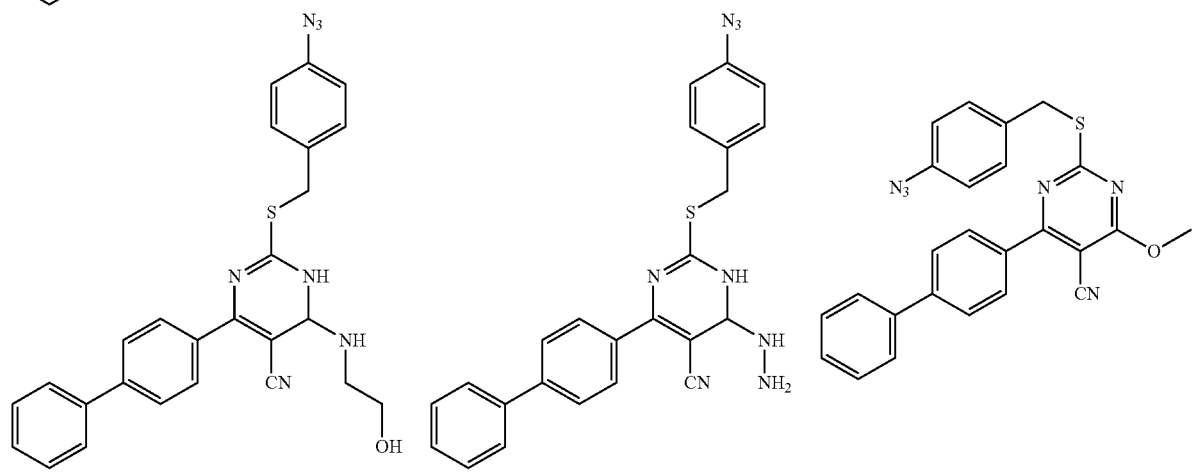
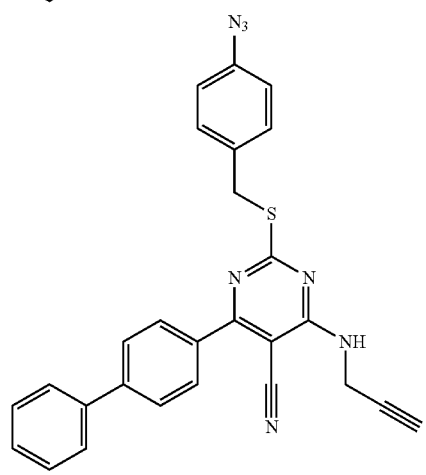

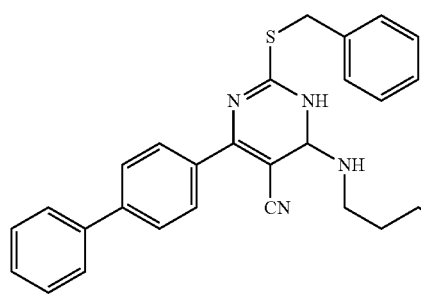
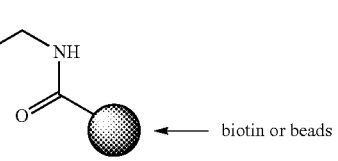
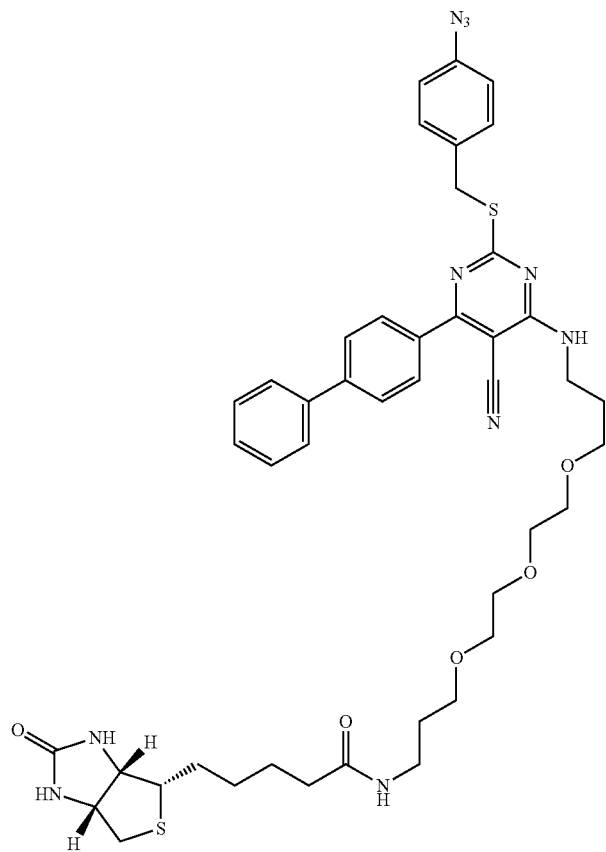
In another embodiment, the compounds of formula X, or a pharmaceutically acceptable salt or a prodrug thereof, is a compound selected from the group consisting of:
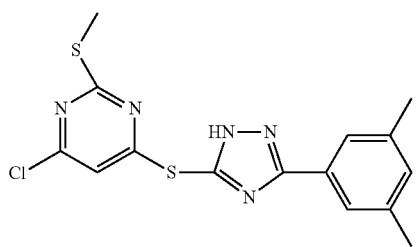
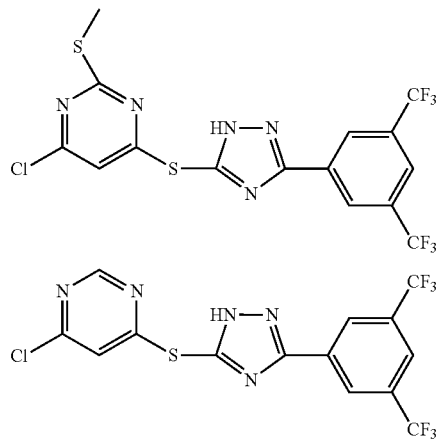

-continued
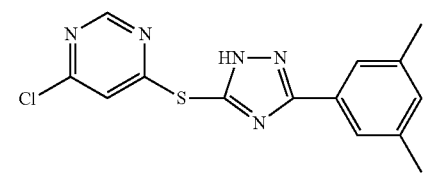
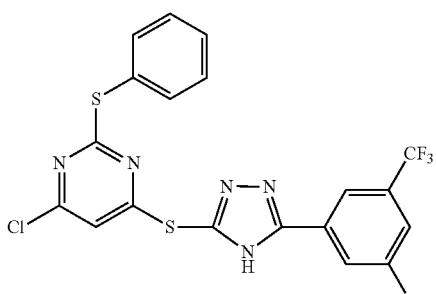
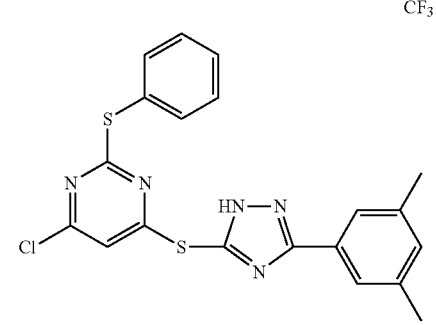
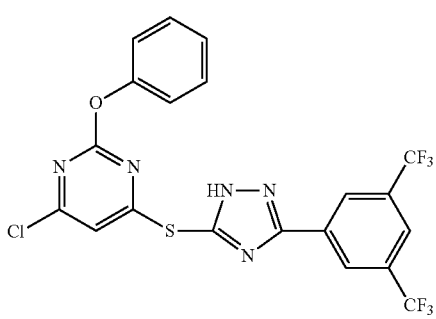
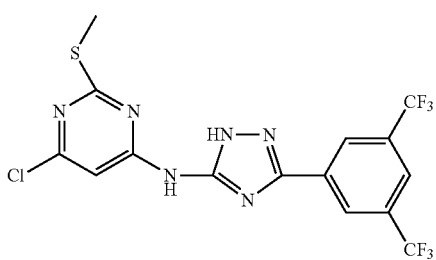
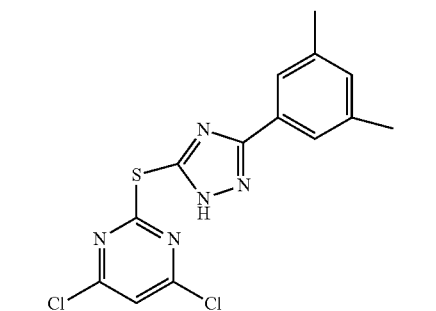
-continued
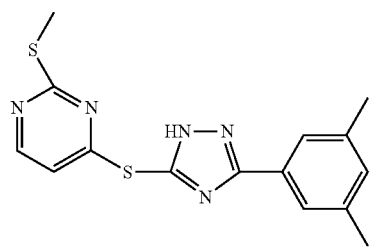

-continued
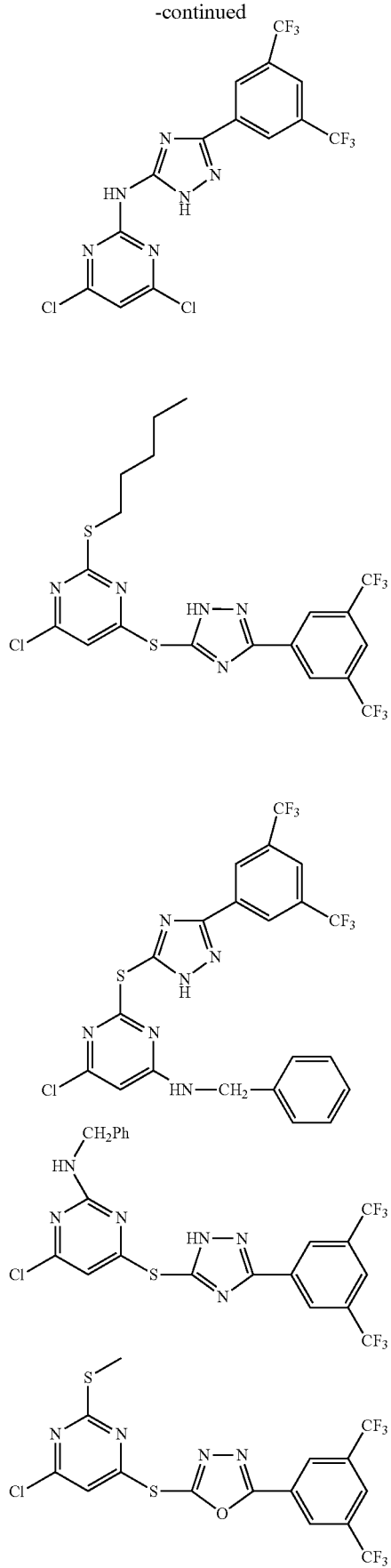
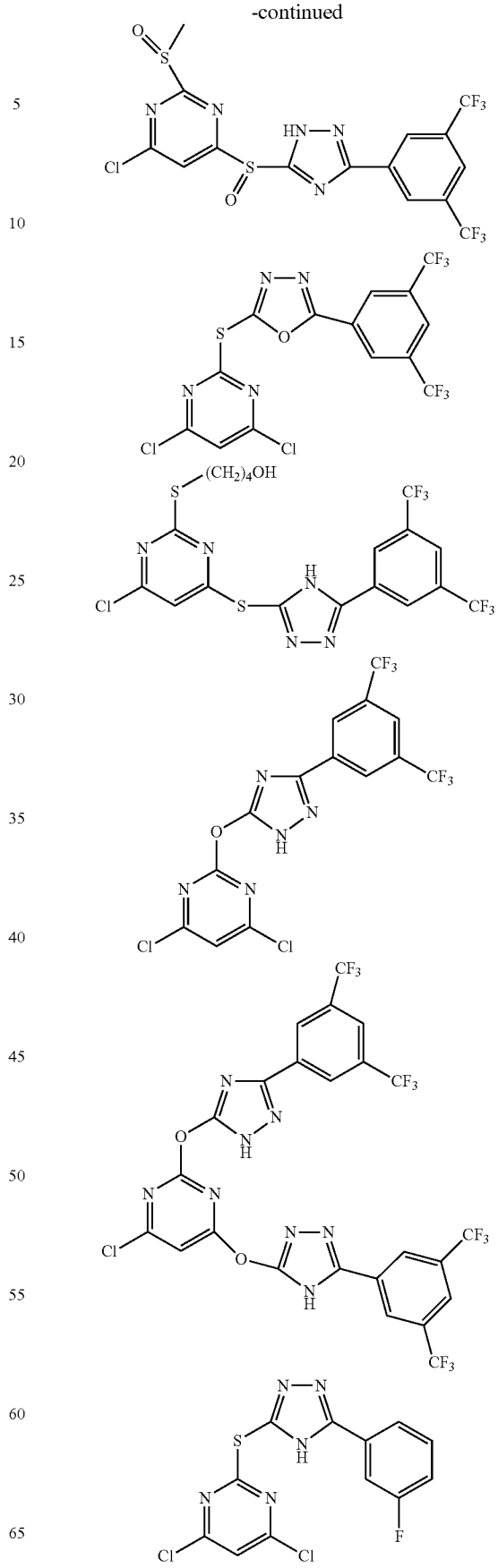

-continued
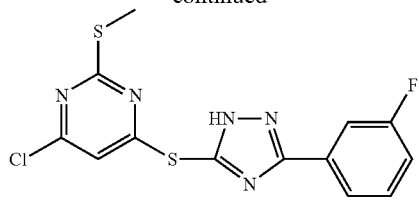
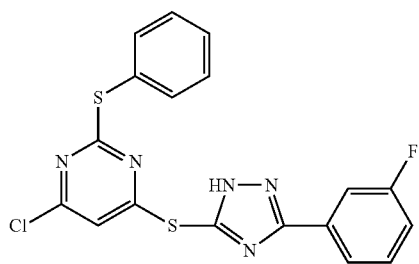
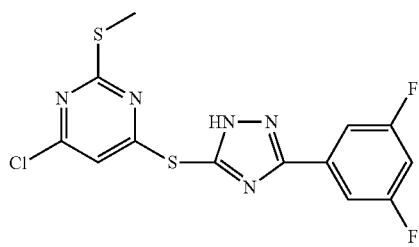
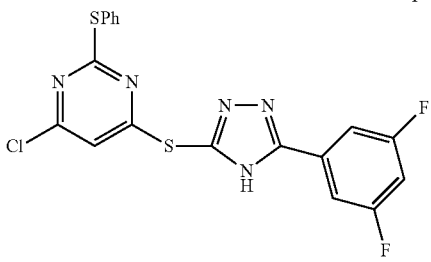
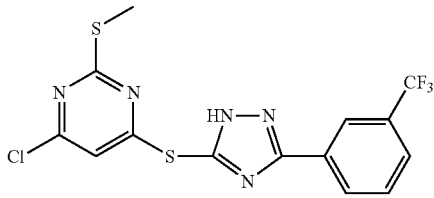
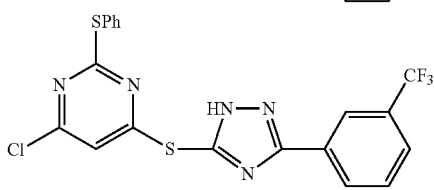
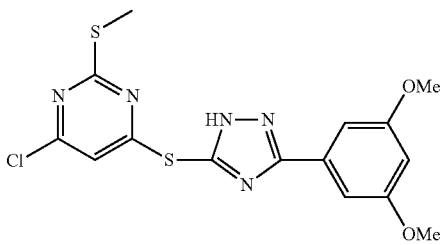
-continued
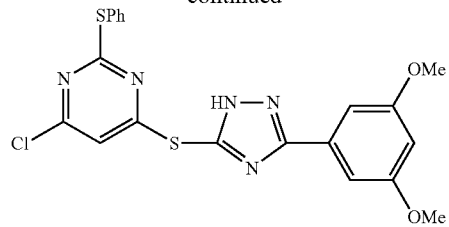
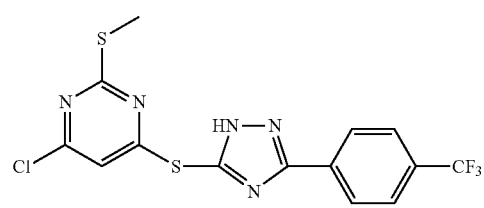
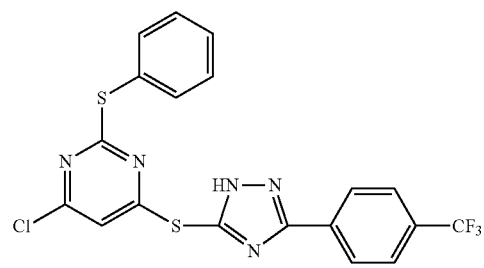
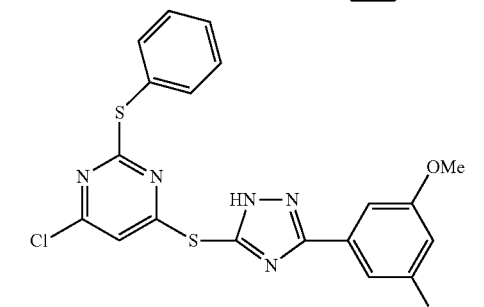
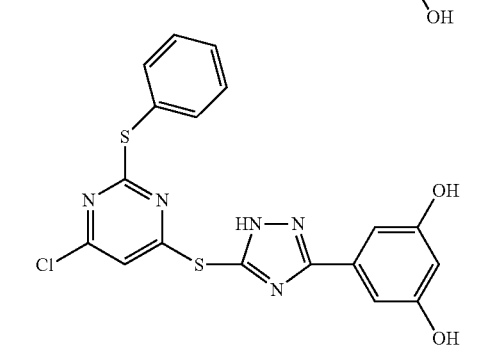
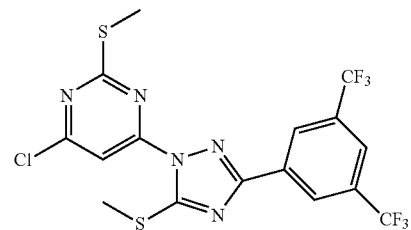

75
-continued
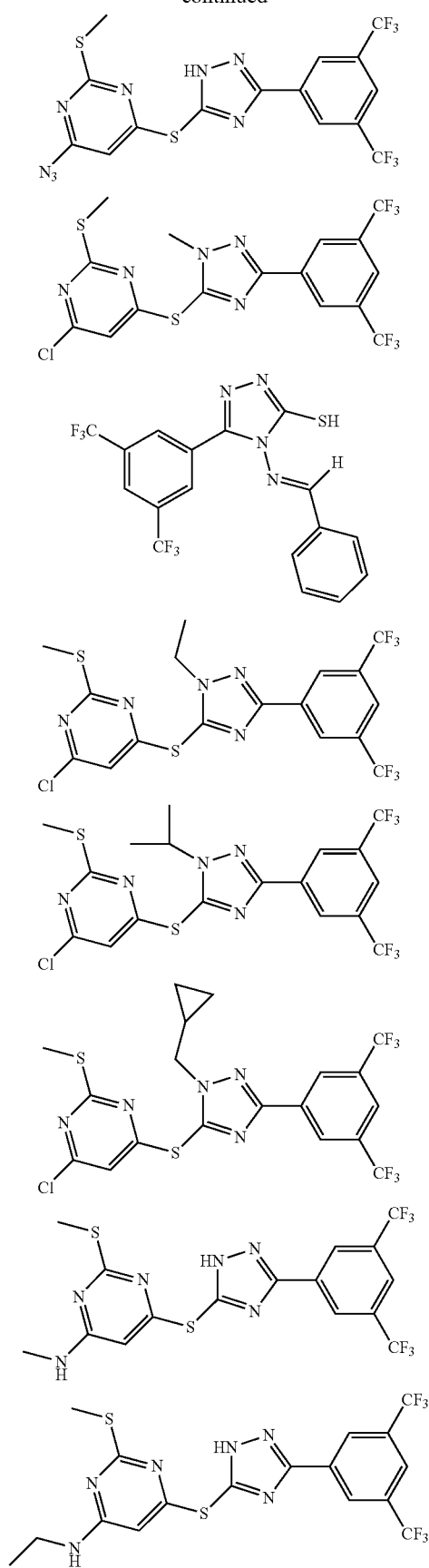
76
-continued
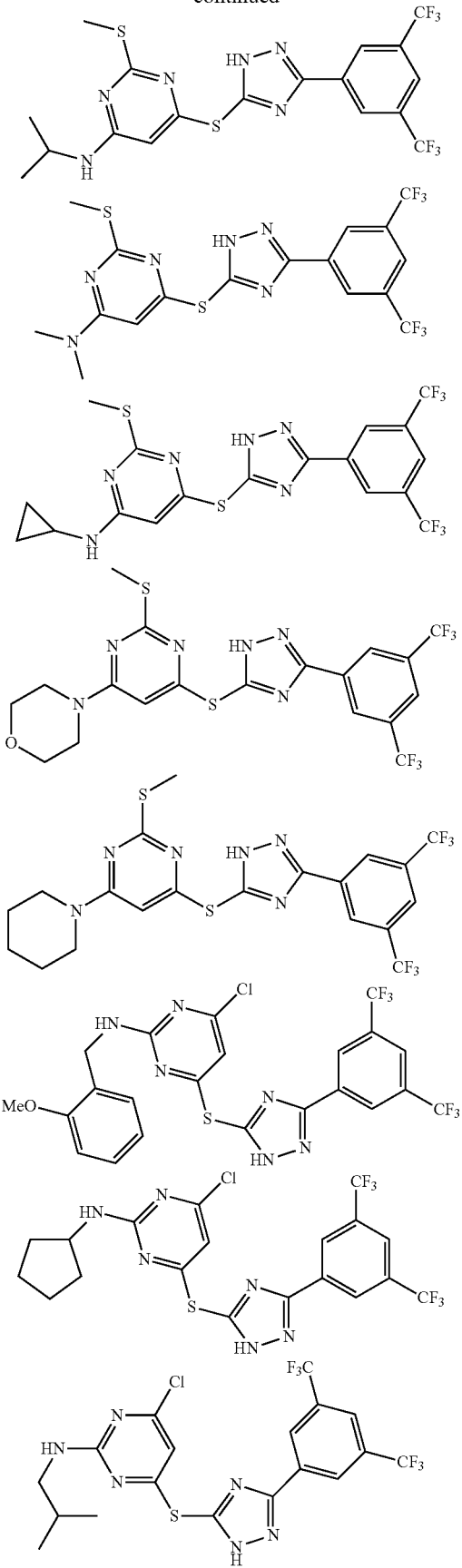

77
-continued
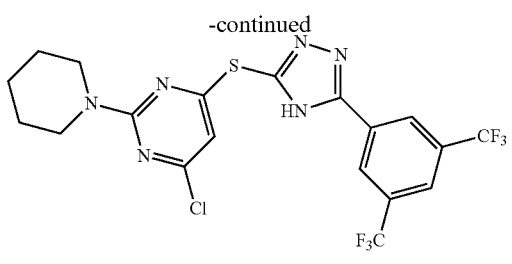
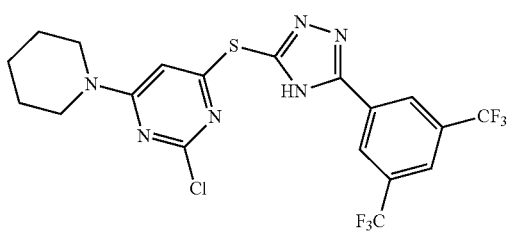
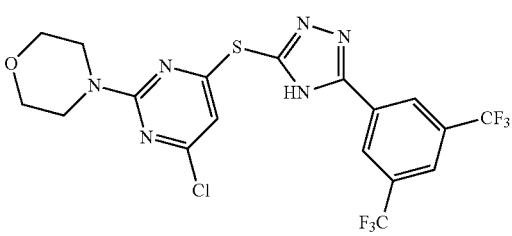
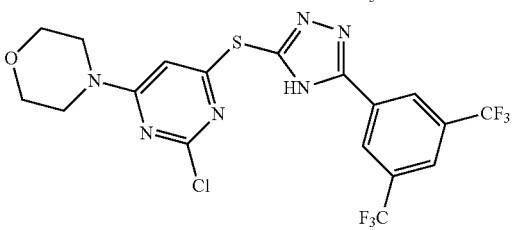
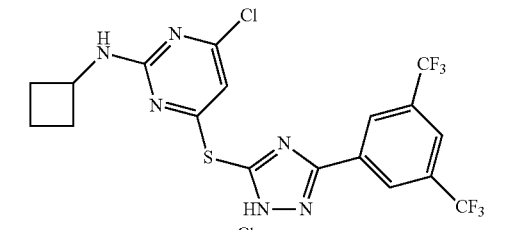
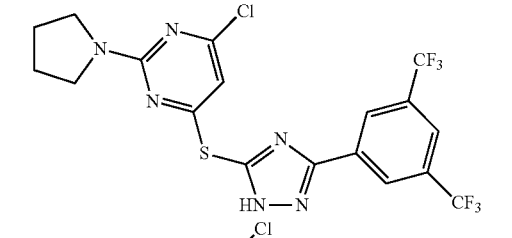
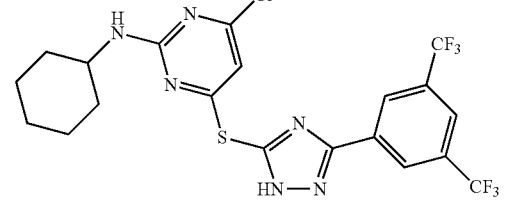
78
-continued
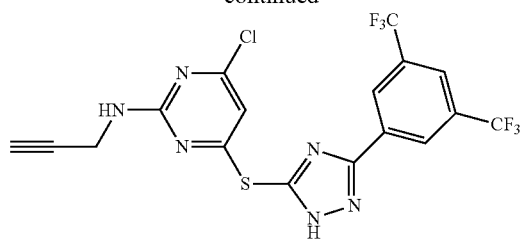
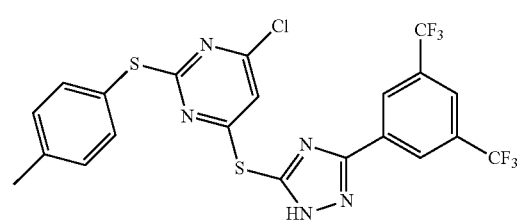
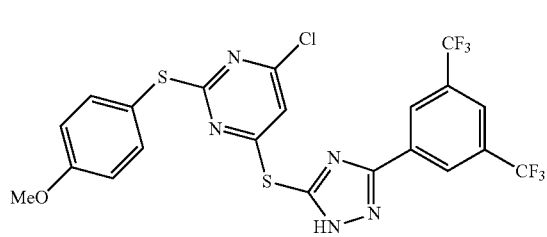
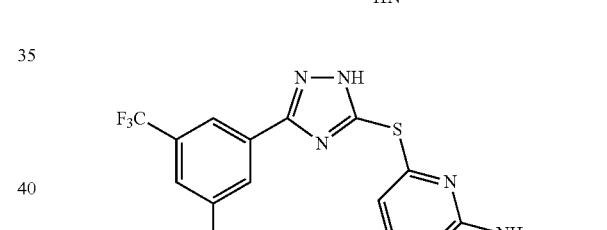
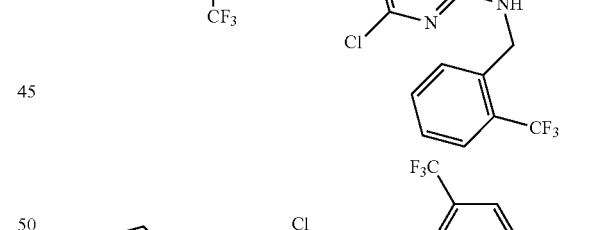
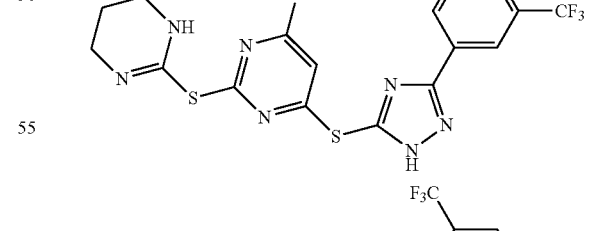
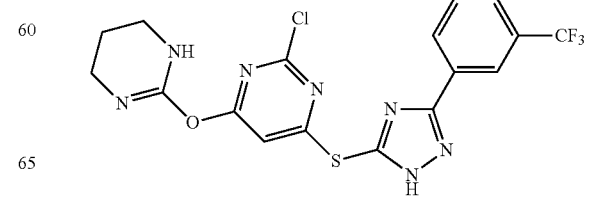

79
-continued
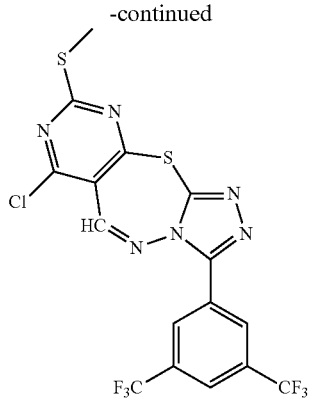
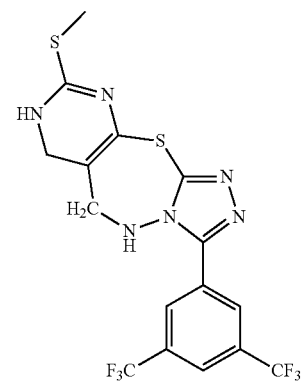
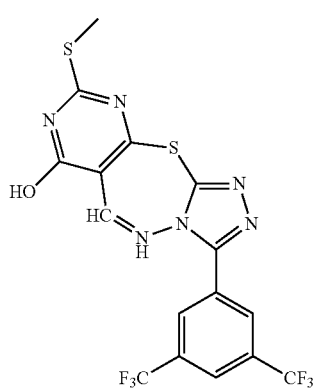
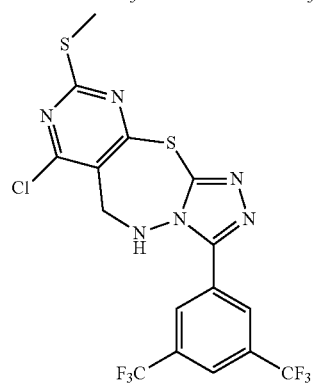
80
-continued
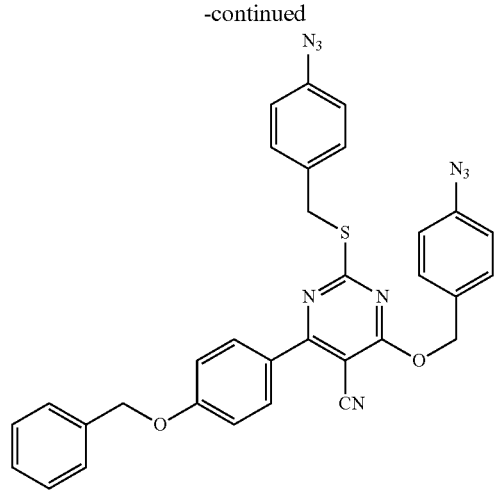
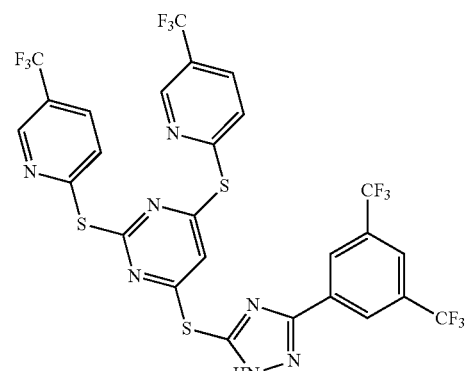
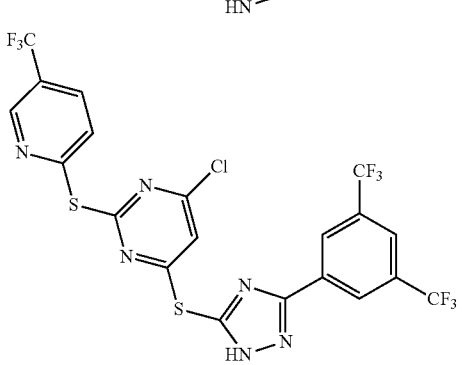
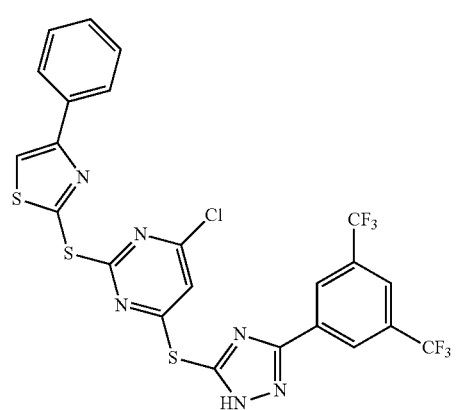

-continued

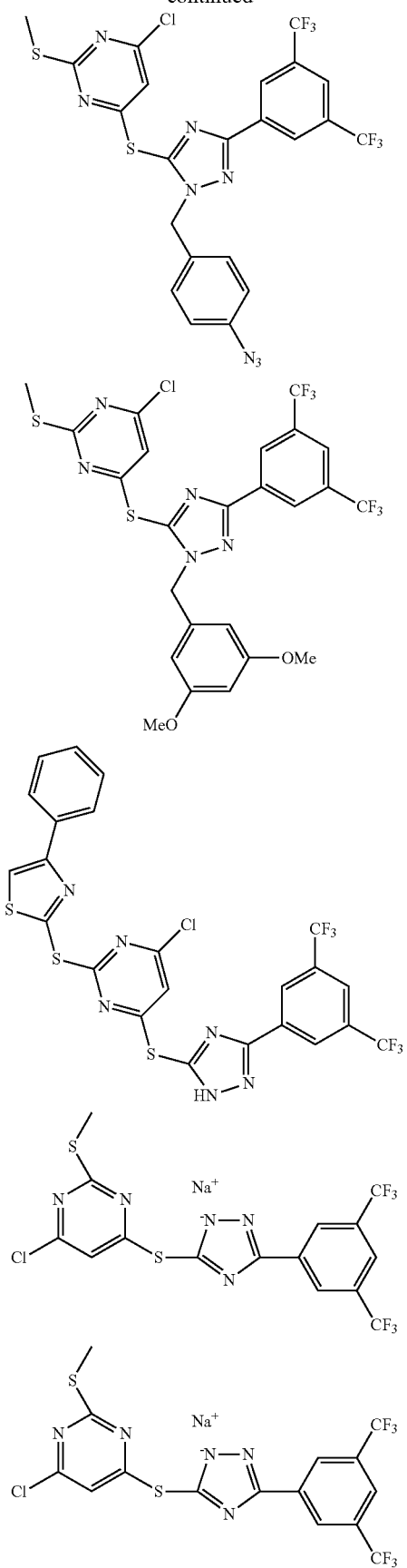

-continued

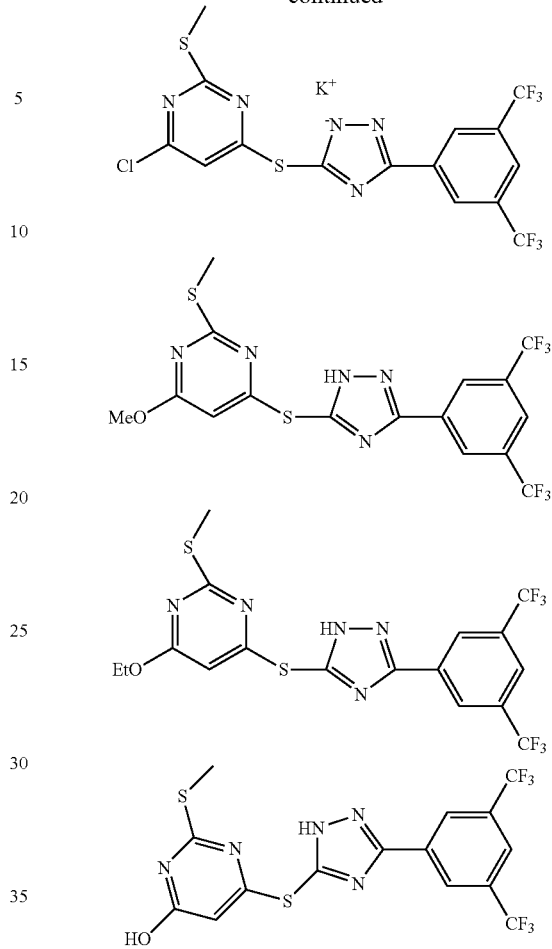

The compounds described herein may have one or more chiral centers, and thus exist as one or more stereoisomers. Such stereoisomers can exist as a single enantiomer, a mixture of enantiomers, a mixture of diastereomers, or a racemic mixture.

As used herein, the term "stereoisomers" refers to compounds made up of the same atoms having the same bond order but having different three-dimensional arrangements of atoms that are not interchangeable. The three-dimensional structures are called configurations. As used herein, the term "enantiomers" refers to two stereoisomers that are non-superimposable mirror images of one another. As used herein, the term "optical isomer" is equivalent to the term "enantiomer". As used herein the term "diastereomer" refers to two stereoisomers which are not mirror images but also not superimposable. The terms "racemate", "racemic mixture" or "racemic modification" refer to a mixture of equal parts of enantiomers. The term "chiral center" refers to a carbon atom to which four different groups are attached. Choice of the appropriate chiral column, eluent, and conditions necessary to effect separation of the pair of enantiomers is well known to one of ordinary skill in the art using standard techniques (see e.g. Jacques, J. et al., "Enantiomers, Racemates, and Resolutions", John Wiley and Sons, Inc. 1981).

The compounds can also be a pharmaceutically acceptable salt of any of the compounds described above. In some cases, it may be desirable to prepare the salt of a compound described above due to one or more of the salt's advantageous physical properties, such as enhanced stability or a desirable solubility or dissolution profile.

Generally, pharmaceutically acceptable salts can be prepared by reaction of the free acid or base forms of a compound described above with a stoichiometric amount of the appropriate base or acid in water, in an organic solvent, or in a mixture of the two. Generally, non-aqueous media including ether, ethyl acetate, ethanol, isopropanol, or acetonitrile are preferred. Lists of suitable salts are found in Remington's Pharmaceutical Sciences, 20th ed., Lippincott Williams & Wilkins, Baltimore, Md., 2000, p. 704; and "Handbook of Pharmaceutical Salts: Properties, Selection, and Use," P. Heinrich Stahl and Camille G. Wermuth, Eds., Wiley-VCH, Weinheim, 2002.

Suitable pharmaceutically acceptable acid addition salts include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids.

Suitable organic acids generally include, for example, aliphatic, cycloaliphatic, aromatic, araliphatic, heterocyclic, carboxylic, and sulfonic classes of organic acids. Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, algenic acid, β-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, tosylate, and undecanoate.

In some cases, the pharmaceutically acceptable salt may include alkali metal salts, including sodium or potassium salts; alkaline earth metal salts, e.g., calcium or magnesium salts; and salts formed with suitable organic ligands, e.g., quaternary ammonium salts. Base salts can also be formed from bases which form non-toxic salts, including aluminum, arginine, benzathine, choline, diethylamine, diolamine, glycine, lysine, meglumine, olamine, tromethamine and zinc salts.

Organic salts may be made from secondary, tertiary or quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups may also be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibuytl, and diamyl sulfates), long chain halides (e.g., decyl, lauryl, myristyl, and stearyl chlorides, bromides, and iodides), arylalkyl halides (e.g., benzyl and phenethyl bromides), and others.

The compound can also be a pharmaceutically acceptable prodrug of any of the compounds described above. Prodrugs are compounds that, when metabolized in vivo, undergo conversion to compounds having the desired pharmacological activity. Prodrugs can be prepared by replacing appropriate functionalities present in the compounds described above with "pro-moieties" as described, for example, in H. Bundgaar, Design of Prodrugs (1985). Examples of prodrugs include ester, ether or amide derivatives of the compounds described above, polyethylene glycol derivatives of the compounds described above, N-acyl amine derivatives, dihydropyridine pyridine derivatives, amino-containing derivatives conjugated to polypeptides, 2-hydroxybenzamide derivatives, carbamate derivatives, N-oxides derivatives that are biologically reduced to the active amines, and N-mannich base derivatives. For further discussion of prodrugs, see, for example, Rautio, J. et al. *Nature Reviews Drug Discovery.* 7:255-270 (2008).

III. Pharmaceutical Formulations

Pharmaceutical formulations are provided containing a therapeutically effective amount of a compound described herein, or a pharmaceutically acceptable salt or prodrug thereof, in combination with one or more pharmaceutically acceptable excipients. Representative excipients include solvents, diluents, pH modifying agents, preservatives, antioxidants, suspending agents, wetting agents, viscosity modifiers, tonicity agents, stabilizing agents, and combinations thereof. Suitable pharmaceutically acceptable excipients are preferably selected from materials that are generally recognized as safe (GRAS), and may be administered to an individual without causing undesirable biological side effects or unwanted interactions.

A. Additional Therapeutics

The compounds described herein can be formulated with one or more additional active agents, such as anti-infectious agents, analgesic, etc.

Pharmaceutical formulations can also include one or more vitamins, minerals, dietary supplements, nutraceutical agents, such as proteins, carbohydrates, amino acids, fatty acids, antioxidants, and plant or animal extracts, or combinations thereof. Suitable vitamins, minerals, nutraceutical agents, and dietary supplements are known in the art, and disclosed, for example, in Roberts et al., (*Nutriceuticals: The Complete Encyclopedia of Supplements, Herbs, Vitamins, and Healing Foods*, American Nutriceutical Association, 2001). Nutraceutical agents and dietary supplements are also disclosed in *Physicians' Desk Reference for Nutritional Supplements,* 1st Ed. (2001) and *The Physicians' Desk Reference for Herbal Medicines,* 1st Ed. (2001).

B. Enteral Formulations

Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art.

Formulations may be prepared using one or more pharmaceutically acceptable excipients, including diluents, preservatives, binders, lubricants, disintegrators, swelling agents, fillers, stabilizers, and combinations thereof.

Excipients, including plasticizers, pigments, colorants, stabilizing agents, and glidants, may also be used to form coated compositions for enteral administration. Delayed release dosage formulations may be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.:

Williams and Wilkins, 1995). These references provide information on excipients, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

Stabilizers are used to inhibit or retard drug decomposition reactions that include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

1. Controlled Release Formulations

Oral dosage forms, such as capsules, tablets, solutions, and suspensions, can for formulated for controlled release. For example, the one or more compounds and optional one or more additional active agents can be formulated into nanoparticles, microparticles, and combinations thereof, and encapsulated in a soft or hard gelatin or non-gelatin capsule or dispersed in a dispersing medium to form an oral suspension or syrup. The particles can be formed of the drug and a controlled release polymer or matrix. Alternatively, the drug particles can be coated with one or more controlled release coatings prior to incorporation in to the finished dosage form.

In another embodiment, the one or more compounds and optional one or more additional active agents are dispersed in a matrix material, which gels or emulsifies upon contact with an aqueous medium, such as physiological fluids. In the case of gels, the matrix swells entrapping the active agents, which are released slowly over time by diffusion and/or degradation of the matrix material. Such matrices can be formulated as tablets or as fill materials for hard and soft capsules.

In still another embodiment, the one or more compounds, and optional one or more additional active agents are formulated into a sold oral dosage form, such as a tablet or capsule, and the solid dosage form is coated with one or more controlled release coatings, such as a delayed release coatings or extended release coatings. The coating or coatings may also contain the compounds and/or additional active agents.

Extended Release Formulations

The extended release formulations are generally prepared as diffusion or osmotic systems, for example, as described in "Remington—The science and practice of pharmacy" (20th ed., Lippincott Williams & Wilkins, Baltimore, Md., 2000). A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly (methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the tradename Eudragit® In further preferred embodiments, the acrylic polymer comprises a mixture of two acrylic resin lacquers commercially available from Rohm Pharma under the tradenames Eudragit® RL30D and Eudragit® RS30D, respectively. Eudragit® RL30D and Eudragit®. RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. Edragit® S-100 and Eudragit® L-100 are also preferred. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids.

The polymers described above such as Eudragit® RL/RS may be mixed together in any desired ratio in order to ultimately obtain a sustained-release formulation having a desirable dissolution profile. Desirable sustained-release multiparticulate systems may be obtained, for instance, from 100% Eudragit®RL, 50% Eudragit® RL and 50% Eudragit® RS, and 10% Eudragit® RL and 90% Eudragit® RS. One skilled in the art will recognize that other acrylic polymers may also be used, such as, for example, Eudragit®L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules. An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including *acacia*, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

Delayed Release Formulations

Delayed release formulations can be created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

Pulsatile Release

The formulation can provide pulsatile delivery of the one or more of the compounds disclosed herein. By "pulsatile" is meant that a plurality of drug doses are released at spaced apart intervals of time. Generally, upon ingestion of the dosage form, release of the initial dose is substantially immediate, i.e., the first drug release "pulse" occurs within about one hour of ingestion. This initial pulse is followed by a first time interval (lag time) during which very little or no drug is released from the dosage form, after which a second dose is then released. Similarly, a second nearly drug release-free interval between the second and third drug release pulses may be designed. The duration of the nearly drug release-free time interval will vary depending upon the dosage form design e.g., a twice daily dosing profile, a three times daily dosing profile, etc. For dosage forms providing a twice daily dosage profile, the nearly drug release-free interval has a duration of approximately 3 hours to 14 hours between the first and second dose. For dosage forms providing a three times daily profile, the nearly drug release-free interval has a duration of approximately 2 hours to 8 hours between each of the three doses.

In one embodiment, the pulsatile release profile is achieved with dosage forms that are closed and preferably sealed capsules housing at least two drug-containing "dosage units" wherein each dosage unit within the capsule provides a different drug release profile. Control of the delayed release dosage unit(s) is accomplished by a controlled release polymer coating on the dosage unit, or by incorporation of the active agent in a controlled release polymer matrix. Each dosage unit may comprise a compressed or molded tablet, wherein each tablet within the capsule provides a different drug release profile. For dosage forms mimicking a twice a day dosing profile, a first tablet releases drug substantially immediately following ingestion of the dosage form, while a second tablet releases drug approximately 3 hours to less than 14 hours following ingestion of the dosage form. For dosage forms mimicking a three times daily dosing profile, a first tablet releases drug substantially immediately following ingestion of the dosage form, a second tablet releases drug approximately 3 hours to less than 10 hours following ingestion of the dosage form, and the third tablet releases drug at least 5 hours to approximately 18 hours following ingestion of the dosage form. It is possible that the dosage form includes more than three tablets. While the dosage form will not generally include more than a third tablet, dosage forms housing more than three tablets can be utilized.

Alternatively, each dosage unit in the capsule may comprise a plurality of drug-containing beads, granules or particles. As is known in the art, drug-containing "beads" refer to beads made with drug and one or more excipients or polymers. Drug-containing beads can be produced by applying drug to an inert support, e.g., inert sugar beads coated with drug or by creating a "core" comprising both drug and one or more excipients. As is also known, drug-containing "granules" and "particles" comprise drug particles that may or may not include one or more additional excipients or polymers. In contrast to drug-containing beads, granules and particles do not contain an inert support. Granules generally comprise drug particles and require further processing. Generally, particles are smaller than granules, and are not further processed. Although beads, granules and particles may be formulated to provide immediate release, beads and granules are generally employed to provide delayed release.

C. Parenteral Formulations

The compounds described herein can be formulated for parenteral administration. "Parenteral administration", as used herein, means administration by any method other than through the digestive tract or non-invasive topical or regional routes. For example, parenteral administration may include administration to a patient intravenously, intradermally, intraperitoneally, intrapleurally, intratracheally, intramuscularly, subcutaneously, by injection, and by infusion.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

1. Controlled Release Formulations

The parenteral formulations described herein can be formulated for controlled release including immediate release, delayed release, extended release, pulsatile release, and combinations thereof.

Nano- and Microparticles

For parenteral administration, the compounds, and optionally one or more additional active agents, can be incorporated into microparticles, nanoparticles, or combinations thereof that provide controlled release. In embodiments wherein the formulations contains two or more drugs, the drugs can be formulated for the same type of controlled release (e.g., delayed, extended, immediate, or pulsatile) or the drugs can be independently formulated for different types of release (e.g., immediate and delayed, immediate and extended, delayed and extended, delayed and pulsatile, etc.).

For example, the compounds and/or one or more additional active agents can be incorporated into polymeric microparticles that provide controlled release of the drug(s). Release of the drug(s) is controlled by diffusion of the drug(s) out of the microparticles and/or degradation of the polymeric particles by hydrolysis and/or enzymatic degradation. Suitable polymers include ethylcellulose and other natural or synthetic cellulose derivatives.

Polymers that are slowly soluble and form a gel in an aqueous environment, such as hydroxypropyl methylcellulose or polyethylene oxide may also be suitable as materials for drug containing microparticles. Other polymers include, but are not limited to, polyanhydrides, poly(ester anhydrides), polyhydroxy acids, such as polylactide (PLA), polyglycolide (PGA), poly(lactide-co-glycolide) (PLGA), poly-3-hydroxybutyrate (PHB) and copolymers thereof, poly-4-hydroxybutyrate (P4HB) and copolymers thereof, polycaprolactone and copolymers thereof, and combinations thereof.

Alternatively, the drug(s) can be incorporated into microparticles prepared from materials which are insoluble in aqueous solution or slowly soluble in aqueous solution, but are capable of degrading within the GI tract by means including enzymatic degradation, surfactant action of bile acids, and/or mechanical erosion. As used herein, the term "slowly soluble in water" refers to materials that are not dissolved in water within a period of 30 minutes. Preferred examples include fats, fatty substances, waxes, wax-like substances and mixtures thereof. Suitable fats and fatty substances include fatty alcohols (such as lauryl, myristyl stearyl, cetyl or cetostearyl alcohol), fatty acids and derivatives, including, but not limited to, fatty acid esters, fatty acid glycerides (mono-, di- and tri-glycerides), and hydrogenated fats. Specific examples include, but are not limited to hydrogenated vegetable oil, hydrogenated cottonseed oil, hydrogenated castor oil, hydrogenated oils available under the trade name Sterotex®, stearic acid, cocoa butter, and stearyl alcohol. Suitable waxes and wax-like materials include natural or synthetic waxes, hydrocarbons, and normal waxes. Specific examples of waxes include beeswax, glycowax, castor wax, carnauba wax, paraffins and candelilla wax. As used herein, a wax-like material is defined as any material that is normally solid at room temperature and has a melting point of from about 30 to 300° C.

In some cases, it may be desirable to alter the rate of water penetration into the microparticles. To this end, rate-controlling (wicking) agents may be formulated along with the fats or waxes listed above. Examples of rate-controlling materials include certain starch derivatives (e.g., waxy maltodextrin and drum dried corn starch), cellulose derivatives (e.g., hydroxypropylmethyl-cellulose, hydroxypropylcellulose, methylcellulose, and carboxymethyl-cellulose), alginic acid, lactose and talc. Additionally, a pharmaceutically acceptable surfactant (for example, lecithin) may be added to facilitate the degradation of such microparticles.

Proteins that are water insoluble, such as zein, can also be used as materials for the formation of drug containing microparticles. Additionally, proteins, polysaccharides and combinations thereof that are water soluble can be formulated with drug into microparticles and subsequently cross-linked to form an insoluble network. For example, cyclodextrins can be complexed with individual drug molecules and subsequently cross-linked.

Encapsulation or incorporation of drug into carrier materials to produce drug containing microparticles can be achieved through known pharmaceutical formulation techniques. In the case of formulation in fats, waxes or wax-like materials, the carrier material is typically heated above its melting temperature and the drug is added to form a mixture comprising drug particles suspended in the carrier material, drug dissolved in the carrier material, or a mixture thereof. Microparticles can be subsequently formulated through several methods including, but not limited to, the processes of congealing, extrusion, spray chilling or aqueous dispersion. In a preferred process, wax is heated above its melting temperature, drug is added, and the molten wax-drug mixture is congealed under constant stirring as the mixture cools. Alternatively, the molten wax-drug mixture can be extruded and spheronized to form pellets or beads. Detailed descriptions of these processes can be found in "Remington—The science and practice of pharmacy", 20th Edition, Jennaro et. al., (Phila, Lippencott, Williams, and Wilkens, 2000).

For some carrier materials it may be desirable to use a solvent evaporation technique to produce drug containing microparticles. In this case drug and carrier material are co-dissolved in a mutual solvent and microparticles can subsequently be produced by several techniques including, but not limited to, forming an emulsion in water or other appropriate media, spray drying or by evaporating off the solvent from the bulk solution and milling the resulting material.

In some embodiments, drug in a particulate form is homogeneously dispersed in a water-insoluble or slowly water soluble material. To minimize the size of the drug particles within the composition, the drug powder itself may be milled to generate fine particles prior to formulation. The process of jet milling, known in the pharmaceutical art, can be used for this purpose. In some embodiments drug in a particulate form is homogeneously dispersed in a wax or wax like substance by heating the wax or wax like substance above its melting point and adding the drug particles while stirring the mixture. In this case a pharmaceutically acceptable surfactant may be added to the mixture to facilitate the dispersion of the drug particles.

The particles can also be coated with one or more modified release coatings. Solid esters of fatty acids, which are hydrolyzed by lipases, can be spray coated onto microparticles or drug particles. Zein is an example of a naturally water-insoluble protein. It can be coated onto drug containing microparticles or drug particles by spray coating or by wet granulation techniques. In addition to naturally water-insoluble materials, some substrates of digestive enzymes can be treated with cross-linking procedures, resulting in the formation of non-soluble networks. Many methods of cross-linking proteins, initiated by both chemical and physical means, have been reported. One of the most common methods to obtain cross-linking is the use of chemical cross-linking agents. Examples of chemical cross-linking agents include aldehydes (gluteraldehyde and formaldehyde), epoxy compounds, carbodiimides, and genipin. In addition to these cross-linking agents, oxidized and native sugars have been used to cross-link gelatin (Cortesi, R., et al., *Biomaterials* 19 (1998) 1641-1649). Cross-linking can also be accomplished using enzymatic means; for example, transglutaminase has been approved as a GRAS substance for cross-linking seafood products. Finally, cross-linking can be initiated by physical means such as thermal treatment, UV irradiation and gamma irradiation.

To produce a coating layer of cross-linked protein surrounding drug containing microparticles or drug particles, a water soluble protein can be spray coated onto the microparticles and subsequently cross-linked by the one of the methods described above. Alternatively, drug containing microparticles can be microencapsulated within protein by coacervation-phase separation (for example, by the addition of salts) and subsequently cross-linked. Some suitable proteins for this purpose include gelatin, albumin, casein, and gluten.

Polysaccharides can also be cross-linked to form a water-insoluble network. For many polysaccharides, this can be accomplished by reaction with calcium salts or multivalent cations that cross-link the main polymer chains. Pectin, alginate, dextran, amylose and guar gum are subject to cross-linking in the presence of multivalent cations. Complexes between oppositely charged polysaccharides can also be formed; pectin and chitosan, for example, can be complexed via electrostatic interactions.

Depot Formulations

Active agents can be formulated for depot injection. In a depot injection, the active agent is formulated with one or more pharmaceutically acceptable carriers that provide for the gradual release of active agent over a period of hours or days after injection. The depot formulation can be administered by any suitable means; however, the depot formulation is typically administered via subcutaneous or intramuscular injection.

A variety of carriers may be incorporated into the depot formulation to provide for the controlled release of the active agent. In some cases, depot formulations contain one or more biodegradable polymeric or oligomeric carriers. Suitable polymeric carriers include, but are not limited to poly(lactic acid) (PLA), poly(lactic-co-glycolic acid) (PLGA), poly(lactic acid)-polyethyleneglycol (PLA-PEG) block copolymers, polyanhydrides, poly(ester anhydrides), polyglycolide (PGA), poly-3-hydroxybutyrate (PHB) and copolymers thereof, poly-4-hydroxybutyrate (P4HB), polycaprolactone, cellulose, hydroxypropyl methylcellulose, ethylcellulose, as well as blends, derivatives, copolymers, and combinations thereof.

In depot formulations containing a polymeric or oligomeric carrier, the carrier and active agent can be formulated as a solution, an emulsion, or suspension. One or more compounds, and optionally one or more additional active agents, can also be incorporated into polymeric or oligomeric microparticles, nanoparticles, or combinations thereof.

In some cases, the formulation is fluid and designed to solidify or gel (i.e., forming a hydrogel or organogel) upon injection. This can result from a change in solubility of the composition upon injection, or for example, by injecting a pre-polymer mixed with an initiator and/or crosslinking agent. The polymer matrix, polymer solution, or polymeric particles entrap the active agent at the injection site. As the polymeric carrier is gradually degraded, the active agent is released, either by diffusion of the agent out of the matrix and/or dissipation of the matrix as it is absorbed. The release rate of the active agent from the injection site can be controlled by varying, for example, the chemical composition, molecular weight, crosslink density, and/or concentration of the polymeric carrier. Examples of such systems include those described in U.S. Pat. Nos. 4,938,763, 5,480, 656 and 6,113,943.

Depot formulations can also be prepared by using other rate-controlling excipients, including hydrophobic materials, including acceptable oils (e.g., peanut oil, corn oil, sesame oil, cottonseed oil, etc.) and phospholipids, ion-exchange resins, and sparingly soluble carriers.

The depot formulation can further contain a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

Implants

Implantation of a slow-release or sustained-release system, such that a constant level of dosage is maintained is also contemplated herein. In such cases, the active agent(s) provided herein can be dispersed in a solid matrix optionally coated with an outer rate-controlling membrane. The compound diffuses from the solid matrix (and optionally through the outer membrane) sustained, rate-controlled release. The solid matrix and membrane may be formed from any suitable material known in the art including, but not limited to, polymers, bioerodible polymers, and hydrogels.

C. Pulmonary Formulations

The compounds described herein can be formulated for parenteral administration. Pharmaceutical formulations and methods for the pulmonary administration are known in the art.

The respiratory tract is the structure involved in the exchange of gases between the atmosphere and the blood stream. The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchioli which then lead to the ultimate respiratory zone, the alveoli, or deep lung, where the exchange of gases occurs.

The alveolar surface area is the largest in the respiratory system and is where drug absorption occurs. The alveoli are covered by a thin epithelium without cilia or a mucus blanket and secrete surfactant phospholipids. Effective delivery of therapeutic agents via pulmonary routes requires that the active agent be formulated so as to reach the alveoli.

In the case of pulmonary administration, formulations can be divided into dry powder formulations and liquid formulations. Both dry powder and liquid formulations can be used to form aerosol formulations. The term aerosol as used herein refers to any preparation of a fine mist of particles, which can be in solution or a suspension, whether or not it is produced using a propellant.

Useful formulations, and methods of manufacture, are described by Caryalho, et al., J Aerosol Med Pulm Drug Deliv. 2011 April; 24(2):61-80. Epub 2011 Mar. 16, for delivery of chemotherapeutic drugs to the lungs.

1. Dry Powder Formulations

Dry powder formulations are finely divided solid formulations containing one or more active agents which are suitable for pulmonary administration. In dry powder formulations, the one or more active agents can be incorporated in crystalline or amorphous form.

Dry powder formulations can be administered via pulmonary inhalation to a patient without the benefit of any carrier, other than air or a suitable propellant. Preferably, however, the dry powder formulations include one or more pharmaceutically acceptable carriers.

The pharmaceutical carrier may include a bulking agent, such as carbohydrates (including monosaccharides, polysaccharides, and cyclodextrins), polypeptides, amino acids, and combinations thereof. Suitable bulking agents include fructose, galactose, glucose, lactitol, lactose, maltitol, maltose, mannitol, melezitose, myoinositol, palatinite, raffinose, stachyose, sucrose, trehalose, xylitol, hydrates thereof, and combinations thereof.

The pharmaceutical carrier may include a lipid or surfactant. Natural surfactants such as dipalmitoylphosphatidylcholine (DPPC) are the most preferred. This is commercially available for treatment of respiratory distress syndrome in premature infants. Synthetic and animal derived pulmonary surfactants include:

Synthetic Pulmonary Surfactants

Exosurf—a mixture of DPPC with hexadecanol and tyloxapol added as spreading agents Pumactant (Artificial Lung Expanding Compound or ALEC)—a mixture of DPPC and PG KL-4—composed of DPPC, palmitoyl-oleoyl phosphatidylglycerol, and palmitic acid, combined with a 21 amino acid synthetic peptide that mimics the structural characteristics of SP-B.

Venticute—DPPC, PG, palmitic acid and recombinant SP-C

Animal Derived Surfactants

Alveofact—extracted from cow lung lavage fluid

Curosurf—extracted from material derived from minced pig lung

Infasurf—extracted from calf lung lavage fluid

Survanta—extracted from minced cow lung with additional DPPC, palmitic acid and tripalmitin Exosurf, Curosurf, Infasurf, and Survanta are the surfactants currently FDA approved for use in the U.S.

The pharmaceutical carrier may also include one or more stabilizing agents or dispersing agents. The pharmaceutical carrier may also include one or more pH adjusters or buffers. Suitable buffers include organic salts prepared from organic acids and bases, such as sodium citrate or sodium ascorbate. The pharmaceutical carrier may also include one or more salts, such as sodium chloride or potassium chloride.

Dry powder formulations are typically prepared by blending one or more active agents with a pharmaceutical carrier. Optionally, additional active agents may be incorporated into the mixture. The mixture is then formed into particles suitable for pulmonary administration using techniques known in the art, such as lyophilization, spray drying, agglomeration, spray coating, extrusion processes, hot melt particle formation, phase separation particle formation (spontaneous emulsion particle formation, solvent evaporation particle formation, and solvent removal particle formation), coacervation, low temperature casting, grinding, milling (e.g., air-attrition milling (jet milling), ball milling), high pressure homogenization, and/or supercritical fluid crystallization.

An appropriate method of particle formation can be selected based on the desired particle size, particle size distribution, and particle morphology. In some cases, the method of particle formation is selected so as to produce a population of particles with the desired particle size, particle size distribution for pulmonary administration. Alternatively, the method of particle formation can produce a population of particles from which a population of particles with the desired particle size, particle size distribution for pulmonary administration is isolated, for example by sieving.

It is known in the art that particle morphology affects the depth of penetration of a particle into the lung as well as uptake of the drug particles. As discussed above, drug particles should reach the alveoli to maximize therapeutic efficacy. Accordingly, dry powder formulations is processed into particles having the appropriate mass median aerodynamic diameter (MMAD), tap density, and surface roughness to achieve delivery of the one or more active agents to the deep lung. Preferred particle morphologies for delivery to the deep lung are known in the art, and are described, for example, in U.S. Pat. No. 7,052,678 to Vanbever, et al.

Particles having a mass median aerodynamic diameter (MMAD) of greater than about 5 microns generally do not reach the lung; instead, they tend to impact the back of the throat and are swallowed. Particles having diameters of about 3 to about 5 microns are small enough to reach the upper- to mid-pulmonary region (conducting airways), but may be too large to reach the alveoli. Smaller particles, (i.e., about 0.5 to about 3 microns), are capable of efficiently reaching the alveolar region. Particles having diameters smaller than about 0.5 microns can also be deposited in the alveolar region by sedimentation, although very small particles may be exhaled.

The precise particle size range effective to achieve delivery to the alveolar region will depend on several factors, including the tap density of particles being delivered. Generally speaking, as tap density decreases, the MMAD of particles capable of efficiently reaching the alveolar region of the lungs increases. Therefore, in cases of particles with low tap densities, particles having diameters of about 3 to about 5 microns, about 5 to about 7 microns, or about 7 to about 9.5 microns can be efficiently delivered to the lungs. The preferred aerodyanamic diameter for maximum deposition within the lungs can be calculated. See, for example, U.S. Pat. No. 7,052,678 to Vanbever, et al.

In some embodiments, the dry powder formulation is composed of a plurality of particles having a median mass aerodynamic diameter between about 0.5 to about 10 microns, more preferably between about 0.5 microns to about 7 microns, most preferably between about 0.5 to about 5 microns. In some embodiments, the dry powder formulation is composed of a plurality of particles having a median mass aerodynamic diameter between about 0.5 to about 3 microns. In some embodiments, the dry powder formulation is composed of a plurality of particles having a median mass aerodynamic diameter between about 3 to about 5 microns. In some embodiments, the dry powder formulation is composed of a plurality of particles having a median mass aerodynamic diameter between about 5 to about 7 microns. In some embodiments, the dry powder formulation is composed of a plurality of particles having a median mass aerodynamic diameter between about 7 to about 9.5 microns.

In some cases, there may be an advantage to delivering particles larger than about 3 microns in diameter. Phagocytosis of particles by alveolar macrophages diminishes precipitously as particle diameter increases beyond about 3 microns. Kawaguchi, H., et al., Biomaterials 7: 61-66 (1986); and Rudt, S. and Muller, R. H., J. Contr. Rel, 22: 263-272 (1992). By administering particles with an aerodynamic volume greater than 3 microns, phagocytic engulfment by alveolar macrophages and clearance from the lungs can be minimized.

In some embodiments, at least about 80%, more preferably at least about 90%, most preferably at least about 95% of the particles in dry powder formulation have aerodynamic diameter of less than about 10 microns, more preferably less than about 7 microns, most preferably about 5 microns. In some embodiments, at least about 80%, more preferably at least about 90%, most preferably at least about 95%, of the particles in dry powder formulation have aerodynamic diameter of greater than about 0.5 microns. In some embodiments, at least about 80%, more preferably at least about 90%, most preferably at least about 95%, of the particles in dry powder formulation have an aerodynamic diameter of greater than about 0.1 microns.

In some embodiments, at least about 80%, more preferably at least about 90%, most preferably at least about 95%, of the particles in dry powder formulation have aerodynamic diameter of greater than about 0.5 microns and less than about 10 microns, more preferably greater than about 0.5 microns and less than about 7 microns, most preferably greater than about 0.5 microns and less than about 5 microns. In some embodiments, at least about 80%, more preferably at least about 90%, most preferably at least about 95% of the particles in dry powder formulation have aerodynamic diameter of greater than about 0.5 microns and less than about 3 microns. In some embodiments, at least about 80%, more preferably at least about 90%, most preferably at least about 95% of the particles in dry powder formulation have aerodynamic diameter of greater than about 3 microns and less than about 5 microns. In some embodiments, at least about 80%, more preferably at least about 90%, most preferably at least about 95% of the particles in dry powder formulation have aerodynamic diameter of greater than about 5 microns and less than about 7 microns. In some embodiments, at least about 80%, more preferably at least about 90%, most preferably at least about 95% of the particles in dry powder formulation have aerodynamic diameter of greater than about 7 microns and less than about 9.5 microns.

In some embodiments, the particles have a tap density of less than about 0.4 g/cm$^3$, more preferably less than about 0.25 g/cm$^3$, most preferably less than about 0.1 g/cm$^3$. Features which can contribute to low tap density include irregular surface texture and porous structure.

In some cases, the particles are spherical or ovoid in shape. The particles can have a smooth or rough surface texture. The particles may also be coated with a polymer or other suitable material to control release of one or more active agents in the lungs.

Dry powder formulations can be administered as dry powder using suitable methods known in the art. Alternatively, the dry powder formulations can be suspended in the liquid formulation s described below, and administered to the lung using methods known in the art for the delivery of liquid formulations 2. Liquid Formulations Liquid formulations contain one or more compounds dissolved or suspended in a liquid pharmaceutical carrier.

Suitable liquid carriers include, but are not limited to distilled water, de-ionized water, pure or ultrapure water, saline, and other physiologically acceptable aqueous solutions containing salts and/or buffers, such as phosphate buffered saline (PBS), Ringer's solution, and isotonic sodium chloride, or any other aqueous solution acceptable for administration to an animal or human.

Preferably, liquid formulations are isotonic relative to physiological fluids and of approximately the same pH, ranging e.g., from about pH 4.0 to about pH 7.4, more preferably from about pH 6.0 to pH 7.0. The liquid pharmaceutical carrier can include one or more physiologically compatible buffers, such as a phosphate buffers. One skilled in the art can readily determine a suitable saline content and pH for an aqueous solution for pulmonary administration.

Liquid formulations may include one or more suspending agents, such as cellulose derivatives, sodium alginate, polyvinylpyrrolidone, gum tragacanth, or lecithin. Liquid formulations may also include one or more preservatives, such as ethyl or n-propyl p-hydroxybenzoate.

In some cases the liquid formulation may contain one or more solvents that are low toxicity organic (i.e., nonaqueous) class 3 residual solvents, such as ethanol, acetone, ethyl acetate, tetrahydofuran, ethyl ether, and propanol. These solvents can be selected based on their ability to readily aerosolize the formulation. Any such solvent included in the liquid formulation should not detrimentally react with the one or more active agents present in the liquid formulation. The solvent should be sufficiently volatile to enable formation of an aerosol of the solution or suspension. Additional solvents or aerosolizing agents, such as a freon, alcohol, glycol, polyglycol, or fatty acid, can also be included in the liquid formulation as desired to increase the volatility and/or alter the aerosolizing behavior of the solution or suspension.

Liquid formulations may also contain minor amounts of polymers, surfactants, or other excipients well known to those of the art. In this context, "minor amounts" means no excipients are present that might adversely affect uptake of the one or more active agents in the lungs.

3. Aerosol Formulations

The dry powder and liquid formulations described above can be used to form aerosol formulations for pulmonary administration. Aerosols for the delivery of therapeutic agents to the respiratory tract are known in the art. The term aerosol as used herein refers to any preparation of a fine mist of solid or liquid particles suspended in a gas. In some cases, the gas may be a propellant; however, this is not required. Aerosols may be produced using a number of standard techniques, including as ultrasonication or high pressure treatment.

Preferably, a dry powder or liquid formulation as described above is formulated into aerosol formulations using one or more propellants. Suitable propellants include air, hydrocarbons, such as pentane, isopentane, butane, isobutane, propane and ethane, carbon dioxide, chlorofluorocarbons, fluorocarbons, and combinations thereof. Suitable fluorocarbons include 1-6 hydrogen containing fluorocarbons, such as $CHF_2CHF_2$, $CF_3CH_2F$, $CH_2F_2CH_3$, and $CF_3CHFCF_3$ as well as fluorinated ethers such as $CF_3$—O—$CF_3$, $CF_2H$—O—$CHF_2$, and $CF_3$—$CF_2$—O—$CF_2$—$CH_3$. Suitable fluorocarbons also include perfluorocarbons, such as 1-4 carbon perfluorocarbons including $CF_3CF_3$, $CF_3CF_2CF_3$, and $CF_3CF_2CF_2CF_3$.

Preferably, the propellants include, but not limited to, one or more hydrofluoroalkanes (HFA). Suitable HFA propellants, include but are not limited to, 1,1,1,2,3,3,-heptafluoro-n-propane (HFA 227), 1,1,1,2-tetrafluoroethane (HFA 134) 1,1,1,2,25 3,3,3-heptafluoropropane (Propellant 227), or any mixture of these propellants.

Preferably, the one or more propellants have sufficient vapor pressure to render them effective as propellants. Preferably, the one or more propellants are selected so that the density of the mixture is matched to the density of the particles in the aerosol formulation in order to minimize settling or creaming of the particles in the aerosol formulation.

The propellant is preferably present in an amount sufficient to propel a plurality of the selected doses of the aerosol formulation from an aerosol canister.

4. Devices for Pulmonary Administration

In some cases, a device is used to administer the formulations to the lungs. Suitable devices include, but are not limited to, dry powder inhalers, pressurized metered dose inhalers, nebulizers, and electrohydrodynamic aerosol devices.

Inhalation can occur through the nose and/or the mouth of the patient. Administration can occur by self-administration of the formulation while inhaling, or by administration of the formulation via a respirator to a patient on a respirator.

Dry Powder Inhalers

The dry powder formulations described above can be administered to the lungs of a patient using a dry powder inhaler (DPI). DPI devices typically use a mechanism such as a burst of gas to create a cloud of dry powder inside a container, which can then be inhaled by the patient.

In a dry powder inhaler, the dose to be administered is stored in the form of a non-pressurized dry powder and, on actuation of the inhaler, the particles of the powder are inhaled by the subject. In some cases, a compressed gas (i.e., propellant) may be used to dispense the powder, similar to pressurized metered dose inhalers (pMDIs). In some cases, the DPI may be breath actuated, meaning that an aerosol is created in precise response to inspiration. Typically, dry powder inhalers administer a dose of less than a few tens of milligrams per inhalation to avoid provocation of cough.

DPIs function via a variety of mechanical means to administer formulations to the lungs. In some DPIs, a doctor blade or shutter slides across the dry powder formulation contained in a reservoir, culling the formulation into a flowpath whereby the patient can inhale the powder in a single breath. In other DPIs, the dry powder formulation is packaged in a preformed dosage form, such as a blister, tabule, tablet, or gelcap, which is pierced, crushed, or otherwise unsealed to release the dry powder formulation into a flowpath for subsequent inhalation. Still others DPIs release the dry powder formulation into a chamber or capsule and use mechanical or electrical agitators to keep the dry powder formulation suspended in the air until the patient inhales.

Dry powder formulations may be packaged in various forms, such as a loose powder, cake, or pressed shape for insertion in to the reservoir of a DPI.

Examples suitable DPIs for the administration of the formulations described above include the Turbohaler® inhaler (Astrazeneca, Wilmington, Del.), the Clickhaler® inhaler (Innovata, Ruddington, Nottingham, UK), the Diskus® inhaler (Glaxo, Greenford, Middlesex, UK), the EasyHaler® (Orion, Expoo, FI), the Exubera® inhaler (Pfizer, N.Y., N.Y.), the Qdose® inhaler (Microdose, Monmouth Junction, N.J.), and the Spiros® inhaler (Dura, San Diego, Calif.).

Pressurized Metered Dose Inhalers

The liquid formulations described above can be administered to the lungs of a patient using a pressurized metered dose inhaler (pMDI).

Pressurized Metered Dose Inhalers (pMDIs) generally include at least two components: a canister in which the liquid formulation is held under pressure in combination with one or more propellants, and a receptacle used to hold and actuate the canister. The canister may contain a single or multiple doses of the formulation. The canister may include a valve, typically a metering valve, from which the contents of the canister may be discharged. Aerosolized drug is dispensed from the pMDI by applying a force on the canister to push it into the receptacle, thereby opening the valve and causing the drug particles to be conveyed from the valve through the receptacle outlet. Upon discharge from the canister, the liquid formulation is atomized, forming an aerosol.

pMDIs typically employ one or more propellants to pressurize the contents of the canister and to propel the liquid formulation out of the receptacle outlet, forming an aerosol. Any suitable propellants, including those discussed above, may be utilized. The propellant may take a variety of forms. For example, the propellant may be a compressed gas or a liquefied gas. Chlorofluorocarbons (CFC) were once commonly used as liquid propellants, but have now been banned. They have been replaced by the now widely accepted hydrofluororalkane (HFA) propellants.

pMDIs are available from a number of suppliers, incuding 3M Corporation, Aventis, Boehringer Ingleheim, Forest Laboratories, Glaxo-Wellcome, Schering Plough and Vectura. In some cases, the patient administers an aerosolized formulation by manually discharging the aerosolized formulation from the pMDI in coordination with inspiration. In this way, the aerosolized formulation is entrained within the inspiratory air flow and conveyed to the lungs.

In other cases, a breath-actuated trigger, such as that included in the Tempo® inhaler (MAP Pharmaceuticals, Mountain View, Calif.) may be employed that simultaneously discharges a dose of the formulation upon sensing inhalation. These devices, which discharge the aerosol formulation when the user begins to inhale, are known as breath-actuated pressurized metered dose inhalers (baMDIs).

Nebulizers

The liquid formulations described above can also be administered using a nebulizer. Nebulizers are liquid aerosol generators that convert the liquid formulation described able, usually aqueous-based compositions, into mists or clouds of small droplets, preferably having diameters less than 5 microns mass median aerodynamic diameter, which can be inhaled into the lower respiratory tract. This process is called atomization. The droplets carry the one or more active agents into the nose, upper airways or deep lungs when the aerosol cloud is inhaled. Any type of nebulizer may be used to administer the formulation to a patient, including, but not limited to pneumatic (jet) nebulizers and electromechanical nebulizers.

Pneumatic (jet) nebulizers use a pressurized gas supply as a driving force for atomization of the liquid formulation. Compressed gas is delivered through a nozzle or jet to create a low pressure field which entrains a surrounding liquid formulation and shears it into a thin film or filaments. The film or filaments are unstable and break up into small droplets that are carried by the compressed gas flow into the inspiratory breath. Baffles inserted into the droplet plume screen out the larger droplets and return them to the bulk liquid reservoir. Examples of pneumatic nebulizers include, but are not limited to, PARI LC Plus®, PARI LC Sprint®, Devilbiss PulmoAide®, and Boehringer Ingelheim Respima®.

Electromechanical nebulizers use electrically generated mechanical force to atomize liquid formulations. The electromechanical driving force can be applied, for example, by vibrating the liquid formulation at ultrasonic frequencies, or by forcing the bulk liquid through small holes in a thin film. The forces generate thin liquid films or filament streams which break up into small droplets to form a slow moving aerosol stream which can be entrained in an inspiratory flow.

In some cases, the electromechanical nebulizer is an ultrasonic nebulizer, in which the liquid formulation is coupled to a vibrator oscillating at frequencies in the ultrasonic range. The coupling is achieved by placing the liquid in direct contact with the vibrator such as a plate or ring in a holding cup, or by placing large droplets on a solid vibrating projector (a horn). The vibrations generate circular standing films which break up into droplets at their edges to atomize the liquid formulation. Examples of ultrasonic nebulizers include DuroMist®, Drive Medical Beetle Neb®, Octive Tech Densylogic®, and John Bunn Nano-Sonic®.

In some cases, the electromechanical nebulizer is a mesh nebulizer, in which the liquid formulation is driven through a mesh or membrane with small holes ranging from 2 to 8 microns in diameter, to generate thin filaments which break up into small droplets. In certain designs, the liquid formulation is forced through the mesh by applying pressure with a solenoid piston driver (for example, the AERx® nebulizer), or by sandwiching the liquid between a piezoelectrically vibrated plate and the mesh, which results in a oscillatory pumping action (for example EFlow®, AerovectRx®, or TouchSpray® nebulizer). In other cases, the mesh vibrates back and forth through a standing column of the liquid to pump it through the holes. Examples of such nebilzers include the AeroNeb Go®, AeroNeb Pro®. PARI EFlow®, Omron 22UE®; and Aradigm AERx®.

Electro Hydro Dynamic Aerosol Devices

The liquid formulations described above can also be administered using an electrohydrodynamic (EHD) aerosol device. EHD aerosol devices use electrical energy to aerosolize liquid drug solutions or suspensions. Examples of EHD aerosol devices are known in the art. See, for example, U.S. Pat. No. 4,765,539 to Noakes et al. and U.S. Pat. No. 4,962,885 to Coffee, R. A.

The electrochemical properties of the formulation may be important parameters to optimize when delivering the liquid formulation to the lung with an EHD aerosol device and such optimization is routinely performed by one of skill in the art.

V. Methods of Treatment

Pharmaceutical formulations containing one or more of the compounds described herein can be administered to treat microbial infections, such as bacterial infection. Assays have been developed to assess compounds for their ability to inhibit enzyme activity, protein transport (using a vesicle or whole cell system), and bacterial viability.

SecA exerts its transporter functions while integrated into membrane in a bound form with the SecYEG complex. However, SecA's ATPase is functional in solution alone or in a membrane. In addition, SecA itself has a C-terminal regulatory sequence. Thus there are several ways to test SecA inhibitory activities. The ATPase activity can be examined using SecA alone in solution (intrinsic/regulated ATPase), truncated SecA without the C-terminal inhibitory sequence in solution (e.g., EcSecAN68, unregulated ATPase), SecA in membrane (membrane ATPase), and SecA in complex with SecYEG in membrane (translocation ATPase).

For functional assays, the in vitro translocation of proOmpA into *E. coli* membrane vesicles (protein translocation), can be used. A sensitive semi-physiological assay for electrophysiological measurement of protein-channel activity in the oocytes has also been developed. This assay is valuable, because of the ease of use, the small amount of materials (nanograms) needed, and the ability to study individual oocytes. The large size of oocytes can easily accommodate various manipulations and electrode penetration. The recording noise is very low from a large number of channels (calculated to be 200-1,000,000 channels). The activity is strictly dependent on the injection of exogenous SecA and membrane vesicles. Liposomes have been developed for measuring SecA activity that allows for easy demonstration that SecA alone can form a protein-conducting channel. The liposome system in the oocytes allows the sensitive detection of channel activities of various SecA (SecA2 has no channel activity) including *S. aureus* SecA1 (SaSecA1) and *S. pyogenes* SecA1 (SpSecA1).

To evaluate antimicrobial activity, the initial enzyme screening was done with the truncated form (unregulated ATPase) or soluble SecA2 because of its ease of use and sensitivity. The truncated EcSecAN68 SecA ATPase, membrane SecA ATPase, and membrane transport experiments revealed the intrinsic ability for the compounds to bind and inhibit the most relevant forms of the transporter/ATPase.

In one embodiment, membrane channel activities may be monitored by introducing a proteo-liposome, such as SecA-liposomes in oocytes. Preferably, the proteo-liposomes are purified reconstituted proteo-liposomes. In this embodiment, the expression of the SecA-liposome is very efficient, reaching up to 80%, preferably up to 90%, more preferably up to 95% of the expression rate, within hours of the injected oocytes. The oocytes can be reconstituted with membrane protein complexes, such as SecYEG and SecDF•YajC, to achieve more specific and efficient ion-channel activities. This method shortens the channel expression time and increases the expression rate, and allows for monitoring channel activities for protein-protein interaction in the oocytes. The injection of liposomes having encapsulated therein SecA homologs also allows similar assessments for other bacterial systems, which otherwise lack the homologs assays due to the strain specificity for translocation ATPase or protein translocation. The inhibitory effect of various SecA inhibitors may be evaluated by injecting liposomes containing either SecA or SecA coupled to SecYEG at various concentrations of a SecA inhibitor. Example 3 demonstrates the inhibitory effect Three structural classes of nM inhibitors of SecA have been developed.

Rose Bengal (RB)

A: RB analogs

SCA-41: R =

SCA-50: R =

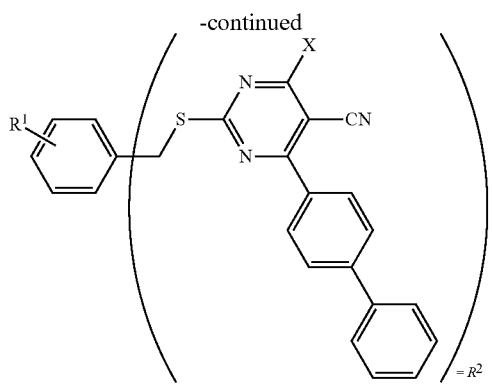

B: Pyrimidine analogs
SCA-8: X = -OH, R¹ = R²
(aka "dimer")
SCA-15: R' = p-N₃
SCA-93: R' = p-N₃, X = -NHOH

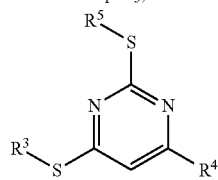

C: Triazole analogs
SCA-21: R⁴ = -SR³, R⁵ = Me-
SCA-107: R⁴ = -Cl, R⁵ = Me-
SCA-112 R⁴ = -Cl, R⁵ = Ph-

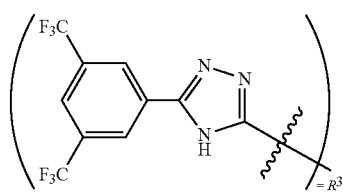

The inhibitors identified include (1) Rose Bengal (RB) analogs (Class A), (2) pyrimidine analogs (Class B), and (3) triazole analogs (Class C). Kinetic studies using selected analogs against EcSecA clearly suggest competitive inhibition against ATP at low ATP concentrations indicating the binding pocket being that of ATP. Such knowledge is critical to the computational work. At high ATP concentrations, the inhibition is non-competitive, presumably because of the existence of a secondary low-affinity ATP binding site.

A number of SecA inhibitors have shown potent inhibition of protein translocation at high nM concentrations in an in vitro (vesicle) model and in vivo oocyte model. For example, RB inhibits protein translocation at $IC_{50}$ of 250 nM. In the oocyte assay, RB (Class A) showed $IC_{50}$ of 400 nM in inhibiting SecA (*S. pyogenes, S. aureus*, and *E. coli*); SCA-8 (Class B) and SCA-107 (Class C) showed $IC_{50}$ of 500-900 nM. The inhibitory sensitivity of these assays parallels that of bacterial growth inhibition.

Selected inhibitors have shown potent antimicrobial effects including against drug-resistant bacteria such as *S. aureus* Mu50. In side-by-side comparisons, the inhibition potency for some SecA inhibitors surpasses that of commonly used antibiotics such as tetracycline (by more than 200 fold) and vancomycin (by up to 12-fold). For example, against drug resistant *S. aureus* Mu50 (MRSA and vancomycin-resistant), the $MIC_{95}$ values are 1.7 and 2.4 μM for RB analogs SCA-41 and SCA-50, 4.5 μM for pyrimidine analog SCA-93, and 1.5, 0.5, and 0.4 μM for triazole analogs SCA-21, SCA-107, and SCA-112. In contrast, the $MIC_{95}$ values are 5 μM for vancomycin, and over 100 μM for kanamycin, gentamycin, tetracycline, erythromycin and other antibiotics tested. For a highly virulent strain of *S. pyogenes*, MGAS5005, the situation is similar. The $MIC_{95}$ values for RB, SCA-15, SCA-21, SCA-50, SCA-93, SCA-107, and SCA-112 are 6.25, 3.13, 0.39, 6.25, 0.78 μM and 0.19 μM respectively.

SecA functions in the membrane as a protein-conducting channel. It is possible that SecA is accessible from the extracellular matrix and thus not susceptible to the effect of efflux, which is a common multidrug resistance (i.e., MDR) mechanism in general and in *S. aureus* and *S. pyogenes*, specifically. I Interestingly, most SecA1 in *S. pyogenes* is present in the membranes as micro-domain 'ExPortal', and it was found that 80-90% of SecA1 are in the membranes of *S. pyogenes* and *S. aureus*. Experimental evidence suggests that expression of various efflux pumps has no effect on the antimicrobial effects of the SecA inhibitors that were tested. For example, it was found that the MIC (bacteriostatic) did not increase and bactericidal (killing) effect was not attenuated for SCA-41 (Class A), SCA-15 (Class B), and SCA-21 (Class C) with the over expression of efflux pumps in *S. aureus*. Bacterial strains used include wild type (*S. aureus* Mu50, 8325 or 6538), deletion strains (NorA−, MepA−) and strains (NorA++, MepA++) with over-expressed efflux pumps. Such results strongly support the hypothesis that SecA inhibitors can overcome the effect of efflux and thus may not be subjected to multi-drug resistance problems.

It has also been demonstrated that SecA inhibition results in inhibition of virulence factor secretion. Specifically, SecA inhibitors such as SCA-15 can inhibit the secretion of hemolysin, enterotoxin B, and toxic shock syndrome toxin (TSST) by the MRSA Mu50 strain.

A summary of the in vitro inhibition effects is shown in Table 1:

TABLE 1

Summary of in vitro inhibition effects.

| $IC_{50}(\mu M)$ | Protein | RB | SCA-41 | SCA-50 | SCA-8 | SCA-15 | SCA-21 | SCA-107 | SCA-112 |
|---|---|---|---|---|---|---|---|---|---|
| Intrinsic ATPase | BsSECA | 20 | 30 | 33 | 8 | >100 | >100 | >200 | >200 |
| | BsSecA2 | 15 | 30 | 20 | 7 | 20 | 45 | 65 | ND |
| | SaSecA2 | 1 | 6 | ND | 3 | 13 | 43 | 50 | ND |
| | EcSecA N68 | 1 | 8 | 4 | 2 | 8 | 18 | 30 | 20 |
| | EcSecA | 60 | 30 | 60 | >100 | 30 | 32 | 28 | ND |
| Translocation ATPase | EcSecA | 1 | 15 | 60 | 6 | 30 | 20 | 28 | ND |

TABLE 1-continued

Summary of in vitro inhibition effects.

| $IC_{50}(\mu M)$ | Protein | RB | SCA-41 | SCA-50 | SCA-8 | SCA-15 | SCA-21 | SCA-107 | SCA-112 |
|---|---|---|---|---|---|---|---|---|---|
| Protein Translocation | EcSecA | 1 | 55 | 38 | 50 | >100 | 21 | 25 | 5 |
| Ion Channel activity | EcSecA | 0.4 | 3.4 | 2.3 | 1.5 | 4.2 | 2.4 | 1.6 | 1.3 |
| | SaSecA1 | 0.4 | 3.4 | 1.1 | 0.5 | 2 | 1.6 | 0.6 | 1 |
| | BGaSecA1 | 0.4 | 3.8 | 1 | 0.9 | 2.8 | 1.5 | 0.7 | 1 |
| | PASecA | 0.3 | 3.6 | 3 | 1.5 | 3.2 | 1.5 | 1.3 | 1.1 |
| | BsSecA | 0.3 | 3 | 2.5 | 1.2 | 3 | 2.6 | 2.1 | 2.3 |
| | MsSecA | 0.4 | 3.5 | 2.5 | 1.3 | 3 | 2 | 2.5 | 2.3 |
| | MtbSecA | 0.5 | 3.2 | 3 | 1.7 | 3.1 | 2 | 2 | 2 |
| | SpSecA | 0.9 | 3 | 1.9 | 1.5 | 3.5 | 1 | 0.7 | 1.3 |

A comparison of the activities of the compounds described herein with other antibiotics is shown in Table 2:

TABLE 2

Comparison of the activities of RB analogs and known antibiotics against SecA inhibition.

| | | Strains | | | |
|---|---|---|---|---|---|
| | | S. aureus Mu50 | | B. anthracis Sterne | |
| | Antbiotics | Bacteriostatic $MIC_{95}$ (µg/ml) | Bactericidal | Bacteriostatic $MIC_{95}$ (µg/ml) | Bacteriostatic |
| RB & analogs | RB | 40.7 | + | 12.2 | ND |
| | SCA-41 | 1.7 | ND | 1.1 | + |
| | SCA-50 | 2.4 | + | 1.7 | + |
| Pyrimidine analogs | SCA-15 | 10.9 | + | 2.2 | + |
| | SCA-93 | 4.5 | ND | 1.6 | ND |
| Bistriazole analogs | SCA-21 | 1.5 | + | 3.0 | + |
| | SCA-112 | 0.4 | ND | 0.8 | ND |
| Glycopeptides | Vancomycin | 5 | + | 2.5 | + |
| Penicillins | Ampicillin | 7.8 | + | >20 | + |
| Aminoclycosides | Gentamycin | >500 | + | 5 | + |
| Polypeptides | Polymyxin B | 15 | + | 10 | + |
| Tetracyclines | Tetracycline | 200 | − | 0.1 | − |
| Macrolides | Erythromycin | >500 | − | 0.3 | − |
| Other | Chloramphenic | >40 | − | 10 | − |

A. Dosages

The precise dosage administered to a patient will depend on many factors, including the physical characteristics of the patient (e.g., weight), the degree of severity of the disease or disorder to be treated, and the presence or absence of other complicating diseases or disorders and can be readily determined by the prescribing physician.

In certain embodiments, the compound(s) is administered at a dosage equivalent to an oral dosage of between about 0.005 mg and about 500 mg per kg of body weight per day, more preferably between about 0.05 mg and about 100 mg per kg of body weight per day, most preferably between about 0.1 mg and about 10 mg per kg of body weight per day.

B. Therapeutic Administration

Pharmaceutical formulations may be administered, for example, in a single dosage, as a continuous dosage, one or more times daily, or less frequently, such as once a week. The pharmaceutical formulations can be administered once a day or more than once a day, such as twice a day, three times a day, four times a day or more. In certain embodiments, the formulations are administered orally, once daily or less.

The pharmaceutical formulations are administered in an effective amount and for an effective period of time to elicit the desired therapeutic benefit. In certain embodiments, the pharmaceutical formulation is administered for a period of at least one week, two weeks, three weeks, four weeks, one month, two months, three months, four months, five months, six months, seven months, eight months, nine months, ten months, eleven months, one year, or longer.

The pharmaceutical formulations may also be administered prophylactically, e.g., to patients or subjects who are at risk for infection.

The exact amount of the formulations required will vary from subject to subject, depending on the species, age, sex, weight and general condition of the subject, extent of the disease in the subject, route of administration, whether other drugs are included in the regimen, and the like. Thus, it is not possible to specify an exact dosages for every formulation. However, an appropriate dosage can be determined by one of ordinary skill in the art using only routine experimentation. For example, effective dosages and schedules for administering the compositions may be determined empirically, and making such determinations is within the skill in the art.

Dosage can vary, and can be administered in one or more dose administrations daily, for one or several days. Guidance can be found in the literature for appropriate dosages for given classes of pharmaceutical products.

1. Co-Administration with Active Agents

In other embodiments, the compounds disclosed herein can be co-administered with one or more additional therapeutic, prophylactic, or diagnostic agents. Co-administration, as used herein, includes administration within the same dosage form or within different dosage forms. For those embodiments where the compounds described herein and the one or more additional therapeutic, prophylactic, or diagnostic agents are administered in different dosage forms, the dosage forms can be administered simultaneously (e.g., at the same time or essentially at the same time) or sequentially. "Essentially at the same time" as used herein generally means within ten minutes, preferably within five minutes, more preferably within two minutes, most preferably within in one minute. Dosage forms administered sequentially can be administered within several hours of each other, e.g., with ten hours, nine hours, eight hours, seven hours, six hours, five hours, four hours, three hours, two hours, one hour, 30 minutes, 20 minutes, or 15 minutes.

EXAMPLES

Example 1

Model SecA Inhibitors

General

Strains and plasmids used in this study were: *E. coli* K-12 strain MC4100, NR698 (MC4100 imp4213), a leaky mutant with increased outer membrane permeability supplied by Thomas J. Slhavy (Princeton University, USA); BA13 (MC4100 secA13(am) supF(ts)), pT7-SecA and pT7div supplied by D. B. Oliver; pIMBB28 obtained from Prof. Anastasios Economou (University of Athens, Greece); F1F0-proton ATPase-enriched membrane of *E. coli* strain KY7485 supplied by Prof. William S. Brusilow (Wayne State University, USA); *B. subtilis* strain 168 (lab stock). Luria-Bertani (LB) liquid and solid (1.5% agar) media with glucose (0.2%) were used for bacterial growth.

Fluorescein analogues were purchased from Sigma-Aldrich (St. Louis, Mo., USA) and were dissolved in $H_2O$ (for Rose Bengal, erythrosin B, and fluorescein) or DMSO (for diiodofluorescein, eosin Y, and dinitrofluorescein).

Bacteriostatic and Bactericidal Effects

Plate assay: A 0.5 mL culture of bacterial cells (exponential phase, OD600=0.5) was mixed with LB (4 mL) supplemented with glucose (0.2%) and soft agar (0.75%) and then poured into petri dishes. After the soft agar solidified, test compound (1 mL) was spotted on the surface of the culture. Bacteriostatic effects were judged by the appearance of a clear zone of growth inhibition after overnight incubation at 37° C.

Liquid culture assay: Bacterial cells of exponential phase (OD600=0.5-0.8) were diluted to an OD600 value of 0.05 with LB supplemented with glucose (0.2%). The diluted culture (90 mL) was incubated with inhibitor or $H_2O$ as control (10 mL) at 37° C. with shaking (1000 rpm, Eppendorf Thermomixer R, Eppendorf, Germany). After 14 h of incubation, the OD600 value was determined. The inhibition of cell growth (or bacteriostatic effects) was evaluated using the relative decrease in the OD600 value.

Bactericidal effect assay: The inhibitor or $H_2O$ as control (40 μL) was added to bacteria cultures (360 μL, exponential phase, OD600=0.5). After 1 h of incubation at 37° C., cultures were spread on LB agar plates after serial dilution, and the colony forming units (CFU) of surviving cells were counted after overnight incubation at 37° C.

Protein Preparation

The N-terminal catalytic domain of SecA from *E. coli* (EcN68) was overexpressed from pIMBB28. EcN68 was used for the early and initial screening because it has higher intrinsic activity and is more sensitive to inhibitors. The full-length SecA from *E. coli* (EcSecA) and *B. subtilis* (BsSecA) were overexpressed from pT7-SecA and pT7div, respectively. SecA proteins were purified as previously described. F1F0-proton ATPase-enriched membrane of *E. coli* strain KY7485 was prepared as described in the literature. F1F0-proton ATPase was partially purified by sucrose-gradient fractionation and then reconstituted into liposomes by dialysis. Non-radiolabeled and [$^{35}$S]-labeled proOmpA were purified as previously described. SecA-depleted BA13 membrane vesicles were prepared as described in the literature,[32] and washed with 6M urea to reduce endogenous ATPase activity.

In vitro ATPase Activity Assay

ATPase activity assays were performed as described previously with minor modifications. For the intrinsic ATPase assay, the reaction mixture (50 μL) contained EcN68 (1.8 μg), EcSecA (1.5 μg), or BsSecA (1.5 μg), ovalbumin (20 μg), ATP (1.2 mM), Tris-HCl (50 mM, pH 7.6), KCl (20 mM), $NH_4Cl$ (20 mM), $Mg(OAc)_2$ (2 mM), and DTT (1 mM). For the membrane ATPase assay, the reaction mixture (50 μL) was supplemented with urea-washed *E. coli* BA13 membrane (3 μg). The reaction mixture for the translocation ATPase assay also contained proOmpA (1 μg) in addition to the BA13 membrane. For the proton ATPase activity, reconstituted liposomes containing partially purified $F_1F_0$-proton ATPase were assayed using the same conditions as in the intrinsic ATPase assay. All reactions were carried out at 40° C. for an appropriate time in the linear ranges of the activity assay that was determined by the release of inorganic phosphate detected by the photometric method, with absorption measured at 660 nm (SmartSpec Plus, Bio-Rad Laboratories, Inc., Hercules, Calif., USA). The inhibitory effects are given as the percentage (%) of remaining ATPase activity relative to the controls in the absence of test compounds. All assays were performed at least in triplicate, and the results are expressed as the mean±standard error of the mean (SEM).

In vitro Protein Translocation Assay

The assay was performed as previously described using [$^{35}$S]-labeled proOmpA as a marker. [34] The protease-resistant translocated proteins were analyzed by SDS-PAGE, autoradiographed, and quantified by a densitometer (GS-800 Calibrated Densitometer, Bio-Rad, Hercules, Calif., USA).

Molecular Simulation of Docking Complexes

The structures of DI, EB, RB and CJ-21058 were docked into the ATP site of EcSecA using DOCK 6 to generate their predicted binding pose. Residues within a radius of 6 angstroms around the center of ATP were defined as the active site to construct a grid. The active site included residues Gly 80, Met81, Arg82, His 83, Phe84, Gln 87, Arg103, Thr 104, Gly 105, Glu 106, Gly 107, Lys 108, Thr 109, Leu110, Arg138, Asp209, Glu 210, Arg 509, and Gln 578. The subsequent computational work was conducted as described previously. Briefly, the docked complexes were solvated by using the TIP3P water model, and then subjected to 500 steps of molecular mechanics minimization and molecular dynamics simulations at 300 K for 1.5 ns using the SANDER module in the AMBER 8 program.

Results

A series of fluorescein analogues were screened against EcSecA using the intrinsic ATPase of the truncated N-terminal catalytic domain EcN68 (unregulated ATPase). Those fluorescein analogues with significant IC50 values are shown in Table 3.

TABLE 3

Screen of fluorescein analogs using EcN68 SecA ATPase

| Compound | IC$_{50}$ [µM] |
| --- | --- |
| Rose bengaL (RB) | 0.5 |
| Erythrosin B (EB) | 2 |
| Diiodofluorescein (DI) | 30 |
| Eosin Y (EY) | 25 |
| Dinitrofluorescein (DN) | 50 |
| Sodium azide | >10 |

[a] Fluorescein analogues were applied to the intrinsic ATPase assay of EcN68 as described in the Experimental Section.

Among the screened compounds, RB and EB were the most effective with IC50 values of 0.5 µM and 2 µM, respectively. Since RB and EB are known to inhibit a number of ATPases from animal tissues, we tested whether these compounds inhibit other *E. coli* ATPases, such as the $F_1F_0$-proton ATPase. The $IC_{50}$ values of RB and EB against $F_1F_0$-proton ATPase are approximately 10 µM and 30 µM, respectively. The data indicate that RB and EB could be general ATPase inhibitors. However, they are more effective on the catalytic SecA ATPase. It has been previously reported that some ATPases from animal tissues can be inhibited by RB and EB through photo-oxidation and subsequent reactions.

In order to fully understand the ability of these fluorescein analogues to inhibit the biological relevant SecA ATPase, the effect of these compounds on all three forms of the SecA ATPase was investigated. The inhibitory effects on the full-length SecA alone (regulated intrinsic ATPase) were evaluateed. As expected, the $IC_{50}$ values (~20-30 µM) for RB and EB are higher than those measured against the unregulated ATPase (truncated SecA, EcN68). The inhibitory effects of RB and EB on the membrane and translocation ATPase activities of EcSecA was also investigated. It is interesting to note that both RB and EB show the following trends in terms of their affinity for the different forms of SecA ATPase: unregulated ATPase (EcN68), translocation ATPase, membrane ATPase and intrinsic ATPase. RB showed $IC_{50}$ values of 0.5, 0.9 and 5 µM for unregulated, translocation and membrane ATPase activities respectively. In the presence of the C-terminal domain (i.e., the native regulated form of SecA ATPase), the IC50 value is higher (25 µM). EB shows a similar trend in inhibiting the different forms of SecA ATPase, that is, higher potency against unregulated ATPase (truncated SecA), translocation and membrane ATPase than the regulated intrinsic ATPase (full-length SecA) activities. However, the potency of EB is lower than that of RB with $IC_{50}$ values of approximately 10-20 µM. The significant differences in sensitivities of the three ATPase forms of EcSecA also indicate that conformational changes of SecA induced by the interaction with membranes and precursors can influence the accessibility of the enzyme to inhibitors. In addition, the inhibition profile of RB and EB on SecA from Gram-positive *B. subtilis* (BsSecA), which has a high homology (51% identity) to EcSecA and much higher intrinsic ATPase activity, was also determined. As expected, both RB and EB show inhibitory effects on the intrinsic ATPase activity of BsSecA, with RB as the more potent inhibitor.

The inhibition of ATPase activity is only relevant if it also results in the inhibition of protein translocation. Therefore, the effects of RB and EB on the SecA-dependent protein translocation in vitro were investigated. It was found that the in vitro translocation of precursor proOmpA into membrane vesicles is severely inhibited by RB and EB. Interestingly, the SecA-dependent protein translocation is about three- to four-times more sensitive to RB and EB than the translocation ATPase activity. Consistent with the result against translocation ATPase activity, RB shows a stronger inhibitory effect on protein translocation (IC50=0.25 µM) than EB (1050=4 µM). Sodium azide is a well-known SecA ATPase inhibitor; however, the intrinsic ATPase of SecA is not inhibited by sodium azide at concentrations as high as 10 mM. According to a previous report, the inhibitory effects of sodium azide against the translocation ATPase activity of SecA ($IC_{50}$=5 mM) and the in vitro protein translocation ($IC_{50}$=0.6 mM) are moderate. On the other hand, RB inhibits both the translocation ATPase activity and in vitro protein translocation very efficiently, with $IC_{50}$ values of 0.9 µM and 0.25 µM, respectively, which are approximately several thousand-times more effective than sodium azide.

The SecA-dependent protein translocation is essential for maintaining the normal physiology of bacteria. The above-mentioned fluorescein analogues inhibit bacterial growth in plate assays. *E. coli* MC4100 (wild-type), a Gram-negative bacteria, is very resistant to the fluorescein analogues, while its permeable leaky mutant NR698 shows high sensitivity. Such results suggest that the outermembrane barrier could be the reason for the observed difference in activity. Among the tested fluorescein analogues, diiodofluorescein (DI), eosin Y (EY), and dinitrofluorescein (DN) show a MIC values in the millimolar range, while RB and EB exhibit stronger inhibitions with MIC values in the micromolar range. RB also completely inhibits the growth of *E. coli* NR698 in liquid culture at low concentrations (50 mm, data not shown). RB demonstrates the same level of bacteriostatic activity with or without 0.2% glucose supplemented to the media, suggesting that F1F0-proton ATPase is not the primary target of the inhibition. The observed inhibition effect against bacterial growth validates the idea that SecA inhibitors can be used as antimicrobial agents. The inhibitory potency of RB is in the single-digit micromolar range, which is similar to the $IC_{50}$ values obtained using truncated SecA and SecA in the presence of membrane and precursor proteins. In the case of EB, the MIC value is much higher than the $IC_{50}$ values obtained in the ATPase inhibition assays. As seen with the results obtained using the wild-type strain of *E. coli*, minimal inhibition is observed. However, when the leaky mutant NR698 was used, the inhibitory potency increased substantially.

It is interesting to note that sodium azide has been reported to inhibit the translocation ATPase activity of SecA and the transport of a Gram-negative bacteria, is very resistant to the fluorescein analogues, while its permeable leaky mutant NR698 shows high sensitivity. Such results suggest that the outermembrane barrier could be the reason for the observed difference in activity. Among the tested fluorescein analogues, diiodofluorescein (DI), eosin Y (EY), and dinitrofluorescein (DN) show a MIC values in the millimolar range, while RB and EB exhibit stronger inhibitions with MIC values in the micromolar range. RB also completely inhibits the growth of *E. coli* NR698 in liquid culture at low concentrations (50 µM). RB demonstrates the same level of bacteriostatic activity with or without 0.2% glucose supplemented to the media, suggesting that $F_1F_0$-proton ATPase is not the primary target of the inhibition.

The observed inhibition effect against bacterial growth validates the idea that SecA inhibitors can be used as antimicrobial agents. The inhibitory potency of RB is in the single-digit micromolar range, which is similar to the $IC_{50}$ values obtained using truncated SecA and SecA in the presence of membrane and precursor proteins. In the case of EB, the MIC value is much higher than the $IC_{50}$ values obtained in the ATPase inhibition assays. Many reasons could contribute to such results. A key consideration is permeability. As seen with the results obtained using the wild-type strain of E. coli, minimal inhibition is observed. However, when the leaky mutant NR698 was used, the inhibitory potency increased substantially.

It is interesting to note that sodium azide has been reported to inhibit the translocation ATPase activity of SecA and the transport of precursor proteins across the inner membrane vesicles in vitro. SecA mutants that lack the stimulated translocation ATPase activity show defects of preprotein translocation in vitro. The in vitro translocation of precursor protein proOmpA into membrane vesicles is also inhibited by RB and EB. The in vitro translocation is even more sensitive to RB and EB than the translocation ATPase of EcSecA. Similar differences are also reported for sodium azide, but the in vitro protein translocation and the cell growth show similar sensitivities. In the case of RB and EB, in vivo growth is significantly less sensitive than in vitro protein translocation. This again could be due to the different membrane permeability of inhibitors. While sodium azide is a small inorganic molecule, RB and EB are much larger organic molecules that presumably exhibit lower permeability through bacterial membranes.

Since the permeability is important for the antibacterial effect of RB and EB, Gram-positive bacteria B. subtilis without the barrier of the outer-membrane were also examined. B. subtilis shows high sensitivities toward fluorescein analogues similar to the leaky E. coli mutant NR698. Indeed, RB and EB are very effective against Gram-positive bacteria where permeability is not a major problem.

In addition to the bacteriostatic studies, bactericidal effects were also investigated. After a one-hour treatment of exponential-phase cells, the colony-forming units (CFU) were determined after overnight incubation. RB showed strong bactericidal effects in a concentration dependent manner. With 100 μM of RB, cell survival decreased about 10 log units in leaky mutant E. coli NR698 and 8 log units in B. subtilis. The cell density did not decrease in the presence of 100 μM RB up to incubation times of 90 min, indicating that the bactericidal effects of RB on both bacteria were not caused by cell lysis. It has been reported that RB can inhibit the growth and kill Staphylococcus aureus in dark with unknown mechanisms, while some halogenated fluoresceins work as the photosensitizer in antimicrobial actions to kill various other bacteria, mainly through photo-oxidation. As discussed earlier, under the experimental condition in this study, photo-oxidation was not likely the primary mechanism of the bacteriostatic and bactericidal effects. Taken together, the results suggest that SecA could be the target of fluorescein analogues, and the inhibition of ATPase and SecA-dependent protein translocation might contribute to the antibacterial effects.

Because of the literature reports of other fluorescein analogues binding to enzymes containing nucleotide binding sites, in silico modeling was performed. Results from kinetic experiments suggest that RB and EB are competitive inhibitors against ATP at low ATP concentrations. Such results indicate that these compounds bind to the high-affinity ATP binding site. Thus, the structures of RB, EB, and DI were docked into the high-affinity ATP binding site. RB and EB show very similar predicted binding profiles, while DI shows a different conformation because of the lack of the diiodo moiety. For comparison, the binding mode of translocation activities of SecA, and bacterial growth might lead to alternative antimicrobial strategies. The fluorescein analogues used in this study are hydroxyxanthenes. Xanthene derivatives are well known and have been used as food additives for some time. Although some xanthene dyes have safety concerns, ten of those dyes could be approved by the US Food and Drug Administration (FDA) for food, drug, or cosmetic use RB is reportedly in phase II clinical trials for the treatment of metastatic melanoma. EB is at present the only xanthene derivative with FDA-approval for use in food. These fluorescein analogues have several advantages as SecA inhibitors: the convenience of commercial availability, high solubility in water, known chemical structure for further modification, and relatively low or no toxicity for food and drug use.

Example 2

Rose Bengal Analogs as SecA Inhibitors

General
Bacterial Strain and Growth Conditions

An outer membrane leaky mutant strain, E. coli NR698 (Ruiz et al., Cell, 2005, 121:307-317; provided by Thomas J Silhavy of Princeton University) and B. subtilis 168 (lab stock) were grown in Luria-Bertani (LB) medium at 37° C.

Protein Preparation

EcSecAN68, a truncated mutant of EcSecA containing the N-terminal catalytic domain, EcSecA, and BsSecA were used to study the in vitro inhibition effect of RB analogs. These proteins were purified as previously described (Chen et al., J. Biol. Chem. 1996, 271:29698-29706; Chen et al., J. Bacteriol. 1998, 180:527-537).

In vitro ATPase Activity Assay

The malachite green colorimetric assay was used to determine the inhibition effect of RB analogs against the ATPase activity of SecA proteins. In this assay, ATPase assays were carried out at different concentrations of the inhibitor, and $IC_{50}$ was defined as the concentration of the compound, which could inhibit 50% ATPase activity of the enzyme. Because RB analogs were dissolved in 100% DMSO, there was 5% DMSO in the final assay.

Bacteriostatic Effect

Bacteriostatic effects were tested by a liquid microdilution method according to the guidelines of the Clinical and Laboratory Standards Institute (*Performance Standards for Antimicrobial Susceptibility Testing*. M100-S21; 21st informational supplement. Clinical and Laboratory Standards Institute, Wayne, Pa. 2011). This assay was performed in a 96-well microtiter tray under normal room light condition. All bacteria were grown in LB broth, and when the $OD_{600}$ reach 0.5, the culture was diluted to $OD_{600} \approx 0.05$. 97.5 μl diluted culture and 2.5 μl of compound were added to each well. Cells were incubated at 37° C. with shaking (250 rpm) for 24 hr. MIC is the lowest concentration of inhibitors at which cells were not able to grow.

Bactericidal Effect

B. subtilis 168 was grown in LB broth. When $OD_{600}$ reached 0.5, 97.5 μl culture and 2.5 μl compound were added into a 1.5-mL Eppendorf tube. After incubation at 37° C. with shaking (1000 rpm) for 1 hr, cultures were serially diluted with LB and spread on LB plate. Bactericidal effect was determined by counting the number of reduced viable colonies. This assay was performed under normal room light condition.

SecA-lipsomes Ion-channel Activity Assays in the Oocytes

The liposomes were prepared as described previously (Hsieh et al., *J. Biol. Chem.* 2011, 286, 44702-44709; Lin et al., *J. Membr. Biol.* 2006, 214, 103-113; Lin et al., *J. Membr. Biol.* 2012, 245, 747-757). *E. coli* total lipids (Avanti) were dried, re-suspended in 150 mM KCl, and sonicated in an ice water bath until the solution became clear (usually for 3-5 mins). Samples of the liposomes were stored at −80° C. and thawed only once before use. Oocytes were obtained from live frog *Xenopus laevis* (*Xenopus* Express, Inc) and injected with sample mixtures as described. 50 nl of the sample mixtures were injected into dark pole site of oocytes using Nanoject II injector (Drummond Scientific Co., Broomall, Pa.). The ion current was recorded three hours after injection. The amount for each component is 120 ng liposomes, 120 ng SecA, 14 ng proOmpA, 2 mM ATP, and 1 mM $Mg^{2+}$. The effective concentration of each component in the oocytes was based on the average volume of oocytes of 500 nl.

Synthesis of Rose Bengal Analogs

3-Bromo-1-(2-hydroxyphenyl) propan-1-one (3)

To a mixture of resorcinol 1 (10 g, 91 mmol) and 3-chloropropionic acid 2 (10 g, 92 mmol) was added trifluoromethane sulfonic acid (29.6 mL) in one portion. After stirring at 80° C. for 30 min, the reaction mixture was cooled to room temperature and poured into 40 mL dichloromethane (DCM) and 40 mL water. The organic layer was separated and the aqueous layer was extracted with DCM twice. The combined organic layers was washed with water and brine, dried over Na2SO4, then filtered, and evaporated under reduced pressure. The crude product 3 (11.4 g) was used directly for the next step.

7-Hydroxychroman-4-one (4)

To a solution of 2 N NaOH 400 mL was added crude product 3 (11.4 g) at 0-5° C. in one portion. The solution was warmed up to room temperature over 2 hr, then acidified with 6N $H_2SO_4$ to pH~4, and finally extracted with ethyl acetate. The combined organic layers was washed with water and brine, dried over $Na_2SO_4$, filtered, and evaporated under reduced pressure to give the crude product 4, which was dried under vacuum overnight and used directly for the next step.

7-Methoxychroman-4-one (5)

To a solution of 4 in 200 mL acetone was added $K_2CO_3$ (10 g, 72.5 mmol) and excess amount of iodomethane (5 mL, 80.1 mmol). Then the reaction mixture was heated at reflux for 3 hr. The solid was filtered off and solvent was evaporated under reduced pressure. The resulting residue was purified by silica gel column chromatography (hexane: ethyl acetate 5:1) to give 5 (8.5 g, 53% for 3 steps). 1H-NMR (CDCl3): δ 7.86-7.83 (d, J=8.8 Hz, 1H), 6.60-6.58 (d, J=8.8 Hz, 1H), 6.42 (s, 1H), 4.54-4.52 (t, J=5.2 Hz, 1H), 3.85 (s, 3H), 2.78-2.75 (t, J=4.8 Hz, 1H); ESIMS: 179.1 [M+H]+.

7-Methoxy-3'-H-spiro[chroman-4,1'-isobenzofuran]-3'-imine (6)

To a solution of 2-bromobenzonitrile (250 mg, 1.37 mmol) in 5 mL THF was added 2.5 M n-BuLi (0.55 mL, 1.37 mmol) at −78° C., The reaction mixture was kept stirring under this condition for 40 min. Then 5 (150 mg, 0.91 mmol) in 4 mL THF was added slowly and the reaction mixture was stirred for another 30 min at the same temperature, before the reaction temperature was warmed up to room temperature over a period of 1 hr. The reaction was stopped with the addition of saturated $NH_4Cl$ and the mixture extracted with DCM. The DCM solution was washed with water and brine, and dried over $Na_2SO_4$. The solid was filtered off and the filtrate was evaporated under reduced pressure. The residue was purified by silica gel column chromatography (hexane: ethyl acetate 5:1) to give 6 (165 mg, 64%). $^1$H-NMR (CDCl$_3$): δ 7.95-7.94 (d, J=6.8 Hz, 1H), 7.59-7.52 (m, 2H), 7.19-7.17 (d, J=6.8 Hz 1H), 6.52-6.46 (m, 2H), 6.40-6.37 (dd, J=2.8, 8.8 Hz, 1H), 4.49-4.47 (dd, J=2.4, 7.2 Hz, 2H), 3.78 (s, 3H), 2.56-2.50 (m, 1H), 2.19-2.15 (d, J=14.8 Hz, 1H); $^{13}$C-NMR (CDCl$_3$): δ 166.3, 161.4, 156.4, 149.6, 132.6, 130.0, 129.6, 129.2, 123.8, 122.0, 113.7, 108.4, 101.3, 84.0, 63.1, 55.2, 36.0; ESI-MS: 282.1 [M+H]$^+$.

7-Methoxy-3'H-spiro[chroman-4,1'-isobenzofuran]-3'-one (7)

To a solution of 6 (205 mg, 0.73 mmol) in 10 mL ethanol and 10 mL water was added NaOH (0.5 g, 12.5 mmol). The reaction mixture was heated at reflux for 3.5 hr before cooling down to room temperature and acidification with 4 N HCl to pH~5. Then the reaction mixture was extracted with ethyl acetate, washed with water and brine, dried over $Na_2SO_4$, and filtered. Solvent evaporation under reduced pressure gave a residue, which was purified by silica gel column chromatography (hexane: ethyl acetate 10:1) to yield 7 (110 mg, 54%). $^1$H-NMR (CDCl$_3$): δ 7.98-7.96 (d, J=7.6 Hz, 1H), 7.71-7.68 (t, J=6.8 Hz 1H), 7.62-7.58 (t, J=7.2 Hz, 1H), 7.29-7.27 (d, J=7.2 Hz, 1H), 6.46-6.35 (m, 3H), 4.52-4.49 (d, J=11.2 Hz, 2H), 3.77 (s, 3H), 2.65-2.57 (m, 1H), 2.18-2.14 (d, J=14.4 Hz, 1H); $^{13}$C-NMR (CDCl$_3$): δ 169.3, 161.7, 156.8, 152.4, 134.5, 129.6, 129.5, 126.9, 125.6, 122.3, 112.4, 108.6, 101.4, 82.6, 63.2, 55.3, 35.9; GC-MS: 282 [M].

7-(Methoxychroman-4-yl)benzoic acid (8)

Compound 8 was synthesized following the same procedure for the preparation of 5a in 92% yield. $^1$H-NMR (CDCl$_3$): δ 8.10-8.08 (dd, J=0.8, 7.6 Hz, 1H), 7.48-7.44 (dt, J=1.2, 7.2 Hz, 1H), 7.35-7.31 (dt, J=1.2, 7.6 Hz, 1H), 7.12-7.09 (t, J=6.0 Hz, 1H), 6.72-6.70 (d, J=8.4 Hz, 1H), 6.47-6.42 (m, 2H), 5.23-5.19 (t, J=6.0 Hz, 1H), 4.22-4.17 (m, 2H), 3.84 (s, 3H), 2.48-2.44 (m, 1H), 2.11-2.04 (m, 1H); $^{13}$C-NMR (CDCl$_3$): δ 172.8, 159.3, 156.3, 148.4, 132.7, 131.4, 131.2, 130.8, 128.4, 126.3, 117.1, 107.7, 101.3, 63.9, 55.2, 36.4, 31.4; ESI-MS: 307.2 [M+Na]$^+$; GC-MS: 284 [M].

2-(7-Hydroxychroman-4-yl)benzoic acid (9)

To a solution of 8 (20 mg, 0.07 mmol) in DCM (2 mL) was slowly added 1M BBr$_3$ (0.21 mL, 0.21 mmol) in DCM at 0-5° C. under N$_2$ atmosphere. After stirring at the same temperature for 2 hr, the reaction was stopped with the addition of ice water before extraction with DCM. The combined organic layers was washed with water and brine, dried over $Na_2SO_4$, and filtered before solvent evaporation under reduced pressure. The crude product was purified by silica gel column chromatography (hexane: acetate 10:1) to afford 9 (12 mg, 64%). $^1$H-NMR (CDCl$_3$): δ 8.09-8.07 (d, d, J=1.6, 8.0 Hz, 1H), 7.48-7.44 (m, 1H), 7.35-7.29 (m, 1H), 7.11-7.09 (d, J=7.6 Hz, 1H), 6.67-6.65 (d, J=8.4 Hz, 1H), 6.41-6.41 (m, 2H), 6.36-6.39 (d, d, J=2.8, 8.4 Hz, 1H), 5.20-5.17 (t, J=9.2 Hz, 1H), 4.19-4.15 (m, 2H), 2.48-2.42 (m, 1H), 2.10-2.05 (m, 1H); $^{13}$C-NMR (CDCl$_3$): δ 156.3, 155.20, 148.3, 132.7, 131.5, 131.3, 130.7, 128.4, 126.3, 117.3, 108.4, 103.2, 63.9, 36.4, 31.4, 30.9; ESI-MS: 293.4 [M+Na]$^+$.

2-(6,8-dibromo-7-hydroxychroman-4-yl)benzoic acid (10a) and 2-(7-hydroxy-6,8-diiodochroman-4-yl)benzoic acid (10b)

For 10a: the same procedure for the preparation of 23a was followed with a 62% yield. $^1$H-NMR (CDCl$_3$): δ 8.21-8.29 (dd, J=1.2, 7.6 Hz, 1H), 7.77-7.73 (dt, J=1.6, 7.6 Hz, 1H), 7.61-7.56 (dt, J=1.2, 7.6 Hz, 1H), 7.40-7.39 (dd, J=0.8, 7.2 Hz, 1H), 7.00 (s, 1H), 4.71-4.68 (m, 1H), 4.32-4.27 (m, 1H), 3.40-3.36 (t, J=8.0 Hz, 1H), 2.48-2.24 (m, 1H), 2.23-2.17 (m, 1H); $^{13}$C-NMR (CDCl$_3$): δ 172.6, 162.7, 161.9, 139.7, 138.6, 135.8, 131.0, 129.4, 127.9, 126.6, 122.5, 106.8, 68.3, 38.3, 30.9, 30.3; ESI-MS: 429.2, 427.4, 426.0 [M+H]$^+$.

10b: the same procedure for the preparation of 23b was used in 65% yield. $^1$H-NMR (CDCl$_3$): δ 8.24-8.22 (d, J=8.0 Hz, 1H), 7.77-7.73 (dt, J=1.2, 7.6 Hz, 1H), 7.62-7.58 (dt, J=1.2, 8.0 Hz, 1H), 7.38-7.36 (d, J=7.6 Hz, 1H), 7.30 (s, 1H), 4.74-4.68 (m, 1H), 4.30-4.24 (m, 1H), 3.32-3.28 (t, J=7.6 Hz, 1H), 2.37-2.19 (m, 2H); ESI-MS: 543.0 [M+Na]$^+$.

1-Bromo-6-methoxynaphthalene (12)

To a suspension of anhydrous CuBr$_2$ (77 mg, 0.35 mmol) in anhydrous MeCN was added tert-butyl nitrite in one portion. The reaction mixture was stirred for 30 min at room temperature under N$_2$ atmosphere. A solution of 11 (50 mg, 0.29 mmol) in 2 mL MeCN was added to the suspension slowly and the resulting mixture was stirred for 1 hr at room temperature, and then poured into 2 mL 1N HCl. The organic phase was separated and the aqueous layer was extracted with ethyl acetate. The combined organic layers was washed with saturated NaHCO$_3$ and brine, and dried over Na$_2$SO$_4$. The solid was filtered off and the solvent was evaporated under reduced pressure. The residue was purified by silica gel column chromatography (hexane: acetate 20:1) to give 12 (10 mg, 14%). $^1$H-NMR (CDCl$_3$): δ 8.22-8.20 (d, J=9.2 Hz, 1H), 7.68-7.66 (d, J=8.0 Hz, 1H), 7.47-7.44 (dd, J=1.2, 7.6 Hz, 1H), 7.38-7.34 (t, J=8.0 Hz, 1H), 7.30-7.27 (dd, J=2.4, 9.2 Hz, 1H), 7.16-7.15 (d, J=2.8 Hz, 1H), 3.95 (s, 3H); $^{13}$C-NMR (CDCl$_3$): δ 158.2, 135.9, 131.9, 126.4, 126.2, 126.0, 126.0, 123.9, 119.7, 106.1, 55.3.

Methyl 2-(6-methoxynaphthalen-1-yl)benzoate (13)

A solution of 12 (50 mg, 0.2 mmol), (2-(methoxycarbonyl)phenyl) boronic acid (80 mg, 0.44 mmol), Pd(PPh$_3$)$_4$ (30 mg, 0.026 mmol), and K$_2$CO$_3$ (65 mg, 0.47 mmol) in 3 mL DMF was heated at 90-100° C. under N$_2$ atmosphere overnight. The reaction mixture was cooled to room temperature before water was added. The reaction mixture was extracted with ethyl acetate. The combined organic layers were washed with water and brine, and dried over Na$_2$SO$_4$. The solid was filtered off and the solvent was evaporated under reduced pressure. The crude product was purified by silica gel column chromatography (hexane: acetate 25:1) to afford 13 (34 mg, 56%). $^1$H-NMR (CDCl$_3$): δ 8.04-8.02 (dd, J=1.2, 8.0 Hz, 1H), 7.78-7.76 (d, J=8.0 Hz, 1H), 7.64-7.60 (dt, J=1.2, 7.6 Hz 1H), 7.54-7.40 (m, 4H), 7.22-7.19 (m, 2H), 7.07-7.04 (dd, J=2.8, 9.2 Hz, 1H), 3.98 (s, 3H), 3.42 (s, 3H), 2.19-2.15; ESI-MS: 293.2 [M+H]$^+$.

2-(6-Methoxynaphthalen-1-yl)benzoic acid (14)

To a solution of 13 (130 mg, 0.4 mmol) in 2.5 mL ethanol was added 1N NaOH (2.2 mL, 2.2 mmol). The reaction mixture was heated at reflux for 4 hr. The reaction mixture was cooled to room temperature and acidified with 2N HCl to pH~5. The mixture was extracted with ethyl acetate. The combined organic layers were washed with water and brine, and dried over Na$_2$SO$_4$. The solid was filtered off and the solvent was evaporated under reduced pressure to afford 14 (123 mg, 100%). $^1$H-NMR (CDCl$_3$): δ 8.10-8.08 (dd, J=1.2, 7.6 Hz, 1H), 7.76-7.74 (d, J=8.0 Hz, 1H), 7.65-7.61 (dt, J=1.2, 7.6 Hz 1H), 7.54-7.36 (m, 4H), 7.20-7.16 (m, 2H), 7.05-7.02 (dd, 9.2 Hz, 1H), 3.98 (s, 3H); ESI-MS: 279.4 [M+H]$^+$, 301.2 [M+Na]$^+$.

2-(6-Hydroxynaphthalen-1-yl)benzoic acid (15)

To a solution of 14 (24 mg, 0.086 mmol) in DCM (2 mL) was added 1M BBr$_3$ (0.26 mL, 0.26 mmol) in DCM slowly at 0-5° C. under N$_2$ atmosphere. After stirring at the same temperature for 2 hr, the reaction was stopped with the addition of ice water. The reaction mixture was extracted with DCM. The combined organic layers were washed with water and brine, and dried over Na$_2$SO$_4$. The solid was filtered off and the solvent was evaporated under reduced pressure. The crude product was purified by silica gel column chromatography (hexane: acetate 10:1) to afford 15 (15 mg, 67%). $^1$H-NMR (CD$_3$OD): δ 7.99-7.97 (dd, J=1.2, 7.6 Hz, 1H), 7.63-7.57 (m, 2H), 7.52-7.48 (dt, J=1.2, 7.6 Hz 1H), 7.39-7.31 (m, 3H), 7.15-7.15 (d, J=2.4 Hz, 1H), 7.08-7.06 (dd, J=2.4, 6.8 Hz, 1H), 6.96-6.93 (dd, J=2.8, 9.2 Hz, 1H), 4.93 (s, br, 1H); $^{13}$C-NMR (CD$_3$OD): δ 169.8, 154.7, 141.4, 139.6, 135.1, 132.3, 131.5, 131.0, 129.4, 127.1, 127.0, 126.9, 125.5, 125.2, 123.0, 117.7, 108.8; ESI-MS: 263.2 [M−H]$^−$.

2-(6-Hydroxy-5-iodonaphthalen-1-yl)benzoic acid (16)

Compound 16 was synthesized following the same procedure as that of 24b in 35% yield. $^1$H-NMR (CD$_3$OD): δ 8.09-8.06 (d, J=8.8 Hz, 1H), 8.01-7.99 (dd, J=1.2, 7.6 Hz, 1H), 7.63-7.594 (dt, J=1.2, 7.2 Hz, 1H), 7.55-7.47 (m, 2H), 7.33-7.13 (t, J=9.2 Hz, 2H), 7.15-7.13 (dd, J=0.8, 6.8 Hz 1H), 7.00-6.98 (d, J=9.2 Hz 1H); $^{13}$C-NMR (CD$_3$OD): δ 169.4, 155.0, 141.1, 140.2, 135.6, 132.1, 131.5, 131.1, 129.8, 129.6, 127.6, 127.5, 127.3, 126.7, 123.7, 116.0, 83.5; ESI-MS: 389.2 [M−H]$^−$.

3,6-Dihydroxy-9H-xanthen-9-one (18a)

2,2',4,4'-Tetrahydroxybenzophenone (5 g, 20.3 mmol) was heated at 210-220° C. (sand bath) in a 75 mL round-bottom pressure flask for 4 hr. The yellow powder in the reaction mixture changed to brown solid. The crude product was used for the next step without purification. $^1$H-NMR (DMSO-D$_6$): δ 10.81 (s, 2H), 7.99-7.97 (d, J=8.8 Hz, 2H), 6.87-6.81 (m, 4H); $^{13}$C-NMR (DMSO-D$_6$): δ 174.3, 163.8, 157.9, 128.2, 114.4, 114.1, 102.5; ESI-MS: 229.2 [M+H]$^+$.

2,4,5,7-Tetrabromo-3,6-dihydroxy-9H-xanthen-9-one (18b)

To a solution of 18 (500 mg, 2.2 mmol) and 49% HBr (1.8 mL, 10.96 mmol) in methanol (11 mL) and water (11 mL) was added 30% H$_2$O$_2$ (1.18 mL, 9.9 mmol) slowly at 0-5° C. The reaction mixture was allowed to warm to room temperature and stirred for an additional 4 hr. The solvent was evaporated under reduced pressure at room temperature, and the crude residue with brown color was purified by silica gel column chromatography (hexane: acetate 10:1) to afford 18b (715 mg, 60%). $^1$H-NMR (DMSO-D$_6$): δ 8.19-8.19 (d, J=0.8 Hz, 2H); $^{13}$C-NMR (CDCl$_3$): δ 172.3, 157.4, 153.2, 128.9, 115.7, 109.1; ESI-MS: 540.9, 542.8, 546.9 [M−H]$^-$.

3,6-Dihydroxy-4,5-diiodo-9H-xanthen-9-one (18c)

To a solution of 18 (500 mg, 2.2 mmol), KI (96 mg, 5.79 mmol) and KIO$_3$ (619 mg, 2.89 mmol) in methanol (4 mL) and water (16 mL) was added 1M HCl (8.93 mL, 8.93 mmol) slowly at room temperature and the reaction mixture was stirred overnight. The reaction was stopped with the addition of ice water and extracted with ethyl acetate. The combined ethyl acetate was washed with water and brine and dried over Na$_2$SO$_4$, and filtered. Solvent evaporation under reduced pressure followed by silica gel column chromatography (hexane: acetate 20:1) afforded 18c (598 mg, 57%). $^1$H-NMR (DMSO-D$_6$): δ 11.70 (s, 2H), 8.02-7.97 (dd, J=0.8, 8.4 Hz, 2H), 7.03-7.01 (dd, J=0.8, 8.4 Hz, 2H); ESI-MS: 480.8 [M+H]$^+$.

3,6-Dimethoxy-9H-xanthen-9-one (19)

In a 100 mL round-bottom flask, 18 (1 g, 4.4 mmol), K$_2$CO$_3$ (0.9 g, 6.6 mmol), MeI (1.1 mL, 17.5 mmol), and 50 mL acetone were added and the reaction mixture was heated at reflux for 3 hr. The reaction mixture was filtered and washed with ethyl acetate twice. The combine organic layers were evaporated and purified by silica gel column chromatography (hexane: acetate 5:1) to give compound 19 (2.3 g, 45% from 17). $^1$H-NMR (CDCl$_3$): δ 8.23-8.20 (dd, J=1.2, 8.8 Hz, 2H), 6.92-6.89 (dt, J=2.0, 8.8 Hz, 1H), 6.83 (s, 6H); $^{13}$C-NMR (CDCl$_3$): δ 176.1, 164.7, 158.0, 128.2, 115.7, 112.9, 100.2, 55.8; ESI-MS: 295.2 [M+K]$^+$.

9-Cyclopentylidene-3,6-dimethoxy-9H-xanthene (20a)

To a suspension of magnesium (307 mg, 12.8 mmol) in 100 mL anhydrous THF was added cyclopropyl bromide (1.4 mL, 12.5 mmol). The mixture was maintained at reflux temperature for 3 hr. At that point, the magnesium was almost completely disappeared. The reaction was cooled down to room temperature. A solution of 19 (1 g, 4.1 mmol) in 20 mL anhydrous THF was added slowly to the reaction mixture. The resulting mixture was stirred at room temperature overnight. Saturated NH$_4$Cl was added before extraction with ethyl acetate. The combined organic layers were washed with water and brine, dried over Na$_2$SO$_4$, and filtered. Solvent evaporation under reduced pressure yields a brown residue. After purification with silica gel column chromatography (hexane: acetate 20:1), 20a (780 mg, 65%) was obtained as a light yellow solid. $^1$H-NMR (CDCl$_3$): δ 7.41-7.99 (t, J=4.8, 4.4 Hz, 2H), 6.72-6.70 (m, 4H), 3.86 (s, 6H), 2.69-2.65 (t, J=6.8 Hz, 4H), 1.72-1.68 (m, 4H); $^{13}$C-NMR (CDCl$_3$): δ 158.9, 154.0, 138.8, 128.6, 119.5, 118.9, 108.8, 101.0, 55.4, 33.5, 25.9; ESI-MS: 309.5 [M+H]$^+$.

3,6-Dimethoxy-9-(propan-2-ylidene)-9H-xanthene (20b)

Compound 20b was synthesized following the same procedure as that of 20a in 55% yield. $^1$H-NMR (CDCl$_3$): δ 7.34-7.32 (d, J=8.4 Hz, 2H), 6.76-6.70 (m, 4H), 3.84 (s, 6H), 2.11 (s, 6H); $^{13}$C-NMR (CDCl$_3$): δ 158.8, 155.0, 128.9, 127.6, 121.7, 119.7, 108.8, 101.4, 55.4, 23.3; ESI-MS: 283.5 [M+H]$^+$.

9-Cyclopentyl-3,6-dimethoxy-9H-xanthene (21a)

To compound 20a (100 mg, 0.32 mmol) in 20 mL methanol was added a catalytic amount of 10% Pd-C. The reaction was degassed under vacuum and flushed with hydrogen 3 times. The reaction mixture was hydrogenated with an H$_2$ balloon for 2 hr. Then the reaction mixture was passed through silica gel in a small funnel and flushed with 2 mL of methanol. After solvent evaporation, the crude product was purified by silica gel column chromatograph (hexane: acetate 15:1) to afford 21a (98 mg, 97%). $^1$H-NMR (CDCl$_3$): δ 7.11-7.09 (d, J=8.4 Hz, 2H), 6.68-6.65 (m, 4H), 3.83 (s, 3H), 3.76-3.74 (d, J=8.4 Hz, 1H), 1.96-1.94 (d, J=6.0 Hz, 1H), 1.61-1.21 (m, 8H); $^{13}$C-NMR (CDCl$_3$): δ 159.0, 153.4, 129.5, 118.1, 109.3, 101.3, 55.4, 50.4, 42.0, 29.4, 24.2; ESI-MS: 311.3 [M+H]$^+$.

9-Isopropyl-3,6-dimethoxy-9H-xanthene (21b)

Compound 21b was synthesized following the same procedure as that of 21a in 87% yield. $^1$H-NMR (CDCl$_3$): δ 7.11-7.08 (dd, J=3.2, 6.8 Hz, 2H), 6.70-6.68 (m, 4H), 3.85 (s, 3H), 3.74 (m, 1H), 1.92 (m, 1H), 0.82-0.80 (dd, J=2.0, 6.8 Hz, 6H); $^{13}$C-NMR (CDCl$_3$): δ 159.1, 153.6, 129.8, 116.6, 109.4, 101.1, 55.3, 44.4, 38.0, 18.8; ESI-MS: 285.2 [M+H]$^+$.

9-Hexyl-3,6-dimethoxy-9H-xanthene (21c)

Compound 21c was synthesized following the same procedure as that of 21a in 78% yield. $^1$H-NMR (CDCl$_3$): δ 7.12-7.12 (d, J=7.6 Hz, 2H), 6.70-6.67 (m, 4H), 3.93 (m, 1H), 3.84 (m, 6H), 1.72-1.70 (m, 2H), 1.25-1.20 (m, J=2.4 Hz, 8H), 0.88-0.85 (t, J=6.4 Hz, 3H); $^{13}$C-NMR (CDCl$_3$): δ 159.0, 152.8, 129.1, 117.8, 109.7, 101.2, 55.3, 41.0, 37.5, 31.8, 29.4, 25.2, 22.6, 14.1; ESI-MS: 325.1 [M+H]$^+$.

9-Cyclohexyl-3,6-dimethoxy-9H-xanthene (21d)

Compound 21d was synthesized following the same procedure as that of 21a in 79% yield. $^1$H-NMR (CDCl$_3$): δ 7.09-7.06 (t, J=4.4 Hz, 2H), 6.99-6.66 (m, 4H), 3.8 (s, 6H), 3.70-3.69 (d, J=4.0 Hz, 1H), 1.69-1.58 (m, 6H), 1.14-0.88 (m, 5H); $^{13}$C-NMR (CDCl$_3$): δ 159.0, 153.7, 129.8, 117.0, 109.4, 101.1, 55.3, 48.0, 44.3, 29.3, 26.5, 26.2; ESI-MS: 325.1 [M+H]$^+$.

9-Cyclopentyl-9H-xanthene-3,6-diol (22a)

To a solution of 20a (440 mg, 1.4 mmol) in DCM (35 mL) was slowly added 1M BBr$_3$ (7 mL, 7 mmol) in DCM at 0-5° C. under N$_2$ atmosphere. After stirring at the same temperature for 2 hr, the reaction was stopped with the addition of ice water and then extracted with DCM. The combined DCM layers was washed with water and brine, dried over $Na_2SO_4$, and filtered. Solvent evaporation under reduced pressure followed by purification by silica gel column chromatography (hexane: acetate 10:1) afforded 22a (254 mg, 64%). $^1$H-NMR (CD$_3$OD): δ 6.94-6.92 (t, J=4.4 Hz, 2H), 6.53-6.51 (m, 4H), 3.54-3.52 (d, J=6.4 Hz 1H), 1.81-1.78 (m, 1H), 1.39-1.29 (m, 6H), 1.15-1.10 (m, 2H); $^{13}$C-NMR (CD$_3$OD): δ 156.2, 153.4, 129.5, 117.2, 109.9, 102.4, 50.4, 41.8, 29.0, 23.9; HRMS-ESI Calcd for $C_{18}H_{18}O_3$: 282.3337. Found: 281.1173 [M−H]$^-$; ESI-MS: 281.3 [M−H]$^-$.

9-Isopropyl-9H-xanthene-3,6-diol (22b)

Compound 22b was synthesized following the same procedure as that of 22a in 63% yield. $^1$H-NMR (CD$_3$OD): δ 6.98-6.96 (d, J=8.4 Hz, 2H), 6.56-6.49 (m, 4H), 3.61-3.60 (d, J=4.0 Hz 1H), 1.81-1.78 (m, 1H), 0.72-0.70 (d, J=6.4 Hz, 6H); $^{13}$C-NMR (CD$_3$OD): δ 156.4, 153.5, 129.6, 115.5, 109.9, 102.1, 44.1, 37.8, 17.8; ESI-MS: 255.1 [M−H]$^-$.

9-Hexyl-9H-xanthene-3,6-diol (22c)

Compound 22c was synthesized following the same procedure as that of 22a in 59.5% yield. $^1$H-NMR (DMSO): δ 9.46 (s, 2H), 7.91-7.89 (d, J=9.6 Hz, 2H), 6.52-6.50 (d, J=8.0 Hz, 2H), 6.43 (s, 2H), 3.81 (m, 1H), 1.98-0.74 (m, 13H); $^{13}$C-NMR (CDCl$_3$): δ 157.1, 152.5, 129.6, 116.1, 111.2, 102.7, 41.0, 36.7, 31.6, 29.1, 24.9, 22.4, 14.3; ESI-MS: 297.3 [M−H]$^-$.

9-Cyclohexyl-9H-xanthene-3,6-diol (22d)

Compound 22d was synthesized following the same procedure as that of 22a in 67% yield. $^1$H-NMR (CD$_3$OD): δ 6.95-6.93 (d, J=8.0 Hz, 2H), 6.54-6.49 (m, 4H), 3.56-3.55 (d, J=4.0 Hz, 1H), 1.62-1.36 (m, 6H), 1.08-0.77 (m, 5H); $^{13}$C-NMR (CD$_3$OD): δ 156.3, 153.6, 129.6, 115.9, 109.9, 102.1, 47.7, 44.0, 29.0, 26.2, 26.1; HRMS-ESI: Calcd for $C_{19}H_{20}O_3$: 296.36. Found: 295.1346 [M−H]$^-$; ESI-MS: 295.0 [M−H]$^-$.

2,4,5,7-Tetrabromo-9-cyclopentyl-9H-xanthene-3,6-diol (23a)

To a solution of 22a (82 mg, 0.29 mmol) and 49% HBr (0.24 mL, 1.45 mmol) in methanol (1 mL) was slowly added 30% $H_2O_2$ (0.15 mL, 1.31 mmol) at 0-5° C. Then the reaction was warmed to room temperature and stirred for an additional 2 hr. The solvent was evaporated under reduced pressure at room temperature and the crude orange product was purified by silica gel column chromatography (hexane: acetate 10:1) afford 23a (103 mg, 60%). $^1$H-NMR (CDCl$_3$): δ 7.41 (S, 2H), 3.75-3.73 (d, J=6.8 Hz, 1H), 2.03-0.89 (m, 9H); $^{13}$C-NMR (CDCl$_3$): δ 150.5, 149.3, 130.5, 119.5, 104.5, 100.0, 49.7, 42.4, 29.0, 23.8; ESI-MS: 596.8, 598.7 [M+H]$^+$.

9-Cyclopentyl-2,4,5,7-tetraiodo-9H-xanthene-3,6-diol (23b and 23c)

To a solution of 22a (134 mg, 0.48 mmol), KI (165.7 mg, 1.28 mmol) and KIO$_3$ (135 mg, 0.63 mmol) in methanol (0.26 mL) and water (1.54 mL) was slowly added 1M HCl (1.99 mL, 1.99 mmol) at room temperature. The the reaction was stirred overnight before the addition of ice water to stop the reaction. The reaction mixture was extracted with ethyl acetate and the combined ethyl acetate layers were washed with water and brine, and dried over $Na_2SO_4$. After filtering off the solid, the solvent was evaporated under reduced pressure. The crude product was purified with silica gel column chromatography (hexane: acetate 20:1) to afford 23b (156 mg, 42%) and 23c (53 mg, 17%). 23b: $^1$H-NMR (CDCl$_3$): δ 7.53 (s, 2H), 5.92 (s, bro, 2H), 3.69-3.67 (d, J=6.8 Hz 1H), 1.90 (m, 1H), 1.61-1.15 (m, 8H); $^{13}$C-NMR (CDCl$_3$): δ 153.3, 153.3, 137.8, 120.8, 74.4, 74.1, 50.0, 42.4, 29.4, 24.0; HRMS-ESI (−): Calcd for $C_{18}H_{14}I_4O_3$: 785.9198. Found: 784.7060 [M−H]$^-$. ESI-MS: 784.8 [M−H]$^-$. 23c: $^1$H-NMR (CDCl$_3$): δ 7.50 (s, 1H), 7.47 (s, 1H), 6.91 (s, 1H), 5.86 (s, bro, 2H), 3.68-3.66 (d, J=6.4 Hz, 1H), 1.87 (m, 1H), 1.54-1.44 (m, 6H), 1.13 (m, 2H); HRMS-ESI: Calcd for $C_{18}H_{15}I_3O_3$: 660.0233. Found: 658.8079 [M−H]$^-$. ESI-MS: 659.1 [M−H]$^-$.

2,4,5,7-Tetraiodo-9-isopropyl-9H-xanthene-3,6-diol (23d)

The synthesis of 23d followed the same procedure as for 23b in yield 43%. $^1$H-NMR (CDCl$_3$): δ 7.50 (s, 2H), 5.93 (s, 2H), 3.65-3.64 (d, J=4.0 Hz 1H), 1.88-1.83 (m, 1H), 0.98-0.74 (m, 6H); $^{13}$C-NMR (CDCl$_3$): δ 153.3, 153.3, 138.1, 119.1, 74.6, 74.0, 44.5, 38.0, 18.6, 14.2; ESI-MS: 758.8 [M−H]$^-$.

2-(3-Acetamidophenoxy)-4-nitrobenzoic acid (26,27)

To a solution of 24 (1.5 g, 7.44 mmol) in DMF (40 mL) was added 25 (1.24 g, 8.19 mmol), K$_2$CO$_3$ (1.5 g, 10.9 mmol) and copper powder (61 mg, 0.85 mmol). The reaction mixture was heated at 130° C. overnight. The reaction was cooled to room temperature and poured slowly over an iced 1N HCl solution (150 mL). The mixture was stirred until a brown solid formed. The solid was filtered and washed with cold water to give 26.

The crude solid was dissolved in concentrated sulfuric acid (10 mL) and heated at 80° C. for 1 hr. After cooling to room temperature, the reaction mixture was poured into ice (150 mL) and stirred for 1 hr. The precipitate was filtered and re-suspended in 2.5% aq. sodium carbonate. The solid was filtered and washed with cold water and dried under vacuum overnight. Product 27 was used for the next step directly without further purification. $^1$H-NMR (DMSO): δ 8.36-8.29 (m, 2H), 8.15-8.13 (m, 2H), 7.88-7.86 (d, J=8.8 Hz, 1H), 6.76-6.55 (m, 4H); ESI-MS: 279.0 [M+Na]$^+$.

3,6-Diamino-9H-xanthen-9-one (28)

To a solution of 27 (1.20 g, 4.22 mmol) in ethanol (100 mL) was added SnCl$_2$ (3.80 g, 16.88 mmol). The mixture was heated at reflux overnight. The solvent was evaporated under reduced pressure and residue was basified with 1N NaOH (80 mL) resulting in brown precipitates, which was directly used for the next step.

3,6-Bis(dimethylamino)-9H-xanthen-9-one (29)

To a solution of 28 (1 g, 4.42 mmol) in 20 mL DMF was added K$_2$CO$_3$ (3.66 g, 26.5 mmol) and iodomethane (1.65 mL, 26.5 mmol). The reaction mixture was heated at 100° C. overnight before being cooled down to room temperature and addition of 100 mL DCM. The reaction mixture was washed with water and brine, dried over Na$_2$SO$_4$, and filtered. Solvent evaporation under reduced pressure gave a crude product, which was purified by column chromatography (hexane: acetate 10:1 to 2:1) to afford 29 (975 mg, 78%). $^1$H-NMR (CDCl$_3$): δ 8.13-8.08 (d, J=5.2 Hz, 2H), 6.77-6.71 (m, 2H), 6.52-6.49 (M, 2H), 3.12 (S, 12H); ESI-MS: 283.1 [M+H]$^+$.

9-Cyclopentyl-N3,N3,N6,N6-tetramethyl-9H-xanthene-3,6-diamine (30)

To a suspension of magnesium (64 mg, 2.67 mmol) in 10 ml anhydrous THF was added cyclopropyl bromide (0.27 mL, 2.5 mmol). The reaction was heated at reflux for 3 hr. At that point the magnesium almost completely disappeared. The reaction was cooled down to room temperature. A solution of 29 (100 mg, 0.35 mmol) in 10 mL anhydrous THF was added slowly to the reaction mixture. The reaction was stirred at room temperature overnight. Saturated NH$_4$Cl was added before extraction of the reaction mixture with ethyl acetate. The combined organic layers were washed with water and brine, dried over Na$_2$SO$_4$, and filtered. Solvent evaporation under reduced pressure resulted in a brown residue, which was directly used for the next step.

To the crude product in 10 mL methanol was added a catalytic amount of 10% Pd-C. The mixture was degassed under vacuum before flushing with hydrogen 3 times. Hydrogenation was carried out at room temperature with a balloon filled with hydrogen. The reaction mixture was passed through silica gel in a small funnel followed by washing 2 times with methanol. Solvent evaporation under reduced pressure followed by purification by silica gel column chromatography (hexane: acetate 15:1) afforded 30 (64 mg, 54%). $^1$H-NMR (CDCl$_3$): δ 7.10-7.08 (d, J=8.0 Hz, 2H), 6.53-6.51 (m, 2H), 3.74 (m, 1H), 3.03 (s, 12H), 2.01 (m, 1H), 1.58-1.46 (m, 8H); $^{13}$C-NMR (CDCl$_3$): δ 153.7, 150.2, 129.4, 114.6, 107.6, 100.2, 50.8, 41.6, 40.7, 29.5, 24.3; ESI-MS: 337.1 [M+H]$^+$.

Results

To evaluate the inhibitory effect of synthesized Rose Bengal ("RB") analogs (Table 4), EcSecA N68 was used for the initial enzymatic ATPase screening assay. EcSecA N68 is a truncated protein of *E. coli* SecA that lacks the down regulatory C-terminus, which allosterically inhibit the ATPase activity, and is the best SecA protein for screening a large number of compounds as described previously (Chen et al., *Bioorg Med Chem* 2010, 18(4), 1617-1625; Huang et al., *Chem Med Chem* 2012, 7(4), 571-577). The initial screening was conducted at 100 μM. As can be seen from FIG. 1, two series of RB analogs, 22a-d and 23a-d showed significant inhibition of enzyme activities. RB analogs containing the 'D-ring;' (ring bearing the carbonyl group) and the chloro groups from ring A removed, exhibited substantially reduced activity or essentially no activity. Compounds with these showed no antimicrobial activity against *E. coli* NR698 (MIC: >250 μM) either. Masking the hydroxyl group in 22a-d with a methyl group (21a-d, Table 4) or replacing hydroxyl group with $^-$N(CH3)$_2$ (30) also resulted in compounds with weak or no activity (FIG. 1).

Analogs that showed substantial inhibition in the initial screening were evaluated in the channel activity assay using both EcSecA and BsSecA. This is a semi-physiological assay in the oocytes (Hsieh et al., *J. Biol. Chem.* 2011, 286, 44702-44709; Lin et al., *J. Membr. Biol.* 2006, 214, 103-113; Lin et al., *J. Membr. Biol.* 2012, 245, 747-757) developed to measure SecA-mediated protein-channel activity in a liposome environment, which closely mimics the situation in bacteria. This method serves as an excellent confirmative assay and is used for the generation of quantitative data for SAR work. In the channel activity assay, many compounds showed potent inhibitory activities (Table 5). The potency is about the same against EcSecA and BsSecA with the exception of 22d, which is more potent against EcSecA than BsSecA by about 2-fold. The results suggest that the 9-position of xanthene can tolerate a fairly large degree of modifications including aryl groups and cycloaliphatic and linear aliphatic substitutions. Further, the synthesized new analogs do not need to have a carboxyl group on the group attached to the 9-position to show potency. Such results suggest that the biologically active form of RB is most like the lactone form, not the ring opening with a free caboxylate group. Such cyclization resulting from a Michael addition type of reaction of the quinoid moiety is well known for this class of compounds including fluorescein. For example, the lactone form is commercially available. Further studies with decarboxylate RB also showed inhibition potency equal or better than RB itself.

To study the antimicrobial effect of these compounds, the active analogs against *E. coli* NR698, a leaky mutant, and *B. subtilis* 168 were evaluated. In the antimicrobial assay, all the non-halogenated analogs (22a-d) showed weak inhibitory activities with MIC in the double-digit micromolar range (Table 5). However, the halogenated analogs (23a-d), although with higher molecular weights, showed potent antimicrobial activities against both *E. coli* NR698 and *B. subtilis* 168. Against *E. coli* NR698, 23a-d showed equal or more potent activities than RB with single digit micromolar MIC values. Against *B. subtilis* 168, RB only showed very weak activity with MIC value of 100 μM. However, 23a had an MIC of 22 μM and the other halogenated analogs (23b-d) had MIC in the single digit micromolar range. The non-halogenated analogs (22a-d) with much lower molecular weight also showed more potent activity than RB with MIC in the range of 13-75 μM. Overall, the synthetic analogs were more potent than RB in antimicrobial assays.

The in vitro enzymatic activity and ion-channel activity assays of these analogs do not always parallel that of antimicrobial activities. On one hand, this is not surprising since antimicrobial activities also depend on permeability and solubility, among other factors. For example, the higher molecular weight and the charged carboxylate group of RB could easily impede its membrane permeability and thus lead to reduced antimicrobial activity. Such phenomenon has been observed in other SecA analogs (Chen et al., *Bioorg Med Chem* 2010, 18:1617-1625; Huang et al., *Chem Med Chem* 2012, 7:571-577). In addition, the modified RB analogs do not have the same planarity issues as RB and thus may not stack and aggregate as much, which should help improve solubility and consequently permeability.

Figure 2:
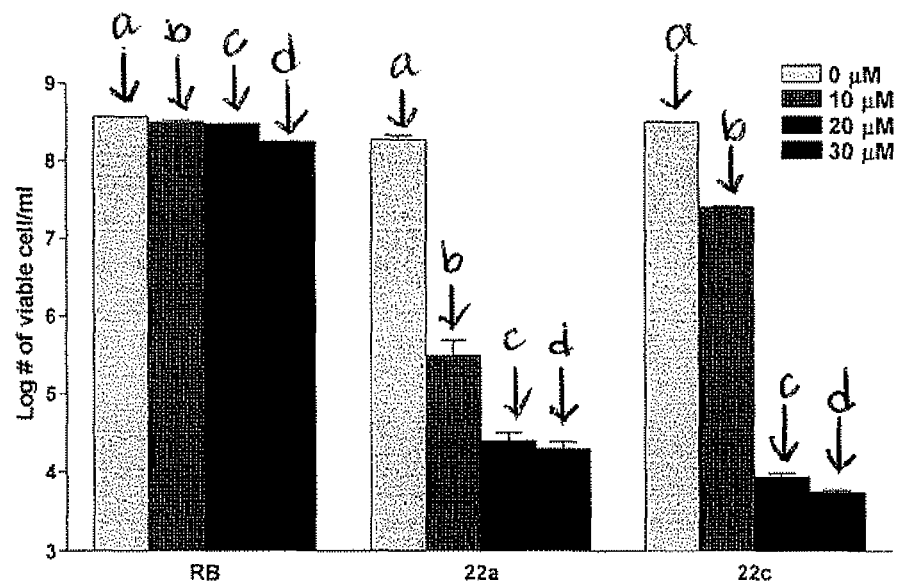
FIG. 2 is a bar graph showing the bactericidal effects of Rose Bengal and selected Rose Bengal analogs against *B. subtilis* 168. The compounds were tested at concentrations ranging from 0 µM (labeled 'a'); 10 µM (labeled 'b'); 20 µM (labeled 'c'); and 30 µM (labeled 'd').

Bactericidal studies were conducted and 20 μM of 22a or 22c was found sufficient to kill 4-5 logs of *B. subtilis* 168 in one hour while RB had little effect (FIG. 2). Thus although the enzymatic inhibition potency of these analogs is not as good as RB, the antimicrobial activity is much stronger. These results also show the importance of using multiple assays in screening and assessing SecA inhibitors.

TABLE 4

Structures of RB analogs

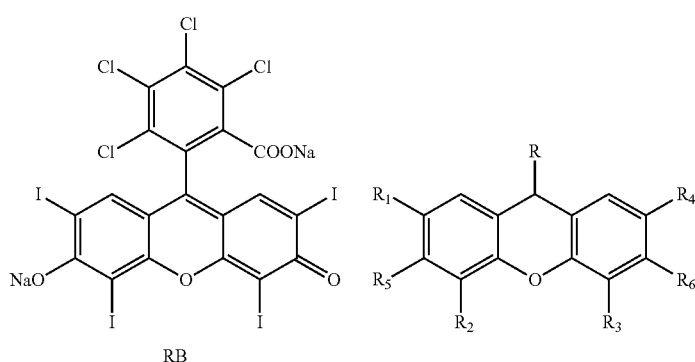

| Comp ID | MW | R | R1 | R2 | R3 | R4 | R5 | R6 |
|---|---|---|---|---|---|---|---|---|
| RB | 1017.6 | chlorinated benzoate | I | I | I | I | NaO | =O |
| 18a | 228.2 | =O | H | H | H | H | OH | OH |
| 18b | 543.8 | =O | Br | Br | Br | Br | OH | OH |
| 18c | 480.0 | =O | H | I | I | H | OH | OH |
| 20a | 308.4 | cyclopentylidene | H | H | H | H | OMe | OMe |
| 20b | 282.3 | propane-2-lidene | H | H | H | H | OMe | OMe |
| 21a | 310.4 | cyclopentane | H | H | H | H | OMe | OMe |
| 21b | 284.4 | iso-propyl | H | H | H | H | OMe | OMe |
| 21c | 326.4 | n-hexyl | H | H | H | H | OMe | OMe |
| 21d | 324.4 | cyclohexane | H | H | H | H | OMe | OMe |
| 22a | 282.3 | cyclopentyl | H | H | H | H | OH | OH |
| 22b | 256.3 | iso-propyl | H | H | H | H | OH | OH |
| 22c | 298.2 | n-hexyl | H | H | H | H | OH | OH |
| 22d | 296.2 | cyclohexyl | H | H | H | H | OH | OH |
| 23a | 597.9 | cyclopentyl | Br | Br | Br | Br | OH | OH |
| 23b | 785.9 | cyclopentyl | I | I | I | I | OH | OH |
| 23c | 660.0 | cyclopentyl | I | I | H | I | OH | OH |
| 23d | 759.9 | iso-propyl | I | I | I | I | OH | OH |
| 30 | 336.1 | cyclopentyl | H | H | H | H | NMe$_2$ | NMe$_2$ |

TABLE 5

Biological activities of RB analogs

| Comp | | Ion channel, IC$_{50}$ (μM) | | MIC (μM) | |
|---|---|---|---|---|---|
| ID | MW | EcSecA | BsSecA | E. coli NR698 | B. subtilis 168 |
| RB | 1017.6 | 0.4 | 0.3 | 5 | 100 |
| 22a | 282.3 | 3.4 | 3.0 | 45 | 25 |
| 22b | 256.3 | 4.3 | 4.9 | 90 | 75 |
| 22c | 298.2 | 2.3 | 2.5 | 19 | 13 |
| 22d | 296.3 | 2.8 | 6.6 | 25 | 22 |
| 23a | 597.9 | 2.3 | 2.4 | 2 | 22 |
| 23b | 785.9 | 2.5 | 3.8 | 1 | 6 |
| 23c | 660.0 | 2.2 | 2.8 | 6 | 6 |
| 23d | 759.9 | 2.8 | 2.5 | 4 | 6 |

Summary

In summary, twenty three new RB analogs were successfully synthesized and evaluated. The result of SAR studies indicated that (1) the xanthene ring is important for activity; (2) the chlorinated benzoate position can tolerate fairly substantial modifications and an aryl ring is not essential; (3) a carboxyl group is not important for activity; and (4) halogen substitution of the xanthene ring is important.

Example 3

Injection of Proteoliposomes in Oocytes as a Tool for Monitoring Membrane Channel Activities Liposomes Preparation E. coli total lipids extracts or synthetic lipids (Avanti Polar Lipid, Inc) were dried in a Thermo Savant vacuum and resuspended in TAK buffer containing Tris-HCl 50 mM pH 7.6, 20 mM NH$_4$Cl and 25 mM KCl. The suspension was subjected to sonication (Fisher Scientific Sonic Dismembrator Model 500) at an amplitude of 70% for 8 to 10 minutes with a two minute pause in a 0° C. ice-water bath. The particle sizes of opalescent liposomes were measured by a Beckman Coulter N5 submicron particle size analyzer and showed a normal distribution with a peak around 130 nm. The liposomes were aliquoted and stored at −80° C. until use. The PC/PS ratio was 2:1 and the PE/PG ratio was 3:1.

Protein Purification

E. coli SecA was purified from BL21(λDE3)/pT7-SecA. SecA homologous from other bacteria were purified similarly from BL21.19. Purified proOmpA were prepared, and SecYEG and SecDF•YajC were purified.

Two Electron Whole Cell Recording

When the channel on the cell membrane is open, ions pass through the membrane and generate an ionic current. Thus, the recording of ionic current could also mean the opening of the protein conducting channel. A two-electrode voltage clamp, connected to an amplifier (Geneclamp 500, Axon instruments Inc., Foster City, Calif.), was used to measure the current across the plasma membranes of oocytes after the oocytes were injected with the inhibitor.

The cells were placed in a recording chamber (BSC-HT, Medical System, Greenvale, N.Y.) on a supporting nylon mesh, so that the perfusion solution washed both the top and the bottom surface of the oocytes. The cells were then impaled using electrodes filled with 3 M KCl. One electrode (1.0-2.0 MΩ) was used for voltage recording. This electrode was connected to the HS-2×1 L headstage (inpot resistance, $10^{11}$Ω). The second electrode (0.3-0.6 MΩ) was used for current recording, which was connected to the HS-2×10 MG headstage (maximum current, 130 μA). The electrodes were connected to the headstage via a silver wire that was freshly chloridized for each experiment. Oocytes were reused for further experiments only if the difference between the leak currents measured before and after the experiments were less than 10% of the peak currents. The leak current was not considered during data analysis. The generated currents were low-pass filtered (Bessel, 4-pole filter, 3 db at 5 kHz), digitized at 5 kHz (12 but resolution), and subsequently analyzed using a pClamp6 (Axon Instruments). The highest and lowest currents recorded were eliminated, and the remaining presented as mean current±S.E. (standard error; n, number of oocytes). The expression rates for each injection sample were also recorded to determine the channel activity efficiency.

Results

Inhibitors Effects

SecA is essential for bacteria growth and serves as an ATPase for protein translocation across membranes. SecA also possesses intrinsic ATPase activity that is increased upon interaction with lipids, and further enhanced with protein precursors. The effective inhibition of channel activity (Table 6) by SecA inhibitor corresponds to inhibition of protein translocation by SecA-dependent ATPase with *E. coli* SecA system. With the proteoliposomes injection methods, the inhibitory effects of various SecA inhibitors on the channel activities for other bacterial systems can also be investigated.

Rose Bengal was used to test the sensitivity of the SecA-dependent channel activity to inhibitors. SecA-liposomes or liposomes containing SecA and SecYEG and various concentrations of Rose Bengal were administered and the $IC_{50}$ for the bacteria's sensitivity to Rose Bengal was recorded.

Inhibition of the channel activity in oocytes injected with BaSecA-, SaSecA-, and PaSecA-liposomes were similar (Table 6). Injection of the various SecA homologs complexed with SecYEG showed intermediate sensitivity to Rose Bengal compared injection with the SecA-liposome alone (Table 6). The PaSecA complex was the only exception. Addition of SecDF•YajC increased the $IC_{50}$ values somewhat.

TABLE 6

Rose Bengal $IC_{50}$ (μM) inhibition of SecA channel activity in oocytes.

| SecAs | Liposomes | BA13/Re-13 | Liposome + SecYEG | +SecYEG + SecDF•C |
|---|---|---|---|---|
| EcSecA | 0.4 | 4.7/0.4 | 3.0 | 3.8 |
| BsSecA1 | 0.3 | 5.8/0.5 | 3.1 | 4.5 |
| PaSecA | 0.3 | 5.1/0.3 | 1.1 | 2 |
| SaSecA1 | 0.4 | 6.1/0.5 | 3.1 | 4.2 |

TABLE 6-continued

Rose Bengal $IC_{50}$ (μM) inhibition of SecA channel activity in oocytes.

| SecAs | Liposomes | BA13/Re-13 | Liposome + SecYEG | +SecYEG + SecDF•C |
|---|---|---|---|---|
| BaSecA1 | 0.3 | 6.1/0.5 | 3.3 | 4.0 |
| MtbSecA1 | 0.5 | — | | |
| MsSecA1 | 0.4 | — | | |

Methods for Assaying Channel Inhibitor Kinetics.

As mentioned, SecA ATPases activities respond differently when interacting with lipids, protein precursors, and SecA inhibitors. SecA-dependent ATPase showed non-competitive inhibition at low ATP concentrations with RB, but competitive inhibition at high ATP concentrations.

Figures 3A, 3B, 3C, 3D:
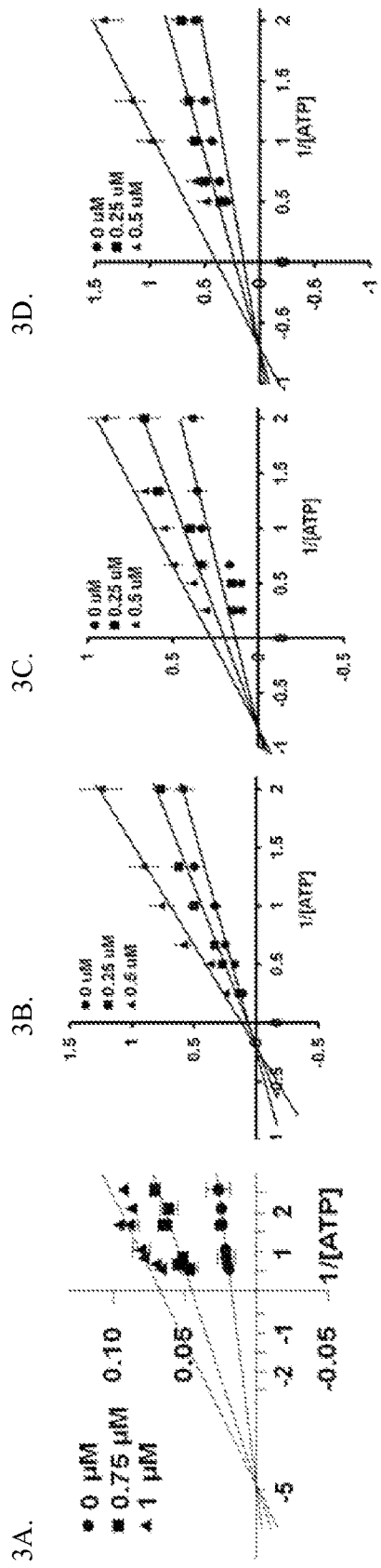
FIGS. 3A-3D are line graphs showing the inhibition kinetics of Rose Bengal in SecA translocation ATPase and channel activity.

FIG. 3A shows non-competitive inhibition of the channel activity of SecA-dependent ATPase. The channel activity on injected EcSecA-liposomes in the oocytes also showed similar non-competitive inhibition in regards to ATP (FIG. 3B). The inhibitor kinetics with other bacterial SecA was also determined Using the injected SecA-liposomes in the oocytes, RB also showed non-competitive inhibition with ATP for the channel activity for PaSecA and SaSecA1 (FIGS. 3C and 3D, respectively).

Example 4

Rose Bengal and Rose Bengal Analogs Inhibitors of SecA Exhibit Antimicrobial Activity, Inhibit Toxins Secretion, and Bypass Some Efflux Pumps Against Methicillin-resistant *Staphylococcus aureus*

Bacterial Strains and Culture Condition

*S. aureus* strains ATCC 35556 and ATCC 6538 were obtained from the American Type Culture collection. *S. aureus* strains Mu50, Mu3, and N315 were kindly provided by Dr. Chung-Dar Lu of Georgia State University. Five efflux pump related *S. aureus* strains 8325-4, K1758 (NorA$^-$), K2361 (NorA$^{++}$), K2908 (MepA$^-$), K2068 (MepA$^{++}$) were kindly provided by Dr. GW Kaatz at Wayne State University School of Medicine and Jon D. Dingell VA Medical Center. All strains were grown on Luria-Bertani (LB) agar plates or broth at 37° C.

Chemical Compounds

Rose Bengal was purchased from SIGMA-ALDRICH. All RB analogs were synthesized as described in Example 2.

Protein Preparation

The SaSecA1 and SaSecA2 genes were amplified from *S. aureus* ATCC35556. The SaSecA1 gene was cloned into pET-21d and the SaSecA2 gene was cloned into pET-29a. Both genes were over-expressed in BL21λDE3 at 20° C. with 0.5 mM IPTG. SaSecA1 and SaSecA2 were purified with His-trap column and Superdex-200 column.

In vitro ATPase Activity Assay

The ATPase activity was determined by malachite green colorimetric assay (described in Example 2). The ATPase assays were carried out with different concentrations of inhibitor at 37° C. for 40 min in the presence of 5% DMSO in room light.

Bacteriostatic Effect

Bacteriostatic effects were tested according to the guidelines of the Clinical and Laboratory Standards Institute (described in Example 2).

Bactericidal Effect

Bactericidal effect was determined in presence of 2.5% DMSO in room light (described in Example 2).

SecA-Lipsomes Ion-channel Activity Assays

The liposomes were prepared as described in Example 3. Oocytes were obtained from live frog *Xenopus laevis* (*Xenopus* Express, Inc) and injected with sample mixtures. 50 nl sample mixtures containing 120 ng liposomes, 120 ng SecA, 14 ng proOmpA, 2 mM ATP, 1 mM $Mg^{2+}$, and different concentration of inhibitors were injected into the dark pole site of oocytes using a Nanoject II injector (Drummond Scientific Co., Broomall, Pa.). The ion current was recorded for 1 min after three hours of incubation at 23° C.

Toxin Secretion

*S. aureus* Mu50 was grown in LB broth at 37° C. Inhibitors were added to the mid-log phase of *S. aureus* Mu50. Cultures were collected after treating with inhibitor for 0 h, 2 hrs (or 2.5 hrs), and 4 hrs. The supernatant and cell pellet were separated by centrifugation followed by filtration through a 0.45 µM filter. Western blots with specific toxin antibodies were used to detect the amount of toxins in the supernatant. Antibodies include α-hemolysin, enterotoxin B, and toxin shock syndrome toxin-1 (TSST-1), which were purchased from Abcam (www.abcam.com).

Results

Inhibition of *S. aureus* SecA Proteins

Figure 4:
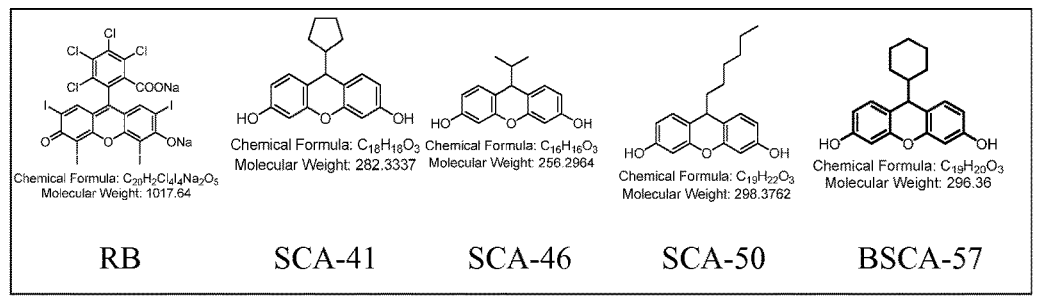
FIG. 4 shows the structures of selected Rose Bengal analogs.

Two SecA homologues have been previously identified in *S. aureus* (Siboo et al., J Bacteriol, 2008. 190:6188-6196). Two low molecular weight RB analogs, SCA-41 and SCA-50 (see FIG. 4), were analyzed for inhibition of SaSecA1 and SaSecA2. SCA-41 and SCA-50 was shown to inhibit the ATPase activities of SaSecA1 and SaSecA2 (Table 7). This is an indication that both compounds have at least two targets in *S. aureus*.

The inhibitory effects of Rose Bengal (RB) and RB analogs against SaSecA1 were further investigated using a SecA-lipsome ion-channel activity assay. To evaluate SecA's function in the membrane, SaSecA1 was injected simultaneously with liposomes into oocytes in the presence or absence of RB and RB analogs. The RB analogs displayed potent inhibition of the ion-channel activity of SaSecA1 ($IC_{50}$ from 0.3 µg/mL to 3.4 µg/mL; Table 7). The RB analog with the highest activity, SCA-50 inhibits SecA-dependent ion channel activity better than that of RB ($IC_{50}$: 0.4 µg/mL).

TABLE 7

Inhibition against activities of SaSecA1 proteins, $IC_{50}$ (µM)

|  | ATPase activity | | Ion-channel activity |
|---|---|---|---|
|  | SaSecA1 | SaSecA2 | SaSecA1 |
| RB | 1.0 | 2.5 | 0.4 |
| SCA-41 | 37.5 | 32.5 | 3.4 |
| SCA-50 | 20 | 17.5 | 1.1 |

Inhibition on the Secretion of *S. aureus* Toxins

In *S. aureus*, Sec-system is responsible for secretion of more than 20 toxins or virulence factors, which play important roles in the pathogenesis of *S. aureus* infection. Therefore, targeting *S. aureus* SecA1, an essential component of Sec-system could reduce virulence of *S. aureus*. To determine whether the SecA inhibitors can inhibit the secretion of *S. aureus* toxins, 10 µM SCA-41 or SCA-50 was added into the mid-log phase of *S. aureus* Mu50. Results from western blot show that these compounds significantly decreased the amount of α-hemolysin, enterotoxin B, and toxin shock syndrome toxin-1 (TSST-1) in the supernatant The OD readings of the control and the supernatant (treated with 10 µM SCA-41 or SCA-50) did not change after 15 hours. This is an indication that protein synthesis was not affected. All three toxins contain Sec-dependent signal peptide. Therefore, it appears that SCA-41 and SCA-50 inhibit the in vivo function of SecA1 Inhibition of SecA could dramatically reduce the virulence of *S. aureus*.

Antimicrobial Activities of Novel RB Analogs Against MRSA Strains

To determine whether the RB analogs possess antimicrobial effect against methicillin resistant *Staphylococcus aureus* (MRSA), the bacteriostatic effects of these compounds against three MRSA strains (N315, Mu3, and Mu50) and one clinical isolated strain of *S. aureus*, ATCC 6538 was investigated. These inhibitors showed bacteriostatic effects against all tested *S. aureus* strains with MICs around 3.7 µg/ml to 25.6 µg/ml (Table 8). The bacteriostatic effects of all tested RB analogs were better than that of RB.

Figure 5:
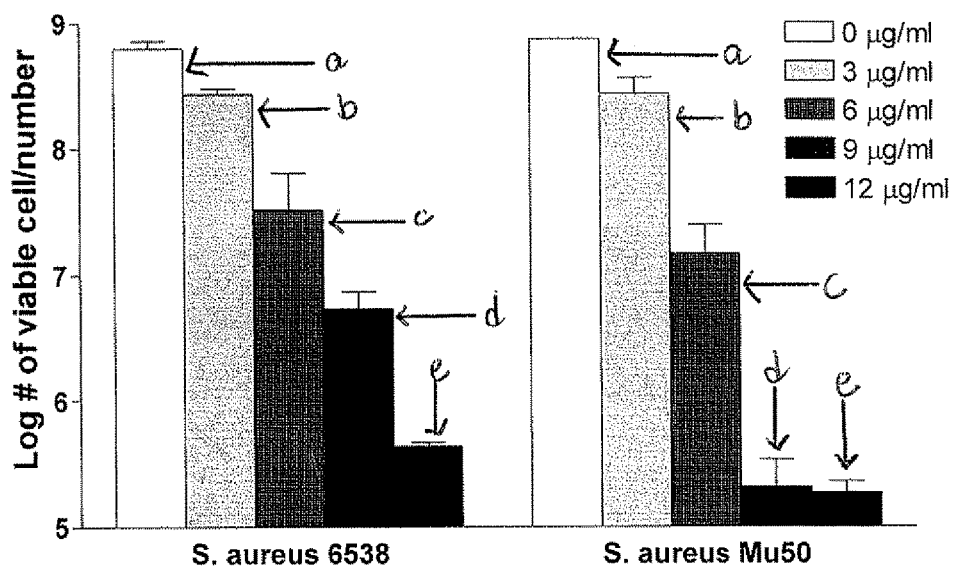
FIG. 5 shows the bactericidal effects of SCA-50 against *S. aureus* for 1 hour at 37° C. SCA-50 was tested at concentrations ranging from 0 µg/ml (labeled 'a'); 3 µg/ml (labeled 'b'); 6 µg/ml (labeled 'c'); 9 µg/ml (labeled 'd'); and 12 µg/ml (labeled 'e').

SCA-50 showed the best bacteriostatic effect and best inhibitory effects against ATPase and ion-channel activities of SaSecAs. Its ability to kill bacteria was tested. MRSA strain Mu50 and a clinical isolated strain *S. aureus* 6538 were employed in this assay. SCA-50 showed a concentration-dependent manner of bactericidal activity for both strains, killing 2 log numbers of *S. aureus* 6538 and more than 3 log numbers of *S. aureus* Mu50 at 9 µg/ml (FIG. 5).

TABLE 8

Bacteriostatic effect, MIC (µg/ml)

|  | *S. aureus* 6538 | *S. aureus* Mu50 | *S. aureus* N315 | *S. aureus* Mu3 |
|---|---|---|---|---|
| RB | 38.2 | 50.8 | 19.1 | 38.2 |
| SCA-41 | 10.6 | 8.8 | 14.1 | 14.1 |
| SCA-46 | 16.0 | 25.6 | 25.6 | 25.6 |
| SCA-50 | 3.7 | 3.7 | 3.7 | 3.7 |
| SCA-57 | 7.4 | 7.4 | 7.4 | 7.4 |

The Effect of Photooxidation

Figure 6:
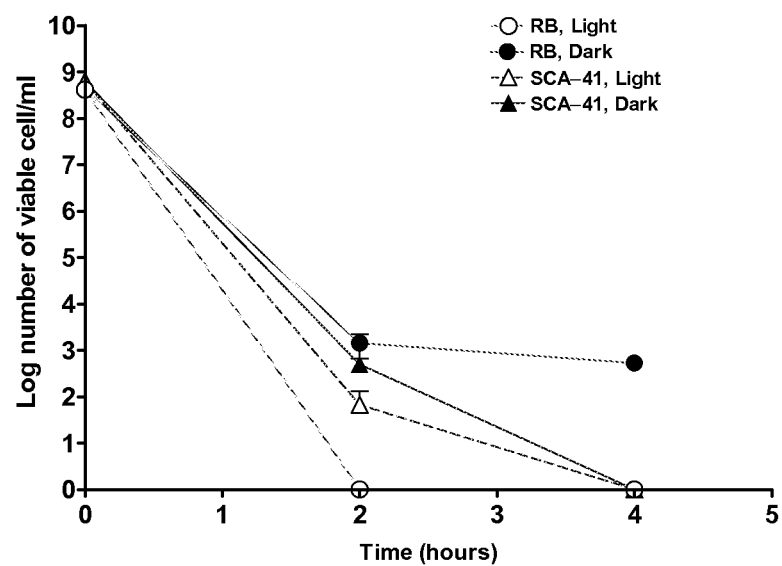
FIG. 6 shows the inhibition of Rose Bengal analogs on the secretion of *S. aureus* toxins over time.

Previous studies demonstrated that part of RB's antimicrobial activities is due to photooxidation (Inbaraj et al., Photochem Photobiol, 2005. 81:81-8; Demidova et al., Antimicrob Agents Chemother, 2005. 49:2329-35; Wang et al., Curr. Microbiol., 2006. 52:1-5). To determine whether the antimicrobial activity of the novel RB analogs were due to photooxidation, the bactericidal effect of RB and SCA-41 were investigated in the dark and under light. In the dark, RB 1 showed little bactericidal effect, and its bactericidal effect was dramatically increased by light (FIG. 6). These results confirmed that photooxidation contribute to part of RB's antimicrobial activity. However the bactericidal effect of SCA-41 was not affected by light. These results indicated that the antimicrobial activity of SCA-41 is not due to a photooxidation mechanism.

The Possibility of Overcoming the Effect of Efflux Pump:

In Gram-positive bacteria, drugs targeting SecA might be directly accessible from the extracellular matrix and exert their effect without entering the cell. Therefore targeting SecA may bypass the negative effect of efflux pumps in bacteria, which is a major concern for the development of current drug-resistance (Zhang et al., Bioorg Med Chem Lett, 2007, 17:707-11; Nikaido et al., Curr Opin Infect Dis, 1999. 12:529-36; Van Bambeke et al., Biochem Pharmacol, 2000, 60: 457-70; Markham et al., Curr Opin Microbiol, 2001, 4:509-14; Levy et al., Symp Ser Soc Appl Microbiol, 2002:65S-71S). *S. aureus* Mu50 and *S. aureus* N315 are resistant to QacA efflux-mediated antibiotics. The SecA inhibitors showed promising bacteriostatic effects against *S. aureus* Mu50 and *S. aureus* N315, suggesting that these SecA inhibitors might be able to overcome QacA mediated efflux.

NorA and MepA are two efflux pumps of *S. aureus* with 23% or 4% overexpression frequencies. To determine whether overexpression of NorA or MepA could affect the antimicrobial effect of the SecA inhibitors, microbial inhibition assay against NorA or MepA deletion or overexpression mutants and the parent *S. aureus* 8325-4 was carried out with RB, SCA-41 and SCA-50. For RB, overexpression NorA increased MIC to 1.5 fold that of NorA deletion mutant and 2.5 fold that of parental strains (Table 9). Overexpression of MepA increased MIC to 1.5 fold that of MepA deletion mutant (Table 9). These results indicate that NorA could pump out RB, though not very efficient. However, for SCA-50 and SCA-41, overexpression or deletion NorA or MepA did not significantly change the MIC (Table 9). Such results strongly suggest that the SecA inhibitors may have the intrinsic ability to overcome the effect of the efflux pumps in drug-resistance development.

TABLE 9

Bacteriostatic effects against *S. aureus* efflux strains, MIC (μg/ml)

| compounds | Strains | | | | |
|---|---|---|---|---|---|
| | WT 8325-4 | NorA⁻ K1758 | NorA⁺⁺ K2361 | MepA⁻ K2908 | MepA⁺⁺ K2068 |
| RB | 13.2 | 22.3 | 34.6 | 10.6 | 17.5 |
| SCA-41 | 11.8 | 14.1 | 11.8 | 14.1 | 11.8 |
| SCA-50 | 3.7 | 3.7 | 3.7 | 3.7 | 3.7 |

RB and RB Analogs Exert Stronger Efficacy than First-line Antibiotics Against MRSA

*S. aureus* Mu50 is a MRSA strain with intermediate level resistance to vancomycin (VISA). As reported in Table 10, the selected SecA inhibitors were far more potent in their antimicrobial activity against *S. aureus* Mu50 than the majority of commonly used antibiotics. The MIC of SCA-50 is 4 μg/ml, which is 250 fold less than the MIC of ampicillin, kanamyin, erythromycin, and rifampicin. MICs of norfloxacin, tetracycline, and polymyxin B are 60 fold to 7 fold higher than that of SCA-50. MIC of vancomycin is two-fold higher than that of SCA-50.

TABLE 10

Comparison of the antimicrobial activities of SecA inhibitors with other antibiotics against *S. aureus* Mu50

| Antibiotics | Bacteriostatic effect MIC (μg/ml) | Bactericidal effect |
|---|---|---|
| RB | 50.8 | + |
| SCA-41 | 8.8 | + |
| SCA-50 | 3.7 | + |
| Vancomycin | 7.8 | + |
| Ampicillin | 1000 | + |
| Kanamycin | 1000 | + |
| Polymxin B | 31.3 | + |
| Tetracycline | 62.5 | − |
| Erythromycin | >1250 | − |
| Norfloxacin | 250 | + |
| Rifampicin | >1000 | + |

Summary

SecA is important in the protein translocation machinery present in all bacteria. In *S. aureus*, SecA is critical for both bacterial survival and virulence, being responsible for secretion of more than 20 toxins or virulence factors, which play important roles in the pathogenesis of *S. aureus* infection. Therefore, targeting *S. aureus* SecA might achieve dual effects-decreasing bacterial survivability and reducing virulence. Two SecA homologues (SecA1 and SecA2) exist in *S. aureus*, making them more attractive targets for the development of novel antimicrobials. Dual target inhibition could increase the chance of combating infection and reducing the occurrence of drug resistance in this bacterium. SecA has no counterpart in mammalian cells, thus providing an ideal target for developing antimicrobial agents. FIG. 7 shows the structures of compounds that were synthesized. Some of the compounds were evaluated for in vitro inhibition activity and/or toxicity.

The tested RB analogs showed promising inhibition against the activities of both SaSecA1 and SaSecA2, and exert better antimicrobial activities than RB. The most active compound, SCA-50 showed potent concentration-dependent bactericidal activity. The MIC of SCA-50 is 4 μg/ml, better than that of vancomycin, which is the last sort against MRSA. Moreover, vancomycin only decreases bacterial survivability, while the SCA-50 decreases bacterial survivability and inhibited toxin secretion simultaneously.

The data showed that the over-productions of NorA and MepA in *S. aureus* strains have no effect on the MIC SCA-41 and SCA-50. Such results strongly suggest that SecA inhibitors may have the intrinsic ability to overcome the effect of the efflux-pumps in drug-resistance development. In such a case, the drug-efflux pump would have less negative effects on the inhibitor's ability to exert antimicrobial activity. This is the first approach, to our best knowledge, of the development of new antimicrobials that have the intrinsic ability to overcome the effects of efflux that bacteria use in developing multi-drug resistance. Given the widespread nature of efflux in bacteria and its importance in drug-resistance, such a finding by itself would be of extraordinary novelty and significance.

In the treatment against bacterial infection, the traditional thinking has been almost solely on achieving bactericidal and/or bacteriostatic effects. Such approaches continue to be very effective and play an important role. However, combination approaches might yield a more effective outcome. These combinatorial approaches may include the regulation and/or inhibition of virulence factor production, inhibition of bacterial quorum sensing, and inhibition or bypassing efflux, which is a key mechanism of multi-drug resistance in bacteria. Some of the additional approaches do not exert the same kind of evolutionary pressure as bactericidal and bacteriostatic agents do and thus are less likely to quickly induce drug resistance. Along this line, targeting SaSecA proteins is a very attractive antimicrobial strategy, because inhibition SecA could decrease bacterial survivability, reducing virulence, and by-passing efflux at the same time.

Example 5

Compounds of Formula I-X as SecA Inhibitors

Bacterial Strain and Growth Conditions

An outer membrane leaky mutant strain, *E. coli* NR698 (Ruiz et al., Cell, 2005, 121:307-317; provided by Thomas J Silhavy of Princeton University) and *B. subtilis* 168 (lab stock) were grown in Luria-Bertani (LB) medium at 37° C.

S. aureus strains Mu50 were kindly provided by Dr. Chung-Dar Lu of Georgia State University. B. anthracis Sterne and S. aureus 6538 were obtained from American Type Culture Center. All strains were grown on Luria-Bertani (LB) agar plates or broth at 37° C.

Protein Preparation

EcSecAN68, a truncated mutant of EcSecA containing the N-terminal catalytic domain, EcSecA, and BsSecA were used to study the in vitro inhibition effect of RB analogs. These proteins were purified as previously described (Chen et al., *J. Biol. Chem.* 1996, 271:29698-29706; Chen et al., *J. Bacteriol.* 1998, 180:527-537).

In vitro ATPase Activity Assay

The malachite green colorimetric assay was used to determine the inhibition effect of RB analogs against the ATPase activity of SecA proteins. In this assay, ATPase assays were carried out at different concentrations of the inhibitor, and $IC_{50}$ was defined as the concentration of the compound, which could inhibit 50% ATPase activity of the enzyme. Because RB analogs were dissolved in 100% DMSO, there was 5% DMSO in the final assay.

Bacteriostatic Effect

Bacteriostatic effects were tested by a liquid microdilution method according to the guidelines of the Clinical and Laboratory Standards Institute (*Performance standards for antimicrobial susceptibility testing.* M100-S21; 21*st informational supplement.* Clinical and Laboratory Standards Institute, Wayne, Pa. 2011). This assay was performed in a 96-well microtiter tray under normal room light condition. All bacteria were grown in LB broth, and when the $OD_{600}$ reach 0.5, the culture was diluted to $OD_{600}\approx 0.05$. 97.5 µl diluted culture and 2.5 µl of compound were added to each well. Cells were incubated at 37° C. with shaking (250 rpm) for 24 hr. MIC is the lowest concentration of inhibitors at which cells were not able to grow.

Figures 2, 8:
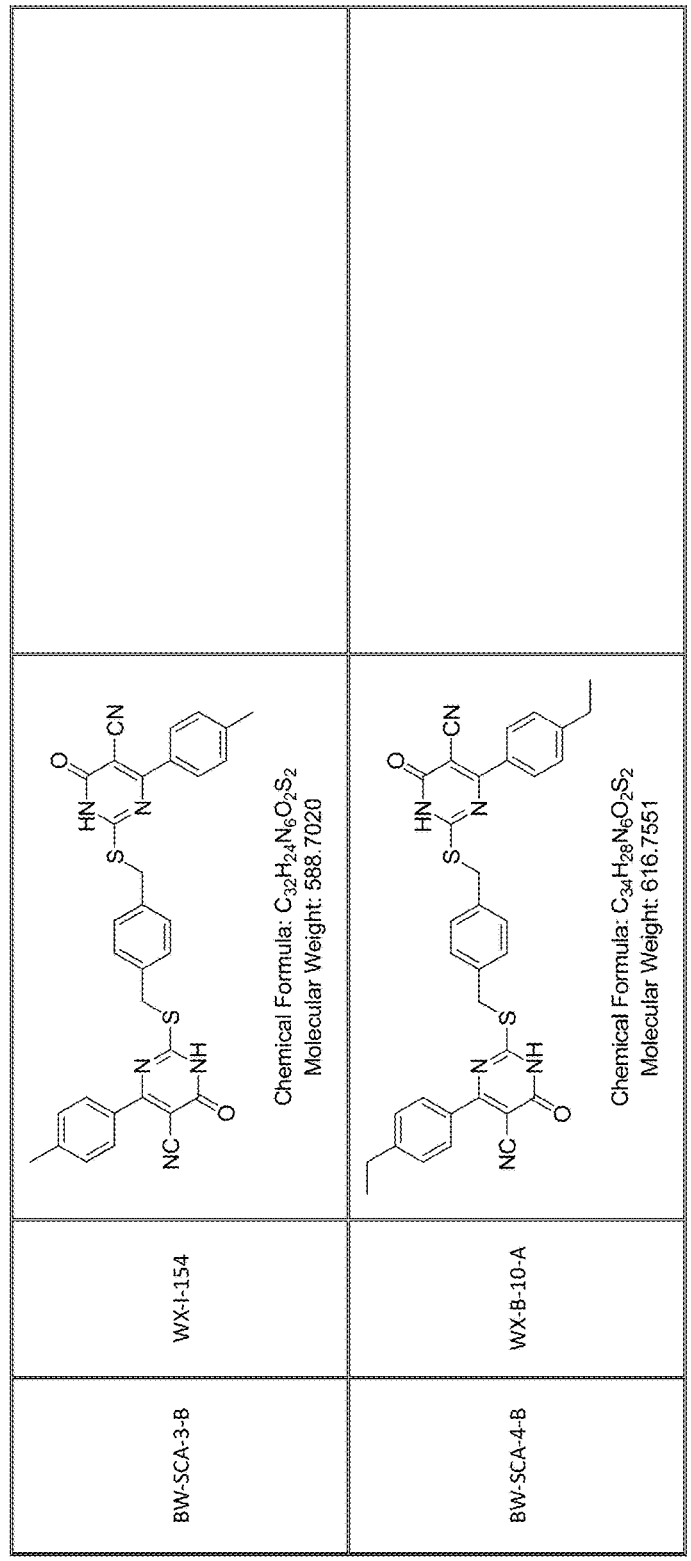
Figures 5, 8:
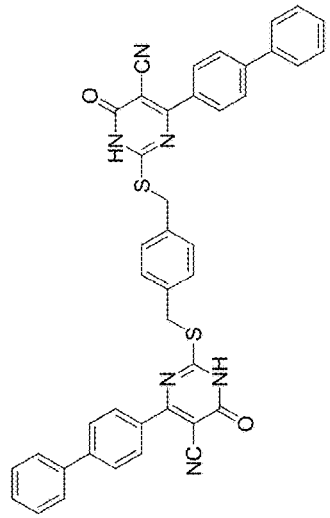
Figure 8:
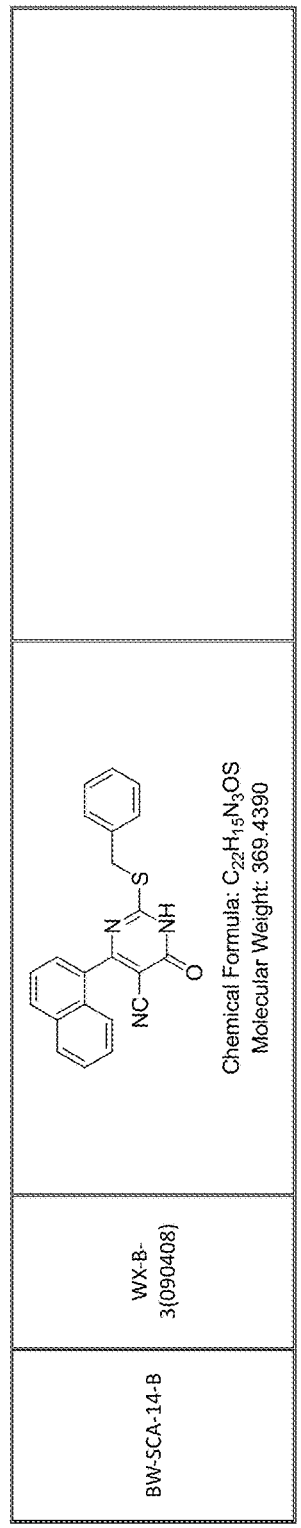
Figures 8, 9, 10, 11, 12, 13, 14, 15:
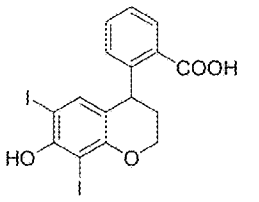
Figures 8, 9, 10, 11, 12, 13, 14, 15, 16:
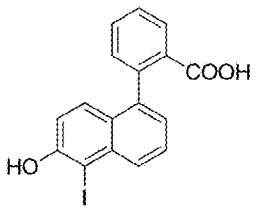
Figures 8, 9, 10, 11, 12, 13, 14, 15, 16, 17:
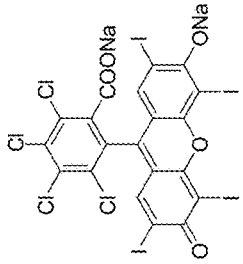
Figures 8, 9, 10, 11, 12, 13, 14, 15, 16, 17, 18, 19, 20, 21, 22, 23, 24, 25:
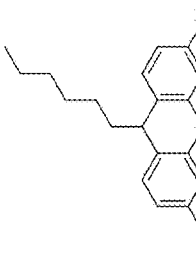
Figures 8, 9, 10, 11, 12, 13, 14, 15, 16, 17, 18, 19, 20, 21, 22, 23, 24, 25, 26, 27, 28, 29, 30, 31, 32:
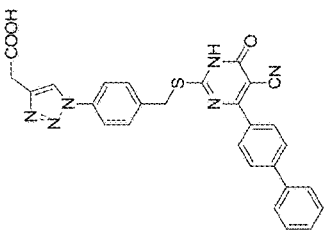
Figures 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49:
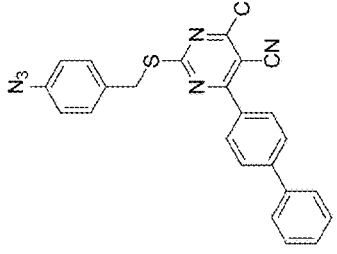
Figures 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52:
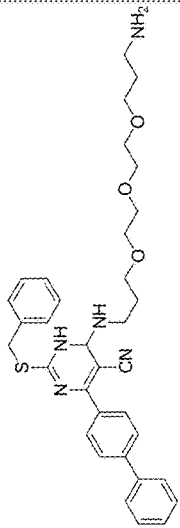
Figures 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54:
Figures 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57:
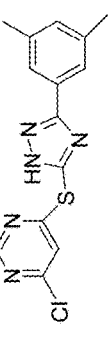
Figures 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58:
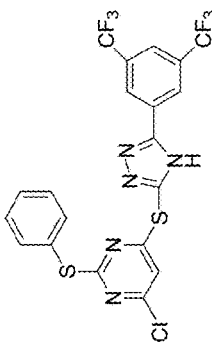
Figures 8, 62:
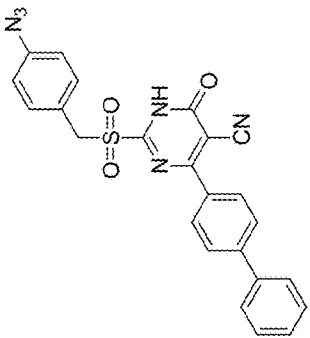
Figures 8, 65:
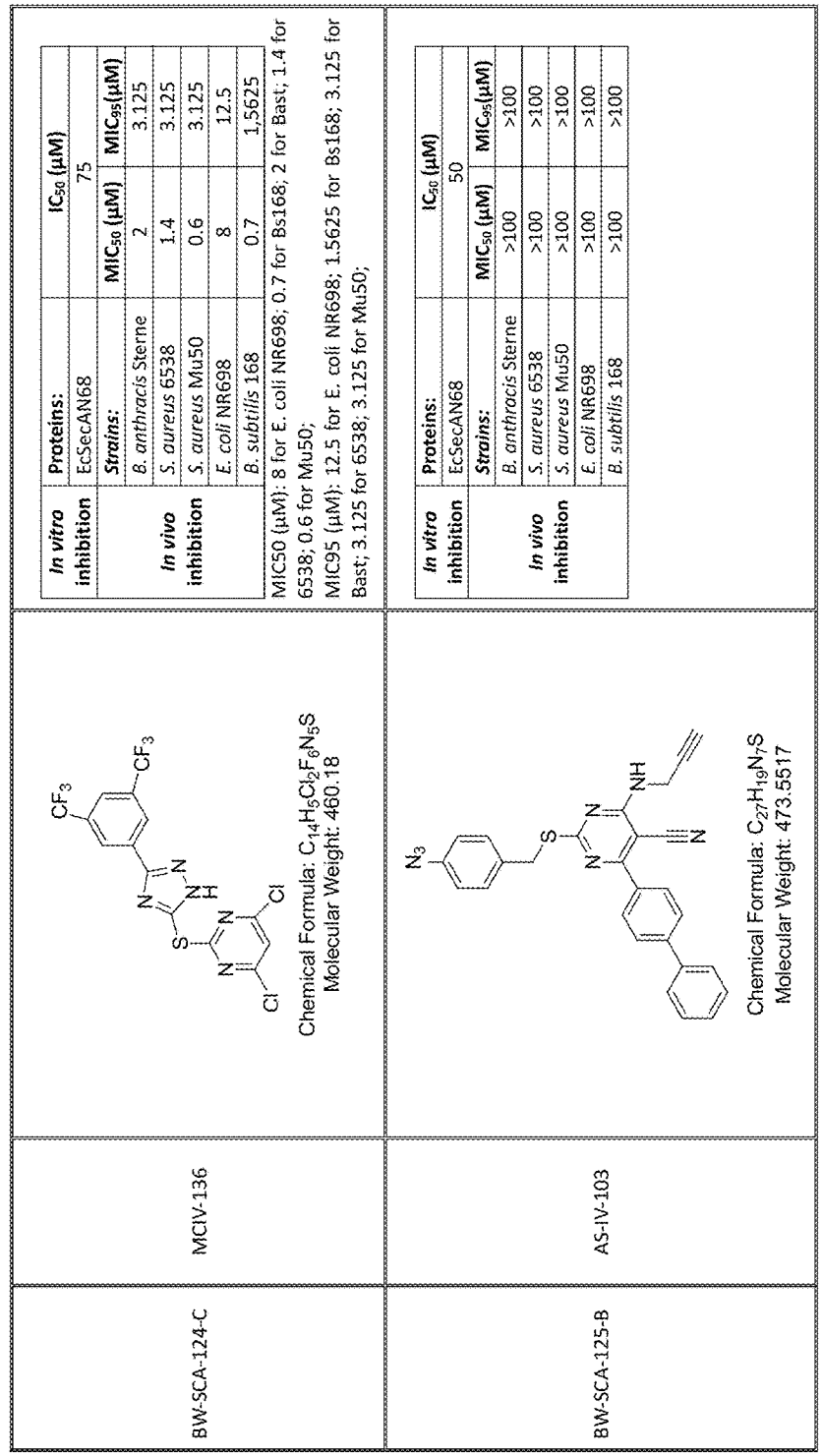
Figures 8, 71:
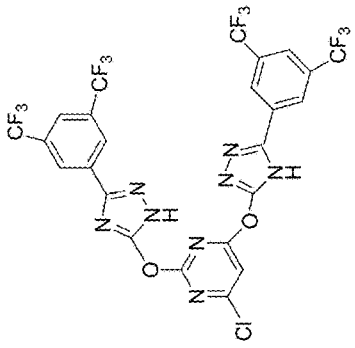
Figures 8, 84:
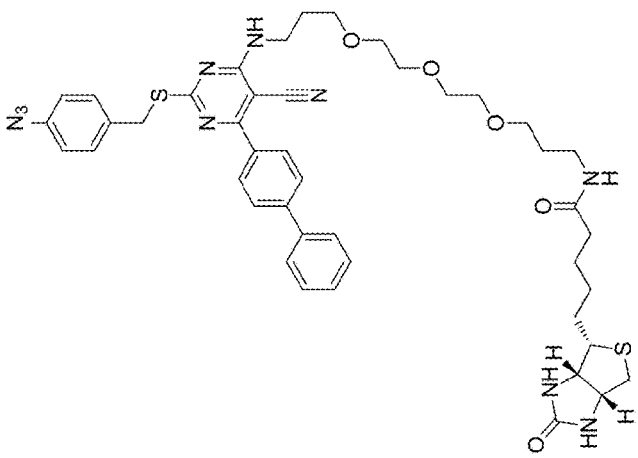
Figures 8, 90:
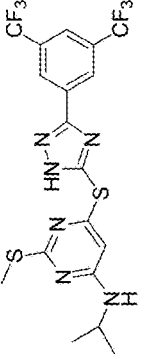
Figures 8, 9, 9I:
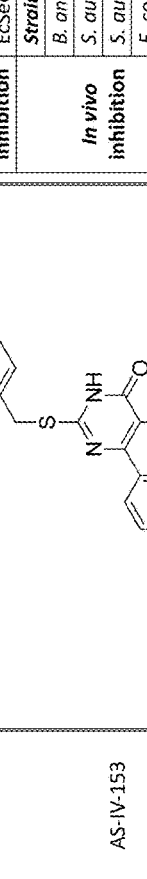
Figure 8:
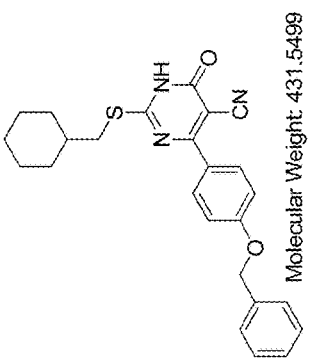
Figure 92:
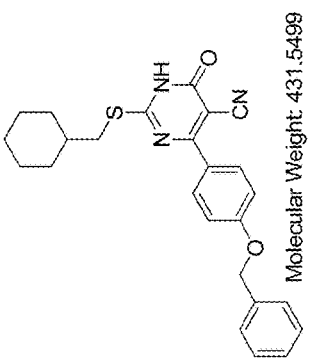
Figure 8:
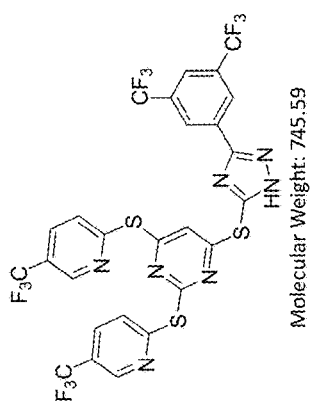
Figure 103:
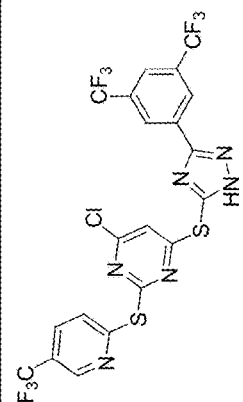
Figure 8:
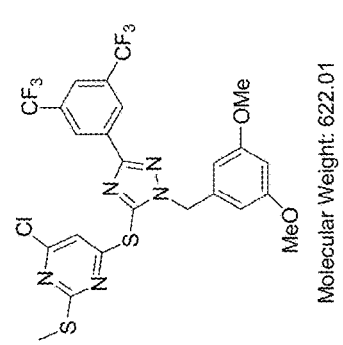
Figure 105:
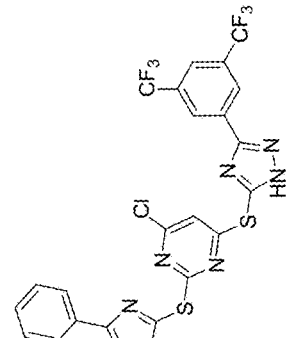
Figures 8, 106:
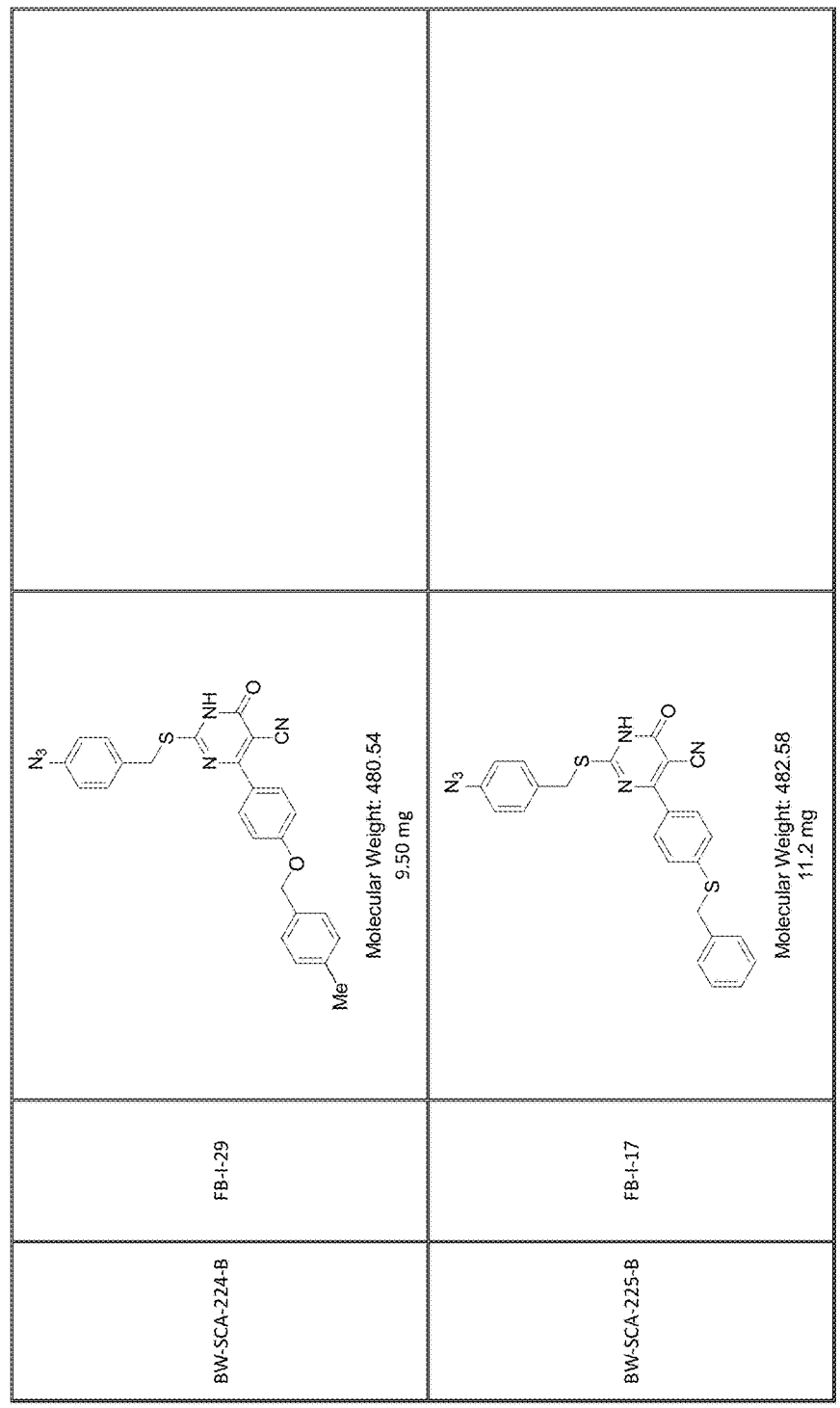
Figures 8, 107:
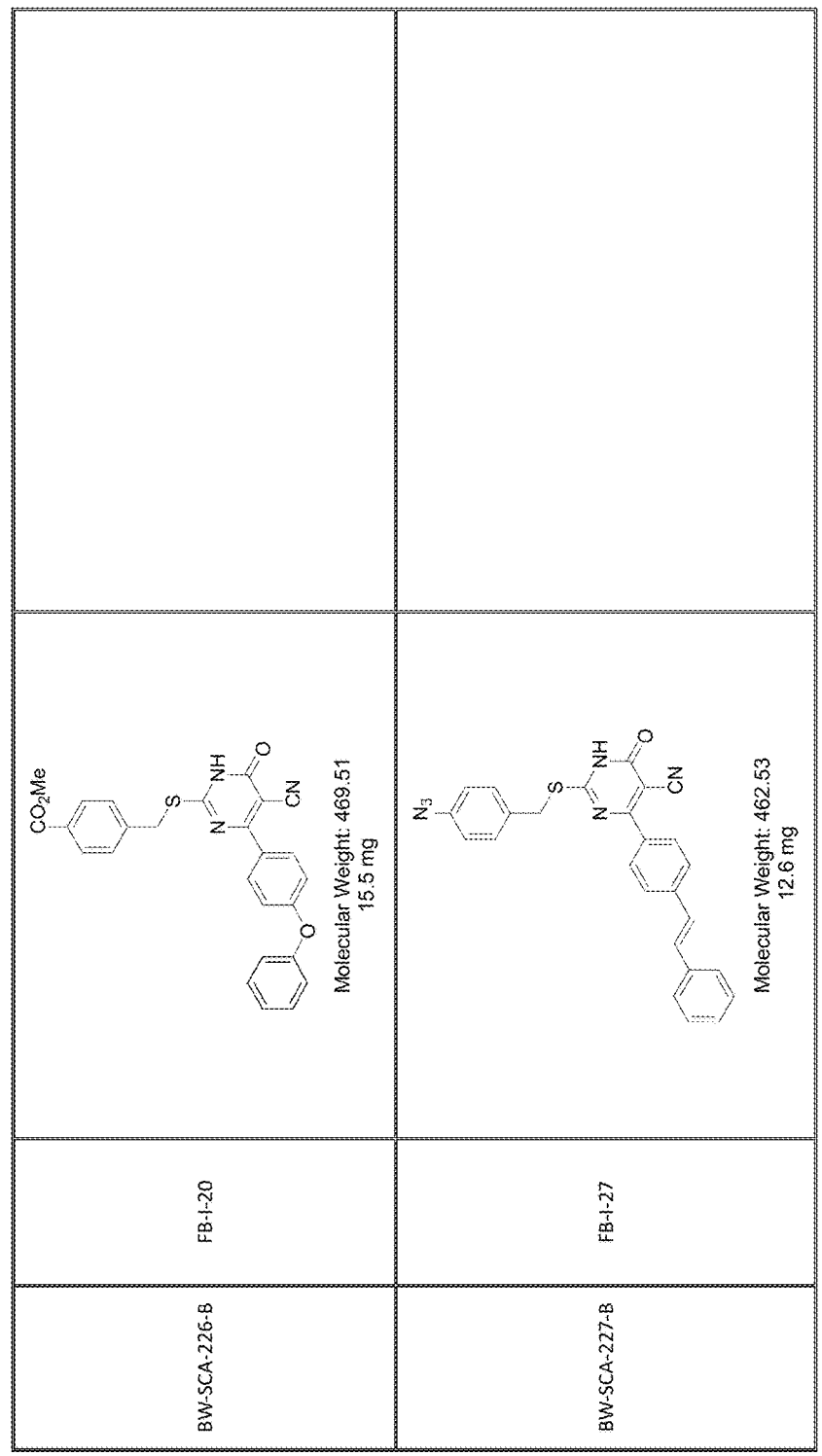
Figures 8, 108:
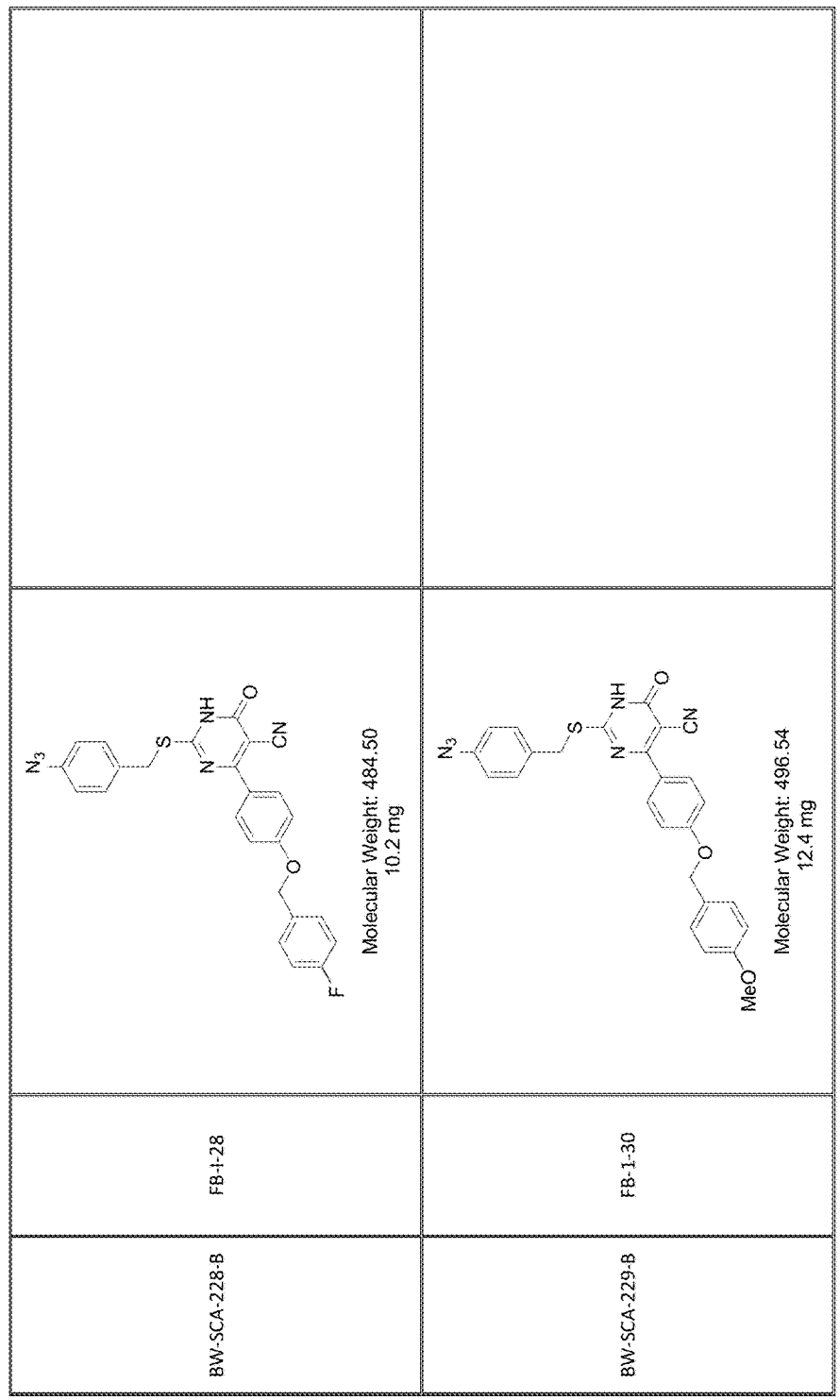
Figures 8, 110:
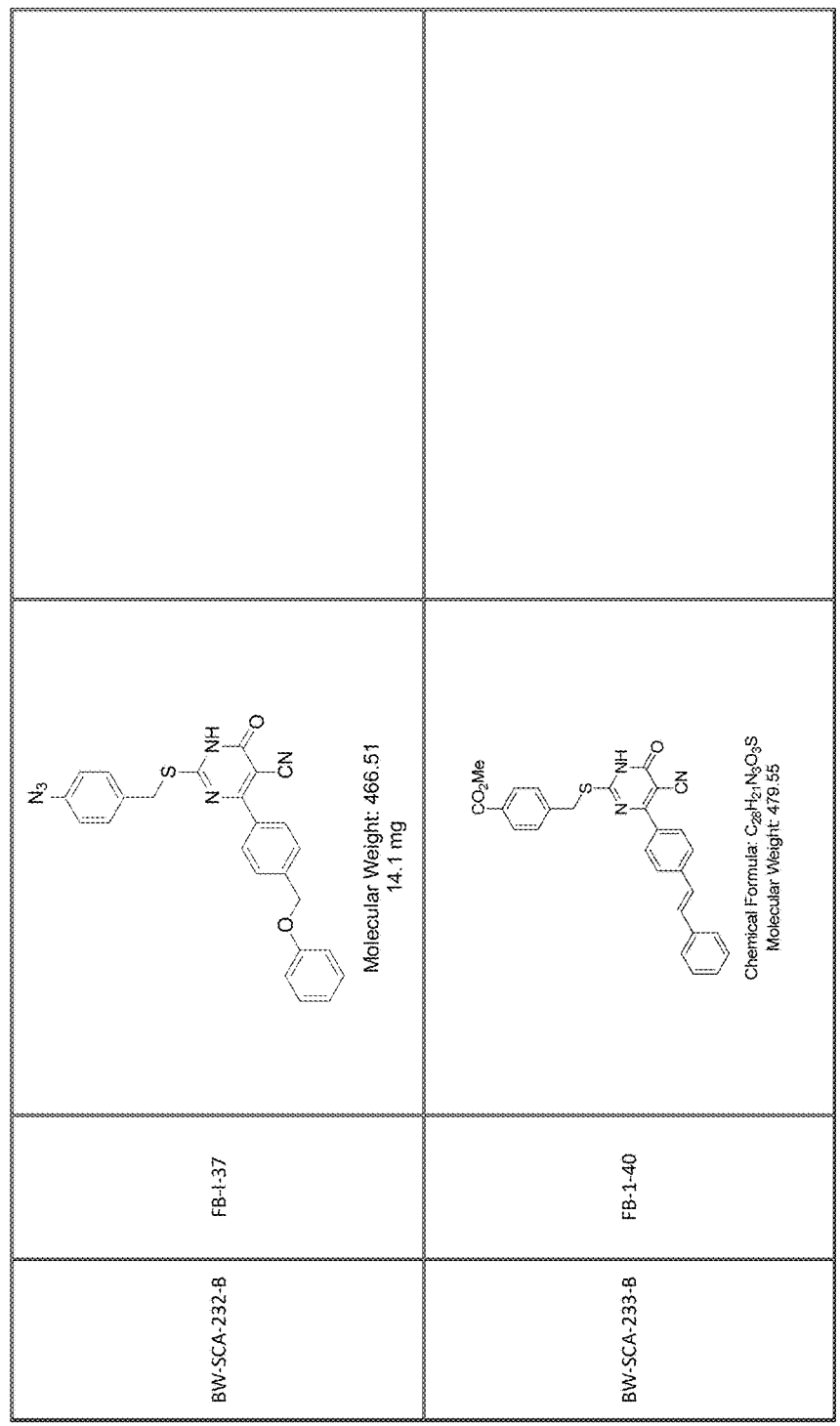
Figures 8, 111:
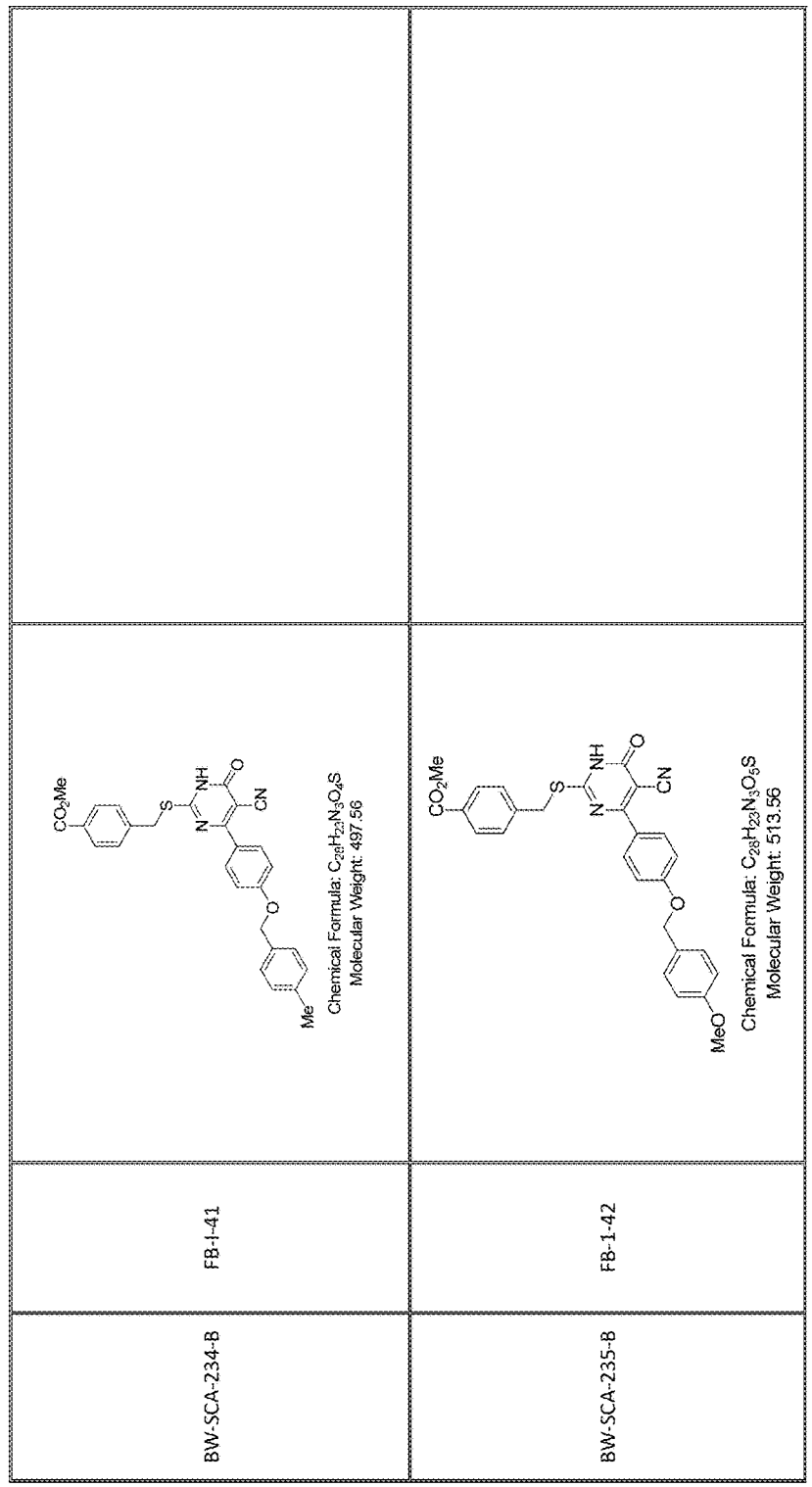
Figures 8, 112:
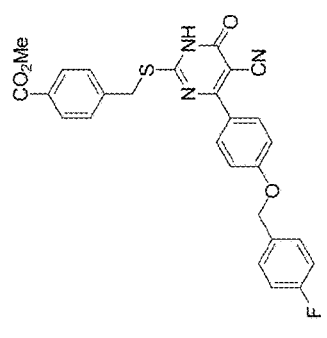
Figures 8, 113:
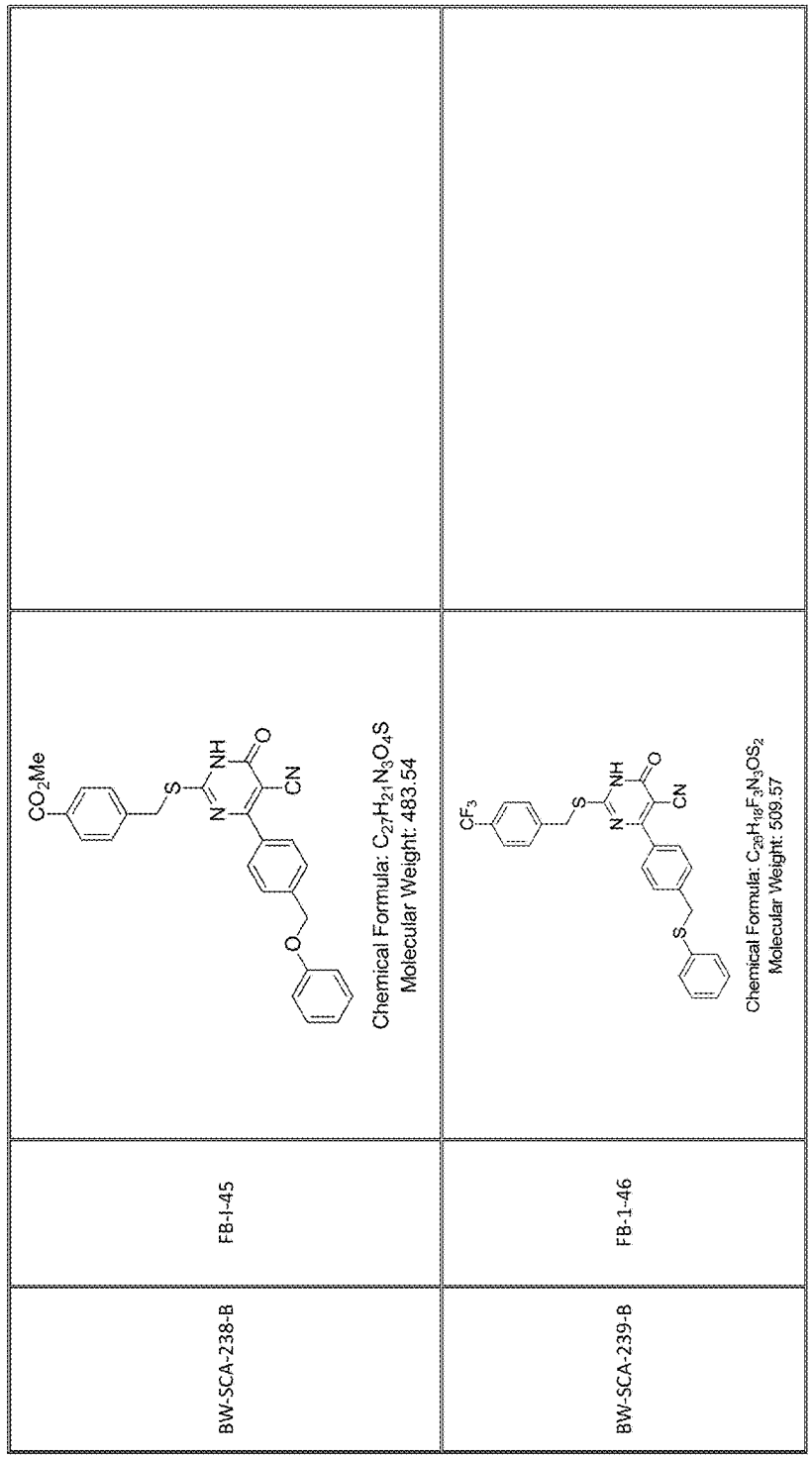
Figure 8:
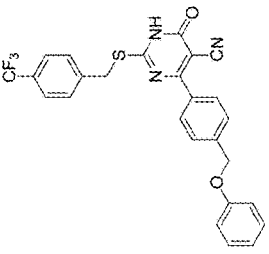
Figure 114:
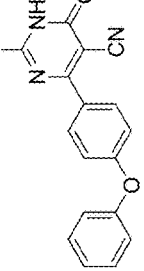
Figures 8, 115:
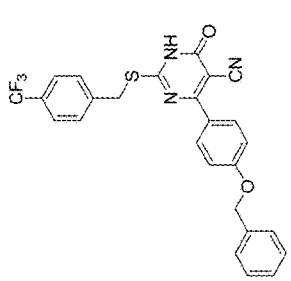
Figures 8, 116:
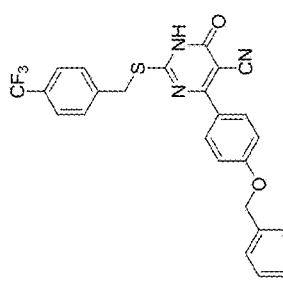
Figures 8, 117:
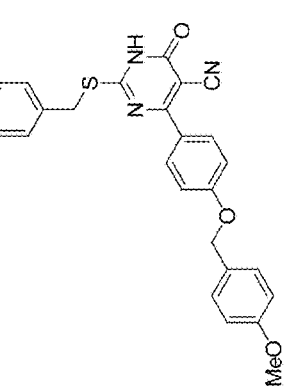
Figures 8, 120:
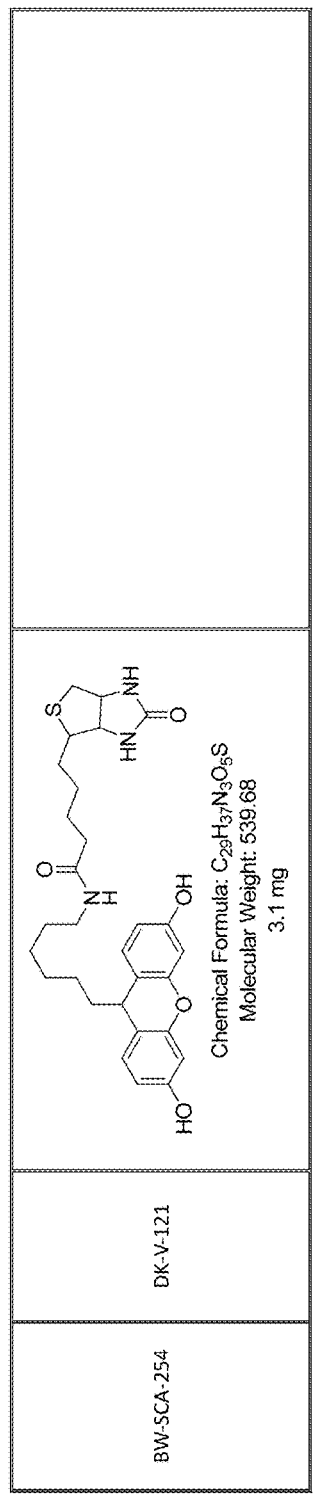

Results:

A series of compounds from the genus described by Formula I-X were screened against EcSecA using the intrinsic ATPase of the truncated N-terminal catalytic domain EcN68(unregulated ATPase). Those compounds with significant 1050 values are shown in FIG. 8.

The compounds were also screened for their inhibitory activitites against the bacterial strains *B. anthracis, S. aureus* 6538, *S. aureus* Mu50, *E. coli* NR698, and *B. subtilis* 168. The inhibitory activities of those compounds with significant $IC_{50}$ values are shown in FIG. 8.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A pharmaceutical composition comprising one or more compounds of the following formula:

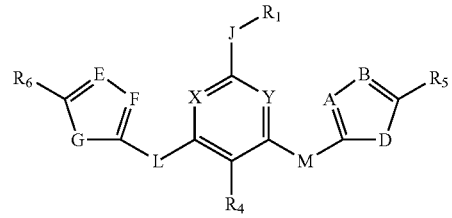

Formula III wherein

X and Y are N;

D and G are independently $NR_7$ or O;

A, B, E, and F are N;

L and M are independently S;

J is S; and $R_1$ and $R_4$ are independently selected from hydrogen, substituted or unsubstituted, linear, branched, hetero $C_1$-$C_{30}$ alkyl, $C_3$-$C_{30}$ cyclic alkyl, $C_2$-$C_{30}$ alkenyl, or $C_2$-$C_{30}$ alkynyl, substituted or unsubstituted aryl or heteroaryl, halogen, substituted or unsubstituted alkoxy, hydroxy, cyano, formyl, acyl, —COOH, —COO⁻, —CONH$_2$, —CONHR$_{17}$, —CONR$_{17}$R$_{17}$, —OCONHR$_{17}$, —NHCOOR$_{17}$, —OCONR$_{17}$R$_{17}$, —NR$_{14}$COOR$_{17}$, —NHCONHR$_{17}$, —NR$_{17}$CONHR$_{17}$, —NHCONR$_{17}$R$_{17}$, —NR$_{17}$CONR$_{17}$R$_{17}$, —CH$_2$OH, —CHR$_{17}$OH, —CR$_{17}$R$_{17}$OH, —COOR$_{17}$, —SH, —NH$_2$, —NHR$_{17}$, —NR$_{17}$R$_{17}$, —SR$_{17}$, —SOR$_{17}$, and —SOOR$_{17}$;

$R_5$ and $R_6$ are substituted or unsubstituted aryl or heteroaryl groups;

$R_7$ and $R_{17}$ are independently selected from hydrogen, substituted or unsubstituted, linear, branched, hetero $C_1$-$C_{30}$ alkyl, $C_3$-$C_{30}$ cyclic alkyl, $C_2$-$C_{30}$ alkenyl, $C_3$-$C_{30}$ cyclic alkenyl, $C_2$-$C_{30}$ alkynyl groups, $C_3$-$C_{30}$ cyclic alkynyl, or aryl group;

wherein substituents of the substituted groups are selected from the group consisting of linear or branched $C_1$-$C_{30}$ alkyl, $C_1$-$C_{30}$ heteroalkyl, $C_3$-$C_{30}$ cyclic alkyl, $C_2$-$C_{30}$ alkenyl, $C_2$-$C_{30}$ alkynyl, phenyl, aryl, heteroaryl, halo, hydroxyl, alkoxy, phenoxy, aroxy, alkylthio, phenylthio, arylthio, cyano, isocyano, carbonyl, carboxyl, amino, amido, sulfonyl, sulfonic acid, phosphoryl, phosphonyl, and polyaryl groups; and wherein the $C_1$-$C_{30}$ alkyl, the $C_1$-$C_{30}$ heteroalkyl, the $C_3$-$C_{30}$ cyclic alkyl, the $C_2$-$C_{30}$ alkenyl, the $C_2$-$C_{30}$ alkynyl, the phenyl, the aryl, the heteroaryl, the alkoxy, the phenoxy, the aroxy, the alkylthio, the phenylthio, the arylthio, the carbonyl, the carboxyl, the amino, the amido, the sulfonyl, the phosphoryl, the phosphonyl, or the polyaryl groups are optionally substituted with one or more halogens or hydroxyl groups;

or pharmaceutically acceptable salts thereof;

wherein the one or more compounds are present in an effective amount to inhibit SecA.

2. A pharmaceutical composition comprising one or more compounds of the following formula:

Formula X

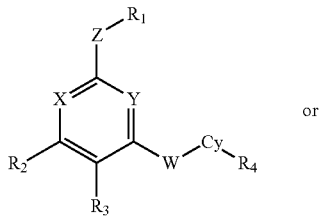

or

Formula Xa

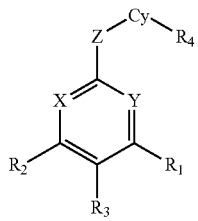

wherein
Z and W are S;
X and Y are N;
Cy is substituted or unsubstituted triazole or an oxadiazole group;
$R_2$ is a halogen;
$R_1$ and $R_3$ are independently selected from hydrogen, substituted or unsubstituted, linear, branched, hetero $C_1$-$C_{30}$ alkyl, $C_2$-$C_{30}$ alkenyl, or $C_2$-$C_{30}$ alkynyl, substituted or unsubstituted aryl, halogen, substituted or unsubstituted alkoxy, hydroxy, cyano, formyl, acyl, —COOH, —COO⁻, —CONH$_2$, —CONHR$_{11}$, —CONR$_{11}$R$_{11}$, —OCONHR$_{11}$, —NHCOOR$_{11}$, —OCONR$_{11}$R$_{11}$, —NR$_{14}$COOR$_{11}$, —NHCONHR$_{11}$, —NR$_{11}$CONHR$_{11}$, —NHCONR$_{11}$R$_{11}$, —NR$_{14}$CONR$_{11}$R$_{11}$, —CH$_2$OH, —CHR$_{11}$OH, —CR$_{11}$R$_{11}$OH, —COOR$_{11}$, —SH, —NH$_2$, —NHR$_{11}$, —NR$_{11}$R$_{11}$, —SR$_{11}$, —SOR$_{11}$, and —SOOR$_{11}$;
$R_4$ is a substituted or unsubstituted aryl or heteroaryl group;
$R_5$ and $R_{11}$ are independently selected from hydrogen, substituted or unsubstituted, linear, branched, or hetero $C_1$-$C_{30}$ alkyl, $C_3$-$C_{30}$ cyclic alkyl, $C_2$-$C_{30}$ alkenyl, $C_3$-$C_{30}$ cyclic alkenyl, $C_2$-$C_{30}$ alkynyl groups, $C_3$-$C_{30}$ cyclic alkynyl, or aryl group;
wherein substituents of the substituted groups are selected from the group consisting of $C_1$-$C_{30}$ alkyl, $C_1$-$C_{30}$ heteroalkyl, $C_3$-$C_{30}$ cyclic alkyl, $C_2$-$C_{30}$ alkenyl, $C_2$-$C_{30}$ alkynyl, phenyl, aryl, heteroaryl, halo, hydroxyl, alkoxy, phenoxy, aroxy, alkylthio, phenylthio, arylthio, cyano, isocyano, carbonyl, carboxyl, amino, amido, sulfonyl, sulfonic acid, phosphoryl, phosphonyl, and polyaryl groups; and wherein the $C_1$-$C_{30}$ alkyl, the $C_1$-$C_{30}$ heteroalkyl, the $C_3$-$C_{30}$ cyclic alkyl, the $C_2$-$C_{30}$ alkenyl, the $C_2$-$C_{30}$ alkynyl, the phenyl, the aryl, the heteroaryl, the alkoxy, the phenoxy, the aroxy, the alkylthio, the phenylthio, the arylthio, the carbonyl, the carboxyl, the amino, the amido, the sulfonyl, the phosphoryl, the phosphonyl, or the polyaryl groups are optionally substituted with one or more halogens or hydroxyl groups;
or pharmaceutically acceptable salts thereof;
wherein the one or more compounds are present in an effective amount to inhibit SecA.

3. The pharmaceutical composition of claim 2, comprising one or more pharmaceutically acceptable carriers.

4. A method of treating a bacterial infection comprising administering the pharmaceutical composition of claim 2.

5. The method according to claim 4, wherein the pharmaceutical composition is administered by one or more routes selected from the group consisting of buccal, sublingual, intravenous, subcutaneous, intradermal, transdermal, intraperitoneal, oral, eye drops, parenteral and topical administration.

6. The pharmaceutical composition of claim 1, wherein the one or more compounds are selected from the group consisting of:

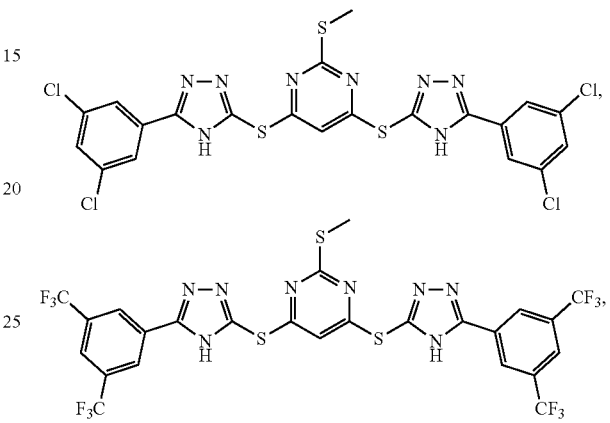

end pharmaceutically acceptable salts thereof.

7. The pharmaceutical composition of claim 2, wherein the one or more compounds are selected from the group consisting of:

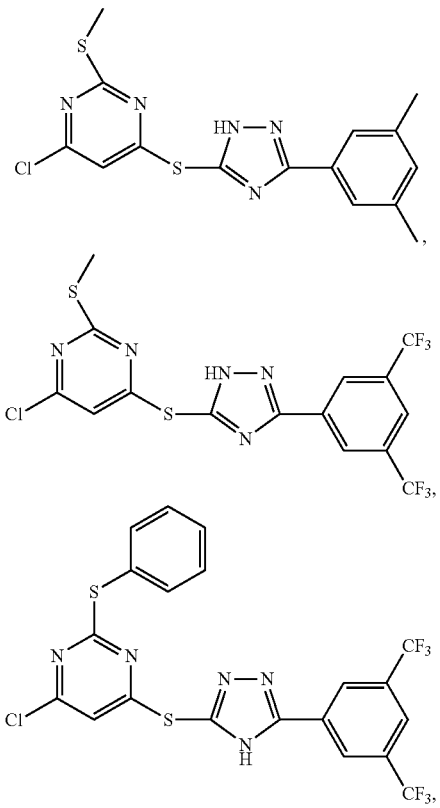

-continued
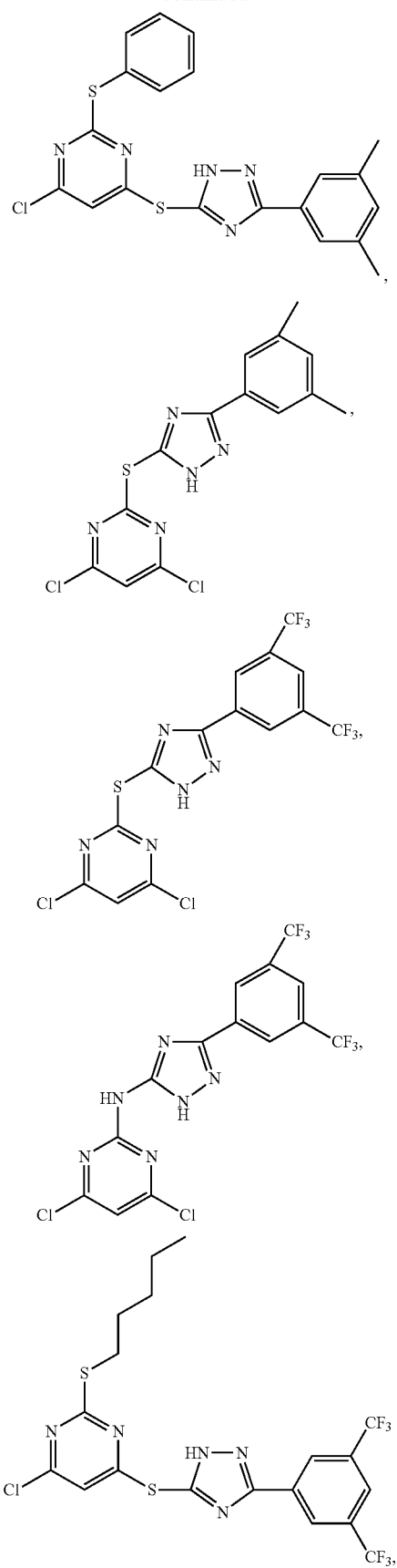
-continued
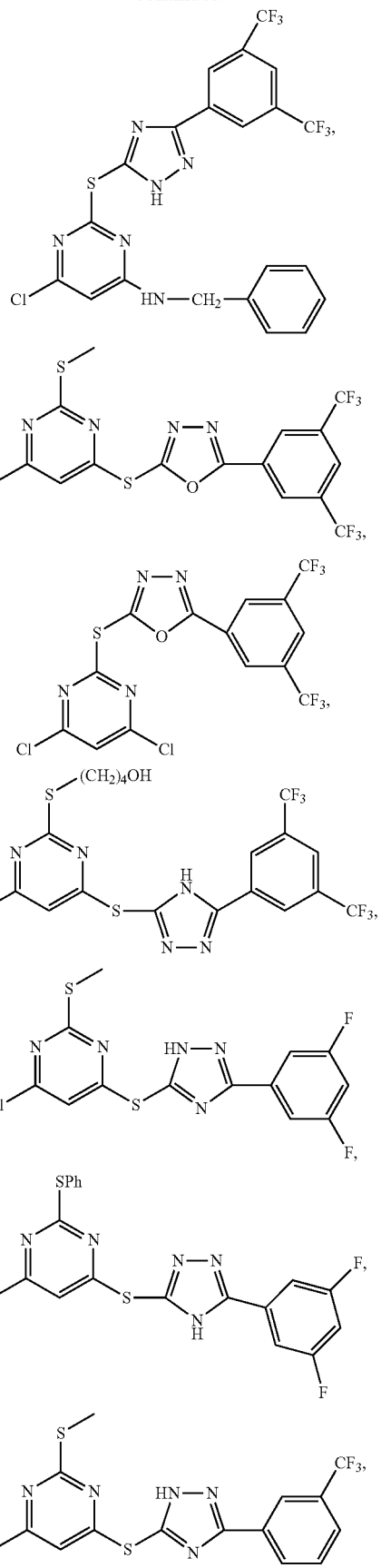

-continued
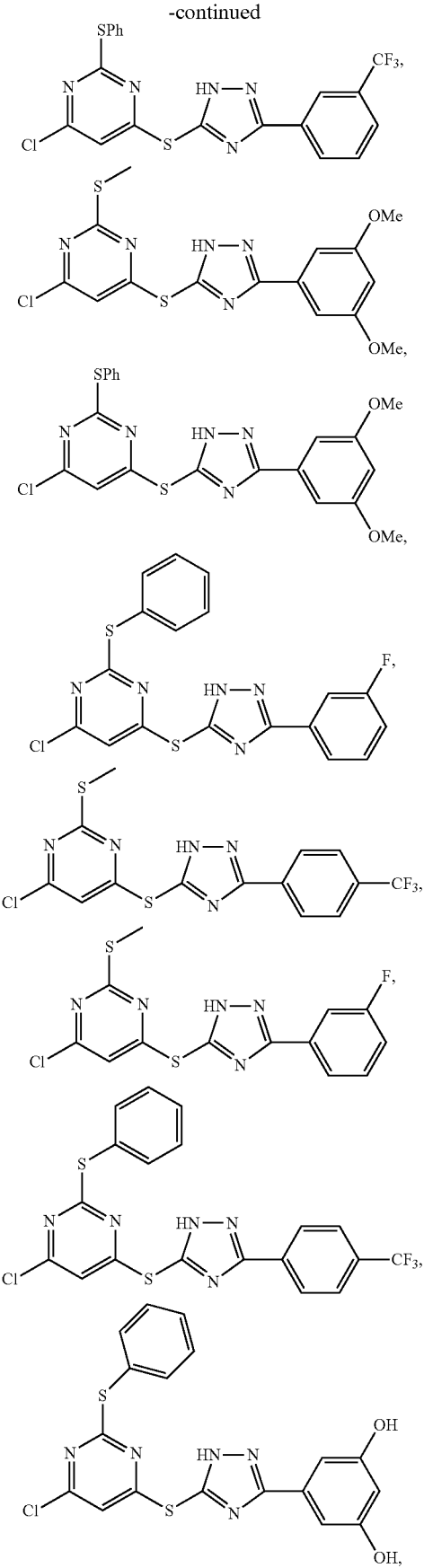
-continued
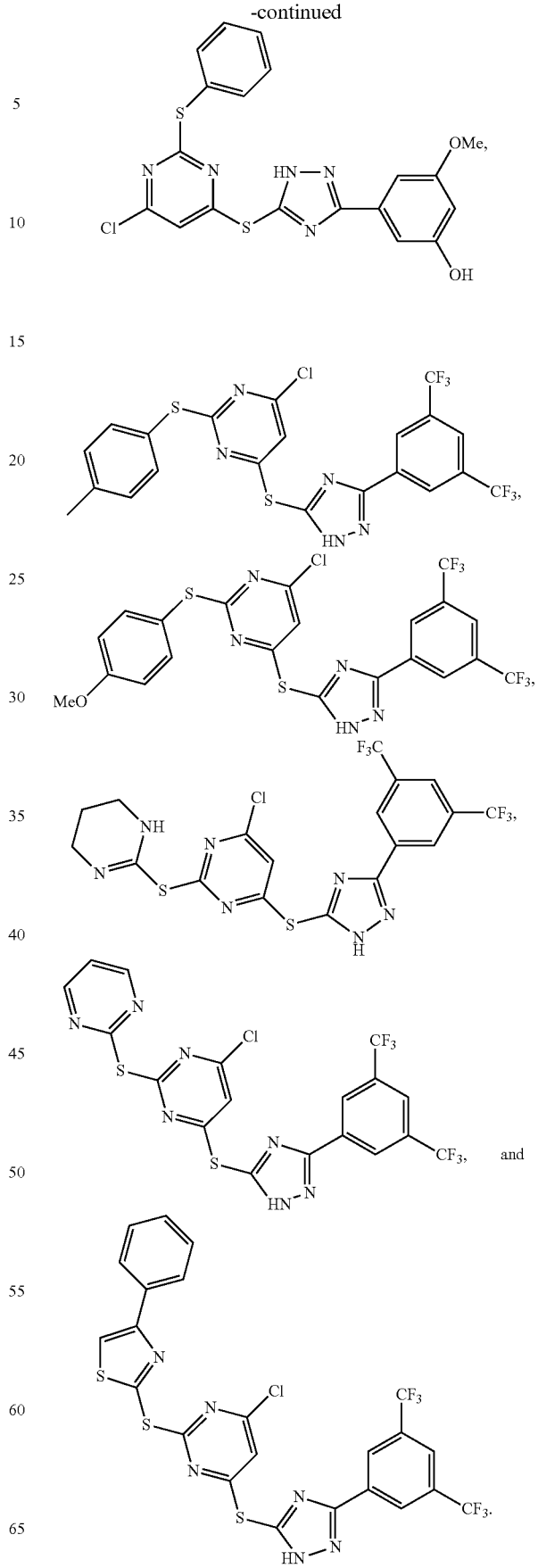

8. The pharmaceutical composition of claim 2, wherein the compound is:

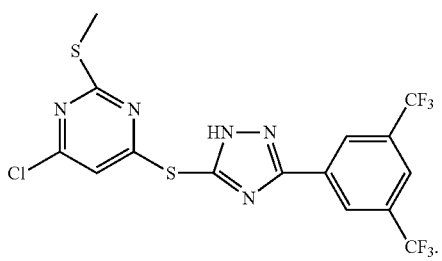 [SMILES: CSc1nc(Cl)cc(Sc2nc(-c3cc(C(F)(F)F)cc(C(F)(F)F)c3)n[nH]2)n1]

9. The pharmaceutical composition of claim 2, wherein the compound is:

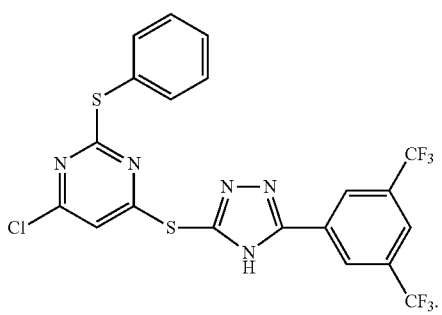 [SMILES: FC(F)(F)c1cc(-c2nnc(Sc3cc(Cl)nc(Sc4ccccc4)n3)[nH]2)cc(C(F)(F)F)c1]

10. The pharmaceutical composition of claim 1, wherein $R_7$ is hydrogen or a $C_1$-$C_{30}$ alkyl.

11. The pharmaceutical composition of claim 1, wherein $R_1$ is a $C_1$-$C_{30}$ alkyl.

12. The pharmaceutical composition of claim 1, wherein $R_5$ and $R_6$ are substituted or unsubstituted aryl groups.

13. The pharmaceutical composition of claim 2, wherein Cy is a triazole ring, and $R_4$ is a substituted or unsubstituted aryl group.

14. The pharmaceutical composition of claim 2, wherein $R_4$ is a substituted or unsubstituted aryl and $R_1$ is an aryl group.

15. The pharmaceutical composition of claim 1, comprising one or more pharmaceutically acceptable carriers.

16. A method of treating a bacterial infection comprising administering the pharmaceutical composition of claim 1.

17. The method according to claim 16, wherein the pharmaceutical composition is administered by one or more routes selected from the group consisting of buccal, sublingual, intravenous, subcutaneous, intradermal, transdermal, intraperitoneal, oral, eye drops, parenteral and topical administration.

* * * * *

UNITED STATES PATENT AND TRADEMARK OFFICE
CERTIFICATE OF CORRECTION

PATENT NO. : 9,957,247 B2  
APPLICATION NO. : 14/406085  
DATED : May 1, 2018  
INVENTOR(S) : Binghe Wang et al.

Page 1 of 2

It is certified that error appears in the above-identified patent and that said Letters Patent is hereby corrected as shown below:

In the Claims

Claim 6, Column 136, Line 30; replace the term "end" with "and".

Claim 7, Column 140, Line 20; replace the structure

" 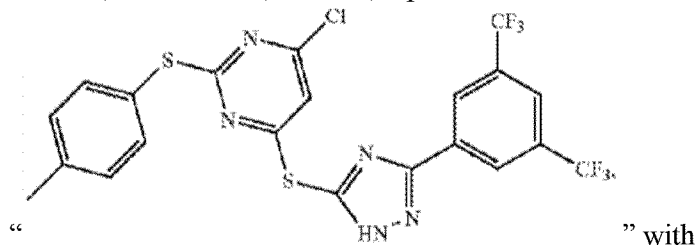 " with

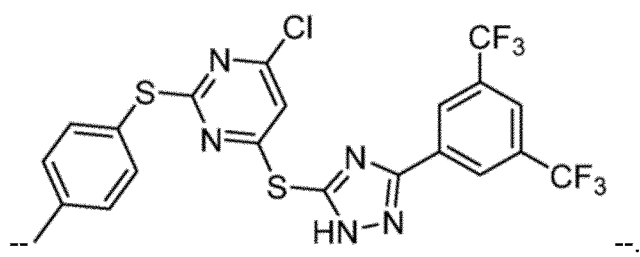 --.

Claim 7, Column 140, Line 30; replace the structure

" 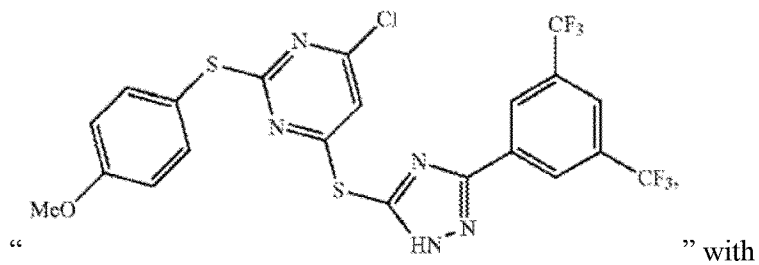 " with

Signed and Sealed this  
Thirtieth Day of October, 2018

Andrei Iancu  
*Director of the United States Patent and Trademark Office*

CERTIFICATE OF CORRECTION (continued)
U.S. Pat. No. 9,957,247 B2

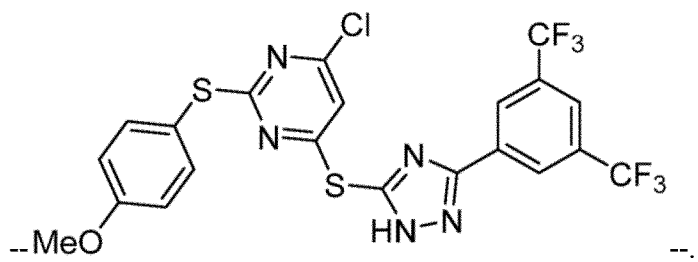

--MeO                                   --.

Claim 7, Column 140, Line 45; please replace the structure

" 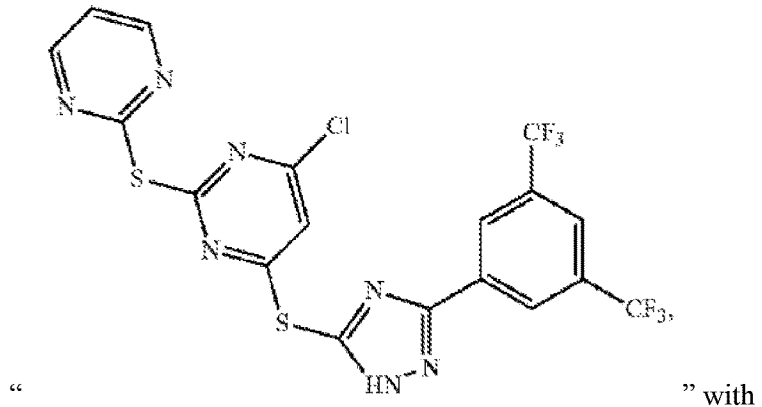 " with

"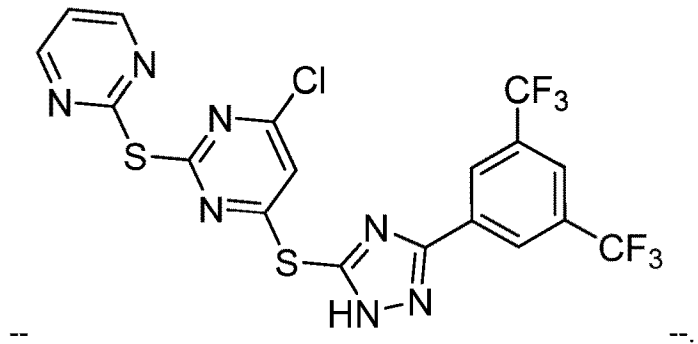

--                                      --.

UNITED STATES PATENT AND TRADEMARK OFFICE
CERTIFICATE OF CORRECTION

| | | |
|---|---|---|
| PATENT NO. | : 9,957,247 B2 | Page 1 of 1 |
| APPLICATION NO. | : 14/406085 | |
| DATED | : May 1, 2018 | |
| INVENTOR(S) | : Binghe Wang et al. | |

It is certified that error appears in the above-identified patent and that said Letters Patent is hereby corrected as shown below:

In the Specification

Column 1, Lines 7-10, replace the following paragraph:
"This invention was made with government support under Agreement Nos. CA123329, CA 883343,GM34766, and GM 084933 awarded by the National Institutes of Health. The government has certain rights in the invention."

With the following paragraph:
--This invention was made with government support under GM084933, CA088343, CA123329, and GM034766 awarded by the National Institutes of Health. The government has certain rights in the invention.--

Signed and Sealed this
Twenty-ninth Day of April, 2025

Coke Morgan Stewart
*Acting Director of the United States Patent and Trademark Office*